(12) United States Patent
Holliger et al.

(10) Patent No.: US 8,435,775 B2
(45) Date of Patent: May 7, 2013

(54) MUTANT PFU DNA POLYMERASE

(75) Inventors: Phillip Holliger, Cambridge (GB);
Nicola Ramsay, Cambridge (GB);
Ann-Sofie Jemth, Uppsala (SE)

(73) Assignee: Medical Research Council, Swindon (GB)

( * ) Notice: Subject to any disclaimer, the term of this patent is extended or adjusted under 35 U.S.C. 154(b) by 508 days.

(21) Appl. No.: 12/440,374

(22) PCT Filed: Aug. 24, 2007

(86) PCT No.: PCT/GB2007/003254
§ 371 (c)(1),
(2), (4) Date: Apr. 27, 2009

(87) PCT Pub. No.: WO2008/029085
PCT Pub. Date: Mar. 13, 2008

(65) Prior Publication Data
US 2010/0035767 A1 Feb. 11, 2010

(30) Foreign Application Priority Data

Sep. 6, 2006 (GB) .................................. 0617565.7
Jun. 22, 2007 (GB) .................................. 0712157.7

(51) Int. Cl.
*C12N 9/00* (2006.01)
*C07H 21/02* (2006.01)
(52) U.S. Cl.
USPC .......................................... 435/183; 536/23.1
(58) Field of Classification Search .......................... None
See application file for complete search history.

(56) References Cited

U.S. PATENT DOCUMENTS

| 5,474,920 A | 12/1995 | Moses |
| 5,985,557 A | 11/1999 | Prudent et al. |
| 2002/0127623 A1 | 9/2002 | Minshull et al. |
| 2006/0240439 A1* | 10/2006 | Smith et al. ....................... 435/6 |

FOREIGN PATENT DOCUMENTS

| WO | WO-95/14782 | 6/1995 |
| WO | WO-02/22869 | 3/2002 |
| WO | WO-2005/024010 | 3/2005 |
| WO | WO-2005/045015 | 5/2005 |
| WO | WO-2008/029085 | 3/2008 |
| WO | WO-2008/050104 | 5/2008 |

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*

(Continued)

*Primary Examiner* — Alexander Kim
(74) *Attorney, Agent, or Firm* — Marshall, Gerstein & Borun LLP

(57) ABSTRACT

The present invention relates to an engineered polymerase with an expanded substrate range characterized in that the polymerase is capable of incorporating an enhanced occurrence of detection agent-labeled nucleotide analogue into nucleic acid synthesized by that engineered polymerase as compared with the wild type polymerase from which it is derived.

17 Claims, 25 Drawing Sheets

OTHER PUBLICATIONS

Wacey et al., Disentangling the perturbational effects of amino acid substitutions in the DNA-binding domain of p53., Hum Genet, 1999, vol. 104, pp. 15-22.*

Anderson et al., "Incorporation of reporter-labeled nucleotides by DNA polymerases", Biotechniques, 38:257-264 (2005).

Augustin et al., "Progress towards single-molecule sequencing: enzymatic synthesis of nucleotide-specifically labeled DNA", J. Biotechnol., 86:289-301 (2001).

Boudsocq et al., "*Sulfolobus solfataricus* P2 DNA polymerase IV (Dpo4): an archaeal DinB-like DNA polymerase with lesion-bypass properties akin to eukaryotic poleta", Nucleic Acids Res. 29:4607-4616 (2001).

Brakmann et al., "The large fragment of *Escherichia coli* DNA polymerase I can synthesize DNA exclusively from fluorecently labeled nucleotides", Chembiochem., 2:772-777 (2001).

Cox et al., "Fluorescent DNA hybridization probe preparation using amine modification and reactive dye coupling", Biotechniques, 36:114-122 (2004).

Derbyshire et al., "Structure-function analysis of 3'- 5'-exonuclease of DNA polymerases", Methods Enzymol., 262:363-385 (1995).

Fogg et al., "Structural basis for uracil recognition by archaeal family B DNA polymerases", Nat Struct Biol., 9:922-927 (2002).

Foldes-Papp et al., "Fluorescent high-density labeling of DNA: error-free substitution for a normal nucleotide", J Biotechnol., 86:237-253 (2001).

Gardner et al., "Determinants of nucleotide sugar recognition in an archaeon DNA polymerase", Nucleic Acids Research, 27:2545-2555 (1999).

Glick et al., "In vitro production and screening of DNA polymerase eta mutants for catalytic diversity", Biotechniques 33:1136-1144 (2002).

Haase et al., "Amplification and detection of lentiviral DNA inside cells", Proc. Natl. Acad. Sci. USA, 87:4971-4975 (1990).

Jäger et al., "Generation and enzymatic amplification of high-ensity functionalized DNA double strands", Angew. Chem., 43:3337-3340 (2004).

Kallioniemi et al., "Comparative genomic hybridization for molecular cytogenetic analysis of solid tumors", Science, 258:818-821 (1992).

Kononen et al., "Tissue microarrays for high-throughput molecular profiling of tumor specimens", Nat Med., 4:844-847 (1998).

Kunkel et al., "DNA replication fidelity", Annu. Rev. Biochem., 69:497-529 (2000).

Lu et al., "Expression in *E. coli* of the thermostable DNA polymerase from *Pyrococcus furiosus*", Protein Expression and Purification, 11:179-184 (1997).

McNeil et al., "Localizing DNA and RNA within nuclei and chromosomes by fluorescence in situ hybridization", Genet Anal Tech Appl., 8:41-58 (1991).

Obayashi et al., "Enzymatic synthesis of labeled DNA by PCR using new fluorescent thymidine nucleotide analogue and superthermophilic KOD dash DNA polymerase", Bioorg Med Chem Lett., 12:1167-1170 (2002).

Oberholzer et al., "Polymerase chain reaction in liposomes", Chem. Biol., 2:677-682 (1995).

Ono et al., "2'-Fluoro modified nucleic acids: polymerase-directed synthesis, properties and stability to analysis by matrix-assisted laser desorption/ionization mass spectrometry", Nucleic Acids Res., 25:4581-4588 (1997).

Ramanathan et al., "High-density polymerase-mediated incorporation of fluorochrome-labeled nucleotides", Anal Biochem., 337:1-11 (2005).

Ried et al., "Simultaneous visualization of seven different DNA probes by in situ hybridization using combinatorial fluorescence and digital imaging microscopy", Proc Natl Acad Sci USA, 89:1388-1392 (1992).

Schena et al., "Quantitative monitoring of gene expression patterns with a complementary DNA microarray", Science, 270:467-470 (1995).

Shendure et al., "Advanced sequencing technologies: methods and goals", Nat Rev Genet., 5:335-344 (2004).

Skerra, "Use of the tetracycline promoter for the tightly regulated production of a murine antibody fragment in *Escherichia coli*.", Gene, 151:131-135 (1994).

Tawfik et al., "Man-made cell-like compartments for molecular evolution", Nature Biotech., 16:652-656 (1998).

Tippen et al., "Error-prone replication for better or worse", Trends in Microbiol., 12:288-295 (2004).

Yu et al., "Cyanine dye dUTP analogs for enzymatic labeling of DNA probes", Nucleic Acids Res., 22:3226-3232 (1994).

Zhu et al., "Family A and family B DNA polymerases are structurally related: evolutionary implications", Nucleic Acids Res., 22:5177-5183 (1994).

Zhu et al., "Molecular mechanism controlling the incorporation of fluorescent nucleotides into DNA by PCR", Cytometry., 28:206-211 (1997).

Zhu et al., "Directly labeled DNA probes using fluorescent nucleotides with different length linkers", Nucleic Acids Res., 22:3418-3422 (1994).

U.S. Appl. No. 12/446,746, Holliger et al.

Amblar et al., Purification and properties of the 5'-3' exonuclease D10A mutant of DNA polymerase I from *Streptococcus pneumoniae*: A new tool for DNA sequencing. *J. Biotechnol.* 63(1): 17-27 (1998).

Darby-Hughes et al., Detailed characterization of conditions for alignment of single-stranded and double-stranded DNA fragments on surfaces. *Biomedical Microdevice*. 5(1): 69-74 (2003).

Evans et al., Improving dideoxynucleotide-triphosphate utilisation by the hyper-thermophilic DNA polymerase from the archaeon *Pyrococcus furiosus*. *Nucl. Acids Res.* 28(5):1059-66 (2000).

Foldes-Papp et al., Fluorescently labeled model DNA sequences for exonucleolytic sequencing. *J. Biotech.* 86(3):203-24 (2001).

Franke-Whittle et al., Comparison of different labeling methods for the production of labeled target DNA microarray hybridization. *J. Microbiol. Meth.* 65(1): 117-26 (2006).

Ghadessy et al., Directed evolution of polymerase function by compartmentalized self-replication. *Proc. Natl. Acad. Sci. USA.* 96(8): 4552-7 (2001).

Ghadessy et al., Generic expansion of the substrate spectrum of a DNA polymerase by direction evolution. *Nature Biotech.* 22(6): 755-9 (2004).

Ravenschlag et al., The use of MasterTaq Kit for PCR with humic material-contaminated DNA. Applications No. 20 <http://www.eppendorf.de/int/index.php?1=2&action=document&sitemap=1&docnode=26726&pb=e4f62a797b085396>, May 2000.

Tasara et al., Incorporation of reporter molecule-labeled nucleotides by DNA polymerase. II. High-density labeling of natural DNA. *Nucl. Acids Res.* 31(10): 2636-46 (2003).

International Search Report, PCT/GB2007/003254, dated Feb. 20, 2008.

International Preliminary Report on Patentability, PCT/GB2007/003254, dated Mar. 19, 2009.

* cited by examiner

|  | | 334 | | | | | | | | | 344 | | | | | | | | | 354 | |
|---|---|---|---|---|---|---|---|---|---|---|---|---|---|---|---|---|---|---|---|---|---|---|
| SEQ ID NO.140 AH12 A motif | E | F | L | P | M | E | I | Q | L | S | R | L | V | G | Q | P | L | W | D | V | S | R | S | S | T | G | N | L | V | E |
| SEQ ID NO.141 55 A motif | E | F | L | P | M | E | I | Q | L | S | R | L | V | G | Q | P | L | W | D | V | S | R | S | S | T | G | N | L | V | E |
| SEQ ID NO.142 23 A motif | E | F | L | P | M | E | I | Q | L | S | R | L | V | G | Q | P | L | W | D | V | S | R | S | S | T | G | N | L | V | E |
| SEQ ID NO.143 15 A motif | E | F | L | P | M | E | I | Q | L | S | R | L | I | G | Q | P | L | W | D | V | S | R | S | S | T | G | N | L | V | E |
| SEQ ID NO.144 Pfu A motif | E | F | L | P | M | E | I | Q | L | S | R | L | V | G | Q | P | L | W | D | V | S | R | S | S | T | G | N | L | V | E |
| SEQ ID NO.145 | E | F | L | P | M | E | I | Q | L | S | R | L | V | G | Q | P | L | W | D | V | S | R | S | S | T | G | N | L | V | E |

364                  374                  384
AH12 A motif  W F L L R K A Y E R N E V A P N K P S E E E Y Q R R L R E S
55 A motif    W F L L R K A Y E R N E V A P N K P S E E E Y Q R R L R E S
23 A motif    W F L L R K A Y E R N E V A P N K P S E E E Y Q R R L R E S
15 A motif    W F L L R K A Y E R N E V A P N K P S E E E Y Q R R L R E S
Pfu A motif   W F L L R K A Y E R N E V A P N K P S E E E Y Q R R L R E S
              W F L L R K A Y E R N E V A P N K P S E E E Y Q R R L R E S
                                            399 400 401 402   407

394                  404                  414
AH12 A motif  Y T G G F V K E P E K G L W D G L A Y L D F I A L Y P S I I
55 A motif    Y T G G F V K E P E K G L W E G I V Y L D F I A L Y P S I I
23 A motif    Y T G G F V K E P E K G L W E D L V Y L D F I A L Y P S I I
15 A motif    Y T G G F V K E P E K G L W D D I V Y L D F I A L Y P S I I
Pfu A motif   Y T G G F V K E P E K G L W E N I V Y L D F R A L Y P S I I
              Y T G G F V K E P E K G L W E   I V Y L D F I A L Y P S I I
              415

424                  434                  444
AH12 A motif  V T H N V S P D T L N L E G C K N Y D I A P Q V G H K F C K
55 A motif    I T H N V S P D T L N L E G C K N Y D I A P Q V G H K F C K
23 A motif    I T H N V S P D T L N L E G C K N Y D I A P Q V G H K F C K
15 A motif    I T H N V S P D T L N L E G C K N Y D I A P Q V G H K F C K
Pfu A motif   I T H N V S P D T L N L E G C K N Y D I A P Q V G H K F C K
              I T H N V S P D T L N L E G C K N Y D I A P Q V G H K F C K
                                                              572

554                  564                  574
AH12 A motif  D I P G F I P S L L G H L L E E R Q K I K T K M K E T Q D P
55 A motif    D I P G F I P S L L G H L L E E R Q K I K T K M K E T Q D P
23 A motif    D I P G F I P S L L G H L L E E R Q K I K T K M K E T H D P
15 A motif    D I P G F I P S L L G H L L E E R Q K I K T K M K E T Q D P
Pfu A motif   D I P G F I P S L L G H L L E E R Q K I K T K M K E T Q D P
              D I P G F I P S L L G H L L E E R Q K I K T K M K E T Q D P

|  |  | 400 |  |  |  |  |  |  |  | 410 |  |  |  |  |  |
|---|---|---|---|---|---|---|---|---|---|---|---|---|---|---|---|
| SEQ ID NO.146 | Pfu | E | N | I | V | Y | L | D | F | R | A | L | Y | P | S | I | I | I |
| SEQ ID NO.147 | 2 | E | N | I | V | Y | L | D | F | R | A | L | Y | P | S | I | I | I |
| SEQ ID NO.148 | 6 | E | N | I | V | Y | L | D | F | R | A | L | Y | P | S | I | I | I |
| SEQ ID NO.149 | 7 | E | N | I | V | Y | L | D | F | R | A | L | Y | P | S | I | I | I |
| SEQ ID NO.150 | 11 | E | N | I | V | Y | L | D | F | R | A | L | Y | P | S | I | I | I |
| SEQ ID NO.151 | 13 | E | N | I | V | Y | L | D | F | R | A | L | Y | P | S | I | I | I |
| SEQ ID NO.152 | 3 | E | G | I | V | Y | L | D | F | I | A | L | Y | P | S | I | I | I |
| SEQ ID NO.153 | 4 | E | D | L | V | Y | L | D | F | I | A | L | Y | P | S | I | I | I |
| SEQ ID NO.154 | 5 | E | G | I | V | Y | L | D | F | I | A | L | Y | P | S | I | I | I |
| SEQ ID NO.155 | 8 | E | D | L | V | Y | L | D | F | I | A | L | Y | P | S | I | I | I |
| SEQ ID NO.156 | 9 | D | D | I | V | Y | L | D | F | I | A | L | Y | P | S | I | I | I |
| SEQ ID NO.157 | 10 | E | G | I | V | Y | L | D | F | I | A | L | Y | P | S | I | I | I |
| SEQ ID NO.158 | 12 | E | G | I | V | Y | L | D | F | I | A | L | Y | P | S | I | I | I |
| SEQ ID NO.159 |  | E |  | I | V | Y | L | D | F | I | A | L | Y | P | S | I | I | I |

A motif

B

|  |  | 490 |  |  |  |  |  |  |  |  | 500 |  |  |  |
|---|---|---|---|---|---|---|---|---|---|---|---|---|---|---|---|
| SEQ ID NO.160 | Pfu | K | L | L | A | N | S | F | Y | G | Y | Y | G | Y | A |
| SEQ ID NO.161 | 2 | K | L | L | A | N | S | V | Y | G | Y | F | G | Y | A |
| SEQ ID NO.162 | 6 | K | L | L | A | N | S | F | Y | G | Y | F | G | Y | T |
| SEQ ID NO.163 | 7 | K | M | A | A | N | S | F | W | G | Y | I | G | Y | T |
| SEQ ID NO.164 | 11 | K | L | L | A | N | S | F | Y | G | Y | F | G | Y | T |
| SEQ ID NO.165 | 13 | K | L | V | A | N | S | F | Y | G | S | Y | G | Y | P |
| SEQ ID NO.166 | 3 | K | L | L | A | N | S | L | Y | G | Y | Y | G | Y | A |
| SEQ ID NO.167 | 4 | K | L | L | A | N | T | F | Y | G | Y | Y | G | Y | A |
| SEQ ID NO.168 | 5 | K | L | L | A | N | S | F | Y | G | Y | F | G | Y | P |
| SEQ ID NO.169 | 8 | K | L | L | A | N | S | F | Y | G | Y | F | G | Y | P |
| SEQ ID NO.170 | 9 | K | L | L | T | N | S | V | Y | G | Y | Y | G | Y | T |
| SEQ ID NO.171 | 10 | K | L | L | A | N | S | F | Y | G | Y | Y | G | Y | P |
| SEQ ID NO.172 | 12 | K | N | L | A | N | C | F | Y | G | Y | I | G | F | A |
| SEQ ID NO.173 |  | K | L | L | A | N | S | F | Y | G | Y | . | G | Y |  |

B motif

|  |  | 410 |
|---|---|---|
| SEQ ID NO.174 | E10 | D D I V Y L D F I A L Y P S I I I |
| SEQ ID NO.175 | 15 | D D I V Y L D F I A L Y P S I I I |
| SEQ ID NO.176 | 5 | D D I V Y L D F I A L Y P S I I I |
| SEQ ID NO.177 | 28 | E G I V Y L D F I A L Y P S I I I |
| SEQ ID NO.178 | 27 | E G I V Y L D F I A L Y P S I I I |
| SEQ ID NO.179 | 25 | E D L V Y L D F I A L Y P S I I I |
| SEQ ID NO.180 | 23 | E G I V Y L D F I A L Y P S I I I |
| SEQ ID NO.181 | 22 | E D L V Y L D F I A L Y P S I I I |
| SEQ ID NO.182 | 13 | E G I V Y L D F I A L Y P S I I I |
| SEQ ID NO.183 | 12 | E G I V Y L D F I A L Y P S I I I |
| SEQ ID NO.184 | 10 | D D I V Y L D F I A L Y P S I I I |
| SEQ ID NO.185 | 9 | D D I V Y L D F I A L Y P S I I I |
| SEQ ID NO.186 | Pfu | E N I V Y L D F R A L Y P S I I I |
| SEQ ID NO.187 |  | E D I V Y L D F I A L Y P S I I I |

A motif

B

|  |  | 540 |
|---|---|---|
| SEQ ID NO.188 | E10 | V L Y I D T D G L H |
| SEQ ID NO.189 | 15 | V I Y I D T D G L L |
| SEQ ID NO.190 | 5 | V L Y I D T D G L H |
| SEQ ID NO.191 | 28 | V L Y I D T D G L H |
| SEQ ID NO.192 | 27 | V L Y I D T D G L H |
| SEQ ID NO.193 | 25 | V L Y I D T D G L L |
| SEQ ID NO.194 | 23 | V L Y I D T D G L H |
| SEQ ID NO.195 | 22 | V L Y I D T D G L H |
| SEQ ID NO.196 | 13 | V L Y I D T D G L H |
| SEQ ID NO.197 | 12 | V L Y I D T D G L H |
| SEQ ID NO.198 | 10 | V L Y I D T D G L L |
| SEQ ID NO.199 | 9 | V L Y I D T D G L H |
| SEQ ID NO.200 | Pfu | V L Y I D T D G L Y |
| SEQ ID NO.201 |  | V L Y I D T D G L H |

C motif

FIG. 7

A) E10 nucleotide sequence (SEQ ID NO.2)
ATGATTTTAGATGTGGATTACATAACTGAAGAAGGAAAAACCTGTTATTAGGCTATTCAAAAAAGAGAAC
GGAAAATTTAAGATAGAGCATGATAGAACTTTTAGACCATACATTTACGCTCTTCTCAGGGATGATTCA
AAGATTGAAGAAGTTAAGAAAATAACGGGGGAAAGGCATGGAAAGATTGTGAGAATTGTTGATGTAGAG
AAGGTTGAGAAAAAGTTTCTCGGCAAGCCTATTACCGTGTGGAAACTTTATTTGGAACATCCTCAGGAT
CAGCCCACTATTAGAGAAAAAGTTAGAGAACATCCAGCAGTTGTGGACATCTTCGAATACGATATTCCA
TTTGCAAAGAGATACCTCATCGACAAAGGCCTAATACCAATGGAGGGGGAAGAAGAGCTAAAGATTCTT
GCCTTCGCGATCGCGACCCTCTATCACGAAGGAGAAGAGTTTGGAAAAGGCCCAATTATAATGATTAGT
TATGCAGATGAAAATGAAGCAAAGGTGATTACTTGGAAAAACATAGATCTTCCATACGTTGAGGTTGTA
TCAAGCGAGAGAGAGATGATAAAGAGATTTCTCAGGATTATCAGGGAGAAGGACCCTGACATTATAGTT
ACTTATAATGGAGACTCATTCGACTTCCCATATTTAGCGAAAAGGGCAGAAAAACTTGGGATTAAATTA
ACCATTGGAAGAGATGGAAGCGAGCCCAAGATGCAGAGAATAGGCGATATGACGGCTGTAGAAGTCAAG
GGAAGAATACATTTCGACTTGTATCATGTAATAACAAGGACAATAAATCTCCCAACATACACACTAGAG
GCTGTATATGAAGCAATTTTTGGAAAGCCAAAGGAGAAGGTATACGCCGACGAGATAGCAAAAGCCTGG
GAAAGTGGAGAGAACCTTGAGGAGTTGCCAAATACTCGATGGAAGATGCAAAGGCAACTTATGAACTC
GGGAAAGAATTCCTTCCAATGGAAATTCAGCTCTCAAGATTAATTGGACAACCTTTATGGGATGTTTCA
AGGTCAAGCACAGGGAACCTTGTAGAGTGGTTCTTACTTAGGAAAGCCTACGAAAGAAACGAAGTAGCT
CCAAACAAGCCAAGTGAAGAGGAGTATCAAAGAAGGCTCAGGGAGAGCTACACAGGTGGATTCGTTAAA
GAGCCAGAAAAGGGGTTGTGGACGACATCGTTTATCTAGATTTCATAGCCCTATATCCTCGATTATA
ATTACCCACAATGTTTCTCCCGATACTCTAAATCTTGAGGGATGCAAGAACTATGATATCGCTCCTCAA
GTAGGCCACAAGTTCTGCAAGGACATCCCTGGTTTTATACCAAGTCTTCTTGGGACATTTGTTAGAGGAA
AGACAAAAGATTAAGACAAAAATGAAGGAAACTCAGGATCCTATAGAAAAATACTCCTTGACTATAGA
CAAAAAGCGATAAAACTCTTAGCAAATTCTTTCTACGGATATTATGGCTATGCAAAAGCAAGATGGTAC
TGTAAGGAGTGTGCTGAGAGCGTTACTGCCTGGGGAAGAAAGTACATCGAGTTAGTATGGAAGGAGCTC
GAAGAAAAGTTTGGATTTAAAGTCCTATACATCGACACTGATGGTCTTCACGCAACTATCCCAGGAGGA
GAAAGTGAGGAGATCAAGAAAAAGGCTCTCGAATTTGTAAAATACATAAATTCAAAGCTCCCTGGACTG
CTCGAGCTTGAATATGAAGGGTTTTATAAGAGGGGATTCTTCGTTACGAAGAAGAGGTATGCAGTAATA
GATGAAGAAGGAAAAGTCATTACTCGTGGTTTAGAGATAGTTAGGAGAGATTGGAGTGAAATTGCAAAA
GAAACTCAAGCTAGAGTTTTGGAGACAATACTAAAACACGGAGATGTTGAAGAAGCTGTGAGAATAGTA
AAAGAAGTAATACAAAAGCTTGCCAATTATGAAATTCCACCAGAGAAGCTCGCAATATATGAGCAGATA
ACAAGACCATTACATGAGTATAAGGCGATAGGTCCTCACGTAGCTGTTGCAAAGAAACTAGCTGCTAAA
GGAGTTAAAATAAAGCCAGGAATGGTAATTGGATACATAGTACTTAGAGGCGATGGTCCAATTAGCAAT
AGGGCAATTCTAGCTGAGGAATACGATCCCAAAAAGCACAAGTATGACGCAGAATATTACATTGAGAAC
CAGGTTCTTCCAGCGGTACTTAGGATATTGGAGGGATTTGGATACAGAAAGGAAGACCTCAGATACCAA
AAGACAAGACAAGTCGGCCTAACTTCCTGGCTTAACATTAAAAAATCCTAA

B) E10 amino acid sequence (SEQ ID NO.1)
MILDVDYITEEGKPVIRLFKKENGKFKIEHDRTFRPYIYALLRDDSKIEEVKKITGERHGKIVRIVDVE
KVEKKFLGKPITVWKLYLEHPQDQPTIREKVREHPAVVDIFEYDIPFAKRYLIDKGLIPMEGEEELKIL
AFAIATLYHEGEEFGKGPIIMISYADENEAKVITWKNIDLPYVEVVSSEREMIKRFLRIIREKDPDIIV
TYNGDSFDFPYLAKRAEKLGIKLTIGRDGSEPKMQRIGDMTAVEVKGRIHFDLYHVITRTINLPTYTLE
AVYEAIFGKPKEKVYADEIAKAWESGENLERVAKYSMEDAKATYELGKEFLPMEIQLSRLIGQPLWDVS
RSSTGNLVEWFLLRKAYERNEVAPNKPSEEEYQRRLRESYTGGFVKEPEKGLWDDIVYLDPIALYPSII
ITHNVSPDTLNLEGCKNYDIAPQVGHKFCKDIPGFIPSLLGHLLEERQKIKTKMKETQDPIEKILLDYR
QKAIKLLANSFYGYYGYAKARWYCKECAESVTAWGRKYIELVWKELEEKFGFKVLYIDTDGLHATIPGG
ESEEIKKKALEFVKYINSKLPGLLELEYEGFYKRGFFVTKKRYAVIDEEGKVITRGLEIVRRDWSEIAK
ETQARVLETILKHGDVEEAVRIVKEVIQKLANYEIPPEKLAIYEQITRPLHEYKAIGPHVAVAKKLAAK
GVKIKPGMVIGYIVLRGDGPISNRAILAEEYDPKKHKYDAEYYIENQVLPAVLRILEGFGYRKEDLRYQ
KTRQVGLTSWLNIKKS*

|  |  | 400 |  |  |  |  |  |  | 410 |  |  |  |  |  |  |
|---|---|---|---|---|---|---|---|---|---|---|---|---|---|---|---|
| SEQ ID NO.146 | Pfu | E | N | I | V | Y | L | D | F | R | A | L | Y | P | S | I | I | I |
| SEQ ID NO.202 | 5 | D | D | I | V | Y | L | D | F | I | A | L | Y | P | S | I | I | I |
| SEQ ID NO.203 | 4 | D | D | I | V | Y | L | D | F | I | A | L | Y | P | S | I | I | I |
| SEQ ID NO.204 | 3 | D | D | I | V | Y | L | D | F | I | A | L | Y | P | S | I | I | I |
| SEQ ID NO.205 | 2 | D | D | I | V | Y | L | D | F | I | A | L | Y | P | S | I | I | I |
| SEQ ID NO.206 | 11 | E | G | I | V | Y | L | D | F | I | A | L | Y | P | S | I | I | I |
| SEQ ID NO.207 | 10 | D | D | I | V | Y | L | D | F | I | A | L | Y | P | S | I | I | I |
| SEQ ID NO.208 | 1 | E | D | L | V | Y | L | D | F | I | A | L | Y | P | S | I | I | I |
| SEQ ID NO.209 | 9 | E | G | I | V | Y | L | D | F | I | A | L | Y | P | S | I | I | I |
| SEQ ID NO.210 | 8 | D | D | I | V | Y | L | D | F | I | A | L | Y | P | S | I | I | I |
| SEQ ID NO.211 | 7 | E | D | L | V | Y | L | D | F | I | A | L | Y | P | S | I | I | I |
| SEQ ID NO.212 | 6 | E | G | I | V | Y | L | D | F | I | A | L | Y | P | S | I | I | I |
| SEQ ID NO.213 |  | . | D | I | V | Y | L | D | F | I | A | L | Y | P | S | I | I | I |

A motif

B

|  |  | 540 |  |  |  |  |  |  |  |  |
|---|---|---|---|---|---|---|---|---|---|---|
| SEQ ID NO.214 | Pfu | V | L | Y | I | D | T | D | G | L | Y |
| SEQ ID NO.215 | 5 | V | L | Y | I | D | T | D | G | L | H |
| SEQ ID NO.216 | 4 | V | L | Y | I | D | T | D | G | L | L |
| SEQ ID NO.217 | 3 | V | L | Y | I | D | T | D | G | L | L |
| SEQ ID NO.218 | 2 | V | L | Y | I | D | T | D | G | L | H |
| SEQ ID NO.219 | 11 | V | L | Y | I | D | T | D | G | L | L |
| SEQ ID NO.220 | 10 | V | L | Y | I | D | T | D | G | L | H |
| SEQ ID NO.221 | 1 | V | I | Y | I | D | T | D | G | L | H |
| SEQ ID NO.222 | 9 | V | I | Y | I | D | T | D | G | L | H |
| SEQ ID NO.223 | 8 | V | L | Y | I | D | T | D | G | L | L |
| SEQ ID NO.224 | 7 | V | L | Y | I | D | T | D | G | L | H |
| SEQ ID NO.225 | 6 | V | L | Y | I | D | T | D | G | L | L |
| SEQ ID NO.226 |  | V | L | Y | I | D | T | D | G | L |  |

C motif

```
                    400                    410
SEQ ID NO.146  Pfu  E N I V Y L D F R A L Y P S I I I
SEQ ID NO.227  F1   E N I V Y L D F R A L Y P S I I I
SEQ ID NO.228  G2   E G I V Y L D F I A L Y P S I I I
SEQ ID NO.229  F2   E G I V Y L D F I A L Y P S I I I
SEQ ID NO.230  E2   E D L V Y L D F I A L Y P S I I I
SEQ ID NO.231  E1   E G I V Y L D F I A L Y P S I I I
SEQ ID NO.232  D2   E G I V Y L D F I A L Y P S I I I
SEQ ID NO.233  D1   E G I V Y L D F I A L Y P S I I I
SEQ ID NO.234  C2   E D L V Y L D F I A L Y P S I I I
SEQ ID NO.235  A3   D D I V Y L D F I A L Y P S I I I
SEQ ID NO.236  A2   D D I V Y L D F I A L Y P S I I I
SEQ ID NO.237       E   I V Y L D F I A L Y P S I I I
                            └─────── A motif ───────┘
```

B

```
                    490                    500
SEQ ID NO.160  Pfu  K L L A N S F Y G Y Y G Y A
SEQ ID NO.238  F1   K L L A N S F Y G Y K G Y P
SEQ ID NO.239  G2   K L L A N S F Y G Y F G Y A
SEQ ID NO.240  F2   K L L A N S F Y G Y F G Y A
SEQ ID NO.241  E2   K R L A N S F Y G Y F S Y T
SEQ ID NO.242  E1   K L L A N S F Y G Y F G Y T
SEQ ID NO.243  D2   K L L A N S F Y G Y F G Y T
SEQ ID NO.244  D1   K L L A N S F Y G Y Y G Y A
SEQ ID NO.245  C2   K L F A N S F Y G Y Y G Y P
SEQ ID NO.246  A3   K L L T N S L Y G Y F G Y P
SEQ ID NO.247  A2   K L F A N S F Y E Y Y G Y A
SEQ ID NO.248       K L L A N S F Y G Y F G Y
                    └──── B motif ────┘
```

FIG. 12

|  |  |  |  |  |  | 10 |  |  |  |  |  |  |  |  |  |  |  | 20 |  |  |
|---|---|---|---|---|---|---|---|---|---|---|---|---|---|---|---|---|---|---|---|---|
| SEQ ID NO.257 Pfu | G | L | W | E | N | I | V | Y | L | D | F | R | A | L | Y | P | S | I | I | I |
| SEQ ID NO.258 Bio32 | G | L | W | N | D | L | V | Y | L | D | F | I | A | L | Y | P | S | I | I | I |
| SEQ ID NO.259 Bio120 | G | L | W | E | D | I | V | Y | L | D | F | R | A | Q | Y | P | S | I | I | I |
| SEQ ID NO.260 Bio187 | G | L | W | E | G | I | V | Y | L | D | F | I | A | L | Y | P | S | I | I | I |
| SEQ ID NO.261 Bio33 | G | L | W | D | S | I | V | Y | L | D | F | I | A | L | Y | P | S | I | I | I |
| SEQ ID NO.262 Bio56 | G | L | W | D | N | I | V | Y | L | D | F | I | A | L | Y | P | S | I | I | I |
| SEQ ID NO.263 Bio80 | G | L | W | D | S | L | V | Y | L | D | F | I | A | L | Y | P | S | I | I | I |
| SEQ ID NO.264 Bio94 | G | L | W | D | D | L | A | Y | L | D | F | K | A | L | Y | P | S | I | I | I |
| SEQ ID NO.265 | G | L | W | . |   | I | V | Y | L | D | F | I | A | L | Y | P | S | I | I | I |

A motif

FIG. 23

A
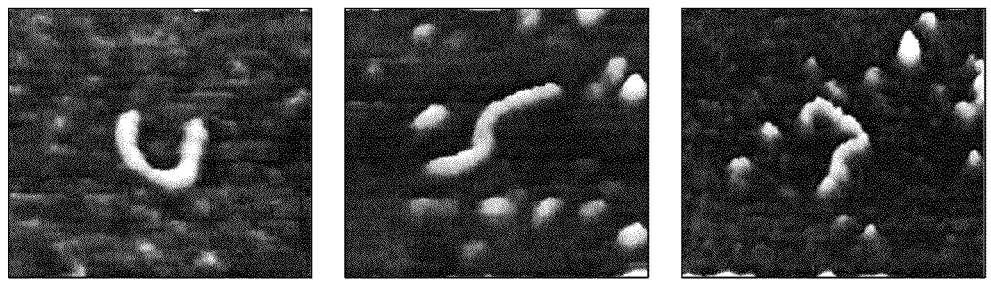
B
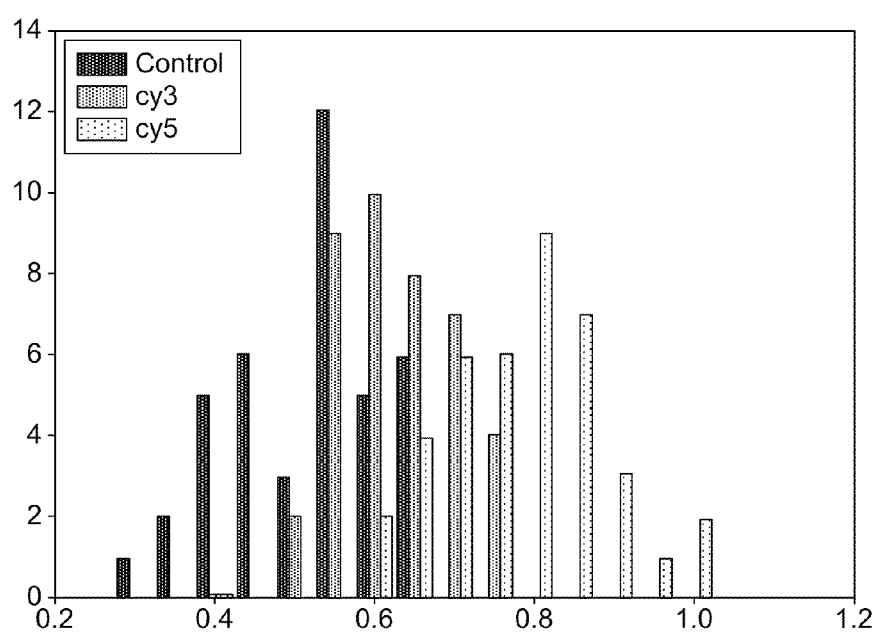
FIG. 25

A
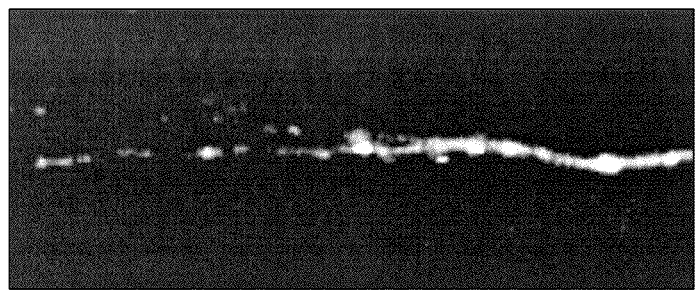
B
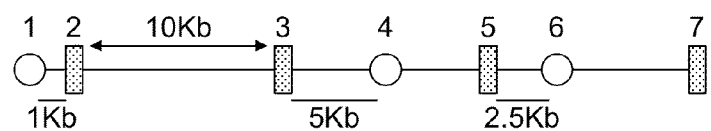
C
| Probe | Label | Length(bp)/Base Composition | Position |
|---|---|---|---|
| 1 | FITC | 933/60%AT | chr8:31626471+31627403 |
| 2 | Cy5 | 919/41%GC | chr8:31628404+31629322 |
| 3 | Cy5 | 925/41%GC | chr8:31639299+31640223 |
| 4 | FITC | 936/61%AT | chr8:31645286+31646222 |
| 5 | Cy5 | 895/36%GC | chr8:31650233+31651127 |
| 6 | FITC | 955/62%AT | chr8:31653626+31654580 |
| 7 | Cy5 | 901/38%GC | chr8:31661123+31662023 |
FIG. 26

MUTANT PFU DNA POLYMERASE

This application is the U.S. national phase of International Application No. PCT/GB2007/003254, filed 24 Aug. 2007, incorporated by reference, which claims priority benefit of Great Britain Patent Application No. 0617565.7 filed Sep. 6, 2006 and Great Britain Patent Application No. 0712157.7 filed Jun. 22, 2007.

FIELD OF THE INVENTION

The present invention relates to DNA polymerases. In particular the invention relates to a method for the generation of DNA polymerases with an enhanced ability to incorporate nucleotide analogues bearing detection agent labelled substituents. Uses of engineered polymerases produced using the methods of the invention are also described.

This application includes a sequence listing submitted electronically as text file 44576_Amended_Sequence_Listing.TXT (created Dec. 21, 2012, 302,085 bytes) and is incorporated herein by reference.

BACKGROUND

Efficient and precise replication of DNA is pivotal to the maintenance, transmission and expression of genetic information. High-fidelity DNA polymerases are the key enzymes responsible for maintaining genome integrity. To avoid the negative consequences of mutations (hereditary and sporadic diseases) high-fidelity DNA polymerases perform an astonishing feat of molecular recognition, selecting the correct nucleotide triphosphate (dNTP) molecule from a pool of very similar substrates and catalysing its incorporation as specified by the template base. DNA synthesis by exonucleolytic proof-reading deficient DNA polymerases occurs with error rates ranging from $10^{-3}$ to $>10^{-6}$ per base-pair (Kunkel and Bebenek, 2000; Tippen et al., 2004). Although in nature high polymerase fidelity is vital for accurate DNA replication it has serious drawbacks for many biotechnological applications. Specifically, it restricts the use of unnatural or modified nucleotide bases and the applications they enable.

Fluorescence-based technologies have superseded radio-isotopic detection as the preferred choice for labelling and detecting biomolecules. The incorporation of fluorescent labelled nucleotides into nucleic acids is central to such techniques as DNA sequencing, gene expression microarray analyses (Schena et al., 1995) tissue microarrays (TMA; Kononen et al., 1998), comparative genome hybridisations (CGH; Kallioniemi et al., 1992) and Fluorescent In-Situ Hybridisation (FISH; McNeil et al., 1991). Nucleic acid fluorescent labelling methodologies have been developed based on either enzymatic (direct incorporation of the fluorescent dye) or chemical modification (indirect incorporation of the fluorescent dye).

Direct incorporation of dye labelled nucleotides employs polymerase enzymes and is limited by the fact that polymerase enzymes have evolved to preserve a high selectivity for their correct nucleotide substrate. As such, most naturally occurring or commercially available polymerase enzymes discriminate against nucleotides bearing bulky side groups such as fluorescent moieties or incorporate them to a low level exhibiting significant sequence bias (Zhu and Waggoner, 1997; Zhu et al., 1994). Most enzymatic fluorescent labelling protocols, therefore, use the dye-labelled nucleotide, spiked at low percentage into a standard reaction mix (Reid et al., 1992). Even under these conditions, however, the polymerase enzyme still favours the natural nucleotide over the modified nucleotide (Zhu et al., 1994).

To overcome the low fluorophore densities achieved with direct labelling methods indirect labelling technologies have been developed whereby a less bulky amine-modified nucleotide is directly incorporated into the nucleic acid and the fluorescent label is chemically coupled to the nucleotide via the reactive amine group post nucleic acid synthesis (Cox and Singer, 2004). Although higher fluorescent nucleic acid labelling densities can be attained by indirect labelling methods complete substitution of every reactive nucleotide has not been achieved.

Nucleic acid probes with a higher density of labels (up to 100% substitution) are desirable as they would be expected to increase detection sensitivity. Furthermore, 100% substitution of every base with its fluorescently modified counterpart is a prerequisite of many single molecule sequencing techniques (Shendure et al., 2004). With current indirect DNA labelling methods unable to label 100% of the available positions research efforts have focussed on identifying naturally occurring or mutant DNA polymerase enzymes that are less stringent with regard to their substrate specificity.

Such efforts have met with modest success. Specifically, several members of the A (PolI-like; Brakmann and Nieckchen, 2001; Anderson et al., 2005; Yu et al., 1994; Tasara et al., 2003; Augustin et al., 2001; Ghadessy et al., 2004; Ramanathan et al., 2005) or B (PolII-like; Anderson et al., 2005; Augustin et al., 2001; Tasara et al., 2003; Földes-Papp et al., 2001; Glick et al., 2002; Jäger and Famulok, 2004; Obayashi et al., 2002; Ono et al., 1997) evolutionary families of DNA polymerase enzymes (Zhu and Ito, 1994) have been identified as able to incorporate fluorescent labelled nucleotides. In the case of enzymes harbouring polymerase as well as proofreading activity the yield of dye-labelled DNA was improved by using their exonuclease deficient mutants.

The ability of the majority of the polymerase enzymes to incorporate fluorescently labelled nucleotides was only investigated by primer extension analyses generating single stranded fluorescently labelled DNA. PCR incorporation of fluorescently labelled nucleotides allows simultaneous labelling and amplification of DNA. However, in contrast to primer extension reactions, following a few cycles of PCR amplification the fluorescent nucleotide is also present in the template strand. This has consequences for PCR amplification as the polymerase frequently pauses or aborts copying and the yield of labelled DNA decreases as the fluorescent nucleotide incorporation increases presumably due to steric crowding effects (Zhu and Waggoner, 1994). Consequently there is a need for polymerase enzymes able to efficiently incorporate fluorescent nucleotide analogues to high density by PCR and there remains a need in the art for polymerases, in particular DNA polymerases which are capable of incorporating a high density of detection label and/or capable of incorporating the detection label into large double stranded DNA fragments.

SUMMARY OF THE INVENTION

The present invention modified the principles of compartmentalised self replication (CSR; Ghadessy et al., 2001) to reduce discrimination against dye labelled nucleotide analogues (detection-agent labels), in particular Cy5-dCTP and Cy3-dCTP (the dye labelled nucleotides most commonly used for labelling of microarray probes). In this way the inventors were able to identify a number of polymerases which allowed the synthesis of nucleic acid probes with high detection agent labels, in particular fluorophore detection agents.

Thus, in the first aspect the present invention provides an engineered (eg. a mutated) polymerase with an expanded substrate range characterised in that the polymerase is capable of incorporating an enhanced density of detection agent-labelled nucleotide analogue into nucleic acid synthesised by that engineered polymerase, as compared with the wild type polymerase from which it is derived.

The term "mutant" is used herein to mean a polypeptide or nucleotide sequence having a sequence which differs from the wild type sequence by one or more additions, substitutions or deletions.

In one embodiment, the engineered polymerase is derived from a Pol B family polymerase. More advantageously, it is a Pfu mutant polymerase. In another embodiment, the engineered polymerase is a Pfu mutant polymerase expressed by the clones selected from the group consisting of the following: 23, AH12, 55, 15, 33, 34, 35 and E10.

In another embodiment of the invention the Pfu mutant is E10, as described herein selected from repertoires of Pfu genes mutated in the A- or A- and B- or A- and C-motifs by a variant of CSR, short-patch CSR (spCSR), for an enhanced ability to incorporate Cy5-dCTP. For example, E10 incorporates Cy5-dCTP when substituted to 100% for dCTP in ELISA extension reactions and PCR (see examples). This is significant since during PCR amplification both the template and product strand become decorated with bulky dye molecules. Advantageously, E10 also incorporates Cy3-dCTP when substituted to 100% for dCTP in ELISA extension reactions and PCR (see examples). DNA labelled by E10 in PCR reactions where 100% of the dCTP had been replaced by Cy3-dCTP resulted in a 7-fold higher fluorescent signal when used in microarray hybridisation experiments (see examples). Surprisingly DNA labelled by E10 in PCR reactions where 10% of the dCTP had been replaced by Cy3-dCTP results in a 4 fold higher fluorescent signal in microarray experiments suggesting that E10 has an enhanced affinity for Cy3 modified dCTP (see examples).

According to the invention described herein, the presence of a detection agent-labelled nucleotide at a given position in the newly synthesised nucleic acid effectively labels that nucleotide position. Such labelling then facilitates the use of the synthesised nucleic acid in any of the following functions: polymerase chain reaction (PCR); single strand DNA sequencing and microarray detection. Those skilled in the art will be aware of other suitable uses for detection-labelled nucleic acid synthesised according to the invention.

Thus in a further aspect the present invention provides a method for enhancing the sensitivity of any one or more of the following: PCR, ELISA, FISH, fibre FISH and microarrays which method comprises the step of utilising a nucleic acid probe which has been Cy5-CTP or Cy3-CTP labelled using a nucleic acid polymerase, suitably, an E10 polymerase according to the invention in that method.

In another embodiment the detection agent label is a dye label. More suitably, it is a fluorescent dye label. Suitable dye labels will be familiar to those skilled in the art and are described in more detail in the detailed description of the invention. In a preferred embodiment of the methods of the invention, the fluorescent label is Cy3 and/or Cy5 labelled dCTP.

According to the present invention, the term 'engineered (eg. mutated) DNA polymerase' refers to a DNA polymerase which has a nucleic acid sequence which is not 100% identical at the nucleic acid level to the one or more DNA polymerase/s or fragments thereof, from which it is derived, and which has been generated using one or more synthetic methods. Advantageously, an engineered DNA polymerase according to the invention is a pol-B family DNA polymerase. Most suitably the engineered polymerase is a Pfu enzyme mutant. As referred to above the term 'engineered DNA polymerase' also includes within its scope fragments, derivatives and homologues of an 'engineered DNA polymerase' as herein defined so long as it exhibits the requisite property of possessing an expanded substrate range as defined herein. In addition, it is an essential feature of the present invention that an engineered DNA polymerase according to the invention includes no more than 10%, 9%, 8%, 7%, 6%, 5%, 4%, 3%, 2%, 1% or substantially 0% (compared to wild type polymerase) of a polymerase without a 3-5' exonuclease activity under the conditions used for the polymerisation reaction. Such a proofreading activity would remove any 3' mismatches incorporated according to the method of the invention, and thus would prevent a polymerase according to the invention possessing an expanded substrate range as defined herein.

As defined herein the term 'expanded substrate range' (of an engineered DNA polymerase) refers to the ability of an engineered polymerase according to the present invention to incorporate an enhanced density of detection agent-labelled nucleotide analogue into nucleic acid synthesised by that engineered polymerase as compared with the wild type polymerase from which it is derived.

In one embodiment, an engineered polymerase according to the invention can incorporate 10% detection-agent labelled nucleotides expressed as a percentage of total nucleotides in the newly synthesised nucleic acid—such as DNA. In a preferred embodiment still, an engineered polymerase according to the invention can incorporate 20, 30, 40, 50, 55, 60, 65, 70, 75, 80, 85, 90, 95% detection labelled nucleotides expressed as a percentage of total nucleotides in the newly synthesised nucleic acid-such as DNA. In one embodiment, the engineered polymerase incorporates 100% detection labelled nucleotides expressed as a percentage of total nucleotides in the newly synthesised nucleic acid—such as DNA.

In a further aspect, there is provided a method for the generation of an engineered polymerase with an expanded substrate range characterised in that the polymerase is capable of incorporating an enhanced occurrence of detection agent-labelled nucleotide analogue into nucleic acid synthesised by that engineered polymerase as compared with the wild type polymerase from which it is derived, which method comprises the steps of:

(a) generating a polymerase repertoire;
(b) performing compartmentalised self replication (CSR) using one of the repertoires of step (a), wherein the CSR is performed in emulsion, utilising primers which anneal 3' and 5' of the region diversified in the library according to step (a) and wherein the emulsion comprises detection agent-labelled dCTP in place of dNTP;
(c) expressing those engineered polymerase repertoire members selected according to step (b) to obtain the protein product (mutant enzyme eg. mutant Pfu enzyme),
(d) selecting those expressed mutant enzymes which are capable of incorporating one or more detection agent-labelled nucleotide analogue/s; and
(e) optionally isolating and/or purifying the selected mutant polymerase.

In one embodiment, the polymerase repertoire according to step (a) is generated from any of the following: a pol A polymerase; a pol B polymerase and a Pfu polymerase or a combination thereof.

In one embodiment, the compartmentalised self replication used in step (b) in the method above is short patch self replication as described herein.

According to the method described above, in one embodiment the detection agent label is a dye label. In another embodiment it is a fluorescent dye label. Suitable dye labels will be familiar to those skilled in the art. In a preferred embodiment of the above aspect of the invention the fluorescent label is either Cy3 or Cy5 labelled dCTP.

In another embodiment an engineered polymerase selected according to the method of the invention can incorporate 10% detection-agent labelled nucleotides expressed as a percentage of total nucleotides in the newly synthesised nucleic acid—such as DNA. In a preferred embodiment still, an engineered polymerase according to the invention can incorporate 20, 30, 40, 50, 55, 60, 65, 70, 75, 80, 85, 90, 95% detection labelled nucleotides expressed as a percentage of total nucleotides in the newly synthesised nucleic acid—such as DNA. In another embodiment, an engineered polymerase incorporates 100% detection labelled nucleotides expressed as a percentage of total nucleic acid in the newly synthesised nucleic acid—such as DNA.

In a further aspect still the present invention provides a method for the incorporation of detection agent-labelled nucleotide analogues into newly synthesised nucleic acid which method comprises the use of an engineered polymerase according to the invention.

In yet a further aspect the present invention provides the use of an engineered polymerase according to the invention in the synthesis of nucleic acid which comprises fluorescently labelled nucleotide analogues.

In a further aspect the present invention provides a Pfu mutant library selected from the following: Pfu A motif library; Pfu A+B motif library and Pfu A+C motif library.

In a further aspect the present invention provides the use of an engineered polymerase with an expanded substrate range according to the invention in one or more techniques in the group consisting of the following: polymerase chain reaction (PCR); microarray analysis (such as gene expression microarray analyses, tissue microarrays, array Comparative Genome Hybridisations); fluorescent in-situ hybridisation (FISH); fibre FISH; comparative genome hybridisations; DNA sequencing, nucleic acid sequencing, (eg. single-stranded nucleic acid sequencing) and single molecule detection.

In another embodiment the engineered polymerase is a Pfu mutant polymerase expressed by the clones selected from the group consisting of the following: 23, AH12, 55, 15, 33, 34, 35 and E10.

In further aspect, there is provided a nucleotide sequence wherein at least 90%, suitably 100% of the Cytidine residues are labelled with Cy5 and/or Cy3. In another embodiment, the nucleotide sequence does not comprise a linker between the C and Cy residues.

The nucleotide sequence may be of synthetic or recombinant origin. The nucleotide sequence may be double-stranded or single-stranded whether representing the sense or antisense strand or combinations thereof. The nucleotide sequence may be DNA. The nucleotide sequence may be prepared by use of recombinant DNA techniques (eg. recombinant DNA).

The nucleotide sequences may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule.

In a further aspect, there is provided a method for analysing the nucleotide sequence, comprising the use of Atomic Force Microscopy, wherein said method comprises the step of depositing the nucleotide sequence onto poly-L-lysine coated mica.

There is also provided the nucleotide sequence bound to poly-L-lysine coated mica.

The use of poly-L-lysine coated mica for analysing the nucleotide sequence is also described.

PCR was carried out in solution or emulsion (CSR) under modified conditions with cells expressing an active Pfu variant (encoded by pASKpfuexo-2) and an inactive Pfu variant (encoded by pASKpfuexo-7) present at a ratio of 1:100 and primers 40 and 41.

The inactive Pfu variant contains a unique XhoI restriction enzyme site at 1218 bp. Restriction digestion with XhoI allows PCR products derived from the inactive and active polymerase genes to be distinguished. In solution there is no compartmentalisation of active and inactive clones and the active Pfu polymerase enzyme amplifies both its own encoding gene and the gene encoding the inactive Pfu variant. After XhoI digestion of reamplified PCR products fragments resistant to digestion (2.4 kb) derived from the active polymerase gene and digested fragments (1.238 kb and 1.166 kb) are observed following agarose gel electrophoresis. By contrast in emulsion individual bacteria expressing either active or inactive or inactive Pfu polymerases are isolated in separate aqueous compartments ensuring that the active polymerase enzyme only amplifies its own encoding gene. PCR products derived from reactions performed in emulsions are resistant to XhoI digestion indicating that the fragment originates from the active polymerase gene and demonstrates a clear enrichment of the active clone over the inactive clone.

Figure 2:
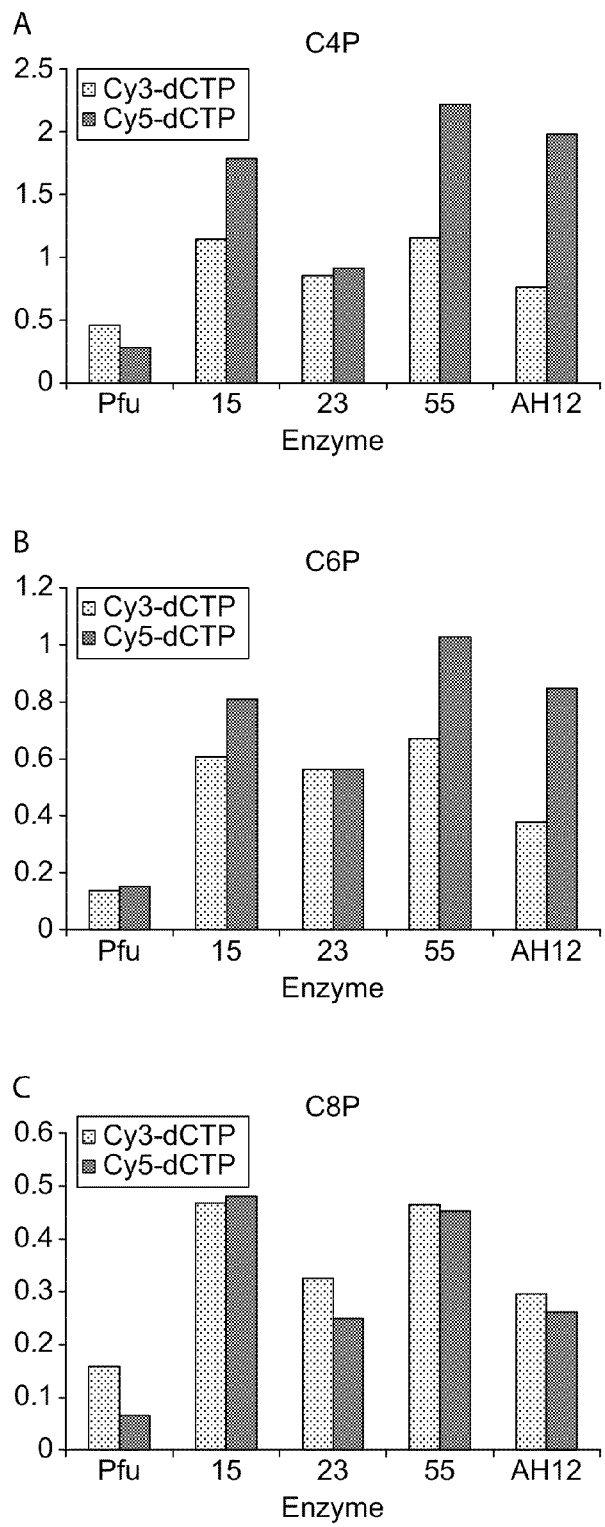

FIG. 2: ELISA activity of Pfu variants selected with Cy5-dCTP from the Pfu A motif repertoire library.

Activity normalised lysates from Pfu and Pfu variants 15, 23, 55 and AH12 selected with Cy5-dCTP from the Pfu A motif repertoire library were assessed for their ability to incorporate (A) 4; primer 33, (B) 6; primer 34 or (C) 8; primer 35 consecutive Cy3- or Cy5-dCTPs. All selected clones are significantly better than Pfu at incorporating Cy5-dCTP, the activity for which they were selected. Additionally, all selected clones are also better able to incorporate Cy3-dCTP than Pfu.

FIG. 3: Amino acid alignment of Pfu variants selected with Cy5-dCTP from the Pfu A motif repertoire library.

ELISAs performed with primers 33, 34 and 35 identified Pfu variants 15, 23, 55 and AH12 as having a significantly enhanced ability to incorporate Cy5-dCTP and Cy3-dCTP (see FIG. 2). Sequence analysis of these clones with primers 44, 36 and 37 over the region amplified and cloned following Cy5-dCTP selection from the Pfu A motif repertoire library identified the following mutations: 15 (V337I, E399D, N400D, R407I), 23 (N400D, I401L, R407I), 55 (N400G, R407I) and AH12 (E399D, N400G, I401L, V402A, R407I, Q572H) compared with the Pfu wild-type amino acid sequence.

Figure 4:
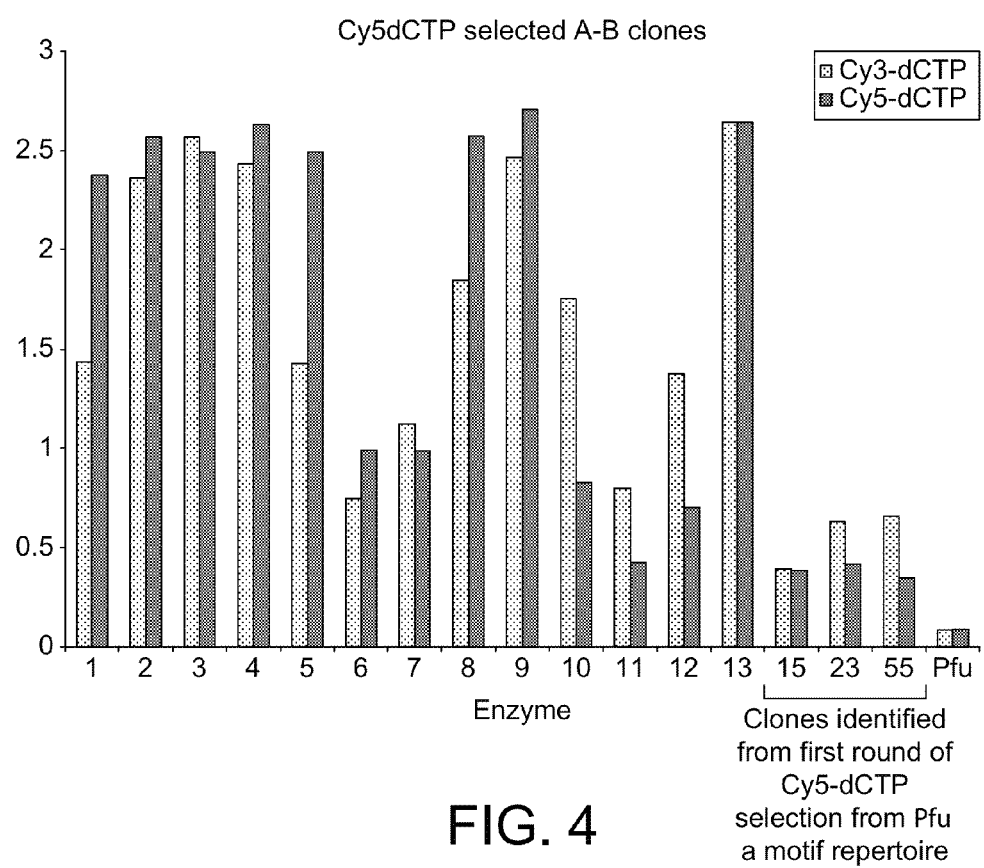

FIG. 4: ELISA activity of Pfu variants selected with Cy5-dCTP from the Pfu A-B motif repertoire library.

Crude lysates from Pfu variants selected with Cy5-dCTP from the Pfu A-B motif repertoire library, Pfu variants 15, 23 and 55 (selected with Cy5-dCTP from the Pfu A motif repertoire library) and Pfu were assessed for their ability to incorporate 8 (primer 35) consecutive Cy3- or Cy5-dCTPs. Clones isolated from the Pfu A-B motif repertoire library are significantly better than Pfu and clones selected from the first round of Cy5-dCTP selection (Pfu A motif repertoire: clones 15, 23 and 55) at incorporating Cy5-dCTP, the activity for which they were selected. Additionally, all selected clones are also better able to incorporate Cy3-dCTP than Pfu and Cy5-dCTP selected A motif library variants (15, 23, and 55).

FIG. 5: Amino acid alignment of Pfu variants selected with Cy5-dCTP from the Pfu A-B motif repertoire library.

ELISAs performed with primer 35 identified Pfu variants 2-13 as having a significantly enhanced ability to incorporate Cy5-dCTP or Cy3-dCTP (see FIG. 4). Sequence analysis of these clones with primer 36 over the A (A) and B (B) motifs diversified during library construction identified mutations in the A and B motifs compared with the Pfu wild-type amino acid sequence. The templates used for A-B motif Pfu repertoire library construction must have been contaminated with some wild-type Pfu sequence since not all selected clones contain diversity in the A-motif although all selected clones contain diversity in the B-motif. Some clones also contained additional mutations not coded for by the diversity primers, but located between the primers (27 and 30) used in the Cy5-dCTP selection.

Figure 6:
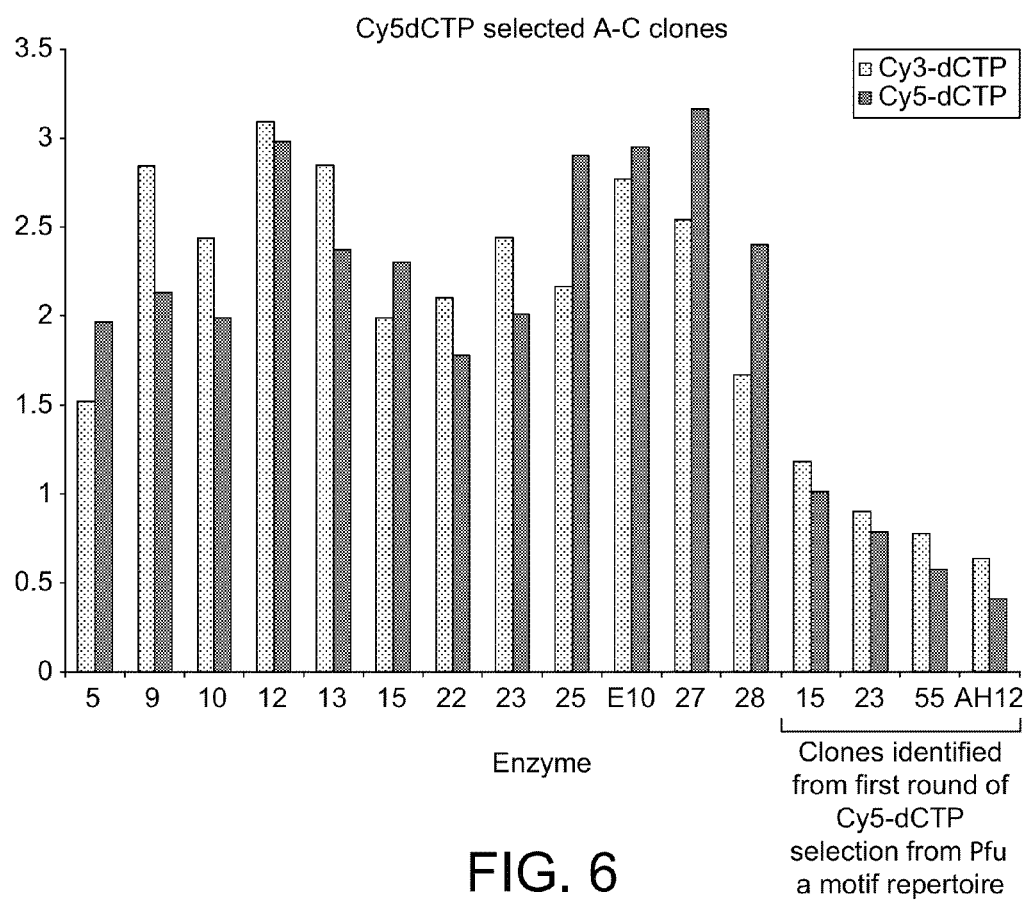

FIG. 6: ELISA activity of Pfu variants selected with Cy5-dCTP from the Pfu A-C motif repertoire library.

Crude lysates from Pfu variants selected with Cy5-dCTP from the Pfu A-C motif repertoire library, Pfu variants 15, 23, 55 and AH12 (selected with Cy5dCTP from the Pfu A motif repertoire library) were assessed for their ability to incorporate 8 (primer 35) consecutive Cy3- or Cy5-dCTPs. Clones isolated from the Pfu A-C motif repertoire library are significantly better than clones selected from the first round of Cy5-dCTP selection (Pfu A motif repertoire: clones 15, 23, 55 and AH12) at incorporating Cy5-dCTP, the activity for which they were selected. Additionally, all selected clones are also better able to incorporate Cy3-dCTP than Cy5-dCTP selected A motif library variants (15, 23, 55 and AH12).

FIG. 7: Amino acid alignment of Pfu variants selected with Cy5-dCTP from the Pfu A-C motif repertoire library.

ELISAs performed with primer 35 identified Pfu variants E10, 5, 9, 10, 12, 13, 15, 22, 23, 25, 27 and 28 as having a significantly enhanced ability to incorporate Cy5-dCTP or Cy3-dCTP (see FIG. 6). Sequence analysis of these clones with primer 36 over the A (A) and C (B) motifs diversified during library construction identified mutations in the A and C motifs compared with the Pfu wild-type amino acid sequence. Some clones also contained additional mutations not coded for by the diversity primers, but located between the primers (27 and 32) used in the Cy5-dCTP selection.

FIG. 8: DNA and amino acid sequence of E10.

Clone E10 selected with Cy5-dCTP from the Pfu A-C motif repertoire library was identified as having a significantly enhanced ability to incorporate both Cy3- and Cy5-dCTP. Sequencing of this clone with primers 36, 37, 39, 44, 45 and 46 identified 14 point mutations of which 9 are silent. The remaining 5 introduce the following mutations: V337I, E399D, N400D, R407I, and Y546H.

Figure 9:
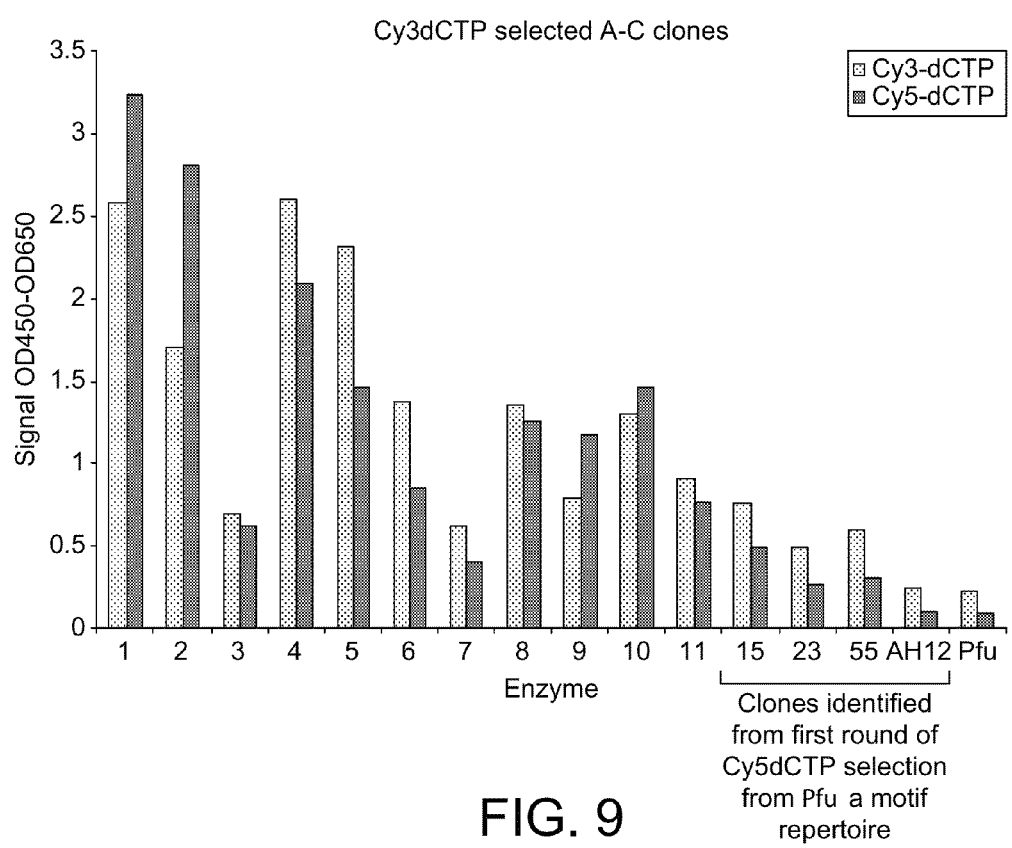

FIG. 9: ELISA activity of Pfu variants selected with Cy3-dCTP from the Pfu A-C motif repertoire library.

Crude lysates from Pfu variants selected with Cy3-dCTP from the Pfu A-C motif repertoire library, Pfu and Pfu variants 15, 23, 55 and AH12 (selected with Cy5dCTP from the Pfu A motif repertoire library) were assessed for their ability to incorporate 8 (primer 35) consecutive Cy3- or Cy5-dCTPs. All clones isolated from the Pfu A-C motif repertoire library are significantly better than Pfu at incorporating Cy3-dCTP, the activity for which they were selected. Additionally, all selected clones are also better able to incorporate Cy5-dCTP than Pfu.

FIG. 10: Amino acid alignment of Pfu variants selected with Cy3-dCTP from the Pfu A-C motif repertoire library.

ELISAs performed with primer 35 identified Pfu variants 1-11 as having a significantly enhanced ability to incorporate Cy5-dCTP or Cy3-dCTP (see FIG. 9). Sequence analysis of these clones with primer 36 over the A (A) and C (B) motifs diversified during library construction identified mutations in the A and C motifs compared with the Pfu wild-type amino acid sequence. Some clones also contained additional mutations not coded for by the diversity primers, but located between the primers (27 and 32) used in the Cy3-dCTP selection.

Figure 11:
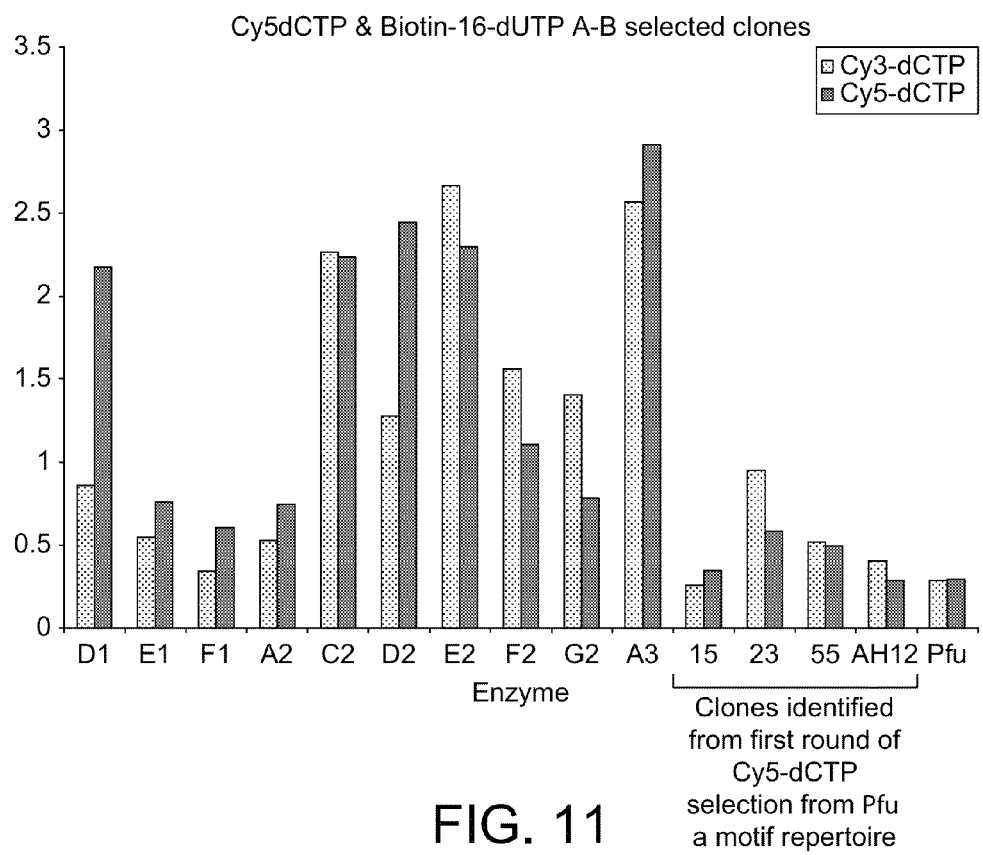

FIG. 11: ELISA activity of Pfu variants selected with Cy5-dCTP and Biotin-16-dUTP from the Pfu A-B motif repertoire library.

Crude lysates from Pfu variants selected with Cy5-dCTP and Biotin-16-dUTP from the Pfu A-B motif repertoire library, Pfu variants 15, 23, 55 and AH12 (selected with Cy5-dCTP from the Pfu A motif repertoire library) and Pfu were assessed for their ability to incorporate 8 (primer 35) consecutive Cy3- or Cy5-dCTPs. Clones isolated from the Pfu A-B motif repertoire library are significantly better than Pfu at incorporating Cy5-dCTP, the activity for which they were selected. Additionally, all selected clones are also better able to incorporate Cy3-dCTP than Pfu.

FIG. 12: Amino acid alignment of Pfu variants selected with Cy5-dCTP & Biotin-16-dUTP from the Pfu A-B motif repertoire library.

ELISAs performed with primer 35 identified Pfu variants D1, E1, F1, A2, C2, D2, E2, F2, G2 and A3 as having an enhanced ability to incorporate Cy5-dCTP or Cy3-dCTP (see FIG. 11). Sequence analysis of these clones with primer 36 over the A (A) and B (B) motifs diversified during library construction identified mutations in the A and B motifs compared with the Pfu wild-type amino acid sequence. The templates used for A-B motif Pfu repertoire library construction must have been contaminated with some wild-type Pfu sequence since not all selected clones contain diversity in the A-motif although all selected clones contain diversity in the B-motif. Some clones also contained additional mutations not coded for by the diversity primers, but located between the primers (27 and 30) used in the Cy5-dCTP selection.

Figure 13:
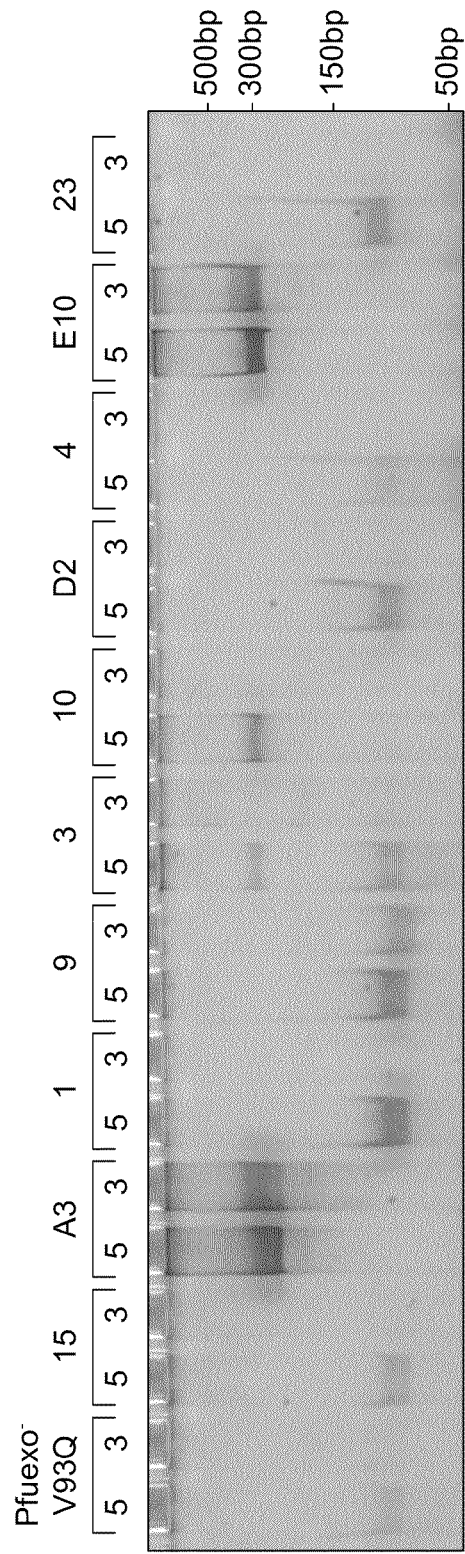

FIG. 13: PAGE analysis of PCR products amplified using selected Pfu variants in reactions where 100% of the dCTP is replaced by Cy3- or Cy5-dCTP.

PCRs were performed with heparin purified activity normalised Pfu V93Q and Pfu variants selected with Cy5-dCTP from the A motif Pfu repertoire library (variant 15), Pfu variants selected with Cy5-dCTP and Biotin-16-dUTP from the A-B Pfu repertoire library (variants A3 and D2) or Pfu variants selected with Cy5-dCTP from the A-C motif Pfu repertoire library (variants 1, 9, 3, 10, 4 and E10). 100% of the dCTP in the PCR reaction was replaced by Cy3-dCTP (3) or Cy5-dCTP (5). A fragment of size 410 bp is amplified with primers 38 and 39 requiring the incorporation of 287 Cy-dye labelled dCTPs.

Figure 14:
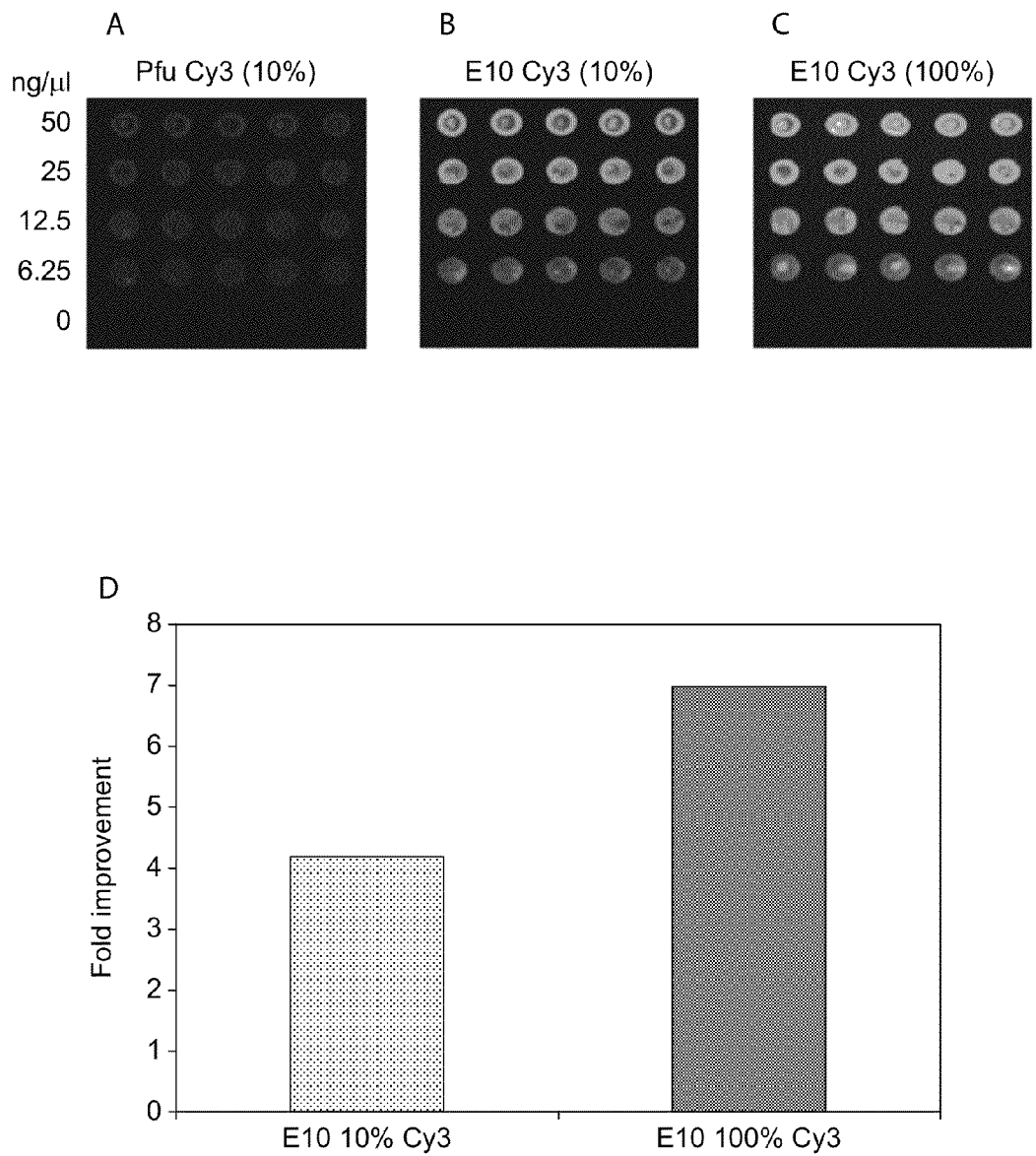

FIG. 14: Microarray analysis with highly E10-labelled Cy3-DNA purified by the freeze-squeeze method.

Fluorescent output measured using ArrayWoRx E scanner (Applied Precision instruments) from experiments where equimolar quantities of PfuCy5$_{10}$ DNA were hybridised with either PfuCy3$_{10}$ DNA (A), E10Cy3$_{10}$ DNA (13) or E10Cy3$_{100}$ DNA (C) to microarray slides on which had been printed a 2-fold dilution series of Pfu polymerase DNA (50-6.25 ng/µL). A 4-fold increase in fluorescent signal was detected from E10Cy3$_{10}$ DNA and a 7-fold increase in Cy3 signal was detected from E10Cy3$_{100}$ DNA (D).

Figure 15:
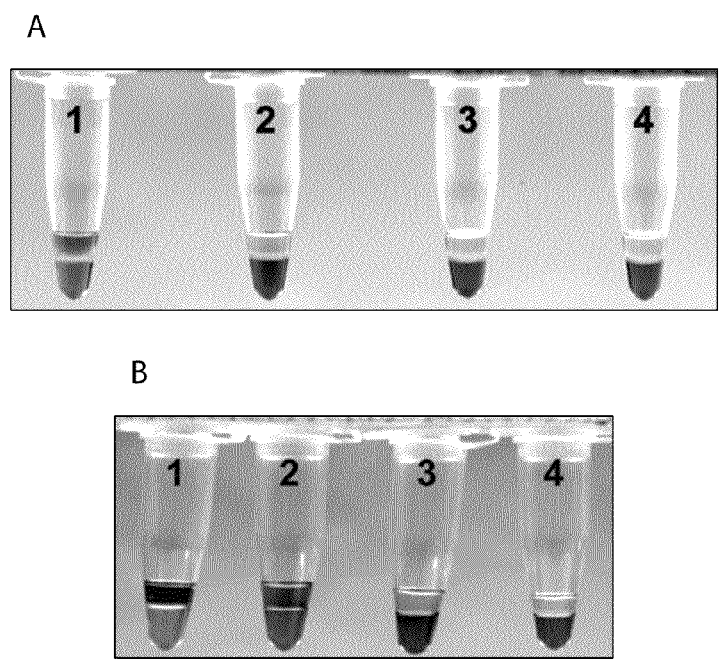

FIG. 15: Highly Cy-dye labelled DNA partitions to the organic phase in the presence of salt on phenol extraction.

Cy5-(FIG. 15A) or Cy3-(FIG. 15B) labelled DNA amplified by E10 was resuspended in either H$_2$O (FIGS. 15A and B 1), 100 mM NaCl (FIGS. 15A and B 2), 150 mM NaCl (FIGS. 15A and B 3) or 200 mM NaCl (FIGS. 15A and 15 4). Following extraction with an equal volume of Tris HCl (pH 7.4) equilibrated phenol the Cy-dye labelled DNA partitions from the upper aqueous phase to the lower organic phenol phase in the presence of salt.

Figure 16:
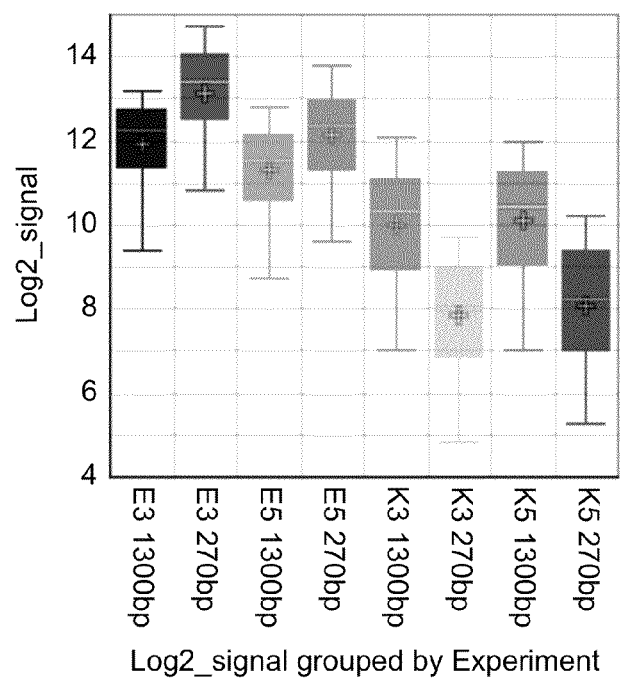

FIG. 16: Fragment length for obtaining maximal signal from highly Cy-dye labelled DNA.

Boxplots of fluorescent signal obtained from co-hybridisation experiments of 270 bp and 1.3 kb fragments directly labelled by E10 (50% replacement of dCTP) with indirectly Klenow-labelled samples scanned using ArrayWoRx E scanner. E=E10; K=Klenow; 3=Cy3-dCTP; 5=Cy5-dCTP.

Figure 17:
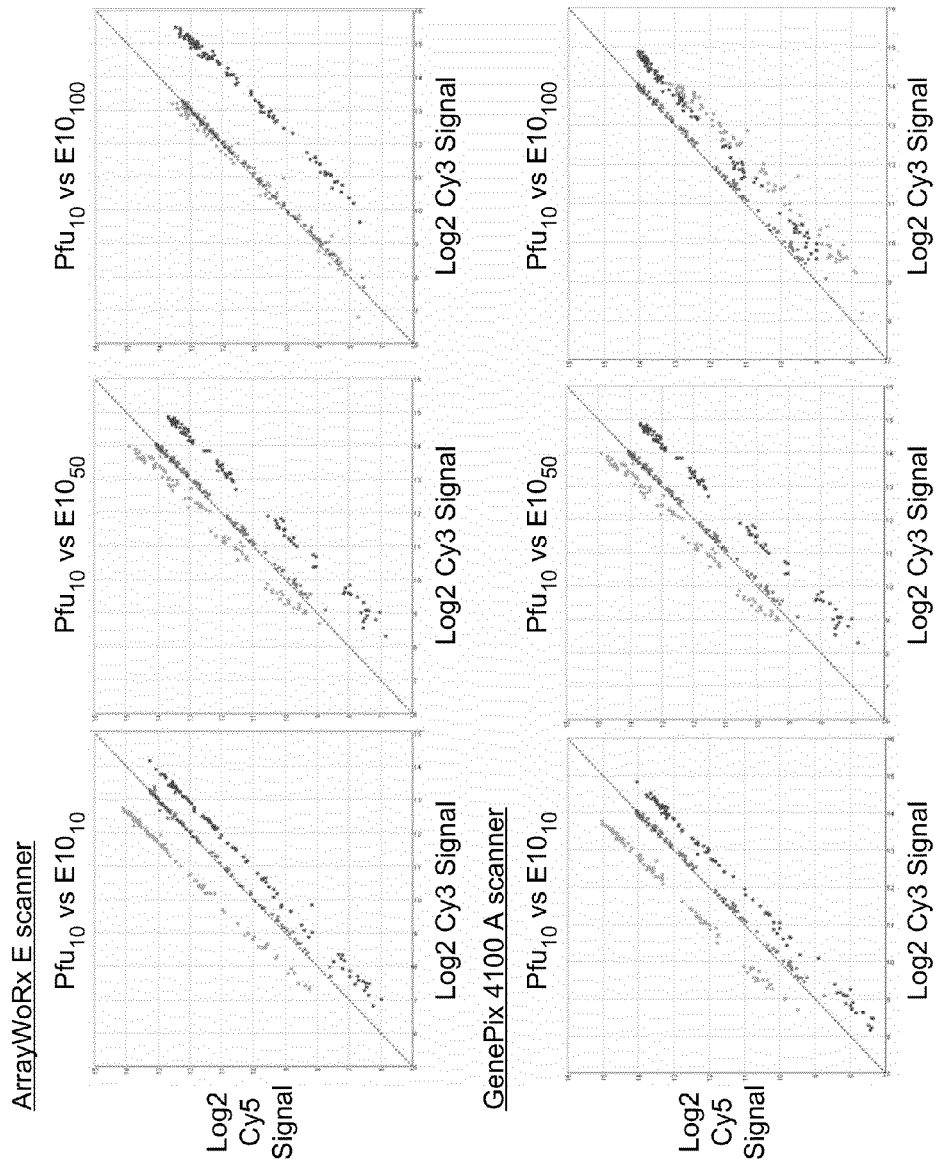

FIG. 17: Label density and choice of scanner for obtaining maximal signal from highly Cy-dye labelled DNA.

Scatterplots of fluorescent signal obtained from co-hybridisation experiments of 270 bp fragments directly labelled by E10 in PCRs where 10% (E10$_{10}$), 50% (E10$_{50}$) or 100% (E10$_{100}$), of the dCTP has been replaced by Cy3- or Cy5-dCTP labelled dCTP with 270 bp fragments directly labelled by Pfuexo- in PCRs where 10% (Pfu$_{10}$) of the dCTP has been replaced by Cy-dye labelled dCTP. Each point represents an individual array feature. Red points=Cy3 and Cy5 signal from 10% Pfuexo-labelled DNA; Green points=Cy5 signal from E10-labelled DNA; Blue points=Cy3 signal from E10-labelled DNA.

Figure 18:
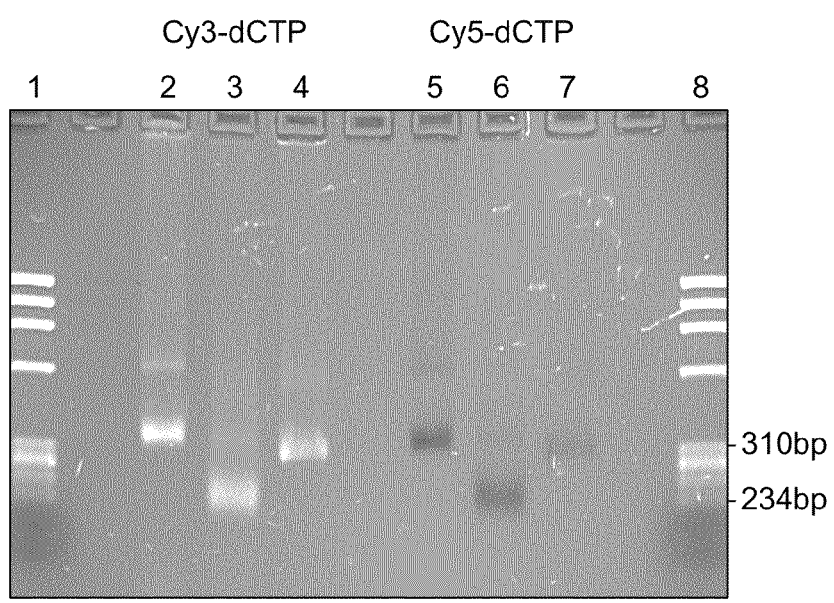

FIG. 18: Restriction digestion of 100% Cy3- or Cy5-dCTP E10-labelled DNA.

Lanes 1 & 7 Marker ØX174 HaeIII, Lanes 2 & 5 DdeI; Lanes 3 & 6 MseI; Lanes 4 & 7 uncut.

Figure 19:
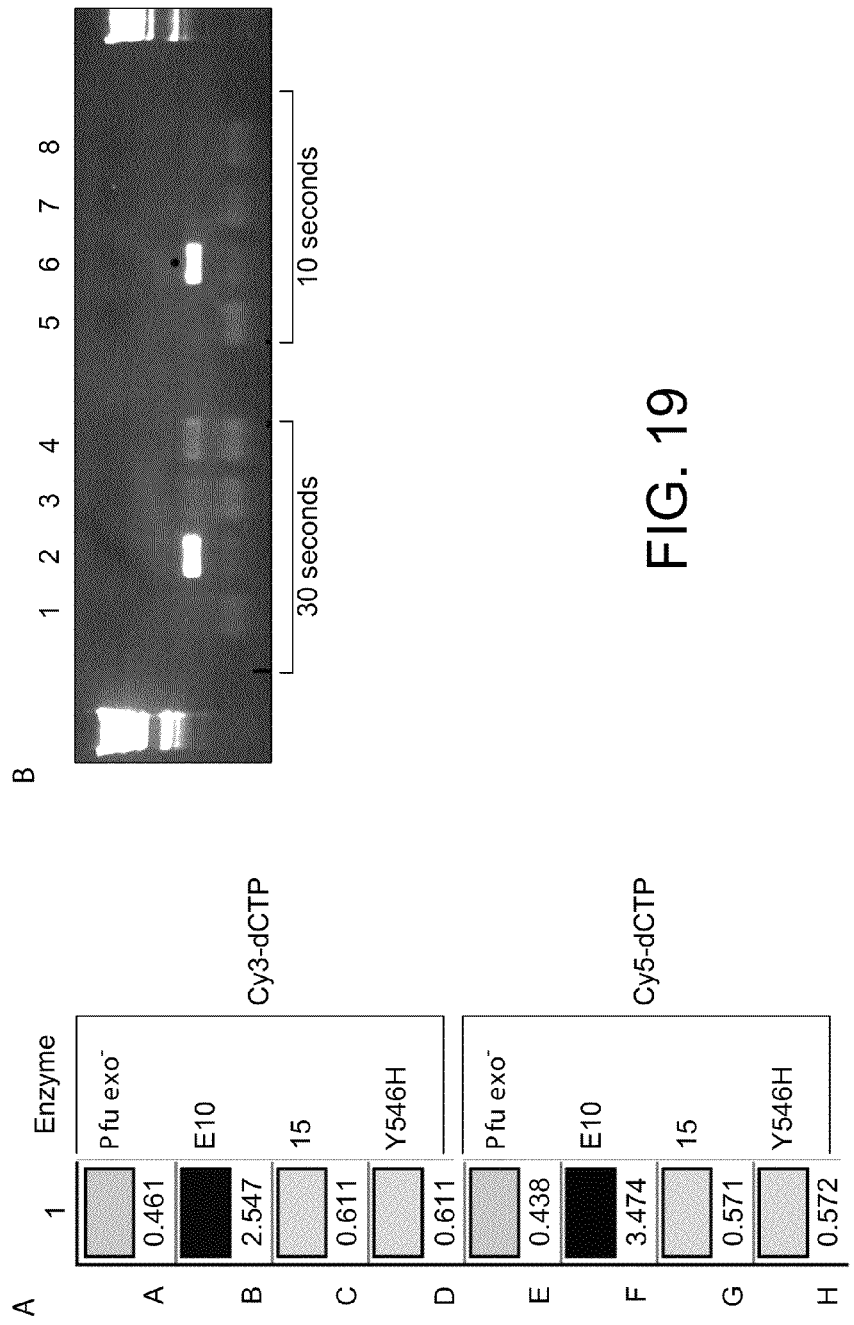

FIG. 19: The contribution of the mutations selected with Cy5-dCTP from the Pfu A motif repertoire (E399D, N400G, R407I and V337I) and the additional mutation selected from the Pfu A and C motif library repertoire (Y546H) to the activity of E10 as assessed by ELISA (FIG. 19A) or PCR (FIG. 19B).

A) ELISAs performed with activity normalised crude lysates of E10 (E10 B and F; E399D, N400G, R407I, V337I, Y546H), clone 15 (15 G and C; E399D, N400G, R407I and V337I), pASKpfuexo-6Y546H (Y546H D and H) or Pfuexo- (A and E; Stratagene) and primer 35 and Cy3 or Cy5-dCTP.

B) Agarose gel (1.2% w/v) electrophoresis of the products of PCRs performed with activity normalised Pfuexo- (1 and 5; Stratagene), E10 (2 and 6), clone 15 (3 and 7) and Y546H (4 and 8) and extension times of either 30 seconds or 10 seconds. With a 10 second extension time only E10 (6) is able to amplify the 270 bp product. Marker=ØX174 HaeIII (HT Biotechnology Ltd).

Figure 20:
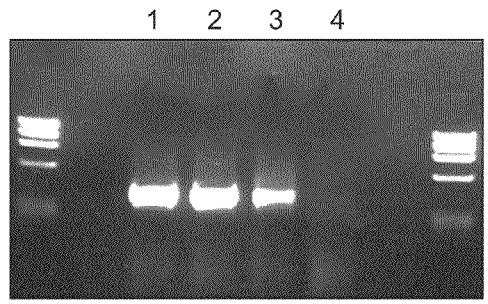

FIG. 20: E10 A motif mutations can compensate for the lack of activity of Tgo Terminator.

A) Sequence alignment of Tgo V93Q exo- (Tgo), Tgo V93Q exo- into which the E10 A motif mutations have been introduced (Tgo E10AMo; V93Q, Exo-, E398D, N399D, R406I), Tgo V93Q exo- Terminator into which the E10 A motif mutations have been introduced (TgoT E10AMo; V93Q, Exo-, A485L, E398D, N399D, R406I).

B) Agarose gel (1.2% w/v) electrophoresis of PCRs performed with crude lysates of Tgo E10AMo (Lane 1; V93Q, exo-, E398D, N399D, R406I), Tgo (Lane 2; V93Q, exo-), TgoT E10AMo (Lane 3; V93Q, Exo-, A485L, E398D, N399D, R406I) TgoT (Lane 4: V93Q, Exo-, A485L). While both Tgo and Tgo E10AMo are able to amplify the 410 bp fragment TgoT is only able to do so in the presence of the E10 A motif mutations.

Figure 21:
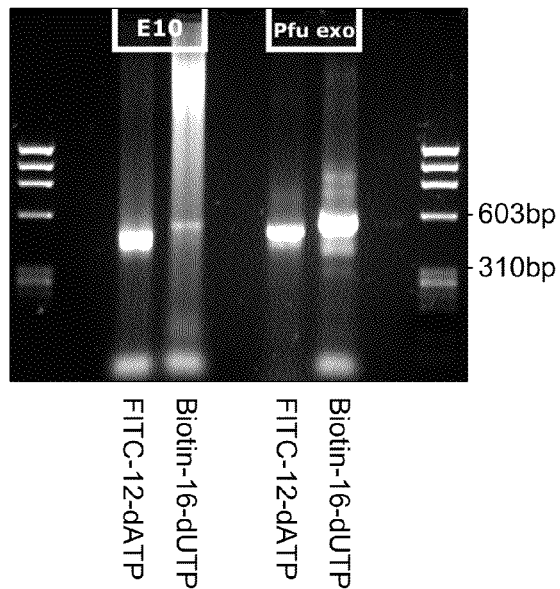

FIG. 21: E10 is able to incorporate 100% FITC-12-dATP or 100% Biotin-16-dUTP.

Agarose gel (1.2% w/v) electrophoresis of PCRs performed E10 or Pfuexo- in the presence of 100% FITC-12-dATP or Biotin-16-dUTP. Marker=ØX174 HaeIII (HT Biotechnology Ltd).

Figure 22:
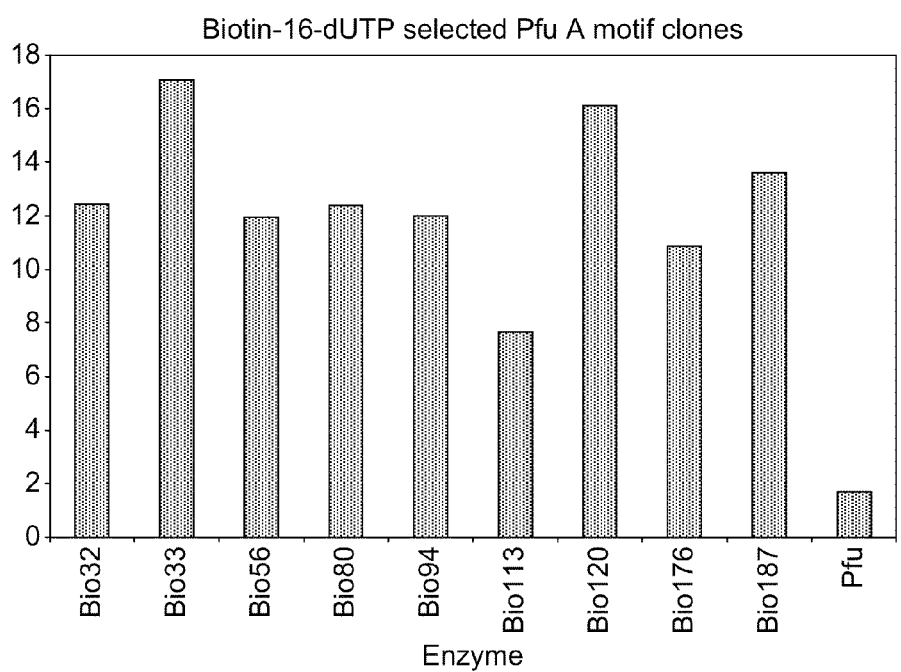

FIG. 22: ELISA activity of Pfu variants selected with Biotin-16-dUTP from the Pfu A motif repertoire library.

Crude lysates from Pfu variants selected with Biotin-16-dUTP from the Pfu A motif repertoire library and Pfu were assessed for their ability to incorporate 12 (primer 60) consecutive Biotin-16-dUTPs. Clones isolated from the Pfu A motif repertoire library are significantly better than Pfu at incorporating Biotin-16-dUTP, the activity for which they were selected.

FIG. 23: Amino acid alignment of Pfu variants selected with Biotin-16-dUTP from the Pfu A motif repertoire library.

ELISAs performed with primer 60 identified Pfu variants Bio187, Bio120, Bio94, Bio80, Bio56, Bio33 and Bio32 as having a significantly enhanced ability to incorporate Biotin-16-dUTP (see FIG. 22). Sequence analysis of these clones with primer 36 over the A motif diversified during library construction identified mutations in the A motif compared with the Pfu wild-type amino acid sequence.

Figure 24:
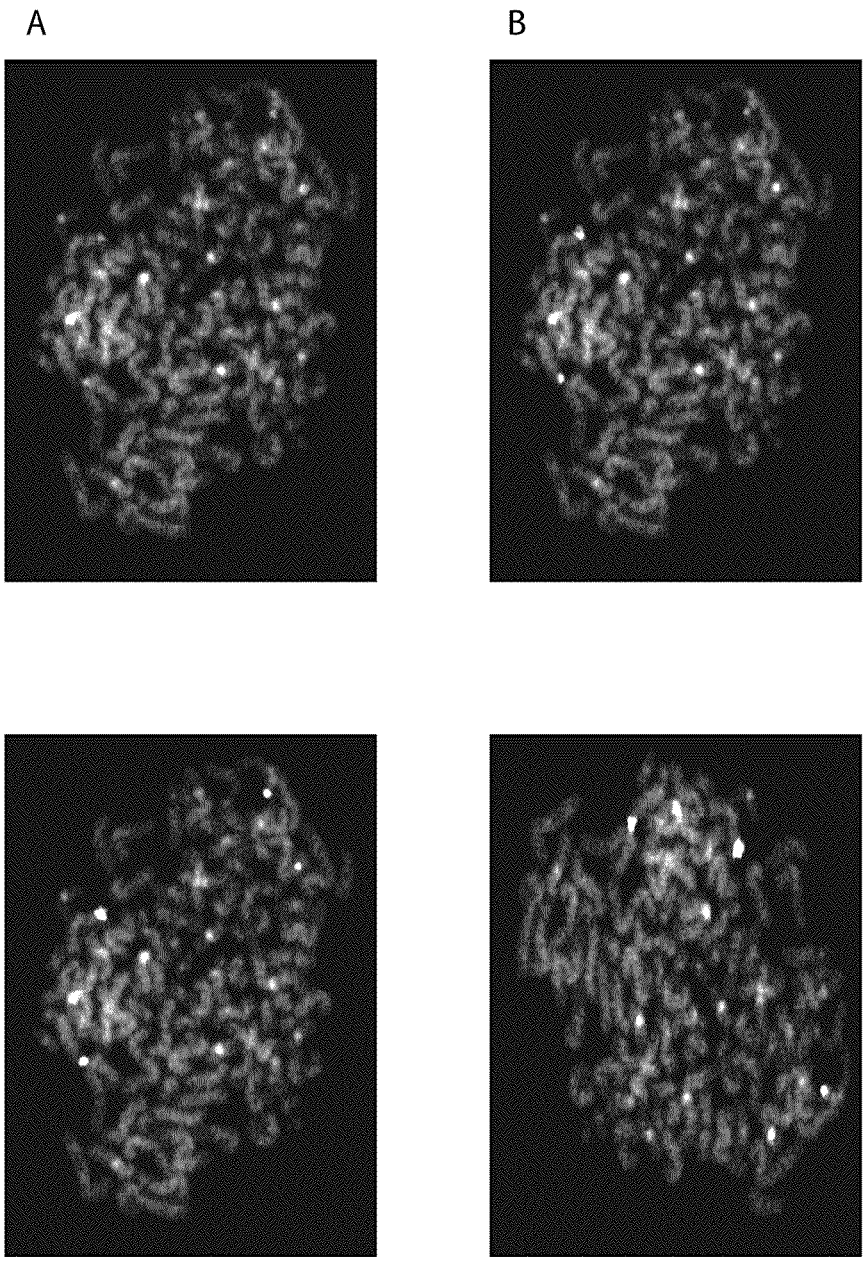

FIG. 24: Fluorescent in-situ hybridisation with E10 generated probes to NRG1, WRN or DCTN6 labelled with Cy3, Cy5 or FITC respectively.

Fluorescent in situ hybridisation of probes to NRG1 (A), WRN (B) or DCTN6 (C) to metaphase spreads of the human pancreatic cancer cell line Suit-2 detects co-localisation of FITC, Cy3 and Cy5 signal to a single chromosome (D; merged image) without the need for secondary signal amplification.

FIG. 25

Atomic force microscopy (AFM) imaging of DNA and CyDNA. (A) Mica-adsorbed DNA and CyDNA (DNA, Cy3-DNA, Cy5-DNA from left to right) fragments of identical length and sequence were imaged using AFM in tapping mode. (B) AFM was used to determine average contour length, stiffness (persistence length) and height. While CyDNA displayed were similar values to standard DNA for contour length and stiffness, Cy3- and in particular Cy5-DNA displayed substantially increased average contour height, presumably due to the dense array of cyanine dyes surrounding the DNA helix.

FIG. 26: Fibre FISH results

A Direct detection of FITC or Cy5 signal on a DAPI stained DNA fibre.

B Organisation of DNA probes along the Neuregulin1 gene The distance of probes 1, 4 and 6 from probes 2, 3, 5 and 7 is indicated. Probes 2, 3, 5 and 7 are spaced 10 Kb apart.

C Probe information.

Figure 27:
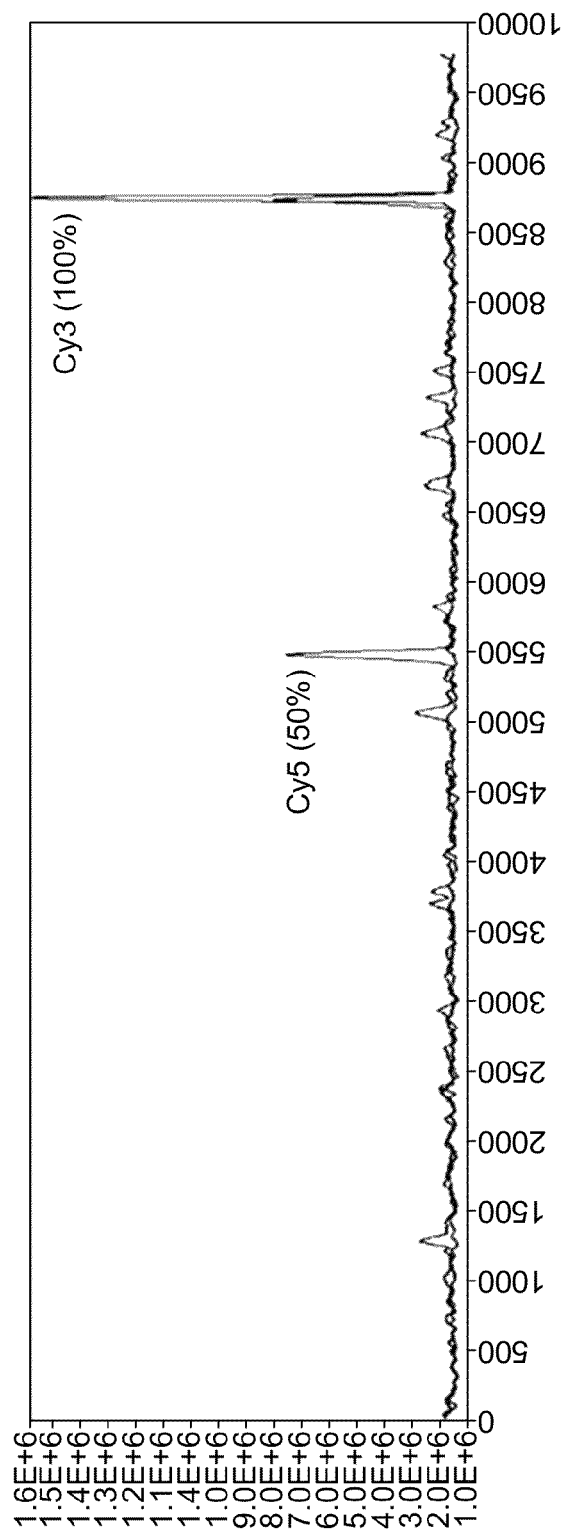

FIG. 27: Microfluidic analysis

A solution of 5 pg/ul each of 50% Cy3-dCTP-labelled and of 100% Cy5-dCTP-labelled 270 mer PCR products was pumped at 30 µl/hr in a fused silica capillary past a sensitive fluorescence detection system (see text). The representative output shows fluorescence (counts per second-vertical axis) at 670 nm (Cy5 maximum-blue trace) and 570 nm (Cy3 maximum-red trace) recorded in consecutive 20 µusec periods (numbered along horizontal axis) and averaged over a sliding window of 40 such periods. Note that Cy3 fluorescence gives a smaller "bleed-through" signal in the Cy5 channel.

DETAILED DESCRIPTION OF THE INVENTION (A) Principles Underlying Compartmentalised Self-Replication Technology The techniques of directed evolution and compartmentalised self replication are detailed in GB 97143002 and GB 98063936 and GB 01275643, in the name of the present inventors. These documents are herein incorporated by reference.

The inventors modified the methods of compartmentalised self replication and surprisingly generated DNA polymerases which exhibited an expanded substrate range as herein defined.

In particular, the inventors realised that for self-replication of Pfu polymerase, compartments must remain stable at the high temperatures of PCR thermocycling. Encapsulation of PCRs has been described previously for lipid vesicles (Oberholzer, T., Albrizio, M. & Luisi, P. L. (1995) *Chem. Biol.* 2, 677-82 and fixed cells and tissues (Haase, A. T., Retzel, E. F. & Staskus, K. A. (1990) *Proc. Natl. Acad. Sci. USA* 87, 4971-5; Embleton, M. J., Gorochov, G., Jones, P. T. & Winter, G. (1992) *Nucleic Acids*) but with low efficiencies.

Further details of the method of compartmentalised self replication in general are given below. Of particular importance in the selection of polymerases which exhibit an enhanced ability to incorporate dye-labelled nucleotide analogues as compared with the polymerase from which they are derived is that the compartmentalised self replication method was modified. These modifications are detailed in section (B) below and also in Example 3 herein.

(i) Microcapsules

The microcapsules used according to the method of the invention require appropriate physical properties to allow the working of the invention.

First, to ensure that the nucleic acids and gene products may not diffuse between microcapsules, the contents of each microcapsule must be isolated from the contents of the surrounding microcapsules, so that there is no or little exchange of the nucleic acids and gene products between the microcapsules over the timescale of the experiment.

Second, the method of the present invention requires that there are only a limited number of nucleic acids per microcapsule. This ensures that the gene product of an individual nucleic acid will be isolated from other nucleic acids. Thus, coupling between nucleic acid and gene product will be highly specific. The enrichment factor is greatest with on average one or fewer nucleic acids per microcapsule, the linkage between nucleic acid and the activity of the encoded gene product being as tight as is possible, since the gene product of an individual nucleic acid will be isolated from the products of all other nucleic acids. However, even if the theoretically optimal situation of, on average, a single nucleic acid or less per microcapsule is not used, a ratio of 5, 10, 50, 100 or 1000 or more nucleic acids per microcapsule may prove beneficial in sorting a large library. Subsequent rounds of sorting, including renewed encapsulation with differing nucleic acid distribution, will permit more stringent sorting of the nucleic acids. In one embodiment, there is a single nucleic acid, or fewer, per microcapsule.

Third, the formation and the composition of the microcapsules must not abolish the function of the machinery the expression of the nucleic acids and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment.

In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

In one embodiment, the microcapsules are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

(ii) Emulsions

Emulsions may be produced from any suitable combination of immiscible liquids. In one embodiment the emulsion has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™80; ICI) and polyoxyethylenesorbitan monooleate (Tween™80; ICI) and Triton-X-100.

The use of anionic surfactants may also be beneficial. Suitable surfactants include sodium cholate and sodium taurocholate. Particularly preferred is sodium deoxycholate, suitably at a concentration of 0.5% w/v, or below. Inclusion of such surfactants can in some cases increase the expression of the nucleic acids and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stirbars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of nucleic acids or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

Details of emulsion/s used when performing the method of the present invention are provided in the Examples.

(iii) Expression within Microcapsules

The processes of expression usually occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. In one embodiment, the mean volume of the microcapsules is less that $5.2\times10^{-16}$ m$^3$, (corresponding to a spherical microcapsule of diameter less than 10 µm, more suitably less than $6.5\times10^{-17}$ m$^3$ (5 µm), more suitably about $4.2\times10^{-18}$ m$^3$ (2 µm) and ideally about $9\times10^{-18}$ m$^3$ (2.6 µm).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2\times10^{-16}$ m$^3$ (corresponding to a sphere of diameter 10 um).

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33\times10^{-22}$ moles). In order to constitute a 2 mM solution, this number of molecules must be contained within a microcapsule of volume $4.17\times10^{-19}$ litres ($4.17\times10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 100 nm.

Therefore, the microcapsule volume is suitably of the order of between $5.2\times10^{-22}$ m$^3$ and $5.2\times10^{-16}$ m$^3$ corresponding to a sphere of diameter between 0.1 um and 10 um, more suitably of between about $5.2\times10^{-19}$ m$^3$ and $6.5\times10^{-17}$ m$^3$ (1 um and 5 um). Sphere diameters of about 2.6 um are most advantageous.

It is no coincidence that the preferred dimensions of the compartments (droplets of 2.6 um mean diameter) closely resemble those of bacteria, for example, *Escherichia* are 1.1–1.5×2.0-6.0 um rods and *Azotobacter* are 1.5-2.0 um diameter ovoid cells. In its simplest form, Darwinian evolution is based on a 'one genotype one phenotype' mechanism. The concentration of a single compartmentalised gene, or genome, drops from 0.4 nM in a compartment of 2 um diameter, to 25 pM in a compartment of 5 um diameter. The prokaryotic transcription/translation machinery has evolved to operate in compartments of ~1-2 um diameter, where single genes are at approximately nanomolar concentrations. A single gene, in a compartment of 2.6 um diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the nucleic acid itself. The volume of the microcapsule should thus be selected bearing in mind not only the requirements for transcription and translation of the nucleic acid/nucleic acid, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given nucleic acid/nucleic acid library, since the ultimately limiting factor will be the size of the microcapsule and thus the number of microcapsules possible per unit volume.

The size of the microcapsules is selected not only having regard to the requirements of the transcription/translation system, but also those of the selection system employed for the nucleic acid/nucleic acid construct. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "nucleic acid" in accordance with the present invention is, typically, a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide.

The nucleic acid portion of the nucleic acid may comprise suitable regulatory sequences, such as those required for efficient expression of the gene product, for example promoters, enhancers, translational initiation sequences, polyadenylation sequences, splice sites and the like.

(iv) Product Selection.

Details of a preferred method of performing the method of the invention are provided in the Examples. However, those skilled in the art will appreciate that the examples given are non-limiting and methods for product selection are discussed in more general terms below.

A ligand or substrate can be connected to the nucleic acid by a variety of means that will be apparent to those skilled in the art (see, for example, Hermanson, 1996). According to the method of the present invention, the ligand or substrate is a 'detection agent label'—such as a dye-labelled nucleotide analogue, in particular Cy3CTP and/or Cy5CTP.

Sorting can be by any method which allows the preferential separation, amplification or survival of the detection agent labelled nucleic acid. Examples include selection by binding (including techniques based on magnetic separation, for example using Dynabeads™), and by resistance to degradation (for example by nucleases, including restriction endonucleases).

When all reactions are stopped and the microcapsules are combined, the nucleic acids encoding the active engineered polymerases selected can be enriched using an antibody or other molecule which binds, or reacts specifically with the "detection agent label". Although both substrates and product have the detection agent label, only the nucleic acids encoding active gene product will co-purify.

The terms "isolating", "sorting" and "selecting", as well as variations thereof, are used herein. Isolation, according to the present invention, refers to the process of separating an entity from a heterogeneous population, for example a mixture, such that it is substantially, suitably totally, free of at least one substance with which it was associated before the isolation process. In one embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired nucleic acids from pools (libraries or repertoires) of nucleic acids which contain the desired nucleic acid. Selecting is used to refer to the process (including the sorting process) of isolating an entity according to a particular property thereof.

Initial selection of a nucleic acid from a nucleic acid library (for example a mutant Pfu library) using the present invention will in most cases require the screening of a large number of variant nucleic acids. Libraries of nucleic acids can be created in a variety of different ways, including the following.

Pools of naturally occurring nucleic acids can be cloned from genomic DNA or cDNA (Sambrook et al., 1989); for example, mutant Pfu libraries or other DNA polymerase libraries, made by PCR amplification repertoires of Pfu or other DNA polymerase genes have proved very effective sources of DNA polymerase fragments. Further details are given in the examples.

Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a nucleic acid or pool of nucleic acids 'randomly' by a variety of techniques in vivo, including; using 'mutator strains', of bacteria such as *E. coli* mutD5 (Liao et al., 1986; Yamagishi et al., 1990; Low et al., 1996). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases (Leung et al., 1989). In a preferred embodiment of the method of the invention, the repertoire of nucleic fragments used is a mutant Taq repertoire which has been mutated using error prone PCR. Details are given in Examples 1. According to the method of the invention, the term 'random' may be in terms of random positions with random repertoire of amino acids at those positions or it may be selected (predetermined) positions with random repertoire of amino acids at those selected positions.

Further diversification can be introduced by using homologous recombination either in vivo (see Kowalczykowski et al., 1994 or in vitro (Stemmer, 1994a; Stemmer, 1994b)).

(V) Microcapsules/Sorting

In addition to the nucleic acids described above, the microcapsules according to the invention will comprise further components required for the sorting process to take place. Other components of the system will for example comprise those necessary for transcription and/or translation of the nucleic acid. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of nucleic acids for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

(Vi) Microcapsule Identification

Microcapsules may be identified by virtue of a change induced by the desired gene product which either occurs or manifests itself at the surface of the microcapsule or is detectable from the outside as described in section iii (Microcapsule Sorting). This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the nucleic acid. A similar procedure has been described previously for the rapid sorting of cells (Keij et al., 1994). Modification of the nucleic acid may result, for example, from coupling a molecular "fluorescent detection agent label", caged by a photolabile protecting group to the nucleic acids: bombardment with photons of an appropriate wavelength leads to the removal of the cage. Afterwards, all microcapsules are combined and the nucleic acids pooled together in one environment. Nucleic acids encoding gene products exhibiting the desired activity can be selected by affinity purification using a molecule that specifically binds to, or reacts specifically with, the "fluorescent label".

(Vii) Multi Step Procedure

It will also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each nucleic acid of a nucleic acid library may take place in a first microcapsule. Each gene product is then linked to the nucleic acid which encoded it (which resides in the same microcapsule). The microcapsules are then broken, and the nucleic acids attached to their respective gene products optionally purified. Alternatively, nucleic acids can be attached to their respective gene products using methods which do not rely on encapsulation. For example, phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified nucleic acid attached to its gene product is put into a second microcapsule containing components of the reaction to be selected. This reaction is then initiated. After completion of the reactions, the microcapsules are again broken and the modified nucleic acids are selected. In the case of complicated multi-step reactions in which many individual components and reaction steps are involved, one or more intervening steps may be performed between the initial step of creation and linking of gene product to nucleic acid, and the final step of generating the selectable change in the nucleic acid.

(Viii) Amplification

In all the above configurations, genetic material comprised in the nucleic acids may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

(B) Modifications to the Standard CSR Procedure

Figure 1:
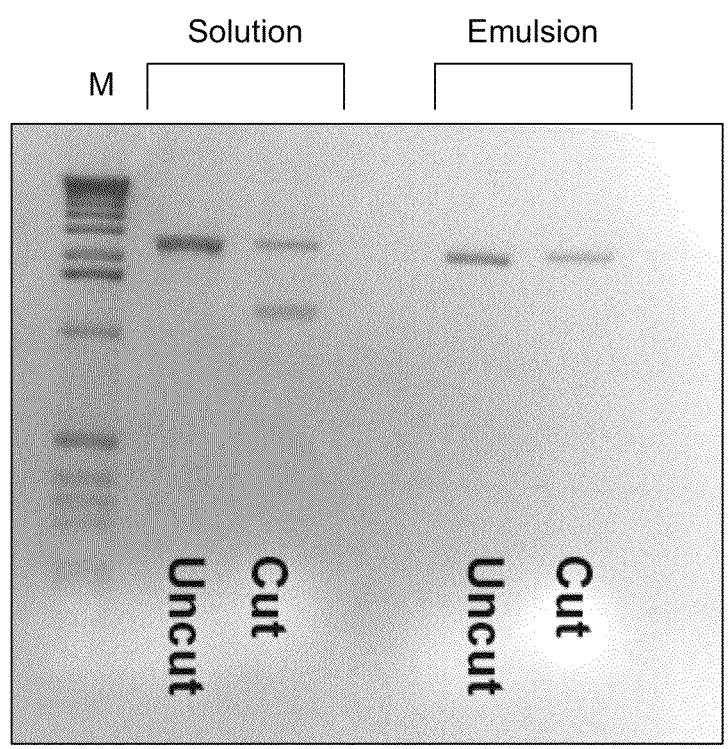
FIG. 1: Enrichment of an active Pfu variant over an inactive variant when present in emulsion at a 1:100 dilution.

Modifications to the previously described CSR protocol are required to enable selection for Pfu variants and especially variants of Pfu able to incorporate dye labelled nucleotide analogues. CSR conditions described previously (Ghadessy et al., 2001), when performed in 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), did not enrich for an active Pfu variant (pASKpfuexo⁻2; see example 1) over an inactive variant (pASKpfuexo⁻7; see example 1) when present at a 1:100 ratio. The aqueous phase of the emulsion had to be modified to include primers (1 µM), dNTPs (0.1 mM each), RNase (10 µg/mL), glycerol (10% v/v), formamide (1% v/v), DTT (1 mM) in 1×Pfu buffer. Cells expressing the active Pfu variant (pASKpfuexo⁻2) were mixed at a ratio of 1:100 with the inactive variant pASKpfuexo⁻7 and subjected to CSR either in solution or in emulsion under the modified conditions described. In solution no significant enrichment of the active variant was observed whereas in emulsion the active variant was enriched for (FIG. 1).

(B) Engineered DNA Polymerases According to the Invention

General.

In a first aspect the present invention provides an engineered polymerase with an expanded substrate range characterised in that the polymerase is capable of incorporating an enhanced occurrence of detection agent-labelled nucleotide analogue/s into nucleic acid synthesised by that engineered polymerase as compared with the wild type polymerase from which it is derived.

As defined herein the term 'expanded substrate range' (of an engineered DNA polymerase) refers to the ability of an engineered polymerase according to the present invention to incorporate an enhanced occurrence of detection agent-labelled nucleotide analogue into nucleic acid synthesised by that engineered polymerase as compared with the wild type polymerase from which it is derived.

In a further embodiment an engineered polymerase according to the invention can incorporate 10% detection-agent labelled nucleotides expressed as a percentage of total nucleotides in the newly synthesised nucleic acid—such as DNA. In a preferred embodiment still, an engineered polymerase according to the invention can incorporate 20, 30, 40, 50, 55, 60, 65, 70, 75, 80, 85, 90, 95% detection labelled nucleotides expressed as a percentage of total nucleotides in the newly synthesised nucleic acid—such as DNA. In another embodiment, the engineered polymerase incorporates 100% detection labelled nucleotides expressed as a percentage of total nucleotides in the newly synthesised nucleic acid—such as DNA.

In another embodiment the detection agent labelled nucleotide analogues are dye labelled analogues. Dye labels may be attached to any of the following nucleotides dATP, dCTP, dGTP and dTTP. Advantageously, the dye label is a fluorescent label. More advantageously, the fluorescent label is Carbocyanaine (Cy). Details of this fluorescently labelled nucleotide are provided in U.S. Pat. No. 6,974,873 which is herein incorporated by reference. Most advantageously, the fluorescent label is $Cy^1$ (Cy3) or $Cy^5$ (Cy5) and the nucleotide is dCTP. Other suitable fluorescently labelled nucleotides will be familiar to those skilled in the art and include those labelled with Alexa Fluor™ dyes (Invitrogen, UK), diethylaminocoumarin, tetramethylrhodamine, N-methylanthraniloyl (MANT), trinitrophenyl, etheno derivatives, biotin or fluorescein.

In one aspect, there is provided a nucleotide sequence wherein at least 50%, 60%, 70%, 80%, 90%, 95%, 99% or 100% of the Cytidine residues are labelled with Cy5 and/or Cy3.

Suitably, the nucleotide sequence is at least about 1 kb in length, at least about 2 kb in length or at least about 3 kb in length—such as from 1 kb to 3 kb in length.

Accordingly, there is also described a nucleotide sequence wherein at least 50% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 60% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 70% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 80% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 90% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 95% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein at least 99% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

There is also described a nucleotide sequence wherein 100% of the Cytidine residues are labelled with Cy5 and/or Cy3 and wherein the nucleotide sequence is at least about 1 kb in length, at least about 2 kb in length or at least about 3 kb in length—such as from 1 kb to 3 kb in length.

(Ci) Pfu Mutants Selected from the a Motif Library with Cy5-dCTP.

Cy5-dCTP selections (see example 5) from the Pfu repertoire library diversified at the A-motif (see example 4) results in the selection of 4 Pfu variants 23, AH12, 55 and 15 which exhibit a significantly enhanced ability to incorporate Cy5 labelled dCTP over the wild-type enzyme as determined in an ELISA extension assay (see example 7) with primer 33, 34 and 35 (FIG. 2; ELISA). Clones were sequenced with primers 36, 37, 39, 44, 45 and 46 and mutations were identified in the regions diversified (FIG. 3; Sequence). Pfu variant 23: N400D, I401L, R407I; Pfu variant AH12: E399D, N400G, I401L, V402A, R407I, Pfu variant 55: N400G, R407I; Pfu variant 15: E399D, N400G, R407I and V337I.

(Cii) Pfu Variants Selected from the A and B Motif Library with Cy5-dCTP.

Pfu variants able to significantly incorporate Cy5-dCTP compared to the ability of the wild-type enzyme are selected from the A-B motif Pfu repertoire library (see example 4) with primers that anneal 5' to the A-motif and 3' of the B-motif (see example 5). Clones exhibiting a significantly enhanced ability to incorporate Cy5-dCTP are ranked by ELISA extension assay with primer 35 (see example 7; FIG. 4). Clones are sequenced with primer 36 and mutations were identified in the regions diversified (FIG. 5; Sequence). The A-B motif repertoire library must have been contaminated with some wild-type Pfu sequence since not all selected clones contain diversity in the A-motif although all selected clones contain diversity in the B-motif.

(Ciii) Pfu Variants Selected from the a and C Motif Library with Cy5-dCTP

Pfu variants able to significantly incorporate Cy5-dCTP compared to the ability of the wild-type enzyme are selected from the A-C motif Pfu repertoire library (see example 4) with primers that anneal 5' to the A-motif and 3' of the C-motif (see example 5). Clones exhibiting a significantly enhanced ability to incorporate Cy5-dCTP are ranked by ELISA extension assay with primer 35 (see example 7; FIG. 6). Clones are sequenced with primer 36 and mutations were identified in the regions diversified (FIG. 7; Sequence). Cy5-dCTP selections from A-C-motif library selected for clone 15, 55 and 23 variants of Pfu in the A-motif and in combination with C-motif residue Y546 mutated to either H or L in 20 of 20 clones sequenced.

(Civ) Pfu Variant Able to Incorporate Cy5dCTP or Cy3dCTP.

One clone, E10, exhibited a significantly enhanced ability to incorporate either Cy3-dCTP or Cy5-dCTP (FIG. 8; E10 sequence). E10 has 14 point mutations (in addition to those introduced during vector construction (see example 1) of which 9 are silent. The remainder introduce mutations at one or more of the following positions: 337, 399, 400, 407 and/or 546, as compared to the wild type sequence as set forth in SEQ ID No. 134. Suitably, the mutations are substitution mutations at one or more of the following positions: 337, 399, 400, 407 and/or 546 as compared to the wild type sequence as set forth in SEQ ID No. 134. More suitably, the mutations are V337I, E399D, N400D, R407I, and/or Y546H as compared to the wild type sequence as set forth in SEQ ID No. 134.

(D) Uses of DNA Polymerases According to the Invention

The present inventors have shown that the use of short-patch compartmentalised self-replication can be used to select for a number of Pfu variant polymerases (engineered DNA polymerases) with a relaxed substrate specificity with respect to the incorporation of dye labelled nucleotide analogue/s.

The unusual properties of the DNA polymerases according to the present invention, in particular E10 as described herein may have immediate uses for example for the improved incorporation of dye-modified nucleotides in sequencing and array labelling and/or the amplification of ultra-long DNA targets. They may prove useful in the amplification of damaged DNA templates in forensics or paelobiology, may permit an expansion of the chemical repertoire of aptamers or deoxi-ribozymes (Benner, Barbas, ribozyme review).

In addition, DNA polymerases according to the invention, in particular E10 polymerase as herein described may serve as a useful framework for mutagenesis and evolution towards polymerases capable of utilizing an ever wider array of modified nucleotide substrates.

(E) Atomic Force Microscopy

Advantageously, the structure of cyDNA can be determined using Atomic Force Microscopy (AFM). However, it has proved difficult to prepare CyDNA samples for AFM analysis. It was, however, possible to analyse samples on mica stubs that had been functionalised with Poly-L-Lysine. Accordingly, AFM can be used to analyse (eg. to determine the structural characteristics of) cyDNA described herein.

Using AFM it was confirmed that CyDNA exists as double stranded B-form DNA.

The lengths and heights of 40 unmodified DNA molecules, 40 Cy3-dCTP modified molecules (where 100% of the dCTP was replaced by Cy3) and 71 Cy5-dCTP molecules (where 100% of the dCTP was replaced by Cy5) were determined. There is a small difference in molecule length between the unmodified and Cy3-dCTP modified DNA molecules (104.0 nm±0.3 vs 97.5 nm±0.25). The height (width) of the Cy3-dCTP and Cy5-dCTP labelled DNA molecules is substantially greater than that of the unmodified DNA molecules (see FIG. 19). Cy5-dCTP labelled DNA molecules are even wider (0.78 nm±0.008) than Cy3-dCTP labelled DNA molecules (0.620 nm±0.008) consistent with Cy5 being a larger fluorophore than Cy3.

Both the Cy5-dCTP Modified and Unmodified DNA Fragments have Similar Persistence Length.

(F) FISH & Fibre FISH

High label density will not necessarily result in an increase in fluorescence due to re-absorption and re-emission effects and quenching. Model microarray experiments identified that PCR fragments labelled in PCRs where of the 50% of the dCTP was replaced by either Cy3- or Cy5-dCTP resulted in higher fluorescent signal than fragments labelled with 100% replacement. Consequently probes used in FISH and Fibre FISH were generated in PCRs where 50% of the unlabelled nucleotide was replaced by its fluorescent counterpart. Pfu exo- is able to incorporate FITC-12-dATP when present at 100% in PCRs. E10 retains this ability. 3 colour FISH with probes labelled with Cy3, Cy5 or FITC was performed on metaphase spreads. 2 colour Fibre FISH was performed with probes labelled with Cy5 or FITC.

(G) Sequence Identity or Sequence Homology

The present invention encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the polymerase.

In the present context, a homologous sequence is taken to include an amino acid sequence which may be at least 70, 75, 80, 85, 90, 95 or 99% identical, preferably at least 95 or 98% identical to the subject (eg. wild type) sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 70, 75, 80, 85, 90% identical, preferably at least 95 or 99% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed-Chapter 18), BLAST 2 (see FEMS Microbiol Lett 1999 174(2): 247-50; FEMS Microbiol Lett 1999 177 (1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Suitably, the amino acid sequence that is at least 70% identical to the engineered polymerases described herein (eg. that designated as E10) retains one or more of the mutations that confer the expanded substrate range described herein (eg. one or more of the following mutations: V337I, E399D, N400D, R407I and/or Y546H).

(H) Kits

The materials for use in the methods of the present invention are ideally suited for preparation of kits.

Such a kit may comprise containers, each with one or more of the various reagents (typically in concentrated form) utilised in the methods—such as for buffers, the appropriate nucleotide triphosphates (e.g., dATP, dCTP, dGTP and dTTP; or rATP, rCTP, rGTP and UTP), DNA polymerase, and one or more oligonucleotides.

A set of instructions will also typically be included.

(I) General Recombinant DNA Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J.

Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

EXAMPLES

The invention will now be described by the following examples which are in no way limiting of the invention claimed herein.

Example 1

Cloning of Pfu Polymerase Open Reading Frame into pASK

The Pfu polymerase open reading frame was amplified by PCR from pETpfu (Lu and Erickson, 1997) using primers 1 and 2. The amplified fragment was restriction digested with NdeI and SalI and ligated into pASKDpo4 (Skerra, 1994) from which the NdeI site at 2421 bp had been eliminated from the pASK vector backbone by site-directed-mutagenesis using primers 3 and 4 thereby creating the expression vector pASKpfu.

The 3'-5' exonuclease activity of the Pfu enzyme was disabled by site-directed-mutagenesis of exonuclease domain I (Derbyshire et al., 1995) using primers 5 and 6 and pASKpfu as a template thereby generating pASKpfuexo⁻.

The XbaI site present in the Pfu sequence at 1683 bp was removed by site-directed-mutagenesis using primers 7 and 8 and pASKpfuexo⁻ as a template thereby generating pASKpfuexo⁻1.

To facilitate library construction by iPCR the BsaI site present in the Pfu sequence at 1636 bp was eliminated by site-directed-mutagenesis using primers 9 and 10 and pASKpfuexo⁻1 as a template thereby generating pASKpfuexo⁻2.

In order to subclone the sequences selected by CSR the BamHI site present in the Pfu sequence at 606 bp was removed by site-directed-mutagenesis using primers 11 and 12 and pASKpfuexo⁻2 as a template thereby generating pASKpfuexo⁻3. A silent mutation was introduced by site-directed-mutagenesis into the Pfu gene to include a unique BamHI (1416 bp) restriction enzyme site using primers 13 and 14 and pASKpfuexo⁻3 as a template thereby generating pASKpfuexo⁻4.

The uracil stalling function (Fogg et al., 2002) of the Pfu enzyme was removed by site-directed-mutagenesis using primers 15 and 16 and pASKpfuexo⁻4 as a template thereby generating pASKpfuexo⁻5.

To facilitate cloning of A-C motif library selections a silent mutation was introduced by site-directed-mutagenesis into the Pfu gene to include a unique XhoI (1726 bp) restriction enzyme site using primers 17 and 18 respectively and pASKpfuexo⁻5 as a template thereby generating pASKpfuexo⁻6.

An inactive Pfu variant was constructed to allow CSR conditions to be evaluated. A XhoI site which introduces a +1 frameshift in the A motif at 1218 bp was generated by site-directed-mutagenesis using primers 19 and 20 and pASKpfuexo⁻4 as a template thereby generating pASKpfuexo⁻7.

Example 2

Pfu Protein Expression

Plasmid constructs or libraries were transformed into *E. coli* Ace6 or TG1TR and expressed as described (Skerra, 1994). Briefly, transformed Ace6 cells are grown overnight at 37° C. in 2×TY, 0.1 mg/mL ampicillin. For expression overnight cultures were diluted 1:50 in 2×TY 0.1 mg/mL ampicillin, grown to an $OD_{595}$ of 0.6 at 37° C. and induced for protein expression by the addition of anhydrotetracycline. Protein expression was induced for 6 hours at 37° C.

Cells were harvested by centrifugation, resuspended in 20 ml (per litre of culture) of buffer A (50 mM Tris pH8.0, 1% glucose, 1 mM EDTA), Buffer B (10 mM Tris pH8.0, 50 mM KCl, 1 mM EDTA, 0.5% NP40) was added to a final volume of 50 ml and cells were lysed for 30 min at 75° C. Debris was pelleted by centrifugation and the NaCl was added to the supernatant to 0.25M final concentration. Then neutralized polyethyleneamine (PEI) was added to a final concentration of 0.1% v/v and precipitate pelleted by centrifugation. The cleared supernatant was diluted 5× with 20 mM Tris pH7.5 and loaded onto a 6/10 Hi-Prep Heparin FF Column (Pharmacia) equilibrated with Column running buffer (CRB) (20 mM Tris pH7.5, 50 mM NaCl, 10% glycerol). The column was washed with 150 ml of CRB and bound polymerase eluted with a NaCl gradient from 0 to 1M. Pfu eluted between 0.2M-0.3M NaCl, 10% glycerol. Eluted polymerase samples were concentrated using Ultra-15 centrifugal filter devices (Amicon), filter dialyzed into 2×Pfu storage buffer (100 mM Tris pH8.0, 2 mM DTT, 0.1% CHAPS) and glycerol was added to 50% final v/v. Samples were stored at −20° C.

Example 3

Pfu Requires Modified CSR Conditions

Modifications to the previously described CSR protocol were required to enable selection for Pfu variants and especially variants of Pfu able to incorporate labelled nucleotide analogues. CSR conditions described previously (Ghadessy et al., 2001), when performed in 1×Pfu buffer (10 mM KCl, 10 mM $(NH_4)_2SO_4$, 20 mM Tris-Cl pH 8.75, 2 mM $MgSO_4$, 0.1% Triton X-100, 100 μg/mL BSA; Stratagene Ltd), did not enrich for an active Pfu variant (pASKpfuexo-2; see example 1) over an inactive variant (pASKpfuexo-7; see example 1) when present at a 1:100 ratio. The aqueous phase of the emulsion had to be modified to include primers (1 μM), dNTPs (0.1 mM each), RNase (10 μg/mL), glycerol (10% v/v), formamide (1% v/v), DTT (1 mM) in 1×Pfu buffer. Cells expressing the active Pfu variant were mixed at a ratio of 1:100 with cells expressing the inactive Pfu variant and subjected to PCR with primers 40 and 41 either in solution or in emulsion (CSR) under the modified conditions described. PCR was performed in emulsion (CSR) or solution with the following cycling parameters: 94° C. 5 min 25 times (94° C. 30 sec, 50° C. 1 min, 72° C. 15 min). Successful amplification results in a product of size 2.5 kb. Following PCR amplification in emulsion the emulsions were extracted with 2 volumes of diethylether. PCR amplifications performed in emulsion and solution were purified using a Qiagen PCR purification kit including an additional wash step with 750 μL 35% guanidium hydrochloride. Purified products were eluted in 50 μL elution buffer. To remove parental plasmid DNA and primers 7 μL of column eluate was digested with DpnI and ExoSAP-IT. 2 μL of DpnI and ExoSAP-IT treated sample was reamplified with a SuperTaq (HT Biotechnology)/PfuTurbo (Stratagene) blend (68 parts Taq: 8 parts PfuTurbo; 1 μL per reaction) in 1× Taq buffer (10 mM Tris-HCl pH 9.0, 1.5 mM $MgCl_2$, 50 mM KCl, 0.1% Triton X-100, 0.01% stabiliser) with primers 42 and 43 (1 μM each), 1% (v/v) formamide and dNTPs (0.5 mM each). Cycling parameters were as follows: 94° C. 4 min 18 times (94° C. 30 sec, 50° C. 30 sec, 72° C. 3 min) 65° C. 10 min. The inactive Pfu variant encoded by pASKpfuexo⁻7 contains an A>C mutation at 1220 bp and a +1 frameshift at 1218 bp resulting from the insertion of a C thereby creating a unique XhoI restriction site at 1218 bp. Restriction digestion with XhoI allows PCR products derived from the inactive and active polymerase genes to be distinguished. In solution no significant enrichment of the active variant was observed whereas in emulsion the active variant was enriched for (FIG. 1).

Example 4

Preparation of Pfu Repertoires with Targeted Diversity

Library diversity was targeted to the Pfu polymerase active site which is comprised of 3 motifs termed the A, B and C motifs these clasp the incoming nucleotide and are involved in primer template binding. Libraries were constructed by iPCR. Briefly iPCR reactions were hot-started by the addition of 3.5 U of Expand High Fidelity polymerase (Roche) to a PCR mix [10 ng of plasmid template, primers (0.4 µM), dNTPs (0.2 mM), in 1× High Fidelity Expand buffer with $MgCl_2$ (Roche)]. Primers including diversity were PAGE purified. Reactions were thermocycled [94° C. for 4 min; 19 times (94° C. for 20 sec, 65° C. for 20 sec −1° C./cycle, and 68° C. for 10 min); 15 times (94° C. for 20 sec, 50° C. for 20 sec, 68° C. for 10 min); 15 times (94° C. for 20 sec, 50° C. for 20 sec, 68° C. for 10 min+15 sec/cycle)]. iPCR reactions were purified with a QIAquick PCR purification kit (Qiagen) and eluted in 50 µL of $H_2O$. Purified DNA was restriction digested overnight with DpnI (New England Biolabs) to remove the input plasmid template. Restricted DNA samples were purified with a QIAquick PCR purification kit (Qiagen) and eluted in 50 µL of $H_2O$. Purified DNA was restriction digested overnight with BsaI (New England Biolabs) after which the reactions were purified with a QIAquick PCR purification kit (Qiagen) and eluted in 50 µL of $H_2O$. 150 µL of the restriction digested DNA was ligated overnight at 16° C. with 1200 U T4 DNA ligase (New England Biolabs) in 1× T4 DNA ligase buffer (New England Biolabs) in a final volume of 200 µL. Ligation reactions were electroporated into E. coli Ace6 or TG1TR cells which were plated onto 2×TY/Amp 0.1 mg/mL plates.

The Pfu A motif library was generated by iPCR using pASKpfuexo⁻2 as template and PCR primer 21 and degenerate primer 22 which introduces random mutations at a rate of 10% in amino acid residues 404 and 406-412 (L and FRALYPS (SEQ ID NO. 136)) avoiding the conserved catalytic aspartate (D405). Residues 399-403 and residue 415 located adjacent to the A motif (ENIVY (SEQ ID NO. 137) & I) were mutated to include the sequence diversity naturally present in B-family polymerase enzymes. The library was transformed into E. coli Ace6.

The Pfu A-B motif library was generated by iPCR using the four best clones selected with Cy5-dCTP from the Pfu A motif library (15, 23, 55 and AH12; see example 6) as template and degenerate PCR primer 23 which introduces random mutations in amino acid residues 488-500 (KLLANS-FYGYYGY (SEQ ID NO. 138)) at a rate of 10% and primer 24. Residue K501 located adjacent to the B motif was mutated to include the sequence diversity naturally present in B-family polymerase enzymes. The library was transformed into E. coli Ace6.

Plasmid DNA was isolated from the Pfu A-B repertoire library in E. coli Ace6 and transformed into E. coli TG1TR. The library in E. coli TG1TR was used in selections.

The Pfu A-C motif library was generated by iPCR using the four best clones selected with Cy5-dCTP from the Pfu A motif library (15, 23, 55 and AH12; see example 6) as template and degenerate PCR primer 25 which introduces random mutations in amino acid residues 537-540, 542 and 544 (VLYI (SEQ ID NO. 139), T and G) at a rate of 10% avoiding the catalytic aspartate residues (D541 and D543) and PCR primer 26. Residues L545 and Y546 were mutated to include the sequence diversity naturally present in B-family polymerase enzymes. The library was transformed into E. coli Ace6. Plasmid DNA was isolated from the Pfu A-C repertoire library in E. coli Ace6 and transformed into E. coli TG1TR. The library in TG1TR was used in selections.

Example 5

Selection of Pfu Variants Able to Incorporate Cy5-dCTP from Pfu Repertoires

Pfu variants were selected from the repertoire libraries (see example 4) for the ability to incorporate dye-labelled nucleotides, specifically Cy5-dCTP. spCSR selections were set up as described in example 3 however, the dCTP was completely replaced by 100 µM of Cy5-dCTP. Primers annealing 5' and 3' of the region diversified were employed in spCSR selections. spCSR was performed due to the difficulty in incorporating dye-labelled nucleotide analogues that initially precludes the amplification of the full length Pfu sequence.

spCSR Cy5-dCTP selections from the A motif library (94° C. for 5 min; 20 times at 94° C. for 30 sec, 50° C. for 1 min, and 72° C. for 18 min followed by a final elongation step at 65° C. for 10 min) were carried out using primers 27 and 28. The aqueous phase was extracted as described in example 3 and purified selection products were reamplified by PCR (94° C. 2 min; 31 times at 94° C. for 30 sec, 54° C. for 1 min, and 72° C. for 3 min followed by a final elongation step at 65° C. for 10 min) using primers 29 and 28 as described in example 3. Reamplified selection products were digested with EcoRI and BamHI and subcloned into pASKpfuexo⁻4 (see Example 1) before transformation into E. coli Ace6.

spCSR Cy5-dCTP selections from the A-B motif library (94° C. for 5 min; 20 times at 94° C. for 30 sec, 50° C. for 1 min, and 72° C. for 10 min) were carried out using primers 27 and 30 as described in example 3. The aqueous phase was extracted as described in Example 3 and purified selection products were reamplified by PCR (94° C. 2 min; 29 times at 94° C. for 30 sec, 54° C. for 1 min, and 72° C. for 1 min 30 sec) using primers 29 and 31. Reamplified selection products were digested with EcoRI and SacI and subcloned into pASKpfuexo⁻6 before transformation into E. coli Ace6.

spCSR Cy5-dCTP selections from the A-C motif library (94° C. for 5 min; 20 times at 94° C. for 30 sec, 50° C. for 1 min, and 72° C. for 10 min) were carried out using primers 27 and 32. The aqueous phase was extracted as described (Ghadessy et al., 2001) and purified selection products were reamplified by PCR (94° C. 2 min; 29 times at 94° C. for 30 sec, 54° C. for 1 min, and 72° C. for 1 min 30 sec) using primers 29 and 32. Reamplified selection products were digested with EcoRI and XhoI and subcloned into pASKpfuexo⁻6.

Example 6

Selection of Pfu Variants Able to Incorporate Cy5-dCTP and Biotin-16-dUTP

Pfu variants were selected from the Pfu A-B repertoire libraries (see example 4) for the ability to incorporate Cy5- dCTP and Biotin-16-dUTP. spCSR selections were set up as described in Example 3 however, the dCTP was completely replaced by 100 µM of Cy5-dCTP and the dTTP was completely replaced by 100 µM Biotin-16-dUTP. Primers annealing 5' and 3' of the region diversified were employed in spCSR selections. spCSR was performed due to the difficulty in incorporating modified nucleotide analogues that initially precludes the amplification of the full length Pfu sequence.

spCSR Cy5-dCTP and Biotin-16-dUTP selections from the A-B motif library (94° C. for 5 min; 20 times at 94° C. for 30 sec, 50° C. for 1 min, and 72° C. for 10 min) were carried out using primers 27 and 30 as described in example 3. The aqueous phase was extracted as described in example 3. Purified selection products were treated with Dpn1 and ExoSAP (as described in example 3) and reamplified using a 2 step pull through procedure. The initial PCR was hot-started by the addition of 2.5 U of Pfuexo⁻ (Stratagene) to a PCR mix [1 µL purified Dpn1/ExoSAP treated purified selection, primers 31 and 29 (1 µM each), 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), 2% (v/v) formamide and dNTPs (0.5 mM each)]. Reactions were thermocycled (94° C. for 2 min; 20 times at 94° C. for 30 sec, 50° C. for 30 sec, and 72° C. for 2 min 30 sec). 1 µL of the Pfuexo⁻ amplified PCR was used as template in a second PCR with primers 31 and 47 and a SuperTaq (HT Biotechnology)/Pfu-Turbo (Stratagene) blend (as described in example 3; 94° C. for 2 min; 20 times at 94° C. for 30 sec, 50° C. for 30 sec, and 72° C. for 1 min 30 sec). Reamplified selection products were digested with EcoRI and SacI and subcloned into pASKpfu-exo⁻6 before transformation into *E. coli* Ace6.

Example 7

Colony Screening by ELISA of Selected Pfu Variants

In order to rank the Cy5-dCTP selected Pfu variants their ability to incorporate Cy-dye labelled dCTP was assessed using an ELISA extension assay. Briefly cells expressing Pfu or selected Pfu variants were washed twice in 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd) and concentrated 10 fold in 1×Pfu buffer. Cells were lysed by incubation at 85° C. for 10 min and cell debris pelleted by centrifugation at 2,000×g for 10 min.

Cleared lysates can be activity normalised in an ELISA extension reaction with primer 48 [1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), dATP (10 µM), dGTP (10 µM), dTTP (9 µM), digoxigenin-11-dUTP (1 µM; Perkin Elmer), dCTP (10 µM), primer (1 µM), 9 µL $H_2O$, 2 µL cell lysate], Primer 48 contains an internal biotin and requires that 20 consecutive nucleotides be incorporated prior to the insertion of digoxigenin-11-dUTP that is used for colorimetric detection.

Crude cleared lysates or activity normalised lysates were screened for the ability to incorporate either Cy5-dCTP or Cy3-dCTP in an ELISA extension reaction [1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), dATP (10 µM), dGTP (10 µM), dTTP (9 µM), digoxigenin-11-dUTP (1 µM; Perkin Elmer), Cy3-dCTP or Cy5-dCTP (10 µM), primer (1 µM), 9 µL $H_2O$, 2 µL cell lysate]. The primers used in the extension reaction contain an internal biotin and require that 4 (Primer 33), 6 (Primer 34) or 8 (Primer 35) consecutive Cy3 or Cy5 labelled dCTP be incorporated prior to the insertion of digoxigenin-11-dUTP that is used for colorimetric detection.

The extension reaction was allowed to proceed at 94° C. for 5 min, 50° C. for 5 min, 72° C. for 5 min. Thereafter 5 µL of the extension reaction was bound for 30 min at room temperature via the biotin, internal to the primer, to a Strepta Well (high capacity) streptavidin coated 96-well microtiter plate (Roche) in 200 µL of 1×PBS-Tween-20 (0.2%). The plate was washed 5× in 1×PBS-Tween-20 (0.2%) and a 1:2,000 dilution (in 200 µL 1×PBS-Tween-20) of an anti-digoxigenin Fab fragment-peroxidase conjugate (Roche) was added to each well and bound for 30 min at room temperature. The plate was then washed 5 times with 1×PBS-Tween-20 and 100 µL of 1-Step Ultra TMB-ELISA substrate was added (Pierce). Colour development was stopped by the addition of 100 µL 1M $H_2SO_4$ and quantified by measuring absorbance at 450 nm-650 nm.

Example 8

Pfu Variants Selected from the A-Motif Library with Cy5-dCTP

Cy5-dCTP selections (see example 5) from the Pfu repertoire library diversified at the A-motif (see example 4) resulted in the selection of 4 Pfu variants 23, AH12, 55 and 15 which exhibited a significantly enhanced ability to incorporate Cy5-dCTP over the wild-type enzyme as determined in an ELISA extension assay with activity normalised lysates (see example 7) performed with primers 33, 34 and 35 (FIG. 2; ELISA). Clones were sequenced with primers 36, 37, 39, 44. 45 and 46 and mutations were identified in the regions diversified (FIG. 3; Sequence). Additional mutations were identified in clones 15 (V337I) and AH12 (Q572H) these lie between primers 27 and 28 which were used in the short patch Cy5-dCTP selection. Pfu variant 23: N400D, I401L, R407I; Pfu variant AH12: E399D, N400G, I401L, V402A, R407I, Q572H; Pfu variant 55: N400G, R407I; Pfu variant 15: E399D, N400G, R407I, V337I.

Example 9

Pfu Variants Selected from the A and B Motif Library with Cy5-dCTP

Pfu variants able to significantly incorporate Cy5-dCTP compared to the ability of the wild-type enzyme were selected from the A-B motif Pfu repertoire library (see example 4) with primers that anneal 5' to the A-motif and 3' of the B-motif (see example 5). Clones exhibiting a significantly enhanced ability to incorporate Cy5-dCTP were ranked by ELISA extension assay with primer 35 (see example 7; FIG. 4). Clones were sequenced with primer 36 and mutations were identified in the regions diversified (FIG. 5; Sequence). The template used for A-B motif Pfu repertoire library construction must have been contaminated with some wild-type Pfu sequence since not all selected clones contain diversity in the A-motif although all selected clones contain diversity in the B-motif.

Example 10

Pfu Variants Selected from the A and C Motif Library with Cy5-dCTP

Pfu variants able to significantly incorporate Cy5-dCTP compared to the ability of the wild-type enzyme were selected from the A-C motif Pfu repertoire library (see example 4) with primers that anneal 5' to the A-motif and 3' of the B-motif (see example 5). Clones exhibiting a significantly enhanced ability to incorporate Cy5-dCTP were ranked by ELISA extension assay with primer 35 (see example 7; FIG. 6). Clones were sequenced with primer 36 and mutations were identified in the regions diversified (FIG. 7; Sequence). Cy5-dCTP selections from A-C-motif library selected for clone 15, 55 and 23 variants of Pfu in the A-motif and in combination with C-motif residue Y546 mutated to either H or L in 20 of 20 clones sequenced. One such clone, E10, (exhibited a significantly enhanced ability to incorporate either Cy3-dCTP or Cy5-dCTP (FIG. 8; E10 sequence). E10 has 14 point mutations (in addition to those introduced during vector construction (see example 1) of which 9 are silent, the remainder introduce the following mutations V337I, E399D, N400D, R407I, and Y546H.

Example 11

Pfu Variants Selected from the A and C Motif Library with Cy3-dCTP

Pfu variants able to significantly incorporate Cy3-dCTP compared to the ability of the wild-type enzyme were selected from the A-C motif Pfu repertoire library (see example 4) with primers that anneal 5' to the A-motif and 3' of the C-motif (see example 5). Clones exhibiting a significantly enhanced ability to incorporate Cy3-dCTP were ranked by ELISA extension assay with primer 35 (see example 7; FIG. 9). Clones were sequenced with primer 36 and mutations were identified in the regions diversified (FIG. 10; Sequence). Cy3-dCTP selections from A-C-motif library selected for clone 15, 55 and 23 variants of Pfu in the A-motif in combination with C-motif residue Y546 mutated to either H or L in 20 of 20 clones sequenced. Some clones contain additional mutations located outside of the regions diversified.

Example 12

Pfu Variants Selected from the A and B Motif Library with Biotin-16-dUTP and Cy5-dCTP Pfu variants able to significantly incorporate Cy5-dCTP compared to the ability of the wild-type enzyme were selected with Cy5-dCTP and Biotin-16-dUTP from the A-B motif Pfu repertoire library (see example 4) with primers that anneal 5' to the A-motif and 3' of the B-motif (see example 5). Clones exhibiting a significantly enhanced ability to incorporate Cy5-dCTP were ranked by ELISA extension assay with primer 35 (see example 7; FIG. 11). Clones were sequenced with primer 36 and mutations identified in the regions diversified (FIG. 12).

Example 13

Some Cy5-dCTP Selected Pfu Variants Isolated from the A Motif, A-B Motif or A-C Motif Repertoire Libraries are Also Able to Incorporate Cy3-dCTP Surprisingly some clones originally selected for an enhanced ability to incorporate Cy5-dCTP or Cy5-dCTP and Biotin-16-dUTP are also able to incorporate Cy3-dCTP as assessed with an ELISA extension assay with primers 33, 34 and 35 (see example 7; FIGS. 2, 4, 6, and 11).

Example 14

PCR Generation of Highly Labelled Fluorescent DNA with Selected Enzymes

Certain Pfu variants identified as being able to incorporate both Cy5-dCTP and Cy3-dCTP in ELISA extension assays (see examples 8, 10, 12 and 13) and wild-type enzyme were expressed and purified (see example 2). Enzymes were normalised for activity in PCR with primers 36 and 37 and long of pASKpfu as template. Activity normalised enzymes were added to PCR reactions containing: 10 ng of plasmid template, 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), 50 µM dGTP, 50 µM dATP, 50 µM dTTP, 50 µM Cy3-dCTP or 50 µM Cy5-dCTP, 1 µM primers, 2% formamide, $H_2O$ to 50 µL. Cycling conditions were as follows: 94° C. 2 min, 50 times at 94° C. for 10 sec, 50° C. for 30 sec, and 72° C. for 20 min. Amplified fragments were analysed on 6% polyacrylamide gels.

The ability of the selected Pfu variants to amplify a 410 bp fragment of the Taq polymerase gene (70% GC) was assessed with primers 38 and 39. This requires that the polymerase enzyme inserts 287 Cy-dye labelled dCTP (FIG. 13 PAGE gel). Several selected enzymes identified as being able to incorporate both Cy3-dCTP or Cy5-dCTP in ELISA (see examples 8, 10, 12 and 13) were also able to perform PCR when 100% of the dCTP was replaced with Cy3-dCTP or Cy5-dCTP.

Example 15

Microarray Analysis with Highly Cy3-Labelled DNA

To assess whether the highly Cy-dye labelled DNA was able to hybridise and result in significant increases in fluorescent signal model microarray experiments were performed. Pfu polymerase DNA was PCR labelled with E10 using primers 36 and 37 in reactions where 10% or 100% of the dCTP in the reaction had been replaced by Cy3-dCTP ($E10Cy3_{10}$ and $E10Cy3_{100}$ respectively) or with wild-type Pfuexo$^-$ in reactions where 10% of the dCTP had been replaced by Cy5-dCTP ($PfuCy5_{10}$). DNA was purified using the "freeze squeeze" method. Briefly Cy-dye labelled DNA was electrophoresed on a 0.8% 1×TBE agarose gel. The labelled fragment was excised from the gel. The excised gel slice was placed into a 0.6 mL Eppendorf tube that had been pierced with a 25 g needle close to the base of the tube. The cap of the tube was closed and the tube dropped into liquid nitrogen. The slice was incubated for 15 min after which the tube was placed into a 1.5 mL Eppendorf tube and immediately centrifuged at 12,000 rpm for 10-20 min at 4° C. Cy-dye labelled DNA was also purified by ethanol precipitation (2.5× sample volume ethanol $\frac{1}{10}^{th}$ sample volume sodium acetate pH 5.2) followed by purification on Autoseq G50 columns (Amersham Biosciences). The extracted labelled DNA is collected in the base of the 1.5 mL Eppendorf tube. Hybridisation of equimolar quantities of purified $PfuCy5_{10}$ DNA with either $E10Cy3_{10}$ or $E10Cy3_{100}$ DNA to microarray slides on which had been printed a dilution series of Pfu polymerase DNA resulted in either 4 or 7-fold increase in Cy3 signal respectively (FIG. 14).

Array Materials and Methods

Array Manufacture

Dilutions series' (100, 50, 25, 12.5, and 6.25 ng/µl) of probe molecules (Pfu and Taq sequences, and sheared salmon testis genomic DNA) were prepared in 150 mM NaPO₄ pH8.5/0.01% SDS and spotted in pentuplicate onto GAPSII aminosilane-coated glass slides (Corning) using a BioRobotics MicroGrid (Genomic Solutions Ltd). Printed slides were baked for 2 hr at 80° C., incubated with agitation for 30 minutes at 42° C. in 5×SSC/1% BSA (Sigma-Aldrich)/0.1% SDS, boiled for 2 min in ultrapure water, washed in 3 changes of ultrapure water at room temperature, rinsed in propan-2-ol and dried by centrifugation.

Array Hybridisation

Labelled-target nomenclature is as follows: Pfu 10% Cy3 or Pfu 10% Cy5 is target DNA that has been labelled using the Pfu enzyme where 10% of the dCTP present in the labelling reaction is Cy3-dCTP or Cy5-dCTP. Likewise, E10 100% Cy5 or E10 10% Cy5 or E10 100% Cy3 or E10 10% Cy3 is target DNA that has been labelled using the E10 enzyme where 100% or 10% of the dCTP present in the labelling reaction is Cy5-dCTP or Cy3-dCTP.

The following competitive hybridisations were performed in duplicate: Pfu 10% Cy3 vs Pfu 10% Cy5 was performed as a control hybridisation; Pfu 10% Cy3 vs E10 10% Cy5 and E10 100% Cy3 vs Pfu 10% Cy5 were performed to measure the improvement in labelling by E10 in the presence of 10% Cy-labelled dCTP; Pfu 10% Cy3 vs E10 100% Cy5 and E10 100% Cy3 vs Pfu 10% Cy5 were performed to measure the improvement in hybridisation signal following labelling by E10 in the exclusive presence of Cy-labelled dCTP.

5 ng of Cy3- and Cy5-labelled products were prepared in 20 µl of hybridisation buffer (1 mM Tris-HCl pH 7.4, 50 mM tetrasodium pyrophosphate, 1×Denhardts solution, 40% deionised formamide, 1% NP-40, 10 mM DTT, 100 µg/ml sheared salmon sperm DNA). Each sample was heated to 95° C. for 5 minutes, centrifuged for 2 min, applied to the surface of an array and covered with a 22×22 mm LifterSlip (Erie Scientific). Hybridisations were performed at 37° C. for 16 hr in a hybridisation chamber (Telechem). Arrays were washed once with 2×SSC/0.1% SDS at room temperature for 5 minutes, and twice with 1×SSC at room temperature for 5 min. Slides were dried by centrifugation and scanned with an ArrayWoRx 'e' (Applied Precision Instruments). To ensure comparability between slides, identical scanning parameters were used for all arrays. Images were analysed using GenePix Pro 4.1 (Axon Instruments) and array features affected by local artifacts were manually excluded from further analysis.

These hybridisation and wash conditions were optimised to provide the largest fold-improvements in signal from highly-labelled DNA without compromising the specificity of hybridisation. Smaller fold-improvements were observed in more stringent conditions, namely elevated hybridisation temperature (42° C.) and increased wash stringency (0.1× SSC at room temperature).

Calculation of Fold-Improvements in Signal $\log_2$ (mean Cy3/mean Cy5) for each array feature was calculated. For each probe type (Pfu, Taq or salmon testis DNA) in each experiment (duplicate arrays of a competitive hybridisation) the mean $\log_2$ ratio for all included array features (max. 50 features i.e. 10 replicate features each of 5 probe dilutions) was calculated.

To normalise the data to the control experiment (Pfu 10% Cy5 vs Pfu 10% Cy3), where equivalent signal is expected in both channels, the Pfu mean $\log_2$ ratio from the control experiment was subtracted from that of every other comparison. If the resulting $\log_2$ ratios are positive or negative, they represent signal improvements in Cy3 and Cy5, respectively, compared to labelling with Pfu at 10% Cy-dye concentration. Fold-improvements for Cy3 and Cy5 are therefore, respectively, the inverse of the resulting mean log 2 ratio and the reciprocal of the inverse of the resulting mean log 2 ratio.

Example 16

Highly Cy-Dye Labelled DNA Partitions to the Organic Phase in the Presence of Salt on Phenol Extraction PCR primers 49 and 50 were used to amplify a 100 bp fragment of the Taq DNA polymerase gene (2152-2251 bp). PCR reactions containing: 10 ng of plasmid template (pASK75 Taq), 1×Pfu buffer (10 mM KCl, 10 mM (NH₄)₂SO₄, 20 mM Tris-Cl pH 8.75, 2 mM MgSO₄, 0.1% Triton X-100, 100 µg/mL BSA; Stratagene Ltd), 50 µM dGTP, 50 µM dATP, 50 µM dTTP, 50 µM Cy3-dCTP or 50 µM Cy5-dCTP, 0.4 µM each primer, 1% (v/v) formamide, H₂O to 25 µL. Reactions were hot-started with E10 polymerase. Cycling conditions were as follows: 94° C. 2 min, 50 times at 94° C. for 10 sec, and 72° C. for 20 min. Amplified fragments were purified by ethanol precipitation (2.5× sample volume ethanol ¹⁄₁₀ᵗʰ sample volume sodium acetate pH 5.2) followed by purification on Autoseq G50 columns (Amersham Biosciences). Following purification NaCl was added to equivalent volumes of Cy-dye labelled DNA to give a final concentration of 0 mM NaCl, 100 mM NaCl or 150 mM NaCl or 200 mM NaCl. Each sample was vortexed with 20 µL of Tris-HCl (pH 7.4) equilibrated phenol. Samples were subsequently centrifuged for 10 min at 13,000 g. Unlike native DNA highly labelled DNA partitions to the organic phenol phase in the presence of salt concentrations commonly found in some restriction enzyme buffers (eg. NEB3; New England Biolabs) following phenol extraction (see FIG. 15). 100% Cy3 labelled DNA partitions entirely to the organic phase in the presence of 200 mM NaCl on phenol extraction whereas 100% Cy5 DNA partitions entirely to the organic phase in the presence of 100 nM NaCl. The labelled DNA can be recovered from the phenol phase by either diluting the aqueous salt containing phase with H₂0 or removing the aqueous salt containing phase and replacing this with an equivalent volume of H₂0. Following vortexing and centrifugation of the samples for 10 min at 13,000 g causes the Cy-dye labelled DNA to partition the aqueous phase. This could form the basis of a novel strategy to purify highly Cy-dye labelled DNA.

Example 17

Fragment Length for Obtaining Maximal Signal from Highly Cy-Dye Labelled DNA

The influence of fragment length on fluorescent signal obtained from highly Cy-dye labelled DNA was investigated using a model array on which had been printed a dilution series (200, 100, 50, 25, and 12.5 ng/ul) of the full-length Pfu polymerase gene 2300 bp), a dilution series of salmon testis DNA (200, 100, 50, 25, and 12.5 ng/µl) and spotting buffer (the latter 2 acting as negative controls). The increase in fluorescent signal from highly Cy-dye E10 labelled DNA of defined length (270 bp or 1.3 kb) was measured relative to Klenow labelled DNA samples where the unlabelled 270 bp or 1.3 kb DNA fragments were used as templates. Klenow labelling results in an average labelled DNA length of 50-100 bp irrespective of the length of the DNA template.

Klenow DNA Labelling:

Fragments of the Pfu polymerase gene of lengths 1300 bp (corresponding to the polymerase domain) and 270 bp (a portion of the polymerase domain from 1047-1312 bp) were amplified with primers 51 and 52 and 36 and 37 respectively. DNA fragments were amplified with 5 U of SuperTaq (HT Biotechnology Ltd) in reactions containing 1×PCR buffer (10 mM TrisHCl pH 9.0, 1.5 mM $MgCl_2$, 50 mM KCl, 0.1% Triton X-100, 0.01% stabiliser; HT Biotechnology Ltd) 1 μM primer 1 and 1 μM primer 2, 10 ng pASKpfuexo⁻5, 250 μM dNTPs and $H_2O$ to 50 L. Reactions hotstarted and thermocycled as follows: 94° C. 2 min, 30 times at 94° C. for 30 sec, 55° C. for 30 sec and 72° C. for 3 min. The DNA products of the PCR amplification were purified using a Qiagen PCR purification kit. 250 ng of purified PCR product of lengths 270 bp or 1.3 kb were used as templates in Klenow labelling reactions (Bioprime DNA labelling System; Invitrogen). Klenow labelling reactions containing 250 ng of PCR product 1× random primer solution (50 mM Tris-HCl pH 6.8, 12.5 mM $MgCl_2$, 10 mM 2-mercaptoethanol, 300 μg/mL random octamer oligodeoxyribonucleotide primers; Bioprime DNA labelling System Invitrogen) in a final reaction volume of 42 μL were mixed by vortexing and heated to 95° C. for 5 min after which they were immediately placed on ice. To the reaction mix was added 200 μM (final concentration) of each of dATP, dTTP and dGTP, 100 μM (final concentration) dCTP, 100 μM (final concentration) Cy3- or Cy5-dCTP and 0.8 U of Klenow Large Fragment of DNA polymerase 1 (Bioprime DNA labelling System Invitrogen). Reactions were incubated for 2 h at 37° C. In these standard reactions 20% of the dCTP is replaced by Cy-dye labelled dCTP. The size distribution of the Klenow labelled DNA populations was analysed using an Agilent 2100 Bioanalyser and shown to peak between 50-100 bp irrespective of template length.

E10 DNA Labelling

DNA fragments of lengths 1.3 kb or 270 bp were labelled with Cy3- or Cy5-dCTP by E10 in PCRs with primers 51 and 52 and 36 and 37 respectively. PCRs were performed in 1×Pfu buffer (10 mM KCl, 10 mM $(N)_2SO_4$, 20 mM Tris-Cl pH 8.75, 2 mM $MgSO_4$, 0.1% Triton X-100, 100 μg/mL BSA; Stratagene Ltd), 1% (v/v) formamide, 1 μM each primer, 50 μM dATP, 50 μM dGTP, 50 μM dTTP, 25 μM dCTP, 25 μM Cy3- or Cy5-dCTP and 10 ng pASKpfuexo⁻5 in a reaction volume of 100 μL $H_2O$. Reactions were hot started with E10 and thermocycled under the following conditions: 94° C. for 2 min 50 times at 94° C. for 10 sec, 50° C. for 10 sec and 68° C. for 20 min. Cy-dye labelled DNA products were purified by ethanol precipitation (2.5× sample volume ethanol $\frac{1}{10}^{th}$ sample volume sodium acetate pH 5.2) followed by purification on Autoseq G50 columns (Amersham Biosciences). In these reactions 50% of the dCTP is replaced by Cy3- or Cy5-dCTP.

Model Array Hybridisations

Labelled-Target Nomenclature is as Follows:

$E10_{270}$ Cy3 or $E10_{270}$ Cy5 refers to a 270 bp target DNA that has been labelled using the E10 enzyme where 50% of the dCTP present in the labelling reaction is Cy3-dCTP or Cy5-dCTP. $E10_{1300}$ Cy3 or $E10_{1300}$ Cy5 is a 1300 bp target DNA that has been labelled using the E10 enzyme where 50% of the dCTP present in the labelling reaction is Cy3-dCTP or Cy5-dCTP.

$Klenow_{270}$ Cy3 or $Klenow_{270}$ Cy5 refers to a 270 bp target DNA that has been labelled using Klenow enzyme where 20% of the dCTP present in the reaction is Cy3-dCTP or Cy5-dCTP. $Klenow_{1300}$ Cy3 or $Klenow_{1300}$ Cy5 refers to a 1300 bp target DNA that has been labelled using Klenow enzyme where 20% of the dCTP present in the reaction is Cy3-dCTP or Cy5-dCTP.

The following competitive hybridisations were performed:
1) $Klenow_{270}$ Cy3 vs $Klenow_{270}$ Cy5
2) $Klenow_{1300}$ Cy3 vs $Klenow_{1300}$ Cy5
3) $E10_{270}$ Cy3 vs $Klenow_{270}$ Cy5
4) $E10_{270}$ Cy5 vs $Klenow_{270}$ Cy3
5) $E10_{1300}$ Cy3 vs $Klenow_{1300}$ Cy5
6) $E10_{1300}$ Cy5 vs $Klenow_{1300}$ Cy3

Competitive hybridisations 1 and 2 were performed as control hybridisations and competitive hybridisations 3, 4, 5 and 6 were performed to measure the influence of fragment length on the level of fluorescent signal obtained following hybridisation.

10 ng of Cy3- and Cy5-labelled products were prepared in 20 μl of hybridisation buffer (1 mM Tris-HCl pH 7.4, 50 mM tetrasodium pyrophosphate, 1×Denhardts solution, 40% deionised formamide, 1% NP-40, 10 mM DTT, 100 μg/ml sheared salmon sperm DNA). Each sample was heated to 95° C. for 5 minutes, centrifuged for 2 min, applied to the surface of an array and covered with a 22×22 mm LifterSlip (Erie Scientific). Hybridisations were performed at 37° C. for 16 h in a hybridisation chamber (Telechem). Arrays were washed once with 2×SSC/0.1% SDS at room temperature for 5 minutes, and twice with 1×SSC at room temperature for 5 min. Slides were dried by centrifugation and scanned with an ArrayWoRx 'e' (Applied Precision Instruments). To ensure comparability between slides, identical scanning parameters were used for all arrays. Images were analysed using GenePix Pro 4.1 (Axon Instruments) and array features affected by local artifacts were manually excluded from further analysis.

Calculation of Fold-Improvements in Signal $Log_2$ (mean Cy3/mean Cy5) for each array feature was calculated. For each probe type (Pfu, or salmon testis DNA) in each experiment the mean log 2 ratio for all included array features (max. 100 Pfu features i.e. 20 replicate features each of 5 Pfu probe dilutions; max. 100 salmon sperm DNA features i.e. 20 replicate features for each of 5 salmon sperm DNA probe dilution; max. 20 spotting buffer features; max. 20 unspotted areas) was calculated. To normalise the data to the control experiment ($Klenow_{270}$ Cy3 vs $Klenow_{270}$ Cy5 or $Klenow_{1300}$ Cy3 vs $Klenow_{1300}$ Cy5), where equivalent signal is expected in both channels, the Klenow mean $log_2$ ratio from the control experiments was subtracted from that of every other comparison. If the resulting $log_2$ ratios are positive or negative, they represent signal improvements in Cy3 and Cy5, respectively, compared to labelling with Klenow at 20% Cy-dye concentration. Fold-improvements for Cy3 and Cy5 are therefore, respectively, the inverse of the resulting mean log 2 ratio and the reciprocal of the inverse of the resulting mean log 2 ratio.

Hybridisation of $E10_{270}$ Cy3 DNA fragment resulted in a 34-fold higher signal whereas hybridisation of the longer $E10_{1300}$ Cy3 DNA fragment resulted in only a 3.6-fold higher signal (see FIG. 16). Hybridisation of $E10_{270}$ Cy5 DNA fragment resulted in a 20-fold higher signal whereas hybridisation of the longer $E10_{1300}$ Cy5 DNA fragment resulted in only a 2.5-fold higher signal (see FIG. 16). These experiments demonstrate that hybridisation of E10-labelled PCR products in model array experiments result in higher (up to 32-fold) fluorescent signal and identifies that fragment length is crucial to obtaining maximal signal from directly E10-labelled samples. No increase in background fluorescence is seen when hybridising highly labelled DNA samples and the fold increase in fluorescence is linear across the dilution series printed on the slide.

Example 18

Label Density for Obtaining Maximal Signal from Highly Cy-Dye Labelled DNA

The influence of label density on fluorescent signal obtained from highly Cy-dye labelled DNA was investigated using a model array on which had been printed a dilution series (200, 100, 50, 25, and 12.5 ng/µl) of the full-length Pfu polymerase gene 2300 bp), a dilution series of salmon testis DNA (200, 100, 50, 25, and 12.5 ng/ul) and spotting buffer (the latter 2 acting as negative controls). The increase in fluorescent signal from a 270 bp Cy-dye E10 labelled DNA fragment labelled in PCRs where 10%, 50% or 100% of the dCTP is replaced by Cy3- or Cy5-dCTP was measured relative to the equivalent 270 bp Cy3- or Cy5-dCTP Pfu labelled fragment amplified in PCRs where 10% of the dCTP is replaced by Cy-dye labelled dCTP.

DNA Labelling

DNA fragments of length 270 bp were labelled with Cy3- or Cy5-dCTP by E10 or Pfu exo⁻ (Stratagene) in PCRs with primers 36 and 37 respectively. PCRs were performed in 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), 10 ng pASKpfuexo⁻5, 1% (v/v) formamide, 1 µM each primer, 50 µM dATP, 50 µM dGTP, 50 µM dTTP, 50 µM Cy3- or Cy5-dCTP (100% labelling) or 25 µM dCTP and 25 µM Cy3- or Cy5-dCTP (50% labelling) or 5 µM Cy3- or Cy5-dCTP and 45 µM dCTP (10% labelling) in a reaction volume of 50 µL $H_2O$. Reactions were hot started with E10 (100%, 50% and 10% dCTP replacement) or Pfu exo⁻ (10% dCTP replacement only) and thermocycled under the following conditions: 94° C. for 2 min 50 times at 94° C. for 10 sec, 50° C. for 10 sec and 68° C. for 20 min. Cy-dye labelled DNA products were purified by ethanol precipitation (2.5× sample volume ethanol $\frac{1}{10}^{th}$ sample volume sodium acetate pH 5.2) followed by purification on Autoseq G50 columns (Amersham Biosciences).

Model Array Hybridisations

Labelled-Target Nomenclature is as Follows:

$E10_{100}$ Cy3 or $E10_{100}$ Cy5 refers to a 270 bp target DNA that has been labelled using the E10 enzyme where 100% of the dCTP present in the labelling reaction is Cy3-dCTP or Cy5-dCTP. $E10_{50}$ Cy3 or $E10_{50}$ Cy5 refers to a 270 bp target DNA that has been labelled using the E10 enzyme where 50% of the dCTP present in the labelling reaction is Cy3-dCTP or Cy5-dCTP. $E10_{10}$ Cy3 or $E10_{10}$ Cy5 refers to a 270 bp target DNA that has been labelled using the E10 enzyme where 10% of the dCTP present in the labelling reaction is Cy3-dCTP or Cy5-dCTP.

$Pfu_{10}$ Cy3 or $Pfu_{10}$ Cy5 refers to a 270 bp target DNA that has been labelled using Pfu exo⁻ enzyme where 10% of the dCTP present in the reaction is Cy3-dCTP or Cy5-dCTP.

The following competitive hybridisations were performed:
1) $Pfu_{10}$ Cy3 vs $Pfu_{10}$ Cy5
2) $E10_{100}$ Cy3 vs $E10_{100}$ Cy5
3) $E10_{50}$ Cy3 vs $E10_{50}$ Cy5
4) $E10_{10}$ Cy3 vs $E10_{10}$ Cy5
5) $E10_{10}$ Cy3 vs $Pfu_{10}$ Cy5
6) $E10_{10}$ Cy5 vs $Pfu_{10}$ Cy3
7) $E10_{50}$ Cy3 vs $Pfu_{10}$ Cy5
8) $E10_{50}$ Cy5 vs $Pfu_{10}$ Cy3
9) $E10_{100}$ Cy3 vs $Pfu_{10}$ Cy5
10) $E10_{100}$ Cy5 vs $Pfu_{10}$ Cy3

Competitive hybridisations 1-4 were performed as control hybridisations and competitive hybridisations 5-10 were performed to measure the influence of labelling density on the level of fluorescent signal obtained following hybridisation.

10 ng of Cy3- and Cy5-labelled products were prepared in 20 µl of hybridisation buffer (1 mM Tris-HCl pH 7.4, 50 mM tetrasodium pyrophosphate, 1×Denhardts solution, 40% deionised formamide, 1% NP-40, 10 mM DTT, 100 µg/ml sheared salmon sperm DNA). Each sample was heated to 95° C. for 5 minutes, centrifuged for 2 min, applied to the surface of an array and covered with a 22×22 mm LifterSlip (Erie Scientific). Hybridisations were performed at 37° C. for 16 hr in a hybridisation chamber (Telechem). Arrays were washed once with 2×SSC/0.1% SDS at room temperature for 5 minutes, and twice with 1×SSC at room temperature for 5 min. Slides were dried by centrifugation and scanned with an ArrayWoRx 'e' (Applied Precision Instruments) and a GenePix 4100A (Axon). To ensure comparability between slides, identical scanning parameters were used for all arrays. Images were analysed using GenePix Pro 4.1 (Axon Instruments) and array features affected by local artifacts were manually excluded from further analysis.

Calculation of Fold-Improvements in Signal $Log_2$ (mean Cy3/mean Cy5) for each array feature was calculated. For each probe type (Pfu, or salmon testis DNA) in each experiment the mean $log_2$ ratio for all included array features (max. 100 Pfu features i.e. 20 replicate features each of 5 Pfu probe dilutions; max. 100 salmon sperm DNA features i.e. 20 replicate features for each of 5 salmon sperm DNA probe dilution; max. 20 spotting buffer features; max. 20 unspotted areas) was calculated. To normalise the data to the control experiment ($Pfu_{10}$ Cy3 vs $Pfu_{10}$ Cy5), where equivalent signal is expected in both channels, the Pfu mean $log_2$ ratio from the control experiments was subtracted from that of every other comparison. If the resulting $log_2$ ratios are positive or negative, they represent signal improvements in Cy3 and Cy5, respectively, compared to labelling with Pfu at 10% Cy-dye concentration. Fold-improvements for Cy3 and Cy5 are therefore, respectively, the inverse of the resulting mean log 2 ratio and the reciprocal of the inverse of the resulting mean log 2 ratio.

Scanning of slides with the GenePix 4100A (Axon) and subsequent analysis of fluorescent signal obtained from experiments where $E10_{10}$ Cy3, $E10_{50}$ Cy3 or $E10_{100}$ Cy3 DNA fragments had been hybridised resulted in 1.7-, 2.4 or 1.6-fold higher fluorescent signal respectively. Scanning of the identical slides with an ArrayWoRx 'e' (Applied Precision Instruments) and subsequent analysis of fluorescent signal resulted in 1.85-fold for $E10_{10}$ Cy3, 3.8-fold for $E10_{50}$ Cy3 and 4.5-fold for $E10_{100}$ increases in fluorescent signal. See FIG. 17.

Scanning of slides with the GenePix 4100A (Axon) and subsequent analysis of fluorescent signal obtained from experiments where $E10_{10}$ Cy5 or $E10_{50}$ Cy5 DNA fragments had been hybridised all resulted in 2.3-fold or 1.65-fold higher fluorescent signal respectively. Scanning of slides with the GenePix 4100A (Axon) and subsequent analysis of fluorescent signal obtained from experiments where $E10_{100}$ Cy5 DNA fragments had been hybridised all resulted in a 2.2-fold decrease in fluorescent signal. Scanning of the identical slides with an ArrayWoRx 'e' (Applied Precision Instruments) and subsequent analysis of fluorescent signal resulted in 2.5-fold for $E10_{10}$ Cy5, 2.3-fold for $E10_{50}$ Cy5 and 0-fold for $E10_{100}$ increases in fluorescent signal. See FIG. 17.

These experiments identify that the increase in fluorescent signal is dependent on the type of scanner used to obtain data suggesting that fluorescent spectra are altered at higher labelling densities or that quenching becomes an issue at higher labelling densities. Additionally labelling density is important to obtain maximal signal from directly E10-labelled samples. No increase in background fluorescence is seen when hybridising highly labelled DNA samples and the fold increase in fluorescence is linear across the dilution series printed on the slide.

Example 19

Highly Cy-Dye E10 Labelled DNA can be Digested by Restriction Enzymes

DNA fragments of length 270 bp were labelled with Cy3- or Cy5-dCTP by E10 in PCRs with primers 36 and 37 respectively. PCRs were performed in 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), 10 ng pASKpfuexo⁻5, 1% (v/v) formamide, 1 µM each primer, 50 µM dATP, 50 µM dGTP, 50 µM dTTP, 50 µM Cy3- or Cy5-dCTP in a reaction volume of 50 µL $H_2O$. Reactions were hot started with E10 and thermocycled under the following conditions: 94° C. for 2 min 50 times at 94° C. for 10 sec, 50° C. for 10 sec and 68° C. for 20 min. Cy-dye labelled DNA products were purified by ethanol precipitation (2.5× sample volume ethanol $1/10^{th}$ sample volume sodium acetate pH 5.2) followed by purification on AutoSeq G50 columns (Amersham Biosciences). Labelled DNA products were digested with the enzymes MseI or DdeI (New England Biolabs). The recognition sequence for MseI is TTAA and would be expected to restrict the DNA if it is double stranded. This was found to be the case (see FIG. 18 lanes 3 and 6) and indicates that 100% Cy3 or Cy5 labelled DNA is, at least in part, double stranded and B-form. The recognition sequence for DdeI is CTNAG it was anticipated that the presence of a modified C's in this site (in the sequence N will also be modified in one of the 2 sites present) will prevent digestion of the labelled DNA. This was found to be the case (see FIG. 18 lanes 2 and 5). That labelled DNA is resistant to restriction digestion presents a novel way to remove parental plasmid DNA following selection since labelled DNA will not restrict (if the enzyme recognition site contains a C) whilst unlabelled parental plasmid DNA will restrict rendering it unamplifiable.

Example 20

E10 Mutations Selected from the Pfu A Motif Repertoire and Pfu C Motif Repertoire are Synergistic To determine the contribution of the mutations selected with Cy5-dCTP from the Pfu A motif repertoire (E399D, N400G, R407I, and V337I) and the additional mutation selected from the Pfu A and C motif repertoire (Y546H) to the activity of E10 the Y546H mutation was introduced into Pfu in the absence of A motif mutations. The E10 mutation Y546H was introduced into pASKpfuexo⁻6 by subcloning a BamHI/XhoI fragment from E10 into pASKpfuexo⁻6 thereby generating pASKpfuexo⁻6Y546H.

Crude lysates of E10 (E399D, N400G, R407I, V337I, Y546H), clone 15 (E399D, N400G, R407I, and V337I) and pASKpfuexo⁻6Y546H (Y546H) were made by growing overnight cultures in 2×TY (100 µg/mL ampicillin) at 30° C. Protein expression was induced by the addition of anhydrous tetracycline (0.4 µg/mL) to the overnight culture and the cultures allowed to grow for 5 h at 37° C. Induced cells were pelleted by centrifugation (13,000 g, 5 min) and 10× lysates were made by resuspension in $1/10^{th}$ of the culture volume of 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd). The cells were lysed by incubation at 85° C. for 10 min and cell debris was removed by centrifugation at 13,000 g for 10 min.

Crude lysates as well as Pfuexo⁻ (5 U; Stratagene) were activity normalised with primer 48 as described in example 7. ELISA experiments designed to determine the contribution of the mutations selected from the Pfu A motif repertoire (E399D, N400G, R407I, and V337I) and Pfu A and C motif repertoire (Y546H) to the activity of E10 were performed activity with normalised crude lysates with primer 35 (requires the incorporation 8 consecutive C's prior to the incorporation of digoxigenin-11-dUTP) and Cy3- or Cy5-dCTP as described in example 7. These experiments show that the contribution of the A motif (and V337I) and C motif mutations are synergistic (FIG. 19).

Crude lysates and Pfuexo⁻ (5 U; Stratagene) were activity normalised in PCRs with primers 36 and 37 and 10 ng of pASKpfuexo⁻5 as template. Activity normalisation of the crude lysates in PCR was performed as follows: 1 µM each primer, 1% (v/v) formamide, 100 µM dNTPs, 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd). Reactions were thermocycled as follows: 94° C. for 2 min 25 times at 94° C. for 30 sec, 55° C. for 30 sec and 72° C. for 2 min. PCRs were set up with activity normalised crude lysates and Pfuexo⁻ (5 U; Stratagene) as described above. Reactions were thermocycled with decreasing extension times (30 sec or 10 sec at 72° C.; see FIG. 19). E10 is able to amplify a 270 bp fragment with a 10 second extension time whereas Pfu exo⁻ (Stratagene), clones 15 and pASKpfuexo⁻6 Y546H cannot.

Example 21

E10 A Motif Mutations can Compensate for the Decrease in Activity of Tgo Polymerase Containing the Therminator Mutation (A485L)

The A motif mutations selected with Cy5-dCTP from the Pfu A motif repertoire were introduced by iPCR into the B family DNA polymerase gene from *Thermococcus gorgonarius* (Tgo) in which the uracil stalling function (V93Q; Fogg et al., 2002) had been removed as well as the 3'-5' exonuclease function (D141A and E143A; Derbyshire et al., 1995) with and without the Therminator mutation (A485L; Gardener and Jack, 1999) with primers 53 and 54 as described in example 4 (see FIG. 20). A motif mutations and the presence or absence of the Therminator mutation were confirmed by sequencing with primer 55 (see FIG. 20).

Tgo (V93Q, Exo⁻), Tgo E10 A motif (V93Q, Exo⁻, E398D, N399D, R406I), Tgo Therminator (V93Q, Exo⁻, A485L) and Tgo Therminator E10 A motif (V93Q, Exo⁻, A485L, E398D, N399D, R406I, A485L) clones were grown overnight at 30° C. in 2×TY (Ampicillin 100 µg/mL). Protein expression was induced the next day by the addition of anhydrous tetracycline (0.4 µg/mL) to the overnight culture and the cultures allowed to grow for 4 h at 37° C. Induced cells were pelleted by centrifugation (13,000 g, 5 min) and 10× lysates were made by resuspension in $1/10^{th}$ of the culture volume of 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd). The cells were lysed by incubation at 85° C. for 10 min and cell debris was removed by centrifugation at 13,000 g for 10 min.

PCRs were hot started by the addition of 2 µL of crude lysate to a reaction containing: 10 ng of pASKTaq, 1 µM primer 56, 1 µM primer 39, 1×Pfu buffer (10 mM KCl, 10 mM $(NH_4)_2SO_4$, 20 mM Tris-Cl pH 8.75, 2 mM $MgSO_4$, 0.1% Triton X-100, 100 µg/mL BSA; Stratagene Ltd), 1% (v/v) formamide and 100 µM dNTPS in a reaction volume of 20 µL. Thermocycling conditions were as follows: 94° C. for 2 min 25 times at 94° C. for 30 sec, 50° C. for 30 sec and 72° C. for 2 min. PCR products were analysed by agarose gel electrophoresis on a 1.2% (w/v) gel (see FIG. 20). The Tgo Terminator clone was unable to amplify the 410 bp product whereas Tgo Terminator clone into which the A motif mutations (E398D, N399D, R406I) had been introduced was.

Example 22

PCR Generation of Highly FITC-12-dATP Labelled or Biotin-16-dUTP Labelled DNA Using E10

Pfuexo⁻ is able to perform PCR with 100% substitution of dATP by FITC-12-dATP or Biotin-16-dUTP. To assess whether E10 retains these properties PCRs were hot started by the addition of 1 μL of E10 or 2.5 U Pfuexo⁻ (Stratagene) to a PCR reaction. For PCRs with 100% replacement of dATP by FITC-12-dATP reactions contained: 10 ng of pASKTaq, 1 μM primer 56, 1 μM primer 39, 1×Pfu buffer (10 mM KCl, 10 mM $(NH_4)_2SO_4$, 20 mM Tris-Cl pH 8.75, 2 mM $MgSO_4$, 0.1% Triton X-100, 100 μg/mL BSA; Stratagene Ltd), 1% (v/v) formamide and 50 μM dNTPs (-dATP) 50 μM FITC-12-dATP in a reaction volume of 12.5 μL. Reactions with 100% replacement of dTTP with Biotin-16-dUTP were performed as described above but with dNTPs lacking dTTP and 50 μM Biotin-16-dUTP. Thermocycling conditions were as follows: 94° C. for 2 min 50 times at 94° C. for 10 sec, 60° C. for 30 sec and 68° C. for 20 min. PCR products were analysed by agarose gel electrophoresis on a 1.2% (w/v) gel (see FIG. 21) and revealed that E10 is able to incorporate either 100% FITC-12-dATP or 100% Biotin-16-dUTP.

Example 23

Selection of Pfu Variants Able to Incorporate Biotin-16-dUTP and Cloning by iPCR Pfu variants were selected from the Pfu A motif repertoire libraries (see example 4) for the ability to incorporate Biotin-16-dUTP. spCSR selections were set up as described in example 3 however, the dTTP was completely replaced by 100 μM of Biotin-16-dUTP. Primers annealing 5' and 3' of the region diversified were employed in spCSR selections.

spCSR Biotin-16-dUTP selections from the Pfu A motif library (94° C. for 5 min; 20 times at 94° C. for 30 sec, 50° C. for 1 min, and 72° C. for 10 min; 1 times at 65° C. for 10 min) were carried out using primers 57 and 37 as described in example 3. The aqueous phase was extracted as described as described in example 3 and purified selection products were reamplified by PCR (94° C. 5 min; 50° C. 5 min; 72° C. 5 min; 26 times at 94° C. for 30 sec, 50° C. for 1 min, and 72° C. for 3 min; 1 times 65° C. 10 min) using primers 58 and 37 as described in example 3. Reamplified selection products were gel purified (QIAquick gel extraction kit; Qiagen) and used as a primer in an iPCR reaction with an equimolar quantity of primer 59 and 10 ng of pASKpfuexo⁻7 as template. iPCR reactions were performed as follows: Briefly iPCR reactions were hot-started by the addition of 3.5 U of Expand High Fidelity polymerase (Roche) to a PCR mix [10 ng of plasmid template, primers (equimolar quantity dependent on yield of selection product), dNTPs (0.2 mM), in 1× High Fidelity Expand buffer with $MgCl_2$ (Roche)]. Reactions were thermocycled [94° C. for 4 min; 19 times (94° C. for 20 sec, 65° C. for 20 sec −1° C./cycle, and 68° C. for 10 min)] at this point 40 μM each of primers 58 and 59 and a further 3.5 U of Expand High Fidelity polymerase (Roche) were added to the iPCRs which were subjected to further thermocycling [15 times (94° C. for 20 sec, 50° C. for 20 sec, 68° C. for 10 min); 15 times (94° C. for 20 sec, 50° C. for 20 sec, 68° C. for 10 min+15 sec/cycle)]. iPCR reactions were purified with a QIAquick PCR purification kit (Qiagen) and eluted in 50 μL of $H_2O$. Purified DNA was restriction digested overnight with DpnI (New England Biolabs) to remove the input plasmid template. Restricted DNA samples were purified with a QIAquick PCR purification kit (Qiagen) and eluted in 50 μL of $H_2O$. Purified DNA was restriction digested overnight with BsaI (New England Biolabs) after which the reactions were purified with a QIAquick PCR purification kit (Qiagen) and eluted in 50 μL of $H_2O$. 50 μL of the restriction digested DNA was ligated overnight at 16° C. with 1600 U T4 DNA ligase (New England Biolabs) in 1× T4 DNA ligase buffer (New England Biolabs) in a final volume of 60 μL. Ligation reactions were extracted with an equal volume of phenol/chloroform (4:1 v/v), ethanol precipitated and then electroporated into *E. coli* Ace6 or TG1TR cells which were plated onto 2×TY/Amp 0.1 mg/mL plates.

Example 24

Pfu Variants Selected from the A-Motif Library with Biotin-16-dUTP

Pfu variants able to significantly incorporate Biotin-16-dUTP compared to the ability of the wild-type enzyme were selected from the A motif Pfu repertoire library (see example 23) with primers that anneal 5' and 3' of the A-motif (see example 5). Clones exhibiting a significantly enhanced ability to incorporate Biotin-16-dUTP were ranked by ELISA extension assay with primer 60 (see example 7; FIG. 22). ELISAs were performed essentially as described in example 7 however the extension reaction contained 20 μM each of dCTP and dGTP, 18 μM dATP, and 20 μM Biotin-16-dUTP. The DIG labelled dUTP in the extension reaction was replaced with 2 μM Fluorescein 12-dATP. The incorporation of Fluorescein 12-dATP was detected by anti-Fluorescein-POD Fab fragments (Roche). Positive clones were identified with the QuantaBlu™ Fluorogenic Peroxidase Substrate Kit (Pierce). Positive clones were sequenced with primer 36 and mutations were identified in the region diversified (FIG. 23).

Example 25

Fluorescence In-Situ Hybridisation (FISH) Analysis with Highly Labelled FITC, Cy3 or Cy5 Probes Generated by E10

Metaphase spreads from the human pancreatic cancer cell line Suit-2 were prepared on Super Frost glass slides (BDH), and denatured by incubations in 50% formamide/1×SSC for 1 min 20 sec at 70° C. and in ice-cold ethanol for 3 min. The chromosomes were dehydrated by 3-minute incubations each in 70%, 90% and 100% ethanol and air-dried at 37° C. until hybridisation.

DNA probes were generated to WRN (chr8:31,150,398-31,150,474; primers 61 & 62, a 766 bp fragment labelled with Cy5-dCTP 32% GC), DCTN6 (chr8:30,133,979-30,134,732; primers 63 & 64, a 754 bp fragment labelled with FITC-12-dATP 59% AT) or NRG1 (chr8:32,718,891-32-32,719,828; primers 65 & 66, a 938 bp fragment labelled with Cy3-dCTP 42% GC). Plasmids containing the fragments to be labelled were used as template in PCRs where 50% of the unlabelled dNTP was replaced by its labelled counterpart. The PCRs were hot-started by the addition of 1 μL of purified E10 to a PCR mix [10 ng plasmid DNA template, primers (0.4 μM each), 1×Pfu buffer (10 mM KCl, 10 mM $(N)_2SO_4$, 20 mM Tris-Cl pH 8.75, 2 mM MgSO$_4$, 0.1% Triton X-100, 100 µg/mL BSA; Stratagene Ltd), formamide and dNTPs (0.05 mM each, 0.025 mM unlabelled counterpart), 0.025 mM Cy3- or Cy5-dCTP or FITC-dATP]. PCRs to generate labelled DNA probes to NRG1 or WRN were performed with a final formamide concentration of 2% (v/v) and PCRs to generate labelled DNA probes to DCTN6 were performed with a final formamide concentration of 1% (v/v). Reactions were thermocycled (94° C. for 2 min; 50 times at 94° C. for 10 sec, annealing for 1 min, and 72° C. for 20 min). The annealing temperatures were 60° C., 55° C. and 58° C. for the NRG1, WRN and DCT respectively. Labelled probes were purified by ethanol precipitation with 2.5× vol of ethanol ¹/₁₀ volume NaAc (pH 5.2) and resuspended in 20 µL of H$_2$O followed by G50 column purification.

Probes labelled with Cy-dyes or FITC (100-150 ng) were mixed with 3 µL human Cot-1 DNA (100 ng/µL; Roche) in 14 µL hybridisation buffer (50% (v/v) formamide, 2×SSC 10 mM Tris-HCl pH 7.5, 0.1% (w/v) Tween 20, 10% dextran sulphate) and incubated at 37° C. for 30 min. The probe mixture was denatured at 95° C. for 10 min, cooled on ice for 2 min and incubated at 37° C. for 1 hr. The probes were applied to denatured metaphase spreads and covered with a glass cover slip. Following hybridisation at 37° C. overnight, the slides were soaked in 1×SSC to remove the cover slips, washed 2 times 5 min in 50% formamide/2×SSC at 42° C. and 2 times 5 min in 1×SSC. The sides were then incubated in 4×SSC, 0.5% BSA (Sigma), 0.05% Tween for 5 min, mounted with Vectashield Mounting Medium with DAPI (Vectashield Laboratories), and viewed with Nikon Eclipse E800 Fluorescence microscope. Cy3, Cy5 and FITC signals from these exceptionally short probes co-localised to a single chromosome in 5 out of 5 cells analysed and could be detected directly without the need for subsequent signal amplification (FIG. 24).

Example 26

Properties of CyDNA

The physico-chemical properties of CyDNA are significantly altered as compared to native DNA.

Analysis of the melting temperature of a 100 bp fragment (70% GC) labelled with E10 in PCRs where 100% of the dCTP was replaced by either Cy3- or Cy5-dCTP revealed that the CyDNA melts at lower temperature than native DNA. DNA fragments (100 bp, 70% GC) for melting temperature analysis were amplified with primers 67 and 68. Reactions were performed in 1×Pfu buffer (Stratagene) containing 10 ng template (pASKwtTaq; Ghadessy et al 2001), 1% formamide (v/v), primers (0.4 µM each) dNTPs (50 µM each). Cy-dye labelled DNA fragments were amplified with E10 and 100% of the dCTP was replaced by Cy3- or Cy5-dCTP. Reactions were hot-started with E10 and thermocycled as follows: 94° C. 2 min; 50 times (94° C. 10 sec, 50° C. 10 sec, 68° C. 20 min). Cy-dye labelled DNA fragments were concentrated and purified by ethanol precipitation followed by additional purification with illustra Microspin G-50 columns (GE Healthcare). Reactions to generate unlabelled control DNA were hot-started with Pfu Turbo (2.5 U Stratagene) and thermocycled as follows: 94° C. 2 min; 30 times (94° C. 30 sec, 50° C. 1 min, 72° C. 1 min). Unlabelled PCR products were purified with QIAquick PCR purification columns (QIAGEN Chatsworth Calif.) followed by gel extraction with QIAquick gel extraction kit (QIAGEN Chatsworth Calif.). Melting temperatures of the labelled and control DNA fragments (1 µm) were determined with a Perkin Elmer Lambda 40 over a temperature range of 60° C.-100° C. The unlabelled DNA melts at 90° C. whereas the Cy5-dCTP labelled DNA melts at 87° C. and the Cy3-dCTP labelled melts at 84° C. This correlates with what others have observed and what we have observed in model microarray experiments where hybridisation temperatures and wash stringencies require reduction. Additionally CyDNA melting is less cooperative than native DNA probably reflecting the presence of additional groups on the duplex.

It is not possible to efficiently purify CyDNA with silica resins in the presence of chaotropic salts or by phenol extraction in the presence of NaCl concentrations commonly found in some restriction enzyme buffers (e.g. NEB3; New England Biolabs). Unlike native DNA 100% Cy3 labelled DNA partitions entirely to the organic phase in the presence of 200 mM NaCl on phenol extraction whereas 100% Cy5 DNA partitions entirely to the organic phase in the presence of 100 mM NaCl. CyDNA can be recovered from the phenol phase into the aqueous phase by either diluting the salt containing phase with H20 or removing the aqueous salt containing phase and replacing this with an equivalent volume of H20. CyDNA cannot be cloned reflecting an inability of the native E. coli polymerase enzymes to replicate this unnatural DNA. However, it is possible to ethanol precipitate CyDNA.

CyDNA exhibits decreased electrophoretic mobility compared to a native DNA fragment amplified with the same primers. Additionally, Cy-dye modified DNA does not fluoresce with ethidium bromide. Presumably the presence of the modifications at the 5' position of the pyrimidine sterically hinders intercalation. However, despite the absence of ethidium bromide intercalation CyDNA is, at least in part, double stranded and B-form as indicated by its digestion with restriction enzymes, such as MseI, whose recognition sequence is devoid of modified C's. The presence of a Cydye modified C in the restriction enzyme recognition site prevents restriction digestion Further evidence that CyDNA exists as double stranded B-form DNA was obtained by Atomic Force Microscopy (AFM). The results of AFM are shown in FIG. 26. DNA fragments (314 bp) for AFM analysis were amplified by PCR with primers 69 and 70. Reactions were performed in 1×Pfu buffer (Stratagene) containing 10 ng template (pASKpfuexo-5), 1% formamide (v/v), primers (1 µM each) dNTPs (50 µM each). Cy-dye labelled DNA fragments were amplified with E10 and 100% of the dCTP was replaced by Cy3- or Cy5-dCTP (GE Healthcare). Reactions were hot-started with E10 and thermocycled as follows: 94° C. 2 min; 50 times (94° C. 10 sec, 50° C. 10 sec, 68° C. 20 min). Labelled DNA fragments were concentrated and purified by ethanol precipitation followed by additional purification with illustra Microspin G-50 columns (GE Healthcare). Reactions to generate unlabelled control DNA were hot-started with Pfu exo- (2.5 U Stratagene) and thermocycled as follows: 94° C. 2 min; 25 times (94° C. 30 sec, 50° C. 30 sec, 72° C. 2 min). Unlabelled PCR products were purified with QIAquick PCR purification columns (QIAGEN Chatsworth Calif.).

The lengths and heights (width) of individual CyDNA molecules amplified with E10 in PCRs where 100% of the dCTP was replaced by either Cy3- or Cy5-dCTP were measured. For AFM imaging the modified and control DNA fragments were diluted to a concentration of 1 nM in buffer X (10 mM Tris-HCl pH 7.4, 10 mM MgCl2, 10 mM NaCl). It proved difficult to prepare the CyDNA samples for analysis on mica stubs presumably due to the hydrophobic nature of the samples. It was, however, possible to analyse samples on mica stubs that had been functionalised with Poly-L-Lysine. Poly-L-lysine coated mica was formed by incubating 50 µL of 0.001% poly-L-lysine (Sigma, Poole, UK) on freshly cleaved mica (Goodfellows, Huntingdon, UK) for 10 min, followed by rinsing with 10 mL MilliQ water (Millipore, Billerica, Mass.), and blown dry with a stream of nitrogen. The DNA fragments were deposited on the poly-L-lysine coated mica by incubating a 10 μL drop of DNA containing solution on the surface for 4 min, the sample was then rinsed with 10 mL MilliQ water and blown dry with a stream of nitrogen. AFM imaging was performed using a Veeco Multimode AFM with a Nanoscope IIIa controller (Veeco, Santa Barbara, Calif.) operated in Tapping mode, using Olympus AC 160TS silicon nitride cantilevers with a resonant frequency of approximately 350 kHz. The images were acquired at 512*512 pixel resolution with a scan size of 3 μm, scan rates were 1.97 Hz. Images were flattened post capture to remove Z offsets and sample tilt. The DNA contour length of individual molecules was measured by approximating the DNA backbone as a series of straight lines using the Nanoscope software (Veeco). The DNA end-end distance was measured by tracing the straight line distance between the two DNA ends.

The lengths and heights of 40 unmodified DNA molecules, 40 Cy3-dCTP modified molecules and 71 Cy5-dCTP molecules were measured. The distribution in length of the Cy5-dCTP modified DNA molecules is not Gaussian this could be due to the presence of smaller termination products present in the PCR amplification making data interpretation difficult. It is possible, however, to conclude that there is a significant difference in molecule length between the unmodified and Cy3-dCTP modified DNA molecules (104.0 nm±0.3 vs 97.5 nm±0.25). The height (width) of the Cy3-dCTP and Cy5-dCTP labelled DNA molecules is significantly greater than that of the unmodified DNA molecules (see FIG. 19). Cy5-dCTP labelled DNA molecules are wider (0.78 nm±0.008) than Cy3-dCTP labelled DNA molecules (0.620 nm±0.008) consistent with Cy5 being a larger fluorophore than Cy3. Additionally, the persistence length (stiffness) of the unmodified and Cy5-dCTP modified DNA molecules was modelled using data from the mean end-to-end distance derived in each case from 61 DNA molecules (i.e. a straight line from one end to the other rather than following the DNA backbone)—the larger the average end-to-end distance the stiffer the molecule. It can be concluded that both the Cy5-dCTP modified and unmodified DNA fragments can be modelled as having the same persistence length. This assumes that both fragments bind to the surface in the same manner, since weaker binding is likely to allow the molecule to equilibrate on the surface better resulting in a larger <R>2 Measured. It was demonstrated previously that the modified DNA binds more weakly to a nonfunctionalised mica surface therefore the persistence length data should be interpreted with caution.

Example 27

FISH & Fibre FISH

High label density will not necessarily result in an increase in fluorescence due to re-absorption and re-emission effects and quenching. Model microarray experiments identified that PCR fragments labelled in PCRs where of the 50% of the dCTP was replaced by either Cy3- or Cy5-dCTP resulted in higher fluorescent signal than fragments labelled with 100% replacement (see Example 18). Consequently probes used in FISH and Fibre FISH were generated in PCRs where 50% of the unlabelled nucleotide was replaced by its fluorescent counterpart. Pfu exo- is able to incorporate FITC-12-dATP when present at 100% in PCRs. E10 retains this ability (see Example 22)

FISH

FISH was performed as described in Example 25.

Fibre FISH

Fibre-FISH was based on the method described by Mann et al. (1997). Briefly, 10 μL of fixed metaphase preparation from the human skin cell line DRM was smeared across the width of a polylysine-coated slide (Polyprep, Sigma, Dorset, UK) approximately 1 cm from the top of the usable slide surface and allowed to dry for a minute before being submerged vertically in lysis buffer (0.5% (w/v) SDS, 50 mM EDTA, 0.2M Tris-HCl pH7.4) in a coplin jar and left to stand with the cell preparation just below the buffer surface. After 5 min 94% ethanol was slowly run on to the buffer surface to form an upper layer until the entire slide was covered. After incubating for 10 min, the slide was pulled out of the solutions slowly and steadily at a 30° angle, submerged in 70% ethanol, incubated for 30 min, and dehydrated in an ethanol series. Slides were hybridized and analysed as for metaphase spreads.

DNA probes of approximately 900 bp in length were generated to the NRG1 gene: Probe 1 (primers 71 and 72; chr8: 31626471+31627403), probe 2 (primers 73 and 74; chr8: 31628404+31629322), probe 3 (primers 75 and 76; chr8: 31639299+31640223) probe 4 (primers 77 and 78; chr8: 31645286+31646222), probe 5 (primers 79 and 80; chr8: 31650233+31651127), probe 6 (primers 81 and 82; chr8: 31653626+31654580), probe 7 (primers 83 and 84; chr8: 31661123+31662023). Probes 1, 4 and 6 were labelled with FITC-dATP (Perkin Elmer) and probes 2, 3, 5 and 7 were labelled with Cy5-dCTP (GE Healthcare). Plasmids containing the fragments to be labelled were used as template in PCRs where 50% of the unlabelled dNTP was replaced by its labelled couterpart. The PCRs were hot-started by the addition of 1 μL of purified E10 to a PCR mix [10 ng plasmid DNA template, primers (1 μM each), 1×Pfu buffer (Stratagene Ltd), 2% formamide (v/v) and dNTPs (0.05 mM each, 0.025 mM unlabelled counterpart), 0.025 mM Cy5-dCTP or FITC-dATP]. Reactions were thermocycled (94° C. for 2 min; 50 times at 94° C. for 10 sec, annealing for 1 min, and 72° C. for 20 min). The annealing temperatures were 55° C. for probes 1, 2, 6 and 7, 60° C. for probe 3, 52° C. for probe 4 and 58° C. for probe 5. Labelled probes were purified by ethanol precipitation with 2.5× volume of ethanol ¹⁄₁₀ volume NaAc (pH 5.2) and resuspended in 20 μL of H₂O followed by S-300 column purification (GE Healthcare). Slides were hybridized and analysed as for metaphase spreads. Fluorescence could be detected from all of these exceptionally short probes, including those separated by just 1 kb (probes 1 and 2), without the need for signal amplification (see FIG. 27).

Example 28

Sensitive Detection in a Microfluidic Device

DNA fragments of length 270 bp were labelled with Cy3- or Cy5-dCTP by E10 in PCRs with primers 36 and 37 respectively. PCRs were performed in 1×Pfu buffer (10 mM KCl, 10 mM: (N)₂SO₄, 20 mM Tris-Cl pH 8.75, 2 mM MgSO₄, 0.1% Triton X-100, 100 μg/mL BSA; Stratagene Ltd), 10 ng pASKpfuexo⁻5, 1% (v/v) formamide, 1 μM each primer, 50 μM dATP, 50 μM dGTP, 50 μM dTTP, 50 μM Cy3- or Cy5-dCTP in a reaction volume of 50 μL H₂O. Reactions were hot started with E10 and thermocycled under the following conditions: 94° C. for 2 min 50 times at 94° C. for 10 sec, 50° C. for 10 sec and 68° C. for 20 min. Cy-dye labelled DNA products were purified by ethanol precipitation (2.5× sample volume ethanol ⅒th sample volume sodium acetate pH 5.2) followed by purification on AutoSeq G50 columns (Amersham Biosciences).

For detection at single- or near-single-molecule levels, a solution was prepared containing 5 pg/μl each of 100% Cy5-dCTP labelled and 50% Cy3-dCTP labelled 270 bp PCR products in water. Based on the sequence of the PCR product, each double-stranded molecule should carry on average 102 Cy3 or 102 Cy5 labels.

This solution was driven through a fused silica capillary (internal diameter ~40 μm) at 30 μl/hr using a syringe pump. Fluorescence was detected at a fixed point inside the lumen of the capillary, using a custom optical unit which consisted of 532/635 nm laser light fed in by a single mode (3/125 μM) silica optical fiber. On emerging from the fiber the light was collected and focused onto the sample using a combination of 0.3 NA and 0.65 NA aspheric lenses, the latter being both the focusing and collecting objective for fluorescence. The working distance of the sample objective was approximately 1.5 mm, and the intensity field in the focal volume had a Guassian profile with a 1/e diameter of approximately 2.5 μM (effective focal volume approximately 8 μm$^3$, or 8 fl). Collected light was filtered of reflected laser energy using a cascaded series of reflective/transmissive filters and then focussed into a receiving fiber which conveyed the light to a Perkin Elmer SPCM module for the final quantitation of intensity. Counts for both Cy3 fluorescence (570 nm; bandwidth ~25 nm) and Cy5 fluorescence (670 nm; bandwidth ~25 nm) were collected in consecutive 20 μsec periods and averaged over a sliding window (centre-weighted) of 40 periods.

A representative section of the output, spanning a total of 0.2 s, is shown in FIG. 28. Since labeled molecules may pass through either the centre or the periphery of the Gaussian detection volume, peak heights are expected to be variable in this system. Also, the overlaps between the Cy3 and Cy5 emission spectra, and the finite bandwidth of the detection filters, means that Cy3 emission causes some signal in the Cy5 channel (though not vice versa). This trace depicts strong detection of one Cy5-labelled molecule (at approximately interval 5500), and of one Cy3-labelled molecule (at approximately interval 8700); smaller peaks are visible, particularly for Cy5—these are believed to represent labeled molecules passing through the edges of the Gaussian detection volume.

The frequency of detection events is approximately that expected if single labeled molecules (rather than aggregates of multiple molecules) were being detected.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

Clones Selected Using the Methods Described Herein, DNA and Amino Acid Sequences:

```
E10 amino acid sequence - SEQ ID NO. 1
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

NLVEWFLLRKAYERNEVAPNKPSEEEYQRRLRESYTGGFVKEPEKGLWDDIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLHATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

E10 nucleotide sequence - SEQ ID NO. 2
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT
```

-continued

```
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAAGTGGAGAGA
ACCTTGAGAGAGTTGCCAAATACTCGATGGAAGATGCAAAGGCAACTTATGAACTCGGGAAGAATTCCT
TCCAATGGAAATTCAGCTCTCAAGATTAATTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAAGGGGTT
GTGGGACGACATCGTTTATCTAGATTTCATAGCCCTATATCCCTCGATTATAATTACCCACAATGTTTCT
CCCGATACTCTAAATCTTGAGGGATGCAAGAACTATGATATCGCTCCTCAAGTAGGCCACAGTTCTGCA
AGGACATCCCTGGTTTTATACCAAGTCTCTTGGGACATTTGTTAGAGGAAAGACAAAAGATTAAGACAAA
AATGAAGGAAACTCAGGATCCTATAGAAAAATACTCCTTGACTATAGACAAAAAGCGATAAAACTCTTA
GCAAATTCTTTCTACGGATATTATGGCTATGCAAAAGCAAGATGGTACTGTAAGGAGTGTGCTGAGAGCG
TTACTGCCTGGGGAAGAAAGTACATCGAGTTAGTATGGAAGGAGCTCGAAGAAAAGTTTGGATTTAAAGT
CCTATACATCGACACTGATGGTCTTCACGCAACTATCCCAGGAGGAGAAAGTGAGGAGATCAAGAAAAAG
GCTCTCGAATTTGTAAAATACATAAATTCAAAGCTCCCTGGACTGCTCGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA
```

Biotin-16-dUTP selected clones.
Bio187-SEQ ID No 3:

```
ATGATTTTAGATGTGGATTACATAACTGAAGAAGGAAAACCTGTTATTAGGCTATTCAAAAAAGAGAACG
GAAAATTTAAGATAGAGCATGATAGAACTTTTAGACCATACATTTACGCTCTTCTCAGGGATGATTCAAA
GATTGAAGAAGTTAAGAAAATAACGGGGGAAAGGCATGGAAAGATTGTGAGAATTGTTGATGTAGAGAAG
GTTGAGAAAAAGTTTCTCGGCAAGCCTATTACCGTGTGGAAACTTTATTTGGAACATCCCCAAGATGTTC
CCACTATTAGAGAAAAAGTTAGAGAACATCCAGCAGTTGTGGACATCTTCGAATACGATATTCCATTTGC
AAAGAGATACCTCATCGACAAAGGCCTAATACCAATGGAGGGGGAAGAAGAGCTAAAGATTCTTGCCTTC
GCGATCGCGACCCTCTATCACGAAGGAGAAGAGTTTGGAAAAGGCCCAATTATAATGATTAGTTATGCAG
ATGAAAATGAAGCAAAGGTGATTACTTGGAAAAACATAGATCTTCCATACGTTGAGGTTGTATCAAGCGA
GAGAGAGATGATAAAGAGATTTCTCAGGATTATCAGGGAGAAGGATCCTGACATTATAGTTACTTATAAT
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAAGTGGAGAGA
ACCTTGAGAGAGTTGCCAAATACTCGATGGAAGATGCAAAGGCAACTTATGAACTCGGGAAGAATTCCT
```

-continued
```
TCCAATGGAAATTCAGCTTTCAAGATTAGTTGGACAACCTTTATGGGGTGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGGCATCGTCTATCTGGATTTTATAGCCCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAAGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 4:
```
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPYTYLEAVYE

AIFGKPKEKVYADEIAKAWESGENLERVAKYSMEDAKATYELGKEFLPMEIQLSRLVGQPLWGVSRSSTG

NLVEWFLLRKAYERNEVAPNKPSEEEYQRRLRESYTGGFVKEPEKGLWEGIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Bio-120-nucleotide sequence: SEQ ID No 5:
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA
```

```
GAGAGAGATGATAAAGAGATTTCTCAGGATTATCAGGGAGAAGGATCCTGACATTATAGTTACTTATAAT
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAAGTGGAGAGA
ACCTTGAGAGAGTTGCCAAATACTCGATGGAAGATGCAAAGGCAACTTATGAACTCGGGAAGAATTCCT
TCCAATGGAAATTCAGCTTTCAAGATTAGTTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAAGGGGTT
GTGGGAAGACATCGTCTATCTAGATTTTAGAGCCCAATATCCCTCGATTATAGTTACCCACAATGTTTCT
CCCGATACTCTAAATCTTGAGGGATGCAAGAACTATGATATCGCTCCTCAAGTAGGCCACAAGTTCTGCA
AGGACATCCCTGGTTTTATACCAAGTCTCTTGGGACATTTGTTAGAGGAAAGACAAAAGATTAAGACAAA
AATGAAGGAAACTCAAGATCCTATAGAAAAATACTCCTTGACTATAGACAAAAAGCGATAAAACTCTTA
GCAAATTCTTTCTACGGATATTATGGCTATGCAAAAGCAAGATGGTACTGTAAGGAGTGTGCTGAGAGCG
TTACTGCCTGGGGAAGAAAGTACATCGAGTTAGTATGGAAGGAGCTCGAAGAAAAGTTTGGATTTAAAGT
CCTCTACATTGACACTGATGGCCTCTATGCAACTATCCCAGGAGGAGAAAGTGAGGAAATAAAGAAAAAG
GCTCTCGAATTTGTAAAATACATATAAATTCAAAGCTCCCTGGACTGCTAGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA
```

Amino acid sequence: SEQ ID No 6.
```
MILDVDYITEEGKPVIRLFKKENGKFKIEHDRTFRPYIYALLRDDSKIEEVKKITGERHGKIVRIVDVEK
VEKKFLGKPITVWKLYLEHPQDVPTIREKVREHPAVVDIFEYDIPFAKRYLIDKGLIPMEGGEELKILAF
AIATLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEDIVYLDFRAQYPSIIVTHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS*
```

Bio32-nucleotide sequence: SEQ ID No 7.
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGATCCTGACATTATAGTTACTTATAAT

GGGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAGGGGTT

GTGGAACGACCTGGTCTATCTAGATTTTATAGCCCTATATCCTTCGATTATAGTTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGCACAAA

AATGAAGGAAACCCAAGATCCTATAGAAAAAATACTCCTTGACTATAGACAAAAAGCGATAAAACTCTTA

GCAAATTCTTTCTACGGATATTATGGCTATGCAAAGCAAGATGGTACTGTAAGGAGTGTGCTGAGAGCG

TTACTGCCTGGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 8.
```
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWNDLVYLDFIALYPSIIVTHNVS
```

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Bio33-nucleotide sequence: SEQ ID No 9.
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAAAG

GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGATCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCACGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGACAGCATCGTTTATCTAGATTTTATAGCCCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAAGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA.

-continued

Amino acid sequence: SEQ ID no 10.
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWDSIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-B motif library clone 3 selected with Cy5-dCTP
SEQ ID No 11:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGGCATCGTTTATCTAGATTTTATAGCCCTATATCCTTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTGTTAGAGGAAAGACAAAAGATTAAGACAAA

AATGAAGGAAACTCAGGATCCTATAGAAAAATACTCCTTGACTATAGACAAAAAGCGATAAAACTCTTG

GCAAATTCTTTATACGGATATTACGGTTATGCCAAAGCAAGATGGTACTGTAAGGAGTGTGCTGAGAGCG

TTACTGCCTGGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

```
ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 12:
```
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEGIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSLYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Pfu A-B motif library clone 4 selected with Cy5-dCTP.
SEQ ID No 13:
```
ATGATTTTAGATGTGGATTACATAACTGAAGAAGGAAAACCTGTTATTAGGCTATTCAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGCACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGACTCGTTAAAGAGCCAGAAAGGGGTT

GTGGGAAGACCTCGTTTATCTAGATTTTATAGCTCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA
```

-continued

```
AATGAAGGAAACTCAGGATCCTATAGAAAAAATACTCCTTGACTATAGACAAAAAGCGATAAAACTCTTA

GCAAATACTTTCTACGGATATTACGGCTATGCCAAAGCAAGATGGTACTGTAAGGAGTGTGCTGAGAGCG

TTACCGCCTGGGGGAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 14:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDFDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGLVKEPEKGLWEDLVYLDFIALYPSIIITHNVS

PDTLNLEGCKNYDIAPQVGHKFCKDIPGFIPSLLGHLLEERQKIKTKMKETQDPIEKILLDYRQKAIKLL

ANTFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-B motif library clone 9 selected with Cy5-dCTP.
SEQ ID No 15:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGCAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA
```

-continued

```
ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGACGACATCGTTTATCTAGATTTCATAGCCCTATATCCCTCGATTATAATTACCCACAATGTTTCT

CCCGATACTCTAAATCTTGAGGGATGCAAGAACTATGATACCGCTCCTCAAGTAGGCCACAAGTTCTGCA

AGGACATCACTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTCTTA

ACAAATTCTGTTTACGGATATTACGGCTATACGAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 16:
MILDVDYITEEGKPVIRLFKKENGKFKIEHDRTFRPYIYALLRDDSKIEEVKKITGERHGKIVRIVDVEK
VEKKFLGKPITVWKLYLEHPQDQPTIREKVREHPAVVDIFEYDIPFAKRYLIDKGLIPMEGEEELKILAF
AIATLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWDDIVYLDFIALYPSIIITHNVS
PDTLNLEGCKNYDTAPQVGHKFCKDITGFIPSLLGHLLEERQKIKTKMKETQDPIEKILLDYRQKAIKLL
TNSVYGYYGYTKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS*

Pfu A-B motif library clone 13 selected with Cy5-dCTP.
SEQ ID No 17:
```
ATGATTTTAGATGTGGATTACATAACTGAAGAAGGAAAACCTGTTATTAGGCTATTCAAAAAAGAGAAACG

GAAAATTTAAGATAGAGCATGATAGAACTTTTAGACCATACATTTACGCTCTTCTCAGGGATGATTCAAA

GATTGAAGAAGTTAAGAAAATAACGGGGAAAGGCATGGAAAGATTGTGAGAATTGTTGATGTAGAGAAG

GTTGAGAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC
```

```
GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAAACATAGTATACCTAGATTTTAGAGCCCTATATCCCTCGATTATAATTACCCACAATGTTTCT

CCCGATACTCTAAATCTTGAGGGATGCAGGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTTGTA

GCAAATTCTTTTTACGGTTCTTACGGCTATCCCAAAGCAAGATGGTACTGTAAGGAGTGTGCTGAGAGCG

TTACTGCCTGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 18:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWENIVYLDFRALYPSIIITHNVS

PDTLNLEGCRNYDIAPQVGHKFCKDIPGFIPSLLGHLLEERQKIKTKMKETQDPIEKILLDYRQKAIKLV

ANSFYGSYGYPKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Pfu A-B motif library clone A3 selected with Cy5-dCTP & Biotin-16-dUTP.
SEQ ID No 19:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAGGCAAACTTATGAACTCGGGAAGAATTCCT

TCCAATGGAAATTCAGCTCTCAAGATTAATTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAGGGGTT

GTGGGACGACATCGTTTATCTAGATTTCATAGCCCTATATCCCTCGATTATAATTACCCACAATGTTTCT

CCCGATACTCTAAATCTTGAGGGATGCAAGAACTATGATATCGCTCCTCAAGTAGGCCACAACTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTCTTA

ACAAATTCTTTATACGGATATTTCGGTTATCCGAAAGCAAGATGGTACTGTAAGGAGTGTGCTGAGAGCG

TTACTGCCTGGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 20:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

-continued

NLVEWFLLRKAYERNEVAPNKPSEEEYQRRLRESYTGGFVKEPEKGLWDDIVYLDFIALYPSIIITHNVS

PDTLNLEGCKNYDIAPQVGHNFCKDIPGFIPSLLGHLLEERQKIKTKMKETQDPIEKILLDYRQKAIKLL

TNSLYGYFGYPKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-B motif library clone C2 selected with Cy5-dCTP & Biotin-16-dUTP.
SEQ ID No 21:
ATGATTTTAGATGTGGATTACATAACTGAAGAAGGAAAACCTGTTATTAGGCTATTCAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGCAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAACTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGACCTCGTTTATCTAGATTTTATAGCTCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGATTATAGACAAAAAGCGATAAAACTCTTC

GCAAATTCTTTCTACGGATATTACGGCTACCCCAAAGCAAGATGGTACTGTAAGGAGTGTGCTGAGAGCG

TTACTGCCTGGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

-continued

```
GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 22:
```
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVTPNKPSEEEYQRRLRESYTGGFVKEPEKGLWEDLVYLDFIALYPSIIITHNVS

PDTLNLEGCKNYDIAPQVGHKFCKDIPGFIPSLLGHLLEERQKIKTKMKETQDPIEKILLDYRQKAIKLF

ANSFYGYYGYPKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Pfu A-B motif library clone D2 selected with Cy5-dCTP & Biotin-16-dUTP.
SEQ ID No 23:
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGGCATCGTTTATCTAGATTTTATAGCCCTATATCCTTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTTTTGGGACATTTGTTAGAGGAAAGACAAAAGATTAAGACAAA

AATGAAGGAAACTCAGGATCCTATAGAAAAATACTCCTTGACTATAGACAAAAAGCGATAAAACTCTTA

GCAAATTCTTTCTACGGATATTTCGGATATACGAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTCGAGCTTGAATATGAAGGGTTTT
```

-continued

```
ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA.
```

Amino acid sequence: SEQ ID No 24:
```
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEGIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYFGYTKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Pfu A-B motif library clone E2 selected with Cy5-dCTP & Biotin-16-dUTP.
SEQ ID No 25:
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGACCTCGTTTATCTAGATTTTATAGCTCTATATCCCTCGATTATAATTACCCACAATGTTTCT
```

```
CCCGATACTCTAAATATTGAGGGATGCAAGAACTATGATATCGCTCCTCAAGTAGGCCACAAGTTCTGCA
AGGACATCCCTGGTTTTATACCAAGTCTCTTGGGACATTTGTTAGAGGAAAGACAAAAGATTAAGACAAA
AATGAAGGAAACTCAGGATCCTATAGAAAAAATACTCCTTGACTATAGACAAAAAGCGATAAAGCGCTTA
GCAAATTCATTCTACGGATATTTCAGCTATACGAAAGCAAGATGGTACTGTAAGGAGTGTGCTGAGAGCG
TTACTGCCTGGGGAAGAAAGTACATCGAGTTAGTATGGAAGGAGCTCGAAGAAAGTTTGGATTTAAAGT
CCTCTACATTGACACTGATGGCCTCTATGCAACTATCCCAGGAGGAGAAAGTGAGGAAATAAAGAAAAAG
GCTCTCGAATTTGTAAAATACATAAATTCAAAGCTCCCTGGACTGCTCGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA.
Amino acid sequence: SEQ ID No 26:
MILDVDYITEEGKPVIRLFKKENGKFKIEHDRTFRPYIYALLRDDSKIEEVKKITGERHGKIVRIVDVEK
VEKKFLGKPITVWKLYLEHPQDQPTIREKVREHPAVVDIFEYDIPFAKRYLIDKGLIPMEGEEELKILAF
AIATLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEDLVYLDFIALYPSIIITHNVS
PDTLNIEGCKNYDIAPQVGHKFCKDIPGFIPSLLGHLLEERQKIKTKMKETQDPIEKILLDYRQKAIKRL
ANSFYGYFSYTKARWYCKECAESVTAWGRKYIELVWKELEEKFGFKVLYIDTDGLYATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS*
Pfu A-C motif library clone 12 selected with Cy5-dCTP.
SEQ ID No 27:
ATGATTTTAGATGTGGATTACATAACTGAAGAAGGAAAACCTGTTATTAGGCTATTCAAAAAAGAGAACG
GAAAATTTAAGATAGAGCATGATAGAACTTTTAGACCATACATTTACGCTCTTCTCAGGGATGATTCAAA
GATTGAAGAAGTTAAGAAAATAACGGGGGAAAGGCATGGAAAGATTGTGAGAATTGTTGATGTAGAGAAG
GTTGAGAAAAAGTTTCTCGGCAAGCCTATTACCGTGTGGAAACTTTATTTGGAACATCCTCAGGATCAGC
CCACTATTAGAGAAAAGTTAGAGAACATCCAGCAGTTGTGGACATCTTCGAATACGATATTCCATTTGC
AAAGAGATACCTCATCGACAAAGGCCTAATACCAATGGAGGGGAAGAAGAGCTAAAGATTCTTGCCTTC
GCGATCGCGACCCTCTATCACGAAGGAGAAGAGTTTGGAAAAGGCCCAATTATAATGATTAGTTATGCAG
ATGAAAATGAAGCAAAGGTGATTACTTGGAAAAACATAGATCTTCCATACGTTGAGGTTGTATCAAGCGA
GAGAGAGATGATAAAGAGATTTCTCAGGATTATCAGGGAGAAGGACCCTGACATTATAGTTACTTATAAT
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
```

-continued

```
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAAGTGGAGAGA
ACCTTGAGAGAGTTGCCAAATACTCGATGGAAGATGCAAAGGCAACTTATGAACTCGGGAAAGAATTCCT
TCCAATGGAAATTCGGCTTTCAAGATTAGTTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAAGGGGTT
GTGGGAAGGCATCGTTTATCTAGATTTTATAGCCCTATATCCTTCGATTATAATTACCCACAATGTTTCT
CCCGATACTCTAAATCTTGAGGGATGCAAGAACTATGATATCGCTCCTCAAGTAGGCCACAAGTTCTGCA
AGGACATCCCTGGTTTTATACCAAGTCTCTTGGGACATTTGTTAGAGGAAAGACAAAAGATTAAGACAAA
AATGAAGGAAACTCAGGATCCTATAGAAAAAATACTCCTTGACTATAGACAAAAAGCGATAAAACTCTTA
GCAAATTCTTTCTACGGATATTATGGCTATGCAAAAGCAAGATGGTACTGTAAGGAGTGTGCTGAGAGCG
TTACTGCCTGGGGAAGAAAGTACATCGAGTTAGTATGGAAGGAGCTCGAAGAAAAGTTTGGATTTAAAGT
CCTCTACATTGACACTGATGGTCTTCACGCAACTATCCCAGGAGGAGAAAGTGAGGAGATCAAGAAAAAG
GCTCTAGAATTTGTAAAATACATAAATTCAAAGCTCCCTGGACTGCTCGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA

Amino acid sequence: SEQ ID No 28:
MILDVDYITEEGKPVIRLFKKENGKFKIEHDRTFRPYIYALLRDDSKIEEVKKITGERHGKIVRIVDVEK
VEKKFLGKPITVWKLYLEHPQDQPTIREKVREHPAVVDIFEYDIPFAKRYLIDKGLIPMEGEEELKILAF
AIATLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIRLSRLVGQPLWDVSRSSTG
NLVEWFLLRKAYERNEVAPNKPSEEEYQRRLRESYTGGFVKEPEKGLWEGIVYLDFIALYPSIIITHNVS
PDTLNLEGCKNYDIAPQVGHKFCKDIPGFIPSLLGHLLEERQKIKTKMKETQDPIEKILLDYRQKAIKLL
ANSFYGYYGYAKARWYCKECAESVTAWGRKYIELVWKELEEKFGFKVLYIDTDGLHATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFGYRKEDLRYQKTRQVGLTSWL
NIKKS*

Pfu A-C motif library clone 25 selected with Cy5-dCTP.
SEQ ID No 29:
ATGATTTTAGATGTGGATTACATAACTGAAGAAGGAAAACCTGTTATTAGGCTATTCAAAAAAGAGAACG
GAAAATTTAAGATAGAGCATGATAGAACTTTTAGACCATACATTTACGCTCTTCTCAGGGATGATTCAAA
GATTGAAGAAGTTAAGAAAATAACGGGGGAAAGGCATGGAAAGATTGTGAGAATTGTTGATGTAGAAAG
GTTGAGAAAAAGTTTCTCGGCAAGCCTATTACCGTGTGGAAACTTTATTTGGAACATCCTCAGGATCAGC
```

```
CCACTATTAGAGAAAAAGTTAGAGAACATCCAGCAGTTGTGGACATCTTCGAATACGATATTCCATTTGC
AAAGAGATACCTCATCGACAAAGGCCTAATACCAATGGAGGGGGAAGAAGAGCTAAAGATTCTTGCCTTC
GCGATCGCGACCCTCTATCACGAAGGAGAAGAGTTTGGAAAAGGCCCAATTATAATGATTAGTTATGCAG
ATGAAAATGAAGCAAAGGTGATTACTTGGAAAAACATAGATCTTCCATACGTTGAGGTTGTATCAAGCGA
GAGAGAGATGATAAAGAGATTTCTCAGGATTATCAGGGAGAAGGACCCTGACATTATAGTTACTTATAAT
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAGTGGAGAGA
ACCTTGAGAGAGTTGCCAAATACTCGATGGAAGATGCAAAGGCAACTTATGAACTCGGGAAAGAATTCCT
TCCAATGGAAATTCAGCTTTCAAGATTAGTTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAAGGGGTT
GTGGGAAGGCATCGTTTATCTAGATTTTATAGCCCTATATCCTTCGATTATAATTACCCACAATGTTTCT
CCCGATACTCTAAATCTTGAGGGATGCAAGAACTATGATATCGCTCCTCAAGTAGGCCACAAGTTCTGCA
AGGACATCCCTGGTTTTATACCAAGTCTCTTGGGACATTTGTTAGAGGAAAGACAAAAGATTAAGGCAAA
AATGAAGGAAACTCAGGATCCTATAGAAAAAATACTCCTTGACTATAGACAAAAAGCGATAAAACTCTTA
GCAAATTCTTTCTACGGATATTATGGCTATGCAAAAGCAAGATGGTACTGTAAGGAGTGTGCTGAGAGCG
TTACTGCCTGGGGAAGAAAGTACATCGAGTTAGTATGGAAGGAGCTCGAAGAAAAGTTTGGATTTAAAGT
CCTCTACATTGACACTGATGGTCTTCACGCAACTATCCCAGGAGGAGAAAGTGAGGAGATCAAGAAAAAG
GCTCTAGAATTTGTAAAATACATAAATTCAAAGCTCCCTGGACTGCTCGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA
```

Amino acid sequence: SEQ ID No 30:

```
MILDVDYITEEGKPVIRLFKKENGKFKIEHDRTFRPYIYALLRDDSKIEEVKKITGERHGKIVRIVDVEK
VEKKFLGKPITVWKLYLEHPQDQPTIREKVREHPAVVDIFEYDIPFAKRYLIDKGLIPMEGEEELKILAF
AIATLYHEGEEFGKGPIIMISYADENEAKVITWKNIDLPYVEVVSSEREMIKRFLRIIREKDPDIIVTYN
GDSFDFPYLAKRAEKLGIKLTIGRDGSEPKMQRIGDMTAVEVKGRIHFDLYHVITRTINLPTYTLEAVYE
AIFGKPKEKVYADEIAKAWESGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEGIVYLDFIALYPSIIITHNVS
PDTLNLEGCKNYDIAPQVGHKFCKDIPGFIPSLLGHLLEERQKIKAKMKETQDPIEKILLDYRQKAIKLL
ANSFYGYYGYAKARWYCKECAESVTAWGRKYIELVWKELEEKFGFKVLYIDTDGLHATIPGGESEEIKKK
ALEFVKYINSKLPGLLELEYEGFYKRGFFVTKKRYAVIDEEGKVITRGLEIVRRDWSEIAKETQARVLET
ILKHGDVEEAVRIVKEVIQKLANYEIPPEKLAIYEQITRPLHEYKAIGPHVAVAKKLAAKGVKIKPGMVI
```

-continued

GYIVLRGDGPISNRAILAEEYDPKKHKYDAEYYIENQVLPAVLRILEGFGYRKEDLRYQKTRQVGLTSWL

NIKKS*

Pfu A-C motif library clone 27 selected with Cy5-dCTP.
SEQ ID No 31:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAAAG

GTTGAGAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGGCATCGTTTATCTAGATTTTATAGCCCTATATCCTTCGATTATAATTACCCACAATGTTTCT

CCCGATACTCTAAATCTTGAGGGATGCGAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGTCTTCACGCAACTATCCCAGGAGGAGAAAGTGAGGAGATCAAGAAAAAG

GCTCTAGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 32:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

-continued

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEGIVYLDFIALYPSIIITHNVS

PDTLNLEGCENYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLHATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-C motif library clone 1 selected with Cy3-dCTP.
SEQ ID No 33:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAGGGGTT

GTGGGAAGACCTCGTTTATCTAGATTTTATAGCTCTATATCCCTCGATTATAATTACCCACAATGTTTCT

CCTGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTGTTAGAGGAAAGACAAAAGATTAAGACAAA

AATGAAGGAAACTCAGGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGGAAGTACATCGAGTTAGTATGGAAGGAGCTCGAAGAAAAGTTTGGATTTAAAGT

CATCTACATTGACACTGATGGTCTTCACGCAACTATCCCAGGAGGAGAAAGTGAGGAGATCAAGAAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

-continued

```
AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence: SEQ ID No 34:
```
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEDLVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVIYIDTDGLHATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

Pfu A-C motif library clone 2 selected with Cy3-dCTP.
SEQ ID No 35:
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTCTCAAGATTAATTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAGGGGTT

GTGGGACGACATCGTTTATCTAGATTTCATAGCCCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGCAAA

AATGAAGGAAACTCAGGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTATATCGAGTTAGTATGGAAGGAGCTCAAGAAAAGTTTGGATTTAAGGT

CCTCTACATCGACACTGATGGTCTTCACGCAACTATCCCAGGAGGAGAAAGTGAGGAGATCAAAAAAACG
```

-continued

```
GCTCTAGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 36:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

NLVEWFLLRKAYERNEVAPNKPSEEEYQRRLRESYTGGFVKEPEKGLWDDIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLHATIPGGESEEIKKT

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-C motif library clone 4 selected with Cy3-dCTP.
SEQ ID No 37:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTCTCAAGATTAATTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT
```

-continued

```
GTGGGACGACATCGTTTATCTAGATTTCATAGCCCTATATCCCTCGATTATAATTACCCACAATGTTTCT

CCCGACACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGTCTTCTCGCAACTATCCCAGGAGGAGAAAGTGAGGAGATCAAGAAAAAG

GCTCTCGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 38:
MILDVDYITEEGKPVIRLFKKENGKFKIEHDRTFRPYIYALLRDDSKIEEVKKITGERHGKIVRIVDVEK

VEKKFLGKPITVWKLYLEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

NLVEWFLLRKAYERNEVAPNKPSEEEYQRRLRESYTGGFVKEPEKGLWDDIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLLATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

Pfu A-C motif library clone 5 selected with Cy3-dCTP.
SEQ ID No 39:
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCTCAGGATCAGC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA
```

```
GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTCTCAAGATTAATTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGACGACATCGTTTATCTAGATTTCATAGCCCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACCATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAGGGAGCTCGAAGAAAAGTTTGGATTTAAAGT

CCTCTACATTGACACTGATGGTCTTCACGCAACTATCCCAGGAGGAGAAAGTGAGGAGATCAAGAAAAAG

GCTCTAGAATTTGTAAAATACATAAATTCAAAGCTCCCTGGACTGCTCGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence: SEQ ID No 40:
MILDVDYITEEGKPVIRLFKKENGKFKIEHDRTFRPYIYALLRDDSKIEEVKKITGERHGKIVRIVDVEK

VEKKFLGKPITVWKLYEHPQDQPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

NLVEWFLLRKAYERNEVAPNKPSEEEYQRRLRESYTGGFVKEPEKGLWDDIVYLDFIALYPSIIITHNVS

PDTLNLEGCKNYDIAPQVGHKFCKDIPGFIPSLLGHLLEERQKIKTKMKETQDPIEKILLDHRQKAIKLL

ANSFYGYYGYAKARWYCKECAESVTAWGRKYIELVWRELEEKFGFKVLYIDTDGLHATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

DNA sequence of clone 23 selected with Cy5-dCTP from Pfu A motif library SEQ
ID NO. 41
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG
```

```
GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGACCTCGTTTATCTAGATTTTATAGCTCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCATGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence of clone 23 selected with Cy5-dCTP from Pfu A motif library
SEQ ID NO. 42

```
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEDLVYLDFIALYPSIIITHNVS

PDTLNLEGCKNYDIAPQVGHKFCKDIPGFIPSLLGHLLEERQKIKTKMKETHDPIEKILLDYRQKAIKLL

ANSFYGYYGYAKARWYCKECAESVTAWGRKYIELVWKELEEKFGFKVLYIDTDGLYATIPGGESEEIKKK
```

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

DNA sequence of clone 15 selected with Cy5-dCTP from Pfu A motif library SEQ ID NO. 43

```
ATGATTTTAGATGTGGATTACATAACTGAAGAAGGAAAACCTGTTATTAGGCTATTCAAAAAAGAGAACG
GAAAATTTAAGATAGAGCATGATAGAACTTTTAGACCATACATTTACGCTCTTCTCAGGGATGATTCAAA
GATTGAAGAAGTTAAGAAAATAACGGGGGAAAGGCATGGAAAGATTGTGAGAATTGTTGATGTAGAAAG
GTTGAGAAAAGTTTCTCGGCAAGCCTATTACCGTGTGGAAACTTTATTTGGAACATCCCCAAGATGTTC
CCACTATTAGAGAAAAAGTTAGAGAACATCCAGCAGTTGTGGACATCTTCGAATACGATATTCCATTTGC
AAAGAGATACCTCATCGACAAAGGCCTAATACCAATGGAGGGGGAAGAAGAGCTAAAGATTCTTGCCTTC
GCGATCGCGACCCTCTATCACGAAGGAGAAGAGTTTGGAAAAGGCCCAATTATAATGATTAGTTATGCAG
ATGAAAATGAAGCAAAGGTGATTACTTGGAAAAACATAGATCTTCCATACGTTGAGGTTGTATCAAGCGA
GAGAGAGATGATAAAGAGATTTCTCAGGATTATCAGGGAGAAGGACCCTGACATTATAGTTACTTATAAT
GGAGACTCATTCGACTTCCCATATTTAGCGAAAAGGGCAGAAAAACTTGGGATTAAATTAACCATTGGAA
GAGATGGAAGCGAGCCCAAGATGCAGAGAATAGGCGATATGACGGCTGTAGAAGTCAAGGGAAGAATACA
TTTCGACTTGTATCATGTAATAACAAGGACAATAAATCTCCCAACATACACACTAGAGGCTGTATATGAA
GCAATTTTTGGAAAGCCAAAGGAGAAGGTATACGCCGACGAGATAGCAAAAGCCTGGGAAAGTGGAGAGA
ACCTTGAGAGAGTTGCCAAATACTCGATGGAAGATGCAAAGGCAACTTATGAACTCGGGAAAGAATTCCT
TCCAATGGAAATTCAGCTCTCAAGATTAATTGGACAACCTTTATGGGATGTTTCAAGGTCAAGCACAGGG
AACCTTGTAGAGTGGTTCTTACTTAGGAAAGCCTACGAAAGAAACGAAGTAGCTCCAAACAAGCCAAGTG
AAGAGGAGTATCAAAGAAGGCTCAGGGAGAGCTACACAGGTGGATTCGTTAAAGAGCCAGAAAGGGGTT
GTGGGACGACATCGTTTATCTAGATTTCATAGCCCTATATCCCTCGATTATAATTACCCACAATGTTTCT
CCCGATACTCTAAATCTTGAGGGATGCAAGAACTATGATATCGCTCCTCAAGTAGGCCACAAGTTCTGCA
AGGACATCCCTGGTTTTATACCAAGTCTCTTGGGACATTTGTTAGAGGAAAGACAAAAGATTAAGCACAAA
AATGAAGGAAACTCAGGATCCTATAGAAAAAATACTCCTTGACTATAGACAAAAAGCGATAAAACTCTTA
GCAAATTCTTTCTACGGATATTATGGCTATGCAAAAGCAAGATGGTACTGTAAGGAGTGTGCTGAGAGCG
TTACTGCCTGGGGAAGAAAGTACATCGAGTTAGTATGGAAGGAGCTGCAAGAAAAGTTTGGATTTAAAGT
CCTCTACATTGACACTGATGGCCTCTATGCAACTATCCCAGGAGGAGAAAGTGAGGAAATAAAGAAAAG
GCTCTCGAATTTGTAAAATACATAAATTCAAAGCTCCCTGGACTGCTAGAGCTTGAATATGAAGGGTTTT
ATAAGAGGGGATTCTTCGTTACGAAGAAGAGGTATGCAGTAATAGATGAAGAAGGAAAAGTCATTACTCG
TGGTTTAGAGATAGTTAGGAGAGATTGGAGTGAAATTGCAAAAGAAACTCAAGCTAGAGTTTTGGAGACA
ATACTAAAACACGGAGATGTTGAAGAAGCTGTGAGAATAGTAAAAGAAGTAATACAAAAGCTTGCCAATT
ATGAAATTCCACCAGAGAAGCTCGCAATATATGAGCAGATAACAAGACCATTACATGAGTATAAGGCGAT
AGGTCCTCACGTAGCTGTTGCAAAGAAACTAGCTGCTAAAGGAGTTAAAATAAAGCCAGGAATGGTAATT
GGATACATAGTACTTAGAGGCGATGGTCCAATTAGCAATAGGGCAATTCTAGCTGAGGAATACGATCCCA
AAAAGCACAAGTATGACGCAGAATATTACATTGAGAACCAGGTTCTTCCAGCGGTACTTAGGATATTGGA
GGGATTTGGATACAGAAAGGAAGACCTCAGATACCAAAAGACAAGACAAGTCGGCCTAACTTCCTGGCTT
AACATTAAAAAATCCTAA
```

-continued

Amino acid sequence of clone 15 selected with Cy5-dCTP from Pfu A motif library
SEQ ID NO. 44
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLIGQPLWDVSRSSTG

NLVEWFLLRKAYERNEVAPNKPSEEEYQRRLRESYTGGFVKEPEKGLWDDIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

DNA sequence of clone 55 selected with Cy5-dCTP from Pfu A motif library SEQ
ID NO. 45
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAGGCATCGTTTATCTAGATTTTATAGCCCTATATCCTTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAGGATCCTATAGAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

-continued

```
ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA
```

Amino acid sequence of clone 55 selected with Cy5-dCTP from Pfu A motif library
SEQ ID NO. 46
```
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWEGIVYLDFIALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

DNA sequence of clone AH12 selected with Cy5-dCTP from Pfu A motif library
SEQ ID NO. 47
```
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCCCAAGATGTTC

CCACTATTAGAGAAAAGTTAGAGAACATCCAGCAGTTGTGGACATCTTCGAATACGATATTCCATTTGC

AAAGAGATACCTCATCGACAAAGGCCTAATACCAATGGAGGGGGAAGAAGAGCTAAAGATTCTTGCCTTC

GCGATCGCGACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGACCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA

GCAATTTTTGGAAAGCCAAAGGAGAAGGTATACGCCGACGAGATAGCAAAAGCTGGGAAAGTGGAGAGA

ACCTTGAGAGAGTTGCCAAATACTCGATGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGACGGCCTGGCTTATCTAGATTTTATAGCCCTATACCCCTCGATTATAGTTACCCACAATGTTTCT

CCCGATACTCTAAATCTTGAGGGATGCAAGAACTATGATATCGCTCCTCAAGTAGGCCACAAGTTCTGCA
```

```
                                                -continued
AGGACATCCCTGGTTTTATACCAAGTCTCTTGGGACATTTGTTAGAGGAAAGACAAAAGATTAAGACAAA

AATGAAGGAAACTCAGGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGCCTCTATGCAACTATCCCAGGAGGAGAAAGTGAGGAAATAAAGAAAAAG

GCTCTCGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAA

Amino acid sequence of clone AH12 selected with Cy5-dCTP from Pfu A motif
library SEQ ID NO. 48
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

AIATLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWDGLAYLDFIALYPSIIVTHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPEVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*

DNA sequence of wild type Pfu DNA polymerase (5'-3') SEQ ID NO. 133
ATGATTTTAGATGTGGATTACATAACTGAAGAAGGAAAACCTGTTATTAGGCTATTCAAAAAAGAGAACG

GAAAATTTAAGATAGAGCATGATAGAACTTTTAGACCATACATTTACGCTCTTCTCAGGGATGATTCAAA

GATTGAAGAAGTTAAGAAAATAACGGGGGAAAGGCATGGAAAGATTGTGAGAATTGTTGATGTAGAGAAG

GTTGAGAAAAAGTTTCTCGGCAAGCCTATTACCGTGTGGAAACTTTATTTGGAACATCCCCAAGATGTTC

CCACTATTAGAGAAAAAGTTAGAGAACATCCAGCAGTTGTGGACATCTTCGAATACGATATTCCATTTGC

AAAGAGATACCTCATCGACAAAGGCCTAATACCAATGGAGGGGAAGAAGAGCTAAAGATTCTTGCCTTC

GATATAGAAACCCTCTATCACGAAGGAGAAGAGTTTGGAAAAGGCCCAATTATAATGATTAGTTATGCAG

ATGAAAATGAAGCAAAGGTGATTACTTGGAAAAACATAGATCTTCCATACGTTGAGGTTGTATCAAGCGA

GAGAGAGATGATAAAGAGATTTCTCAGGATTATCAGGGAGAAGGATCCTGACATTATAGTTACTTATAAT

GGAGACTCATTCGACTTCCCATATTTAGCGAAAAGGGCAGAAAAACTTGGGATTAAATTAACCATTGGAA

GAGATGGAAGCGAGCCCAAGATGCAGAGAATAGGCGATATGACGGCTGTAGAAGTCAAGGGAAGAATACA

TTTCGACTTGTATCATGTAATAACAAGGACAATAAATCTCCCAACATACACACTAGAGGCTGTATATGAA
```

```
-continued
GCAATTTTTGGAAAGCCAAAGGAGAAGGTATACGCCGACGAGATAGCAAAAGCCTGGGAAAGTGGAGAGA

ACCTTGAGAGAGTTGCCAAATACTCGATGGAAGATGCAAAGGCAACTTATGAACTCGGGAAAGAATTCCT

TCCAATGGAAATTCAGCTTTCAAGATTAGTTGGACAACCTTTATGGGATGTTTCAAGGTCAAGCACAGGG

AACCTTGTAGAGTGGTTCTTACTTAGGAAAGCCTACGAAAGAAACGAAGTAGCTCCAAACAAGCCAAGTG

AAGAGGAGTATCAAAGAAGGCTCAGGGAGAGCTACACAGGTGGATTCGTTAAAGAGCCAGAAAAGGGGTT

GTGGGAAAACATAGTATACCTAGATTTTAGAGCCCTATATCCCTCGATTATAATTACCCACAATGTTTCT

CCCGATACTCTAAATCTTGAGGGATGCAAGAACTATGATATCGCTCCTCAAGTAGGCCACAAGTTCTGCA

AGGACATCCCTGGTTTTATACCAAGTCTCTTGGGACATTTGTTAGAGGAAAGACAAAAGATTAAGACAAA

AATGAAGGAAACTCAAGATCCTATAGAAAAAATACTCCTTGACTATAGACAAAAAGCGATAAAACTCTTA

GCAAATTCTTTCTACGGATATTATGGCTATGCAAAAGCAAGATGGTACTGTAAGGAGTGTGCTGAGAGCG

TTACTGCCTGGGGAAGAAAGTACATCGAGTTAGTATGGAAGGAGCTCGAAGAAAAGTTTGGATTTAAAGT

CCTCTACATTGACACTGATGGTCTCTATGCAACTATCCCAGGAGGAGAAAGTGAGGAAATAAAGAAAAAG

GCTCTAGAATTTGTAAAATACATAAATTCAAAGCTCCCTGGACTGCTAGAGCTTGAATATGAAGGGTTTT

ATAAGAGGGGATTCTTCGTTACGAAGAAGAGGTATGCAGTAATAGATGAAGAAGGAAAAGTCATTACTCG

TGGTTTAGAGATAGTTAGGAGAGATTGGAGTGAAATTGCAAAAGAAACTCAAGCTAGAGTTTTGGAGACA

ATACTAAAACACGGAGATGTTGAAGAAGCTGTGAGAATAGTAAAAGAAGTAATACAAAAGCTTGCCAATT

ATGAAATTCCACCAGAAGCTCGCAATATATGAGCAGATAACAAGACCATTACATGAGTATAAGGCGAT

AGGTCCTCACGTAGCTGTTGCAAAGAAACTAGCTGCTAAAGGAGTTAAAATAAAGCCAGGAATGGTAATT

GGATACATAGTACTTAGAGGCGATGGTCCAATTAGCAATAGGGCAATTCTAGCTGAGGAATACGATCCCA

AAAAGCACAAGTATGACGCAGAATATTACATTGAGAACCAGGTTCTTCCAGCGGTACTTAGGATATTGGA

GGGATTTGGATACAGAAAGGAAGACCTCAGATACCAAAAGACAAGACAAGTCGGCCTAACTTCCTGGCTT

AACATTAAAAAATCCTAG

Amino acid sequence of wild type Pfn DNA polymerase SEQ ID NO. 134
MILDVDYITEEGKPVIRLFKKENGKFKIEHDRTFRPYIYALLRDDSKIEEVKKITGERHGKIVRIVDVEK

VEKKFLGKPITVWKLYLEHPQDVPTIREKVREHPAVVDIFEYDIPFAKRYLIDKGLIPMEGEEELKILAF

DIETLYHEGEEFGKGPIIMISYADENEAKVITWKNIDLPYVEVVSSEREMIKRFLRIIREKDPDIIVTYN

GDSFDFPYLAKRAEKLGIKLTIGRDGSEPKMQRIGDMTAVEVKGRIHFDLYHVITRTINLPTYTLEAVYE

AIFGKPKEKVYADEIAKAWESGENLERVAKYSMEDAKATYELGKEFLPMEIQLSRLVGQPLWDVSRSSTG

NLVEWFLLRKAYERNEVAPNKPSEEEYQRRLRESYTGGFVKEPEKGLWENIVYLDFRALYPSIIITHNVS

PDTLNLEGCKNYDIAPQVGHKFCKDIPGFIPSLLGHLLEERQKIKTKMKETQDPIEKILLDYRQKAIKLL

ANSFYGYYGYAKARWYCKECAESVTAWGRKYIELVWKELEEKFGFKVLYIDTDGLYATIPGGESEEIKKK

ALEFVKYINSKLPGLLELEYEGFYKRGFFVTKKRYAVIDEEGKVITRGLEIVRRDWSEIAKETQARVLET

ILKHGDVEEAVRIVKEVIQKLANYEIPPEKLAIYEQITRPLHEYKAIGPHVAVAKKLAAKGVKIKPGMVI

GYIVLRGDGPISNRAILAEEYDPKKHKYDAEYYIENQVLPAVLRILEGFGYRKEDLRYQKTRQVGLTSWL

NIKKS*
```

REFERENCES

Anderson J P, Angerer B and Loeb L A (2005) Incorporation of reporter-labeled nucleotides by DNA polymerases. Biotechniques 38 p 257-264.

Augustin M A, Ankenbauer W and Angerer B (2001) Progress towards single-molecule sequencing: enzymatic synthesis of nucleotide-specifically labeled DNA. J. Biotechnol. 86 p 289-301.

Boudsocq F, Iwai S, Hanaoka F, Woodgate R. (2001) *Sulfolobus solfataricus* P2 DNA polymerase IV (Dpo4): an archaeal DinB-like DNA polymerase with lesion-bypass properties akin to eukaryotic poleta. Nucleic Acids Res. 29:4607-16

Brakmann S and Nieckchen P (2001) The large fragment of *Escherichia coli* DNA polymerase I can synthesize DNA exclusively from fluorescently labeled nucleotides. Chembiochem. 2 p 773-777.

Cox W G and Singer V L (2004) Fluorescent DNA hybridization probe preparation using amine modification and reactive dye coupling. Biotechniques 36 p 114-122

Derbyshire V, Pinsonneault J K and Joyce C M (1995) Structure-function analysis of 3'-5'-exonuclease of DNA polymerases. Methods Enzymol. 262 p 363-385.

Fogg M J, Pearl L H and Connolly B A (2002) Structural basis for uracil recognition by archaeal family B DNA polymerases. Nat Struct Biol. 9 p 922-927.

Földes-Papp Z, Angerer B, Ankenbauer W and Rigler R (2001) Fluorescent high-density labeling of DNA: error-free substitution for a normal nucleotide. J. Biotechnol. 86 p 237-253.

Gardner A F and Jack W E (1999) Determinants of nucleotide sugar recognition in an archaeon DNA polymerase. Nucleic Acids Research 27 p 2545-2555 1999

Glick E, Anderson J P and Loeb L A (2002) In vitro production and screening of DNA polymerase eta mutants for catalytic diversity. Biotechniques 2002 33 p 1136-1144.

Ghadessy F J, Ramsay N, Boudsocq F, Loakes D, Brown A, Iwai S, Vaisman A, Woodgate R and Holliger P (2004) Generic expansion of the substrate spectrum of a DNA polymerase by directed evolution. Nat. Biotechnol. 22 p 755-759.

Ghadessy F J, Ong J L and Holliger P (2001) Directed evolution of polymerase function by compartmentalised self-replication. PNAS 98 p 4552-4557.

Jäger and Famulok (2004) Generation and enzymatic amplification of high-density functionalized DNA double strands. Angew. Chem. 43 p 2-5.

Kallioniemi A, Kallioniemi O P, Sudar D, Rutovitz D, Gray J W, Waldman F and Pinkel D (1992) Comparative genomic hybridization for molecular cytogenetic analysis of solid tumors. Science 258 p 818-821.

Kononen J, Bubendorf L, Kallioniemi A, Barlund M, Schraml P, Leighton S, Torhorst J, Mihatsch M J, Sauter G and Kallioniemi O P (1998) Tissue microarrays for high-throughput molecular profiling of tumor specimens. Nat. Med. 4 p 844-847.

Kunkel T A and Bebenek K (2000) DNA replication fidelity. Annu. Rev. Biochem. 69 p 497-529.

Lu C and Erickson H P (1997) Expression in *E. coli* of the thermostable DNA polymerase from *Pyrococcus furiosus* Protein Expression and Purification. 11 p 179-184.

McNeil J A, Johnson C V, Carter K C, Singer R H and Lawrence J B (1991) Localizing DNA and RNA within nuclei and chromosomes by fluorescence in situ hybridization. Genet Anal Tech Appl. 8 p 41-58.

Obayashi T, Masud M M, Ozaki A N, Ozaki H, Kuwahara M and Sawai H (2002) Enzymatic synthesis of labeled DNA by PCR using new fluorescent thymidine nucleotide analogue and superthermophilic KOD dash DNA polymerase. Bioorg Med Chem. Lett. 12 p 1167-1170.

Ono T, Scalf M, Smith L M (1997) 2'-Fluoro modified nucleic acids: polymerase-directed synthesis, properties and stability to analysis by matrix-assisted laser desorption/ionization mass spectrometry. Nucleic Acids Res. 25 p 4581-4588.

Ramanathan A, Pape L and Schwartz D C (2005) High-density polymerase-mediated incorporation of fluorochrome-labeled nucleotides. Anal Biochem. 2005 337 p 1-11.

Ried T, Baldini A, Rand T C and Ward D C (1992) Simultaneous visualization of seven different DNA probes by in situ hybridization using combinatorial fluorescence and digital imaging microscopy. Proc Natl Acad Sci USA 1992 89 p 1388-1392.

Schena M, Shalon D, Davis R W and Brown P O (1995). Quantitative monitoring of gene expression patterns with a complementary DNA microarray. Science 270 p 467-470.

Shendure J, Mitra R D, Varma C and Church G M (2004) Advanced sequencing technologies: methods and goals. Nat Rev Genet. 5 p 335-344.

Skerra, A (1994) Use of the tetracycline promoter for the tightly regulated production of a murine antibody fragment in *Escherichia coli*. Gene 151 p 131-135.

Tasara T, Angerer B, Damond M, Winter H, Dorhofer S, Hubscher U and Amacker M (2003) Incorporation of reporter molecule-labeled nucleotides by DNA polymerases. II. High-density labeling of natural DNA. Nucleic Acids Res. 31 p 2636-2646.

Tawfik D S and Griffiths A D (1998) Man-made cell-like compartments for molecular evolution. Nature Biotech. 16 p 652-656.

Tippen B, Pham P and Goodman N E (2004) Error-prone replication for better or worse. Trends in Microbiol. 12 p 288-295.

Yu H, Chao J, Patek D, Mujumdar R, Mujumdar S and Waggoner A S (1994) Cyanine dye dUTP analogs for enzymatic labeling of DNA probes. Nucleic Acids Res. 22 p 3226-3232.

Zhu W and Ito J (1994) Family A and family B DNA polymerases are structurally related: evolutionary implications. Nucleic Acids Res. 22 p 5177-5183.

Zhu Z and Waggoner A S (1997) Molecular mechanism controlling the incorporation of fluorescent nucleotides into DNA by PCR. Cytometry. 1997 28 p 206-211.

Zhu Z, Chao J, Yu H and Waggoner A S (1994) Directly labeled DNA probes using fluorescent nucleotides with different length linkers. Nucleic Acids Res. 22 p 3418-3422.

```
Primers
1:
                                          SEQ ID No. 49
CAG GAA ACA GCT ATG ACC ATA TGA TTT TAG ATG TGG

ATT ACA TAA CTG-

2:
                                          SEQ ID No. 50
AGT AGC GGC GTC GAC TTA GGA TTT TTT AAT GTT AAG

CCA GGA AG-

3:
                                          SEQ ID No. 51
GTT GTT TTT CTA ATC CGC ATG TGA TCA ATT CAA GGC

CG-

4:
                                          SEQ ID No. 52
CGG CCT TGA ATT GAT CAC ATG CGG ATT AGA AAA ACA

AC-

5:
                                          SEQ ID No. 53
CTA AAG ATT CTT GCC TTC GCG ATC GCG ACC CTC TAT

CAC GAA GGA GAA-

6:
                                          SEQ ID No. 54
TTC TCC TTC GTG ATA GAG GGT CGC GAT CGC GAA GGC

AAG AAT CTT TAG-
```

7:
SEQ ID No. 55
GAG GAA ATA AAG AAA AAG GCT CTC GAA TTT GTA AAA TAC ATA AAT TC-

8:
SEQ ID No. 56
GAA TTT ATG TAT TTT ACA AAT TCG AGA GCC TTT TTC TTT ATT TCC TC-

9:
SEQ ID No. 57
CTA CAT TGA CAC TGA TGG CCT CTA TGC AAC TAT CCC A-

10:
SEQ ID No. 58
TGG GAT AGT TGC ATA GAG GCC ATC AGT GTC AAT GTA G-

11:
SEQ ID No. 59
CAG GAT TAT CAG GGA GAA GGA CCC TGA CAT TAT AGT TAC TTA T-

12:
SEQ ID No. 60
ATA AGT AAC TAT AAT GTC AGG GTC CTT CTC CCT GAT AAT CCT G-

13:
SEQ ID No. 61
GAC AAA AAT GAA GGA AAC TCA GGA TCC TAT AGA AAA AAT ACT CC-

14:
SEQ ID No. 62
GGA GTA TTT TTT CTA TAG GAT CCT GAG TTT CCT TCA TTT TTG TC-

15:
SEQ ID No. 63
GAA ACT TTA TTT GGA ACA TCC TCA GGA TCA GCC CAC TAT TAG AGA AAA AG-

16:
SEQ ID No. 64
CTT TTT CTC TAA TAG TGG GCT GAT CCT GAG GAT GTT CCA AAT AAA GTT TC-

17:
SEQ ID No. 65
CAA AGC TCC CTG GAC TGC TCG AGC TTG AAT ATG AAG GG-

18:
SEQ ID No. 66
CCC TTC ATA TTC AAG CTC GAG CAG TCC AGG GAG CTT TG-

19:
SEQ ID No. 67
GAA AAC ATA GTA CTA GAT TTC TCG AGC CCT ATA TCC CTC GAT TAT-

20:
SEQ ID No. 68
ATA ATC GAG GGA TAT AGG GCT CGA GAA ATC TAG GTA TAC TAT GTT TTC-

21:
SEQ ID No. 69
GAG TAG GTC TCT ACC CCT TTT CTG GCT CTT TAA CG-

22:
SEQ ID No. 70
5'-GGA AAG GTC TCA GGG TTG TGG RAM RRC MTS RYY TMT CTA GAT TTT AGA GCC CTA TAT CCC TCG ATT ATA RTT ACC CAC AAT G-3'-
Underlined 90% wild-type 10% other sequence.

23:
SEQ ID No. 71
5'-GGA AAG GTC TCA GAC AAA AAG CGA TAA AAC TCT TAG CAA ATT CTT TCT ACG GAT ATW WCG GCT ATV CSA AAG CAA GAT GGT ACT-3'-
Underlined 90% wild-type 10% other sequence.

24:
SEQ ID No. 72
GAG TAG GTC TCT TGT CTA TAG TCA AGG AGT ATT TTT TCT ATA GG-

25:
SEQ ID No. 73
5'-GAG TAG GTC TCA GGA TAG TTG CGW GAR GAC CAT CAG TGT CAA TGT AGA GGA CTT TAA ATC CAA ACT TTT CTT C-3'-
Underlined 90% wild-type 10% other sequence.

26:
SEQ ID No. 74
GGA AAG GTC TCT ATC CCA GGA GGA GAA AGT GAG GAG ATC AAG AAA AAG GCT CTA GA-

27:
SEQ ID No. 76
CAG GAA ACA GCT ATG ACA AAC GGG AAA GAA TTC CTT CCA ATG G-

28:
SEQ ID No. 77
GTA AAA CGA CGG CCA GTA CCT CTA TAG GAT CCT GAG TTT CCT TC-

29:
SEQ ID No. 78
CAG GAA ACA GCT ATG ACA AA-

30:
SEQ ID No. 79
GTA AAA CGA CGG CCA GTA CCC TTT TCT TCG AGC TCC TTC CAT AC-

31:
SEQ ID No. 80
CTT TTC TTC GAG CTC CTT CCA TAC-

32:
SEQ ID No. 81
GTAAAACGACGGCCAGTACCATATTCAAGCTCGAGCAGTCCAGGGAG-

33:
SEQ ID No. 82
TAG CTA CCA GGG GCT CCG GCT TCC GTC GCG ACC ACG TTP5 TTC GTG GTC GCG ACG AAA GCC G-
Where P5 is biotin-dT.

34:
SEQ ID No. 83
TAG CTA CCA GGG GGG CTC CGG CTT CCG TCG CGA CCA
CGT TP5T TCG TGG TCG CGA CGG AAG CCG-
Where P5 is biotin-dT.

35:
SEQ ID No. 84
Where P5 is biotin-dT.

36:
SEQ ID No. 85
AGG GAA CCT TGT AGA GTG GT-

37:
SEQ ID No. 86
CTT GAG GAG CGA TAT CAT AGT TC-

38:
SEQ ID No. 87
GGG TAC GTG GAG ACC CTC TTC GGC C-

39:
SEQ ID No. 88
ACC ACC GAA CTG CGG GTG ACG CCA AGC G-

40:
SEQ ID No. 89
CAG GAA ACA GCT ATG ACG AGA AAA GTG AAA TGA ATA
GTT CGA C-

41:
SEQ ID No. 90
GTA AAA CGA CGG CCA GTA CCA CCG AAC TGC GGG TGA
CGC CAA GCG-

42:
SEQ ID No. 91
CAG GAA ACA GCT ATG ACC ATA TGA TTT TAG ATG TGG
ATT ACA TAA CTG-

43:
SEQ ID No. 92
GTA AAA CGA CGG CCA GT-

44:
SEQ ID No. 93
GCG AGA GAG AGA TGA TAA AG-

45:
SEQ ID No. 94
TCG AAA TGT ATT CTT CCC TT-

46:
SEQ ID No. 95
AAG AGG TAT GCA GTA ATA GA-

47:
SEQ ID No. 96
CGG GAA AGA ATT CCT TCC AAT GG-

48:
SEQ ID No. 97
GAC TTC CTT GCC TGC TCG TCG TCG GCA TCC GTC GCG
ACC ACG TT5 TTC GTG GTC GCG ACG GAT GCC G-
Where P5 is biotin-dT.

49:
SEQ ID No. 98
GGT ACG TGG AGA CCC TCT TC-

50:
SEQ ID No. 99
TGT TGA AGG CCA TGC GCT CGG-

51:
SEQ ID No. 100
CAG GAA ACA GCT ATG ACG AAC TCG GGA AAG AAT TC-

52:
SEQ ID No. 101
GTA AAA CGA CGG CCA GTA CCG TCG ACT TAG GAT TTT
TTA ATG TTA AGC-

53:
SEQ ID No. 102
GGA AAG GTC TCA GTG GGA CGA CAT CGT GTA TCT GGA
CTT CAT ATC CCT GTA TCC-

54:
SEQ ID No. 103
GAG TAG GTC TCT CCA CAG TCC CCT TTC GGG CTC CTT G-

55:
SEQ ID No. 104
GCT GAG GAA GGC CTA CGA GAG-

56:
SEQ ID No. 105
GGG TAC GTG GAG ACC CTC TTC GGC C-

57:
SEQ ID No. 106
ACA GGA AAC AGC TAT GAC AAA GGT CTC AGT TAA AGA
GCC AGA AAG GGT TG-

58:
SEQ ID No. 107
CAG GAA ACA GCT ATG ACA AA-

59:
SEQ ID No. 108
GAG TAG GTC TCT TAA CGA ATC CAC CTG TGT AGC TC-

60:
SEQ ID No. 109
TAG CTC GGT AAA AAA AAA AAA CGC CGG CTT CCG TCG
CGA CCA CGT TP5T TCG TGG TCG CGA CGG AAG CCG-
Where P5 is biotin-dT.

61:
SEQ ID No. 110
ACT TCA TCT GCA GAG AGA AAG AG-

62:
SEQ ID No. 111
AAT ATT CAG TAT GAA AAA CAT TG-

63:
SEQ ID No. 112
CCT GGA CTT GAA CTG TGA CAC-

64:
SEQ ID No. 113
CGG AGA AGA AGC CAA ACT TCC-

65:
SEQ ID No. 114
CTA TTC AGG CAG AGA CAG AAA G-

66:
SEQ ID No. 115
AAC CCA CAG TTT TCG TGG GAC A-

67:
SEQ ID No. 75
GGG TAC GTG GAG ACC CTC TTC-

68:
SEQ ID No. 116
TGT TGA AGG CCA TGC GCT CGG-

-continued

69:
SEQ ID No. 117
TAG CCC CCT TAT TAG CGT TTG CCA AGG GAA CCT TGT AGA GTG GT-

70:
SEQ ID No. 118
TAG CCC CCT TAT TAG CGT TTG CCA CTT GAG GAG CGA TAT CAT AGT TC-

71:
SEQ ID No. 119
CTA ATG CAC GTG GAG TAG TGG-

72:
SEQ ID No 120
AGT TAA CTA TGG TGC ATC CAT TG-

73:
SEQ ID No 121
GAG AAA GTT CAG TCA TTT GTG-

74:
SEQ ID No 122
GGA CGA ATC TGA GAT TTG TTA AG-

75:
SEQ ID No 123
AGC TGT AAG TAG CAT TTG TGC-

76:
SEQ ID No 124
ACA GCC CTT ACA CCA AAC CAG-

77:
SEQ ID No 125
GAT CAT TGG TTT AGA TAG ATC CC-

78:
SEQ ID No 126
AGG ATC GCT TGT GCC CAG AAG-

79:
SEQ ID No 127
AGA CAT CAT CCC TAG AGG TTC-

80:
SEQ ID No 128
AGA CAC CAG ACA CAG AAG GGC-

81:
SEQ ID No 129
CAC CCC ATA TCT GCT TAA TCA G-

82:
SEQ ID No 130
GTG ATC CTC TGA CAT CGG TGG-

83:
SEQ ID No 131
GAT GGT TTT TGA AGG ATG GTC-

84:
SEQ ID No 132
TCC ATG CAC CTT GTG ATA TTC-

---

The invention claimed is:

1. A purified engineered DNA polymerase comprising an amino acid sequence, wherein the engineered polymerase has an expanded substrate range and incorporates an enhanced occurrence of a dye-labelled nucleotide analogue into nucleic acid synthesized by the engineered polymerase as compared with the wild type polymerase from which it is derived, wherein the engineered DNA polymerase has at least 90% identity to SEQ ID NO: 1, 4, 8, 12, 14, 16, 20, 22, 24, 26, 28, 30, 32, 34, 36, 38, 40, 42, 44, 46 or 48, and wherein the engineered DNA polymerase comprises the following substitution mutations compared with the *Pyrococcus furiosus* (Pfu) wild-type DNA polymerase amino acid sequence set forth in SEQ ID NO: 134: N400G/N400D and R407I.

2. The purified engineered DNA polymerase according to claim 1 wherein the dye-labelled nucleotide analogue is a fluorescent labelled nucleotide analogue.

3. The purified engineered DNA polymerase according to claim 2 wherein the fluorescent label is Alexa Fluor™ dye, diethylaminocoumarin, tetramethylrhodamine, N-methylanthraniloyl, trinitrophenyl, etheno derivatives, fluorescein, or carbocyanine.

4. The purified engineered DNA polymerase according to claim 3 wherein the dye-labelled nucleotide analogue is a carbocyanine labelled nucleotide analogue.

5. The purified engineered DNA polymerase according to claim 4, wherein the dye-labelled nucleotide analogue is Cy5-dNTP or Cy3-dNTP.

6. The purified engineered DNA polymerase according to claim 5, wherein the dye-labelled nucleotide analogue is Cy5-dCTP or Cy3-dCTP.

7. The purified engineered DNA polymerase according to claim 1, wherein the engineered polymerase further has one or more of the mutations V337I, E399D and Y546H compared with the Pfu wild-type amino acid sequence.

8. The purified engineered DNA polymerase according to claim 1 comprising the amino acid sequence set out in SEQ ID NO: 46 or an amino acid sequence at least identical to SEQ ID NO: 46.

9. The purified, engineered DNA polymerase of claim 1 that has substantially 0% of a 3'-5' exonuclease activity of the Pfu wild-type DNA polymerase.

10. A method for the incorporation of dye-labeled nucleotide analogues into newly synthesized nucleic acid comprising:
incubating a nucleic acid template, a primer, a polymerase, a buffer, and nucleotide synthesis reagents, including a dye-labeled nucleotide analogue, under conditions in which the polymerase synthesizes nucleic acid, wherein the polymerase is the purified engineered DNA polymerase according to claim 1.

11. The method of claim 10 wherein the dye-labeled nucleotide analogue is a fluorescent dye-labelled nucleotide analogue.

12. The method of claim 11 wherein the fluorescent dye-labelled nucleotide analogue is Cy3-CTP or Cy5-CTP.

13. The method of claim 11 wherein the method comprises a polymerase chain reaction; a microarray analysis; fluorescent in-situ hybridisation (FISH); fibre FISH; a comparative genome hybridisation; DNA sequencing; nucleic acid sequencing; or single molecule detection.

14. The method of claim 11 wherein the engineered DNA polymerase has the amino acid sequence set out in SEQ ID NO: 46 or an amino acid sequence at least identical to SEQ ID NO: 46.

15. A kit for incorporating an enhanced occurrence of dye-labelled nucleotide analogue into nucleic acid, the kit comprising the purified engineered DNA polymerase according to claim 1.

16. The kit of claim 15 wherein the purified engineered DNA polymerase has the amino acid sequence set out in SEQ ID NO: 46 or an amino acid sequence at least 90% identical to SEQ ID NO: 46.

17. The kit according to claim 15, wherein the kit further includes a dye-labeled nucleotide analogue.

* * * * *

UNITED STATES PATENT AND TRADEMARK OFFICE
CERTIFICATE OF CORRECTION

PATENT NO.        : 8,435,775 B2
APPLICATION NO.   : 12/440374
DATED             : May 7, 2013
INVENTOR(S)       : Holliger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Eighth Day of September, 2015

Michelle K. Lee
*Director of the United States Patent and Trademark Office*

SEQUENCE LISTING

<160> NUMBER OF SEQ ID NOS: 265

<210> SEQ ID NO 1
<211> LENGTH: 775
<212> TYPE: PRT
<213> ORGANISM: Artificial
<220> FEATURE:
<223> OTHER INFORMATION: Clone sequence

<400> SEQUENCE: 1

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

-continued

```
Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Ser Ser Glu Arg Glu Met Ile Lys
        180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Ile Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
        370                 375                 380

Tyr Thr Gly Gly Phe Val Lys Glu Pro Glu Lys Gly Leu Trp Asp Asp
385                 390                 395                 400

Ile Val Tyr Leu Asp Phe Ile Ala Leu Tyr Pro Ser Ile Ile Ile Thr
            405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
        530                 535                 540

Leu His Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
            565                 570                 575
```

```
Glu Leu Glu Tyr Glu Gly Phe Tyr Lys Arg Gly Phe Val Thr Lys
                580                 585                 590
Lys Arg Tyr Ala Val Ile Asp Glu Glu Gly Lys Val Ile Thr Arg Gly
595                 600                 605
Leu Glu Ile Val Arg Arg Asp Trp Ser Glu Ile Ala Lys Glu Thr Gln
610                 615                 620
Ala Arg Val Leu Glu Thr Ile Leu Lys His Gly Asp Val Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
                675                 680                 685
Ala Lys Gly Val Lys Ile Lys Pro Gly Met Val Ile Gly Tyr Ile Val
                690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
                740                 745                 750
Lys Glu Asp Leu Arg Tyr Gln Lys Thr Arg Gln Val Gly Leu Thr Ser
                755                 760                 765
Trp Leu Asn Ile Lys Lys Ser
                770                 775

<210> SEQ ID NO 2
<211> LENGTH: 2328
<212> TYPE: DNA
<213> ORGANISM: Artificial
<220> FEATURE:
<223> OTHER INFORMATION: Clone sequence

<400> SEQUENCE: 2 atgatttttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat tctctcaggat tatcagggag      600 aaggaccctg acattatagt tacttataat ggagactcat tcgacttccc atatttagcg     660
aaaagggcag aaaacttggg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaatttttg gaaagccaaa ggagaaggta tacgccgacg agatagcaaa agcctgggaa     900
```

| | |
|---|---|
| agtggagaga accttgagag agttgccaaa tactcgatgg aagatgcaaa ggcaacttat | 960 |
| gaactcggga aagaattcct tccaatggaa attcagctct caagattaat tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aaagagccag aaaagggggtt gtgggacgac | 1200 |
| atcgtttatc tagatttcat agccctatat ccctcgatta taattaccca caatgtttct | 1260 |
| cccgatactc taaatcttga gggatgcaag aactatgata tcgctcctca agtaggccac | 1320 |
| aagttctgca aggacatccc tggttttata ccaagtctct tgggacattt gttagaggaa | 1380 |
| agacaaaaga ttaagacaaa aatgaaggaa actcaggatc ctatagaaaa aatactcctt | 1440 |
| gactatagac aaaaagcgat aaaactctta gcaaattctt tctacggata ttatggctat | 1500 |
| gcaaaagcaa gatggtactg taaggagtgt gctgagagcg ttactgcctg gggaagaaag | 1560 |
| tacatcgagt tagtatggaa ggagctcgaa gaaaagtttg gatttaaagt cctatacatc | 1620 |
| gacactgatg gtcttcacgc aactatccca ggaggagaaa gtgaggagat caagaaaaag | 1680 |
| gctctcgaat ttgtaaaata cataaattca aagctccctg gactgctcga gcttgaatat | 1740 |
| gaagggtttt ataagagggg attcttcgtt acgaagaaga ggtatgcagt aatagatgaa | 1800 |
| gaaggaaaag tcattactcg tggtttagag atagttagga gagattggag tgaaattgca | 1860 |
| aaagaaactc aagctagagt tttggagaca atactaaaac acggagatgt tgaagaagct | 1920 |
| gtgagaatag taaagaagt aatacaaaag cttgccaatt atgaaattcc accagagaag | 1980 |
| ctcgcaatat atgagcagat aacaagacca ttacatgagt ataaggcgat aggtcctcac | 2040 |
| gtagctgttg caaagaaact agctgctaaa ggagttaaaa taaagccagg aatggtaatt | 2100 |
| ggatacatag tacttagagg cgatggtcca attagcaata gggcaattct agctgaggaa | 2160 |
| tacgatccca aaaagcacaa gtatgacgca gaatattaca ttgagaacca ggttcttcca | 2220 |
| gcggtactta ggatattgga gggatttgga tacagaaagg aagacctcag ataccaaaag | 2280 |
| acaagacaag tcggcctaac ttcctggctt aacattaaaa aatcctaa | 2328 |

<210> SEQ ID NO 3
<211> LENGTH: 2328
<212> TYPE: DNA
<213> ORGANISM: Artificial
<220> FEATURE:
<223> OTHER INFORMATION: Clone sequence

<400> SEQUENCE: 3

| | |
|---|---|
| atgattttag atgtggatta cataactgaa gaaggaaaac ctgttattag gctattcaaa | 60 |
| aaagagaacg gaaaatttaa gatagagcat gatagaactt ttagaccata catttacgct | 120 |
| cttctcaggg atgattcaaa gattgaagaa gttaagaaaa taacggggga aaggcatgga | 180 |
| aagattgtga gaattgttga tgtagagaag gttgagaaaa agtttctcgg caagcctatt | 240 |
| accgtgtgga aactttattt ggaacatccc caagatgttc ccactattag agaaaaagtt | 300 |
| agagaacatc cagcagttgt ggacatcttc gaatacgata ttccatttgc aaagagatac | 360 |
| ctcatcgaca aaggcctaat accaatggag ggggaagaag agctaaagat tcttgccttc | 420 |
| gcgatcgcga ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat ttctcaggat tatcagggag | 600 |
| aaggatcctg acattatagt tacttataat ggagactcat tcgacttccc atatttagcg | 660 |

-continued

```
aaaagggcag aaaaacttgg gattaaatta accattggaa gagatggaag cgagcccaag    720
atgcagagaa taggcgatat gacgctgta gaagtcaagg gaagaataca tttcgacttg     780
tatcatgtaa taacaaggac aataaatctc ccaacataca cactagaggc tgtatatgaa    840 gcaattttg gaaagccaaa ggagaaggta tacgccgacg agatagcaaa agcctgggaa     900
agtggagaga accttgagag agttgccaaa tactcgatgg aagatgcaaa ggcaacttat    960
gaactcggga agaattcct tccaatgaaa attcagcttt caagattagt tggacaacct     1020
ttatggggtg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaagggggtt gtgggaaggc    1200
atcgtctatc tggattttat agccctatat ccctcgatta taattaccca caatgtttct    1260
cccgatactc taaatcttga gggatgcaag aactatgata tcgctcctca agtaggccac    1320
aagttctgca aggacatccc tggttttata ccaagtctct gggacatttt gttagaggaa    1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gcctctatgc aactatccca ggaggagaaa gtgaggaaat aaagaaaaag    1680
gctctcgaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa                2328
```

<210> SEQ ID NO 4
<211> LENGTH: 775
<212> TYPE: PRT
<213> ORGANISM: Artificial
<220> FEATURE:
<223> OTHER INFORMATION: Clone sequence

<400> SEQUENCE: 4

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80
```

```
Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
               100                 105                 110

Asp Ile Pro Phe Ala Lys Arg Tyr Leu Ile Asp Lys Gly Leu Ile Pro
               115                 120                 125

Met Glu Gly Glu Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Arg Glu Met Ile Lys
                180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Gly Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Gly
385                 390                 395                 400

Ile Val Tyr Leu Asp Phe Ile Ala Leu Tyr Pro Ser Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
```

```
                  500             505             510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Ser Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Arg Tyr Ala Val Ile Asp Glu Glu Gly Lys Val Ile Thr Arg Gly
                595                 600                 605
Leu Glu Ile Val Arg Arg Asp Trp Ser Glu Ile Ala Lys Glu Thr Gln
                610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
                675                 680                 685
Ala Lys Gly Val Lys Ile Lys Pro Gly Met Val Ile Gly Tyr Ile Val
                690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
                740                 745                 750
Lys Glu Asp Leu Arg Tyr Gln Lys Thr Arg Gln Val Gly Leu Thr Ser
                755                 760                 765
Trp Leu Asn Ile Lys Lys Ser
770                 775

<210> SEQ ID NO 5
<211> LENGTH: 2328
<212> TYPE: DNA
<213> ORGANISM: Artificial
<220> FEATURE:
<223> OTHER INFORMATION: Clone sequence

<400> SEQUENCE: 5
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag gggggagaag agctaaagat tcttgccttc     420
gcgatcgcga ccctctatca cgaaggagaa gagtttggaa aaggcccaat tataatgatt     480
agttatgcag atgaaaatga agcaaggtg attacttgga aaaacataga tcttccatac      540
```

```
gttgaggttg tatcaagcga gagagagatg ataaagagat ttctcaggat tatcagggag    600
aaggatcctg acattatagt tacttataat ggagactcat tcgacttccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg atagcaaa agcctgggaa       900 agtggagaga accttgagag agttgccaaa tactcgatgg aagatgcaaa ggcaacttat    960
gaactcggga agaattcct tccaatggaa attcagcttt caagattagt tggacaacct     1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggggtt gtgggaagac   1200 atcgtctatc tagattttag agcccaatat ccctcgatta tagttaccca caatgtttct    1260
cccgatactc taaatcttga gggatgcaag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gcctctatgc aactatccca ggaggagaaa gtgaggaaat aagaaaaag     1680 gctctcgaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt   2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa                 2328
```

<210> SEQ ID NO 6
<211> LENGTH: 775
<212> TYPE: PRT
<213> ORGANISM: Artificial
<220> FEATURE:
<223> OTHER INFORMATION: Clone sequence

<400> SEQUENCE: 6

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45
```

-continued

```
Glu Glu Val Lys Lys Ile Thr Gly Glu Arg His Gly Lys Ile Val Arg
     50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Gly Glu Leu Lys Ile Leu Ala Phe Ala Ile Ala Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asp
385                 390                 395                 400

Ile Val Tyr Leu Asp Phe Arg Ala Gln Tyr Pro Ser Ile Ile Val Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480
```

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Ile Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
            770                 775

<210> SEQ ID NO 7
<211> LENGTH: 2328
<212> TYPE: DNA
<213> ORGANISM: Artificial
<220> FEATURE:
<223> OTHER INFORMATION: Clone sequence

<400> SEQUENCE: 7 atgatttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatccc caagatgttc ccactattag agaaaaagtt    300
agagaacatc cagcagttgt ggacatcttc gaatacgata ttccatttgc aaagagatac    360

```
ctcatcgaca aaggcctaat accaatggag ggggaagaag agctaaagat tcttgccttc    420
gcgatcgcga ccctctatca cgaaggagaa gagtttggaa aagcccaat tataatgatt    480 agttatgcag atgaaaatga agcaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgacttccc atatttagcg    660
aaaagggcag aaaacttgg gattaaatta accattggaa gagatggaag cgagcccaag    720
atgcagagaa taggcgatat gacggctgta aagtcaagg aagaatacat tttcgacttg    780
tatcatgtaa taacaaggac aataaatctc ccaacataca cactagaggc tgtatatgaa    840
gcaatttttg aaaagccaaa ggagaaggta tacgccgacg atagcaaa agcctgggaa    900 agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaagggggtt gtggaacgac   1200 ctggtctatc tagattttat agccctatat ccttcgatta tagttaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa acccaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gcctctatgc aactatccca ggaggagaaa gtgaggaaat aaagaaaaag   1680
gctctcgaat ttgtaaaata cataaaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa atcctaa              2328
```

<210> SEQ ID NO 8
<211> LENGTH: 775
<212> TYPE: PRT
<213> ORGANISM: Artificial
<220> FEATURE:
<223> OTHER INFORMATION: Clone sequence

<400> SEQUENCE: 8

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg

-continued

```
                20                  25                  30
Thr Phe Arg Pro Tyr Ile Tyr Ala Leu Leu Arg Asp Asp Ser Lys Ile
             35                  40                  45
Glu Glu Val Lys Lys Ile Thr Gly Glu Arg His Gly Lys Ile Val Arg
         50                  55                  60
Ile Val Asp Val Glu Lys Val Glu Lys Lys Phe Leu Gly Lys Pro Ile
 65                  70                  75                  80
Thr Val Trp Lys Leu Tyr Leu Glu His Pro Gln Asp Val Pro Thr Ile
                 85                  90                  95
Arg Glu Lys Val Arg Glu His Pro Ala Val Val Asp Ile Phe Glu Tyr
             100                 105                 110
Asp Ile Pro Phe Ala Lys Arg Tyr Leu Ile Asp Lys Gly Leu Ile Pro
         115                 120                 125
Met Glu Gly Glu Glu Leu Lys Ile Leu Ala Phe Ala Ile Ala Thr
         130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                 165                 170                 175
Asp Leu Pro Tyr Val Glu Val Ser Ser Glu Arg Glu Met Ile Lys
             180                 185                 190
Arg Phe Leu Arg Ile Ile Arg Glu Lys Asp Pro Asp Ile Ile Val Thr
         195                 200                 205
Tyr Asn Gly Asp Ser Phe Asp Phe Pro Tyr Leu Ala Lys Arg Ala Glu
     210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                 245                 250                 255
His Phe Asp Leu Tyr His Val Ile Thr Arg Thr Ile Asn Leu Pro Thr
             260                 265                 270
Tyr Thr Leu Glu Ala Val Tyr Glu Ala Ile Phe Gly Lys Pro Lys Glu
         275                 280                 285
Lys Val Tyr Ala Asp Glu Ile Ala Lys Ala Trp Glu Ser Gly Glu Asn
     290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                 325                 330                 335
Val Gly Gln Pro Leu Trp Asp Val Ser Arg Ser Ser Thr Gly Asn Leu
             340                 345                 350
Val Glu Trp Phe Leu Leu Arg Lys Ala Tyr Glu Arg Asn Glu Val Ala
         355                 360                 365
Pro Asn Lys Pro Ser Glu Glu Tyr Gln Arg Arg Leu Arg Glu Ser
     370                 375                 380
Tyr Thr Gly Gly Phe Val Lys Glu Pro Glu Lys Gly Leu Trp Asn Asp
385                 390                 395                 400
Leu Val Tyr Leu Asp Phe Ile Ala Leu Tyr Pro Ser Ile Ile Val Thr
                 405                 410                 415
His Asn Val Ser Pro Asp Thr Leu Asn Leu Glu Gly Cys Lys Asn Tyr
             420                 425                 430
Asp Ile Ala Pro Gln Val Gly His Lys Phe Cys Lys Asp Ile Pro Gly
         435                 440                 445
```

| | | | | | | | | | | | | | |
|---|---|---|---|---|---|---|---|---|---|---|---|---|---|
|Phe|Ile|Pro|Ser|Leu|Leu|Gly|His|Leu|Leu|Glu|Glu|Arg|Gln|Lys|Ile|
| |450| | | |455| | | |460| | | | |

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 9
<211> LENGTH: 2328
<212> TYPE: DNA
<213> ORGANISM: Artificial
<220> FEATURE:
<223> OTHER INFORMATION: Clone sequence

<400> SEQUENCE: 9
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa agtttctcgg caagcctatt     240

```
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgacttccc atatttagcg    660
aaaagggcag aaaacttgg gattaaatta accattggaa gagatggaag cgagcccaag    720
atgcagagaa taggcgatat gacggctgta gaagtcaagg gaagaataca tttcgacttg    780
tatcacgtaa taacaaggac aataaatctc ccaacataca cactagaggc tgtatatgaa    840 gcaattttg aaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggacagc   1200
atcgtttatc tagattttat agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gcctctatgc aactatccca ggaggagaaa gtgaggaaat aaagaaaaag   1680
gctctcgaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa                2328
```

<210> SEQ ID NO 10
<211> LENGTH: 775
<212> TYPE: PRT
<213> ORGANISM: Artificial
<220> FEATURE:
<223> OTHER INFORMATION: Clone sequence

<400> SEQUENCE: 10

-continued

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Asp Ser
385                 390                 395                 400

Ile Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
```

```
                420             425             430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
        450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
770                 775

<210> SEQ ID NO 11
<211> LENGTH: 2328
<212> TYPE: DNA
<213> ORGANISM: Artificial
<220> FEATURE:
<223> OTHER INFORMATION: Clone sequence

<400> SEQUENCE: 11
atgattttag atgtggatta cataactgaa gaaggaaaac ctgttattag gctattcaaa      60
```

-continued

| | |
|---|---|
| aaagagaacg gaaaatttaa gatagagcat gatagaactt ttagaccata catttacgct | 120 |
| cttctcaggg atgattcaaa gattgaagaa gttaagaaaa taacgggga aaggcatgga | 180 |
| aagattgtga gaattgttga tgtagagaag gttgagaaaa agtttctcgg caagcctatt | 240 |
| accgtgtgga aactttattt ggaacatcct caggatcagc ccactattag agaaaaagtt | 300 |
| agagaacatc cagcagttgt ggacatcttc gaatacgata ttccatttgc aaagagatac | 360 |
| ctcatcgaca aaggcctaat accaatggag ggggaagaag agctaaagat tcttgccttc | 420 |
| gcgatcgcga ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat ttctcaggat tatcagggag | 600 |
| aaggaccctg acattatagt tacttataat ggagactcat tcgacttccc atatttagcg | 660 |
| aaaagggcag aaaaacttgg gattaaatta accattggaa gagatggaag cgagcccaag | 720 |
| atgcagagaa taggcgatat gacggctgta gaagtcaagg gaagaataca tttcgacttg | 780 |
| tatcatgtaa taacaaggac aataaatctc ccaacataca cactagaggc tgtatatgaa | 840 |
| gcaattttg gaaagccaaa ggagaaggta tacgccgacg agatagcaaa agcctgggaa | 900 |
| agtggagaga accttgagag agttgccaaa tactcgatgg aagatgcaaa ggcaacttat | 960 |
| gaactcggga agaattcct tccaatggaa attcagcttt caagattagt tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aaagagccag aaaaggggtt gtgggaaggc | 1200 |
| atcgtttatc tagattttat agccctatat ccttcgatta taattaccca caatgtttct | 1260 |
| cccgatactc taaatcttga gggatgcaag aactatgata tcgctcctca agtaggccac | 1320 |
| aagttctgca aggacatccc tggttttata ccaagtctct tgggacattt gttagaggaa | 1380 |
| agacaaaaga ttaagacaaa aatgaaggaa actcaggatc ctatagaaaa aatactcctt | 1440 |
| gactatagac aaaaagcgat aaaactcttg gcaaattctt tatacggata ttacggttat | 1500 |
| gccaaagcaa gatggtactg taaggagtgt gctgagagcg ttactgcctg gggaagaaag | 1560 |
| tacatcgagt tagtatggaa ggagctcgaa gaaaagtttg gatttaaagt cctctacatt | 1620 |
| gacactgatg gcctctatgc aactatccca ggaggagaaa gtgaggaaat aaagaaaaag | 1680 |
| gctctcgaat ttgtaaaata cataaattca aagctccctg gactgctcga gcttgaatat | 1740 |
| gaagggtttt ataagagggg attcttcgtt acgaagaaga ggtatgcagt aatagatgaa | 1800 |
| gaaggaaaag tcattactcg tggtttagag atagttagga gagattggag tgaaattgca | 1860 |
| aaagaaactc aagctagagt tttggagaca atactaaaac acgagatgt tgaagaagct | 1920 |
| gtgagaatag taaagaagt aatacaaaag cttgccaatt atgaaattcc accagagaag | 1980 |
| ctcgcaatat atgagcagat aacaagacca ttacatgagt ataaggcgat aggtcctcac | 2040 |
| gtagctgttg caaagaaact agctgctaaa ggagttaaaa taaagccagg aatggtaatt | 2100 |
| ggatacatag tacttagagg cgatggtcca attagcaata gggcaattct agctgaggaa | 2160 |
| tacgatccca aaaagcacaa gtatgacgca gaatattaca ttgagaacca ggttcttcca | 2220 |
| gcggtactta ggatattgga gggatttgga tacagaaagg aagacctcag ataccaaaag | 2280 |
| acaagacaag tcggcctaac ttcctggctt aacattaaaa aatcctaa | 2328 |

<210> SEQ ID NO 12
<211> LENGTH: 775
<212> TYPE: PRT

<213> ORGANISM: Artificial
<220> FEATURE:
<223> OTHER INFORMATION: Clone sequence

<400> SEQUENCE: 12

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Gly
385                 390                 395                 400
```

Ile Val Tyr Leu Asp Phe Ile Ala Leu Tyr Pro Ser Ile Ile Thr
            405                 410                 415

His Asn Val Ser Pro Asp Thr Leu Asn Leu Glu Gly Cys Lys Asn Tyr
        420                 425                 430

Asp Ile Ala Pro Gln Val Gly His Lys Phe Cys Lys Asp Ile Pro Gly
    435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Leu Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 13
<211> LENGTH: 2328
<212> TYPE: DNA
<213> ORGANISM: Artificial
<220> FEATURE:
<223> OTHER INFORMATION: Clone sequence

<400> SEQUENCE: 13

```
atgattttag atgtggatta cataactgaa gaaggaaaac ctgttattag gctattcaaa        60
aaagagaacg gaaaatttaa gatagagcat gatagaactt ttagaccata catttacgct       120
cttctcaggg atgattcaaa gattgaagaa gttaagaaaa taacggggga aaggcatgga       180
aagattgtga gaattgttga tgtagagaag gttgagaaaa agtttctcgg caagcctatt       240
accgtgtgga aactttattt ggaacatcct caggatcagc ccactattag agaaaaagtt       300
agagaacatc cagcagttgt ggacatcttc gaatacgata ttccatttgc aaagagatac       360
ctcatcgaca aaggcctaat accaatggag ggggaagaag agctaaagat tcttgccttc       420
gcgatcgcga ccctctatca cgaaggagaa gagtttggaa aaggcccaat tataatgatt       480
agttatgcag atgaaaatga agcaaaggtg attacttgga aaaacataga tcttccatac       540
gttgaggttg tatcaagcga gagagagatg ataaagagat ttctcaggat tatcagggag       600
aaggaccctg acattatagt tacttataat ggagactcat tcgacttccc atatttagcg       660
aaaagggcag aaaaacttgg gattaaatta accattggaa gagatggaag cgagcccaag       720
atgcagagaa taggcgatat gacggctgta gaagtcaagg gaagaataca tttcgacttg       780
tatcatgtaa taacaaggac aataaatctc ccaacataca cactagaggc tgtatatgaa       840
gcaattttg gaaagccaaa ggagaaggta tacgccgacg agatagcaaa agcctgggaa       900
agtggagaga accttgagag agttgccaaa tactcgatgg aagatgcaaa ggcaacttat       960
gaactcggga agaattcct tccaatggaa attcagcttt caagattagt tggacaacct      1020
ttatgggatg tttcaaggtc aagcacaggg aaccttgtag agtggttctt acttaggaaa      1080
gcctacgaaa gaacgaagt agctccaaac aagccaagtg aagaggagta tcaaagaagg      1140
ctcagggaga gctacacagg tggactcgtt aaagagccag aaaaggggtt gtgggaagac      1200
ctcgtttatc tagattttat agctctatat ccctcgatta taattaccca caatgtttct      1260
cccgatactc taaatcttga gggatgcaag aactatgata tcgctcctca gtaggccac      1320
aagttctgca aggacatccc tggttttata ccaagtctct tgggacattt gttagaggaa      1380
agacaaaaga ttaagacaaa aatgaaggaa actcaggatc ctatagaaaa aatactcctt      1440
gactatagac aaaaagcgat aaaactctta gcaaatactt tctacggata ttacggctat      1500
gccaaagcaa gatggtactg taaggagtgt gctgagagcg ttaccgcctg ggggagaaag      1560
tacatcgagt tagtatggaa ggagctcgaa gaaaagtttg gatttaaagt cctctacatt      1620
gacactgatg gcctctatgc aactatccca ggaggagaaa gtgaggaaat aaagaaaaag      1680
gctctcgaat tgtaaaaata cataaattca aagctccctg gactgctcga gcttgaatat      1740
gaagggtttt ataagagggg attcttcgtt acgaagaaga ggtatgcagt aatagatgaa      1800
gaaggaaaag tcattactcg tggtttagag atagttagga gagattggag tgaaattgca      1860
aaagaaactc aagctagagt tttggagaca atactaaaac acggagatgt tgaagaagct      1920
gtgagaatag taaaagaagt aatacaaaag cttgccaatt atgaaattcc accagagaag      1980
ctcgcaatat atgagcagat aacaagacca ttacatgagt ataaggcgat aggtcctcac      2040
gtagctgttg caaagaaact agctgctaaa ggagttaaaa taaagccagg aatggtaatt      2100
ggatacatag tacttagagg cgatggtcca attagcaata gggcaattct agctgaggaa      2160
tacgatccca aaaagcacaa gtatgacgca gaatattaca ttgagaacca ggttcttcca      2220
gcggtactta ggatattgga gggatttgga tacagaaagg aagacctcag ataccaaaag      2280
acaagacaag tcggcctaac ttcctggctt aacattaaaa aatcctaa                   2328
```

<210> SEQ ID NO 14
<211> LENGTH: 775
<212> TYPE: PRT
<213> ORGANISM: Artificial
<220> FEATURE:
<223> OTHER INFORMATION: Clone sequence

<400> SEQUENCE: 14

| | | | | | | | | | | | | | | |
|---|---|---|---|---|---|---|---|---|---|---|---|---|---|---|
| Met | Ile | Leu | Asp | Val | Asp | Tyr | Ile | Thr | Glu | Glu | Gly | Lys | Pro | Val | Ile |
| 1 | | | | 5 | | | | | 10 | | | | | 15 | |
| Arg | Leu | Phe | Lys | Lys | Glu | Asn | Gly | Lys | Phe | Lys | Ile | Glu | His | Asp | Arg |
| | | | 20 | | | | | 25 | | | | | 30 | | |
| Thr | Phe | Arg | Pro | Tyr | Ile | Tyr | Ala | Leu | Leu | Arg | Asp | Asp | Ser | Lys | Ile |
| | | 35 | | | | | 40 | | | | | 45 | | | |
| Glu | Glu | Val | Lys | Lys | Ile | Thr | Gly | Glu | Arg | His | Gly | Lys | Ile | Val | Arg |
| | 50 | | | | | 55 | | | | | 60 | | | | |
| Ile | Val | Asp | Val | Glu | Lys | Val | Glu | Lys | Phe | Leu | Gly | Lys | Pro | Ile |
| 65 | | | | | 70 | | | | | 75 | | | | | 80 |
| Thr | Val | Trp | Lys | Leu | Tyr | Leu | Glu | His | Pro | Gln | Asp | Gln | Pro | Thr | Ile |
| | | | | 85 | | | | | 90 | | | | | 95 | |
| Arg | Glu | Lys | Val | Arg | Glu | His | Pro | Ala | Val | Val | Asp | Ile | Phe | Glu | Tyr |
| | | | 100 | | | | | 105 | | | | | 110 | | |
| Asp | Ile | Pro | Phe | Ala | Lys | Arg | Tyr | Leu | Ile | Asp | Lys | Gly | Leu | Ile | Pro |
| | | 115 | | | | | 120 | | | | | 125 | | | |
| Met | Glu | Gly | Glu | Glu | Glu | Leu | Lys | Ile | Leu | Ala | Phe | Ala | Ile | Ala | Thr |
| | 130 | | | | | 135 | | | | | 140 | | | | |
| Leu | Tyr | His | Glu | Gly | Glu | Glu | Phe | Gly | Lys | Gly | Pro | Ile | Ile | Met | Ile |
| 145 | | | | | 150 | | | | | 155 | | | | | 160 |
| Ser | Tyr | Ala | Asp | Glu | Asn | Glu | Ala | Lys | Val | Ile | Thr | Trp | Lys | Asn | Ile |
| | | | | 165 | | | | | 170 | | | | | 175 | |
| Asp | Leu | Pro | Tyr | Val | Glu | Val | Val | Ser | Ser | Glu | Arg | Glu | Met | Ile | Lys |
| | | | 180 | | | | | 185 | | | | | 190 | | |
| Arg | Phe | Leu | Arg | Ile | Ile | Arg | Glu | Lys | Asp | Pro | Asp | Ile | Ile | Val | Thr |
| | | 195 | | | | | 200 | | | | | 205 | | | |
| Tyr | Asn | Gly | Asp | Ser | Phe | Asp | Phe | Pro | Tyr | Leu | Ala | Lys | Arg | Ala | Glu |
| | 210 | | | | | 215 | | | | | 220 | | | | |
| Lys | Leu | Gly | Ile | Lys | Leu | Thr | Ile | Gly | Arg | Asp | Gly | Ser | Glu | Pro | Lys |
| 225 | | | | | 230 | | | | | 235 | | | | | 240 |
| Met | Gln | Arg | Ile | Gly | Asp | Met | Thr | Ala | Val | Glu | Val | Lys | Gly | Arg | Ile |
| | | | | 245 | | | | | 250 | | | | | 255 | |
| His | Phe | Asp | Leu | Tyr | His | Val | Ile | Thr | Arg | Thr | Ile | Asn | Leu | Pro | Thr |
| | | | 260 | | | | | 265 | | | | | 270 | | |
| Tyr | Thr | Leu | Glu | Ala | Val | Tyr | Glu | Ala | Ile | Phe | Gly | Lys | Pro | Lys | Glu |
| | | 275 | | | | | 280 | | | | | 285 | | | |
| Lys | Val | Tyr | Ala | Asp | Glu | Ile | Ala | Lys | Ala | Trp | Glu | Ser | Gly | Glu | Asn |
| | 290 | | | | | 295 | | | | | 300 | | | | |
| Leu | Glu | Arg | Val | Ala | Lys | Tyr | Ser | Met | Glu | Asp | Ala | Lys | Ala | Thr | Tyr |
| 305 | | | | | 310 | | | | | 315 | | | | | 320 |
| Glu | Leu | Gly | Lys | Glu | Phe | Leu | Pro | Met | Glu | Ile | Gln | Leu | Ser | Arg | Leu |
| | | | | 325 | | | | | 330 | | | | | 335 | |
| Val | Gly | Gln | Pro | Leu | Trp | Asp | Val | Ser | Arg | Ser | Ser | Thr | Gly | Asn | Leu |
| | | | 340 | | | | | 345 | | | | | 350 | | |
| Val | Glu | Trp | Phe | Leu | Leu | Arg | Lys | Ala | Tyr | Glu | Arg | Asn | Glu | Val | Ala |
| | | 355 | | | | | 360 | | | | | 365 | | | |

```
Pro Asn Lys Pro Ser Glu Glu Glu Tyr Gln Arg Arg Leu Arg Glu Ser
        370                 375                 380

Tyr Thr Gly Gly Leu Val Lys Glu Pro Glu Lys Gly Leu Trp Glu Asp
385                 390                 395                 400

Leu Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Thr Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 15
```

<211> LENGTH: 2328
<212> TYPE: DNA
<213> ORGANISM: Artificial
<220> FEATURE:
<223> OTHER INFORMATION: Clone sequence

<400> SEQUENCE: 15

| | | | | | | |
|---|---|---|---|---|---|---|
| atgattttag | atgtggatta | cataactgaa | gaaggaaaac | ctgttattag | gctattcaaa | 60 |
| aaagagaacg | gaaaatttaa | gatagagcat | gatagaactt | ttagaccata | catttacgct | 120 |
| cttctcaggg | atgattcaaa | gattgaagaa | gttaagaaaa | taacgggga | aaggcatgga | 180 |
| aagattgtga | gaattgttga | tgtagagaag | gttgagaaaa | agtttctcgg | caagcctatt | 240 |
| accgtgtgga | aactttattt | ggaacatcct | caggatcagc | ccactattag | agaaaaagtt | 300 |
| agagaacatc | cagcagttgt | ggacatcttc | gaatacgata | ttccatttgc | aaagagatac | 360 |
| ctcatcgaca | aaggcctaat | accaatggag | ggggaagaag | agctaaagat | tcttgccttc | 420 |
| gcgatcgcga | ccctctatca | cgaaggagaa | gagtttggaa | aaggcccaat | tataatgatt | 480 |
| agttatgcag | atgaaaatga | agcaaaggtg | attacttgga | aaaacataga | tcttccatac | 540 |
| gttgaggttg | tatcaagcga | gagagagatg | ataaagagat | ttctcaggat | tatcagggag | 600 |
| aaggaccctg | acattatagt | tacttataat | ggagactcat | tcgacttccc | atatttagcg | 660 |
| aaaagggcag | aaaacttgg | gattaaatta | accattggaa | gagatggaag | cgagcccaag | 720 |
| atgcagagaa | taggcgatat | gacggctgta | gaagtcaagg | gaagaataca | tttcgacttg | 780 |
| tatcatgtaa | taacaaggac | aataaatctc | ccaacataca | cactagaggc | tgtatatgaa | 840 |
| gcaatttttg | gaaagccaaa | ggagaaggta | tacgccgacg | agatagcaaa | agcctgggaa | 900 |
| agtggagaga | accttgagag | agttgccaaa | tactcgatgg | aagatgcaaa | ggcaacttat | 960 |
| gaactcggga | agaattcct | tccaatggaa | attcagcttt | caagattagt | tggacaacct | 1020 |
| ttatgggatg | tttcaaggtc | aagcacaggg | aaccttgtag | agtggttctt | acttaggaaa | 1080 |
| gcctacgaaa | gaaacgaagt | agctccaaac | aagccaagtg | aagaggagta | tcaaagaagg | 1140 |
| ctcagggaga | gctacacagg | tggattcgtt | aaagagccag | aaaagggtt | gtgggacgac | 1200 |
| atcgtttatc | tagatttcat | agccctatat | ccctcgatta | taattaccca | caatgtttct | 1260 |
| cccgatactc | taaatcttga | gggatgcaag | aactatgata | ccgctcctca | agtaggccac | 1320 |
| aagttctgca | aggacatcac | tggtttata | ccaagtctct | tgggacattt | gttagaggaa | 1380 |
| agacaaaaga | ttaagacaaa | aatgaaggaa | actcaggatc | ctatagaaaa | aatactcctt | 1440 |
| gactatagac | aaaaagcgat | aaaactctta | acaaattctg | tttacggata | ttacggctat | 1500 |
| acgaaagcaa | gatggtactg | taaggagtgt | gctgagagcg | ttactgcctg | gggaagaaag | 1560 |
| tacatcgagt | tagtatggaa | ggagctcgaa | gaaaagtttg | gatttaaagt | cctctacatt | 1620 |
| gacactgatg | gcctctatgc | aactatccca | ggaggagaaa | gtgaggaaat | aagaaaaag | 1680 |
| gctctcgaat | ttgtaaaata | cataaattca | agctccctg | gactgctcga | gcttgaatat | 1740 |
| gaagggtttt | ataagagggg | attcttcgtt | acgaagaaga | ggtatgcagt | aatagatgaa | 1800 |
| gaaggaaaag | tcattactcg | tggtttagag | atagttagga | gagattggag | tgaaattgca | 1860 |
| aaagaaactc | aagctagagt | tttggagaca | atactaaaac | acggagatgt | tgaagaagct | 1920 |
| gtgagaaatag | taaagaagt | aatacaaaag | cttgccaatt | atgaaattcc | accagagaag | 1980 |
| ctcgcaatat | atgagcagat | aacaagacca | ttacatgagt | ataaggcgat | aggtcctcac | 2040 |
| gtagctgttg | caaagaaact | agctgctaaa | ggagttaaaa | taaagccagg | aatggtaatt | 2100 |
| ggatacatag | tacttagagg | cgatggtcca | attagcaata | gggcaattct | agctgaggaa | 2160 |

```
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa               2328
```

<210> SEQ ID NO 16
<211> LENGTH: 775
<212> TYPE: PRT
<213> ORGANISM: Artificial
<220> FEATURE:
<223> OTHER INFORMATION: Clone sequence

<400> SEQUENCE: 16

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
```

-continued

```
                340                 345                 350
Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Asp Asp
385                 390                 395                 400

Ile Val Tyr Leu Asp Phe Ile Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Thr Ala Pro Gln Val Gly His Lys Phe Cys Lys Asp Ile Thr Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Thr Asn Ser Val Tyr Gly
                485                 490                 495

Tyr Tyr Gly Tyr Thr Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765
```

Trp Leu Asn Ile Lys Lys Ser
    770             775

<210> SEQ ID NO 17
<211> LENGTH: 2328
<212> TYPE: DNA
<213> ORGANISM: Artificial
<220> FEATURE:
<223> OTHER INFORMATION: Clone sequence

<400> SEQUENCE: 17

| | | | | | |
|---|---|---|---|---|---|
| atgattttag | atgtggatta | cataactgaa | gaaggaaaac | ctgttattag | gctattcaaa     60 |
| aaagagaacg | gaaaatttaa | gatagagcat | gatagaactt | ttagaccata | catttacgct    120 |
| cttctcaggg | atgattcaaa | gattgaagaa | gttaagaaaa | taacgggga | aaggcatgga    180 |
| aagattgtga | gaattgttga | tgtagagaag | gttgagaaaa | agtttctcgg | caagcctatt    240 |
| accgtgtgga | aactttattt | ggaacatcct | caggatcagc | ccactattag | agaaaaagtt    300 |
| agagaacatc | cagcagttgt | ggacatcttc | gaatacgata | ttccatttgc | aaagagatac    360 |
| ctcatcgaca | aaggcctaat | accaatggag | ggggaagaag | agctaaagat | tcttgccttc    420 |
| gcgatcgcga | ccctctatca | cgaaggagaa | gagtttggaa | aaggcccaat | tataatgatt    480 |
| agttatgcag | atgaaaatga | agcaaggtg | attacttgga | aaaacataga | tcttccatac    540 |
| gttgaggttg | tatcaagcga | gagagagatg | ataaagagat | tctctcaggat | tatcagggag    600 |
| aaggaccctg | acattatagt | tacttataat | ggagactcat | tcgacttccc | atatttagcg    660 |
| aaaagggcag | aaaaacttgg | gattaaatta | accattggaa | gagatggaag | cgagcccaag    720 |
| atgcagagaa | taggcgatat | gacggctgta | gaagtcaagg | gaagaataca | tttcgacttg    780 |
| tatcatgtaa | taacaaggac | aataaatctc | ccaacataca | cactagaggc | tgtatatgaa    840 |
| gcaatttttg | gaaagccaaa | ggagaaggta | tacgccgacg | agatagcaaa | gcctgggaa    900 |
| agtggagaga | accttgagag | agttgccaaa | tactcgatgg | aagatgcaaa | ggcaacttat    960 |
| gaactcggga | agaattcct | tccaatggaa | attcagcttt | caagattagt | tggacaacct   1020 |
| ttatgggat | tttcaaggtc | aagcacaggg | aaccttgtag | agtggttctt | acttaggaaa   1080 |
| gcctacgaaa | gaaacgaagt | agctccaaac | aagccaagtg | aagaggagta | tcaaagaagg   1140 |
| ctcagggaga | gctacacagg | tggattcgtt | aaagagccag | aaaagggtt | gtgggaaaac   1200 |
| atagtatacc | tagattttag | agccctatat | ccctcgatta | taattaccca | caatgtttct   1260 |
| cccgatactc | taaatcttga | gggatgcagg | aactatgata | tcgctcctca | gtaggccac   1320 |
| aagttctgca | aggacatccc | tggttttata | ccaagtctct | tgggacattt | gttagaggaa   1380 |
| agacaaaaga | ttaagacaaa | aatgaaggaa | actcaggatc | ctatagaaaa | atactccttt   1440 |
| gactatagac | aaaaagcgat | aaaacttgta | gcaaattctt | tttacggttc | ttacggctat   1500 |
| cccaaagcaa | gatggtactg | taaggagtgt | gctgagagcg | ttactgcctg | gggaagaaag   1560 |
| tacatcgagt | tagtatggaa | ggagctcgaa | gaaaagtttg | gatttaaagt | cctctacatt   1620 |
| gacactgatg | gcctctatgc | aactatccca | ggaggagaaa | gtgaggaaat | aaagaaaaag   1680 |
| gctctcgaat | ttgtaaaata | cataaattca | agctccctg | gactgctcga | gcttgaatat   1740 |
| gaagggtttt | ataagagggg | attcttcgtt | acgaagaaga | ggtatgcagt | aatagatgaa   1800 |
| gaaggaaaag | tcattactcg | tggtttagag | atagttagga | gagattggag | tgaaattgca   1860 |
| aaagaaactc | aagctagagt | tttggagaca | atactaaac | acggagatgt | tgaagaagct   1920 |
| gtgagaatag | taaagaagt | aatacaaaag | cttgccaatt | atgaaattcc | accagagaag   1980 |
| ctcgcaatat | atgagcagat | aacaagacca | ttacatgagt | ataaggcgat | aggtcctcac   2040 |

```
gtagctgttg caaagaaact agctgctaaa ggagttaaaa taaagccagg aatggtaatt      2100
ggatacatag tacttagagg cgatggtcca attagcaata gggcaattct agctgaggaa      2160
tacgatccca aaaagcacaa gtatgacgca gaatattaca ttgagaacca ggttcttcca      2220
gcggtactta ggatattgga gggatttgga tacagaaagg aagacctcag ataccaaaag      2280
acaagacaag tcggcctaac ttcctggctt aacattaaaa aatcctaa                  2328
```

<210> SEQ ID NO 18
<211> LENGTH: 775
<212> TYPE: PRT
<213> ORGANISM: Artificial
<220> FEATURE:
<223> OTHER INFORMATION: Clone sequence

<400> SEQUENCE: 18

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320
```

-continued

```
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Thr Gly Asn Leu
            340                 345                 350
Val Glu Trp Phe Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Arg Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Val Ala Asn Ser Phe Tyr Gly
                485                 490                 495
Ser Tyr Gly Tyr Pro Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
```

```
                740                 745                 750
Lys Glu Asp Leu Arg Tyr Gln Lys Thr Arg Gln Val Gly Leu Thr Ser
            755                 760                 765

Trp Leu Asn Ile Lys Lys Ser
    770                 775

<210> SEQ ID NO 19
<211> LENGTH: 2328
<212> TYPE: DNA
<213> ORGANISM: Artificial
<220> FEATURE:
<223> OTHER INFORMATION: Clone sequence

<400> SEQUENCE: 19
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat tctctcagga tatcagggag     600
aaggaccctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactgaggc tgtatatgaa      840 gcaattttg gaaagccaaa ggagaaggta tacgccgacg agatagcaaa agcctgggaa     900
agtggagaga accttgagag agttgccaaa tactcgatgg aagatgcaaa ggcaacttat     960
gaactcggga agaattcct tccaatggaa attcagctct caagattaat tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggacgac    1200
atcgtttatc tagatttcat agccctatat ccctcgatta aattaccca caatgttct     1260 cccgatactc taaatcttga gggatgcaag aactatgata tcgctcctca gtaggccac    1320 aacttctgca aggacatccc tggttttata ccaagtctct tgggacattt gttagaggaa    1380
agacaaaaga ttaagacaaa aatgaaggaa actcaggatc ctatagaaaa aatactcctt    1440
gactatagac aaaaagcgat aaaactctta acaaattctt tatacggata tttcggttat    1500
ccgaaagcaa gatggtactg taaggagtgt gctgagagcg ttactgcctg ggaagaaag    1560 tacatcgagt tagtatggaa ggagctcgaa gaaaagtttg gatttaaagt cctctacatt    1620
gacactgatg gcctctatgc aactatccca ggaggagaaa gtgaggaaat aaagaaaaag    1680
gctctcgaat ttgtaaaata cataaattca aagctccctg gactgctcga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
```

```
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa               2328

<210> SEQ ID NO 20
<211> LENGTH: 775
<212> TYPE: PRT
<213> ORGANISM: Artificial
<220> FEATURE:
<223> OTHER INFORMATION: Clone sequence

<400> SEQUENCE: 20
```

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

```
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Ile Gly Gln Pro Leu Trp Asp Val Ser Arg Ser Ser Thr Gly Asn Leu
                340                 345                 350
Val Glu Trp Phe Leu Leu Arg Lys Ala Tyr Glu Arg Asn Glu Val Ala
                355                 360                 365
Pro Asn Lys Pro Ser Glu Glu Tyr Gln Arg Arg Leu Arg Glu Ser
370                 375                 380
Tyr Thr Gly Gly Phe Val Lys Glu Pro Glu Lys Gly Leu Trp Asp Asp
385                 390                 395                 400
Ile Val Tyr Leu Asp Phe Ile Ala Leu Tyr Pro Ser Ile Ile Ile Thr
                405                 410                 415
His Asn Val Ser Pro Asp Thr Leu Asn Leu Glu Gly Cys Lys Asn Tyr
                420                 425                 430
Asp Ile Ala Pro Gln Val Gly His Asn Phe Cys Lys Asp Ile Pro Gly
            435                 440                 445
Phe Ile Pro Ser Leu Leu Gly His Leu Leu Glu Glu Arg Gln Lys Ile
450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Thr Asn Ser Leu Tyr Gly
                485                 490                 495
Tyr Phe Gly Tyr Pro Lys Ala Arg Trp Tyr Cys Lys Glu Cys Ala Glu
                500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Arg Tyr Ala Val Ile Asp Glu Glu Gly Lys Val Ile Thr Arg Gly
            595                 600                 605
Leu Glu Ile Val Arg Arg Asp Trp Ser Glu Ile Ala Lys Glu Thr Gln
610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
            675                 680                 685
Ala Lys Gly Val Lys Ile Lys Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
```

```
Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
    770             775

<210> SEQ ID NO 21
<211> LENGTH: 2328
<212> TYPE: DNA
<213> ORGANISM: Artificial
<220> FEATURE:
<223> OTHER INFORMATION: Clone sequence

<400> SEQUENCE: 21
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacgggggga aaggcatgga   180 aagattgtga gaattgttga tgtagagaag gttgagaaaa agtttctcgg caagcctatt    240
accgtgtgga aactttattt ggaacatcct caggatcagc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggaccctg acattatagt tacttataat ggagactcat tcgacttccc atatttagcg    660
aaaagggcag aaaaacttgg gattaaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt aactccaaac aagccaagtg aagaggagta tcaaagaagg   1140
ctcagggaga gctacacagg tggattcgtt aaagagccag aaaagggggtt gtgggaagac   1200 ctcgtttatc tagattttat agctctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaggatc ctatagaaaa aatactcctt   1440
gattatagac aaaaagcgat aaaactcttc gcaaattctt tctacggata ttacggctac   1500
cccaaagcaa gatggtactg taaggagtgt gctgagagcg ttactgcctg ggaagaaag   1560 tacatcgagt tagtatggaa ggagctcgaa gaaaagtttg gatttaaagt cctctacatt   1620
gacactgatg gcctctatgc aactatccca ggaggagaaa gtgaggaaat aaagaaaaag   1680
gctctcgaat ttgtaaaaata cataaattca aagctccctg gactgctcga gcttgaatat   1740
```

```
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag     1980
ctcgcaatat atgagcagat aacaagacca ttcatgagt ataaggcgat aggtcctcac     2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa atcctaa                  2328
```

<210> SEQ ID NO 22
<211> LENGTH: 775
<212> TYPE: PRT
<213> ORGANISM: Artificial
<220> FEATURE:
<223> OTHER INFORMATION: Clone sequence

<400> SEQUENCE: 22

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
```

```
            260                 265                 270
Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Thr
                355                 360                 365

Pro Asn Lys Pro Ser Glu Glu Glu Tyr Gln Arg Arg Leu Arg Glu Ser
                370                 375                 380

Tyr Thr Gly Gly Phe Val Lys Glu Pro Glu Lys Gly Leu Trp Glu Asp
385                 390                 395                 400

Leu Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
                435                 440                 445

Phe Ile Pro Ser Leu Leu Gly His Leu Leu Glu Glu Arg Gln Lys Ile
                450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Phe Ala Asn Ser Phe Tyr Gly
                485                 490                 495

Tyr Tyr Gly Tyr Pro Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
                515                 520                 525

Leu Glu Glu Lys Phe Gly Phe Lys Val Leu Tyr Ile Asp Thr Asp Gly
                530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
                595                 600                 605

Leu Glu Ile Val Arg Arg Asp Trp Ser Glu Ile Ala Lys Glu Thr Gln
                610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
                675                 680                 685
```

```
Ala Lys Gly Val Lys Ile Lys Pro Gly Met Val Ile Gly Tyr Ile Val
    690             695             700
Leu Arg Gly Asp Gly Pro Ile Ser Asn Arg Ala Ile Leu Ala Glu Glu
705             710             715             720
Tyr Asp Pro Lys Lys His Lys Tyr Asp Ala Glu Tyr Tyr Ile Glu Asn
                725             730             735
Gln Val Leu Pro Ala Val Leu Arg Ile Leu Glu Gly Phe Gly Tyr Arg
            740             745             750
Lys Glu Asp Leu Arg Tyr Gln Lys Thr Arg Gln Val Gly Leu Thr Ser
        755             760             765
Trp Leu Asn Ile Lys Lys Ser
    770             775

<210> SEQ ID NO 23
<211> LENGTH: 2328
<212> TYPE: DNA
<213> ORGANISM: Artificial
<220> FEATURE:
<223> OTHER INFORMATION: Clone sequence

<400> SEQUENCE: 23
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggaccctg acattatagt tacttataat ggagactcat tcgacttccc atatttagcg     660
aaaagggcag aaaaacttgg gattaaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaatttttg aaagccaaa ggagaaggta tacgccgacg atagcaaa agcctgggaa     900 agtggagaga accttgagag agttgccaaa tactcgatgg aagatgcaaa ggcaacttat     960
gaactcggga agaattcct tccaatgaaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggtt gtgggaaggc    1200 atcgtttatc tagattttat agccctatat ccttcgatta taattaccca caatgtttct    1260
cccgatactc taaatcttga gggatgcaag aactatgata tcgctcctca gtaggccac    1320 aagttctgca aggacatccc tggttttata ccaagtcttt tgggacattt gttagaggaa    1380
agacaaaaga ttaagacaaa aatgaaggaa actcaggatc ctatagaaaa aatactcctt    1440
gactatagac aaaaagcgat aaaactctta gcaaattctt tctacggata tttcggtat    1500 acgaaagcaa gatggtactg taaggagtgt gctgagagcg ttactgcctg gggaagaaag    1560
```

```
tacatcgagt tagtatggaa ggagctcgaa gaaaagtttg gatttaaagt cctctacatt   1620
gacactgatg gcctctatgc aactatccca ggaggagaaa gtgaggaaat aaagaaaaag   1680
gctctcgaat ttgtaaaata cataaattca aagctccctg gactgctcga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa                2328
```

<210> SEQ ID NO 24
<211> LENGTH: 775
<212> TYPE: PRT
<213> ORGANISM: Artificial
<220> FEATURE:
<223> OTHER INFORMATION: Clone sequence

<400> SEQUENCE: 24

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240
```

```
Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
                340                 345                 350

Val Glu Trp Phe Leu Leu Arg Lys Ala Tyr Glu Arg Asn Glu Val Ala
                355                 360                 365

Pro Asn Lys Pro Ser Glu Glu Tyr Gln Arg Arg Leu Arg Glu Ser
            370                 375                 380

Tyr Thr Gly Gly Phe Val Lys Glu Pro Glu Lys Gly Leu Trp Glu Gly
385                 390                 395                 400

Ile Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Phe Gly Tyr Thr Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
                515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
```

```
                        660                665                 670
Glu Tyr Lys Ala Ile Gly Pro His Val Ala Val Ala Lys Lys Leu Ala
                    675                 680                 685
Ala Lys Gly Val Lys Ile Lys Pro Gly Met Val Ile Gly Tyr Ile Val
                690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 25
<211> LENGTH: 2328
<212> TYPE: DNA
<213> ORGANISM: Artificial
<220> FEATURE:
<223> OTHER INFORMATION: Clone sequence

<400> SEQUENCE: 25
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga aattgttga tgtagagaag gttgagaaaa agtttctcgg caagcctatt     240
accgtgtgga aactttattt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggaccctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaatttttg gaaagccaaa ggagaaggta tacgccgacg atatagcaaa agcctgggaa     900
agtggagaga accttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggggtt gtgggaagac    1200 ctcgtttatc tagattttat agctctatat ccctcgatta taattaccca caatgttct    1260 cccgatactc taaatattga gggatgcaag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaggatc ctatagaaaa aatactcctt    1440
```

-continued

```
gactatagac aaaaagcgat aaagcgctta gcaaattcat tctacggata tttcagctat    1500
acgaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gcctctatgc aactatccca ggaggagaaa gtgaggaaat aaagaaaaag    1680
gctctcgaat tgtaaaata cataaattca aagctcccctg gactgctcga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caagaaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa                 2328
```

<210> SEQ ID NO 26
<211> LENGTH: 775
<212> TYPE: PRT
<213> ORGANISM: Artificial
<220> FEATURE:
<223> OTHER INFORMATION: Clone sequence

<400> SEQUENCE: 26

| Met | Ile | Leu | Asp | Val | Asp | Tyr | Ile | Thr | Glu | Glu | Gly | Lys | Pro | Val | Ile |
|---|---|---|---|---|---|---|---|---|---|---|---|---|---|---|---|
| 1 | | | | 5 | | | | | 10 | | | | | 15 | |

| Arg | Leu | Phe | Lys | Lys | Glu | Asn | Gly | Lys | Phe | Lys | Ile | Glu | His | Asp | Arg |
| | | | 20 | | | | | 25 | | | | | 30 | | |

| Thr | Phe | Arg | Pro | Tyr | Ile | Tyr | Ala | Leu | Leu | Arg | Asp | Asp | Ser | Lys | Ile |
| | | 35 | | | | | 40 | | | | | 45 | | | |

| Glu | Glu | Val | Lys | Lys | Ile | Thr | Gly | Glu | Arg | His | Gly | Lys | Ile | Val | Arg |
| | 50 | | | | | 55 | | | | | 60 | | | | |

| Ile | Val | Asp | Val | Glu | Lys | Val | Glu | Lys | Lys | Phe | Leu | Gly | Lys | Pro | Ile |
| 65 | | | | | 70 | | | | | 75 | | | | | 80 |

| Thr | Val | Trp | Lys | Leu | Tyr | Leu | Glu | His | Pro | Gln | Asp | Gln | Pro | Thr | Ile |
| | | | 85 | | | | | 90 | | | | | 95 | | |

| Arg | Glu | Lys | Val | Arg | Glu | His | Pro | Ala | Val | Val | Asp | Ile | Phe | Glu | Tyr |
| | | | 100 | | | | | 105 | | | | | 110 | | |

| Asp | Ile | Pro | Phe | Ala | Lys | Arg | Tyr | Leu | Ile | Asp | Lys | Gly | Leu | Ile | Pro |
| | | 115 | | | | | 120 | | | | | 125 | | | |

| Met | Glu | Gly | Glu | Glu | Leu | Lys | Ile | Leu | Ala | Phe | Ala | Ile | Ala | Thr |
| | 130 | | | | | 135 | | | | | 140 | | | |

| Leu | Tyr | His | Glu | Gly | Glu | Glu | Phe | Gly | Lys | Gly | Pro | Ile | Ile | Met | Ile |
| 145 | | | | 150 | | | | | 155 | | | | | 160 |

| Ser | Tyr | Ala | Asp | Glu | Asn | Glu | Ala | Lys | Val | Ile | Thr | Trp | Lys | Asn | Ile |
| | | | 165 | | | | | 170 | | | | | 175 | | |

| Asp | Leu | Pro | Tyr | Val | Glu | Val | Val | Ser | Ser | Glu | Arg | Glu | Met | Ile | Lys |
| | | | 180 | | | | | 185 | | | | | 190 | | |

| Arg | Phe | Leu | Arg | Ile | Ile | Arg | Glu | Lys | Asp | Pro | Asp | Ile | Ile | Val | Thr |
| | | | 195 | | | | | 200 | | | | | 205 | | |

```
Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asp
385                 390                 395                 400

Leu Val Tyr Leu Asp Phe Ile Ala Leu Tyr Pro Ser Ile Ile Ile Thr
                405                 410                 415

His Asn Val Ser Pro Asp Thr Leu Asn Ile Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Arg Leu Ala Asn Ser Phe Tyr Gly
                485                 490                 495

Tyr Phe Ser Tyr Thr Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640
```

| | | | | | | | | | | |
|---|---|---|---|---|---|---|---|---|---|---|
|Val|Arg|Ile|Val|Lys|Glu|Val|Ile|Gln|Lys|Leu|Ala|Asn|Tyr|Glu|Ile|
| | | |645| | | |650| | | |655| | | | |

Val Arg Ile Val Lys Glu Val Ile Gln Lys Leu Ala Asn Tyr Glu Ile
              645              650              655

Pro Pro Glu Lys Leu Ala Ile Tyr Glu Gln Ile Thr Arg Pro Leu His
              660              665              670

Glu Tyr Lys Ala Ile Gly Pro His Val Ala Val Ala Lys Lys Leu Ala
              675              680              685

Ala Lys Gly Val Lys Ile Lys Pro Gly Met Val Ile Gly Tyr Ile Val
    690              695              700

Leu Arg Gly Asp Gly Pro Ile Ser Asn Arg Ala Ile Leu Ala Glu Glu
705               710              715            720

Tyr Asp Pro Lys Lys His Lys Tyr Asp Ala Glu Tyr Tyr Ile Glu Asn
              725              730              735

Gln Val Leu Pro Ala Val Leu Arg Ile Leu Glu Gly Phe Gly Tyr Arg
              740              745              750

Lys Glu Asp Leu Arg Tyr Gln Lys Thr Arg Gln Val Gly Leu Thr Ser
              755              760              765

Trp Leu Asn Ile Lys Lys Ser
770               775

<210> SEQ ID NO 27
<211> LENGTH: 2328
<212> TYPE: DNA
<213> ORGANISM: Artificial
<220> FEATURE:
<223> OTHER INFORMATION: Clone sequence

<400> SEQUENCE: 27

| | | | | |
|---|---|---|---|---|
|atgattttag|atgtggatta|cataactgaa|gaaggaaaac|ctgttattag gctattcaaa|60|
|aaagagaacg|gaaaatttaa|gatagagcat|gatagaactt|ttagaccata catttacgct|120|
|cttctcaggg|atgattcaaa|gattgaagaa|gttaagaaaa|taacggggga aaggcatgga|180|
|aagattgtga|gaattgttga|tgtagagaag|gttgagaaaa|agtttctcgg caagcctatt|240|
|accgtgtgga|aactttattt|ggaacatcct|caggatcagc|ccactattag agaaaaagtt|300|
|agagaacatc|cagcagttgt|ggacatcttc|gaatacgata|ttccatttgc aaagagatac|360|
|ctcatcgaca|aaggcctaat|accaatggag|ggggaagaag|agctaaagat tcttgccttc|420|
|gcgatcgcga|ccctctatca|cgaaggagaa|gagtttggaa|aaggcccaat tataatgatt|480|
|agttatgcag|atgaaaatga|agcaaggtg|attacttgga|aaaacataga tcttccatac|540|
|gttgaggttg|tatcaagcga|gagagagatg|ataaagagat|ttctcaggat tatcagggag|600|
|aaggaccctg|acattatagt|tacttataat|ggagactcat|tcgacttccc atatttagcg|660|
|aaaagggcag|aaaaacttgg|gattaaatta|accattggaa|gagatggaag cgagcccaag|720|
|atgcagagaa|taggcgatat|gacggctgta|gaagtcaagg|gaagaataca tttcgacttg|780|
|tatcatgtaa|taacaaggac|aataaatctc|ccaacataca|cactagaggc tgtatatgaa|840|
|gcaattttg|gaaagccaaa|ggagaaggta|tacgccgacg|agatagcaaa agcctgggaa|900|
|agtggagaga|accttgagag|agttgccaaa|tactcgatgg|aagatgcaaa ggcaacttat|960|
|gaactcggga|agaattcct|tccaatggaa|attcggcttt|caagattagt tggacaacct|1020|
|ttatgggatg|tttcaaggtc|aagcacaggg|aaccttgtag|agtggttctt acttaggaaa|1080|
|gcctacgaaa|gaaacgaagt|agctccaaac|aagccaagtg|aagaggagta tcaaagaagg|1140|
|ctcaggagga|gctacacagg|tggattcgtt|aagagccag|aaaagggtt gtgggaaggc|1200|
|atcgtttatc|tagattttat|agccctatat|ccttcgatta|taattaccca caatgtttct|1260|

```
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaggatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtcttcacgc aactatccca ggaggagaaa gtgaggagat caagaaaaag   1680
gctctagaat ttgtaaaata cataaattca aagctccctg gactgctcga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa              2328
```

<210> SEQ ID NO 28
<211> LENGTH: 775
<212> TYPE: PRT
<213> ORGANISM: Artificial
<220> FEATURE:
<223> OTHER INFORMATION: Clone sequence

<400> SEQUENCE: 28

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
    130                 135                 140

Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
```

-continued

```
                180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Arg Leu Ser Arg Leu
            325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Glu Tyr Gln Arg Arg Leu Arg Glu Ser
370                 375                 380
Tyr Thr Gly Gly Phe Val Lys Glu Pro Glu Lys Gly Leu Trp Glu Gly
385                 390                 395                 400
Ile Val Tyr Leu Asp Phe Ile Ala Leu Tyr Pro Ser Ile Ile Ile Thr
            405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
            530                 535                 540
Leu His Ala Thr Ile Pro Gly Gly Glu Ser Glu Ile Lys Lys Lys
545                 550                 555                 560
Ala Leu Glu Phe Val Lys Tyr Ile Asn Ser Lys Leu Pro Gly Leu Leu
            565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
            595                 600                 605
```

| | | | | | | | | | | | |
|---|---|---|---|---|---|---|---|---|---|---|---|
|Leu|Glu|Ile|Val|Arg|Arg|Asp|Trp|Ser|Glu|Ile|Ala|Lys|Glu|Thr|Gln|
| |610| | | |615| | | |620| | | | | | |

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 29
<211> LENGTH: 2328
<212> TYPE: DNA
<213> ORGANISM: Artificial
<220> FEATURE:
<223> OTHER INFORMATION: Clone sequence

<400> SEQUENCE: 29

```
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240
accgtgtgga aactttattt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat tctcaggat tatcagggag     600
aaggaccctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaattttg gaaagccaaa ggagaaggta tacgccgacg agatagcaaa agcctgggaa     900
agtggagaga accttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
```

```
ctcagggaga gctacacagg tggattcgtt aaagagccag aaaaggggtt gtgggaaggc    1200
atcgtttatc tagattttat agccctatat ccttcgatta taattaccca caatgtttct    1260
cccgatactc taaatcttga gggatgcaag aactatgata tcgctcctca agtaggccac    1320
aagttctgca aggacatccc tggttttata ccaagtctct tgggacattt gttagaggaa    1380
agacaaaaga ttaaggcaaa aatgaaggaa actcaggatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtcttcacgc aactatccca ggaggagaaa gtgaggagat caagaaaaag    1680
gctctagaat ttgtaaaata cataaattca agctccctg actgctcga gcttgaatat    1740 gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa                2328
```

<210> SEQ ID NO 30
<211> LENGTH: 775
<212> TYPE: PRT
<213> ORGANISM: Artificial
<220> FEATURE:
<223> OTHER INFORMATION: Clone sequence

<400> SEQUENCE: 30

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160
```

-continued

Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
    370                 375                 380
Tyr Thr Gly Gly Phe Val Lys Glu Pro Glu Lys Gly Leu Trp Glu Gly
385                 390                 395                 400
Ile Val Tyr Leu Asp Phe Ile Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Ala Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu His Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys

|  |  |  | 580 |  |  |  |  | 585 |  |  |  |  | 590 |  |
|---|---|---|---|---|---|---|---|---|---|---|---|---|---|---|
| Lys | Arg | Tyr | Ala | Val | Ile | Asp | Glu | Glu | Gly | Lys | Val | Ile | Thr | Arg | Gly |
|  |  | 595 |  |  |  |  | 600 |  |  |  |  | 605 |  |  |

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
    755                 760                 765

Trp Leu Asn Ile Lys Lys Ser
770                 775

<210> SEQ ID NO 31
<211> LENGTH: 2328
<212> TYPE: DNA
<213> ORGANISM: Artificial
<220> FEATURE:
<223> OTHER INFORMATION: Clone sequence

<400> SEQUENCE: 31

```
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240
accgtgtgga actttatttt ggaacatcct caggatcagc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gcgatcgcga ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggaccctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaattttg aaagccaaa ggagaaggta tacgccgacg agatagcaaa gcctgggaa       900
agtggagaga acctttgagag agttgccaaa tactcgatga agatgcaaa ggcaacttat     960
```

```
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggaaggc    1200
atcgtttatc tagattttat agccctatat ccttcgatta taattaccca caatgtttct    1260
cccgatactc taaatcttga gggatgcgag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaggatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg ggaagaaag    1560
tacatcgagt tagtatggaa ggagctcgaa gaaaagtttg gatttaaagt cctctacatt    1620
gacactgatg gtcttcacgc aactatccca ggaggagaaa gtgaggagat caagaaaag    1680
gctctagaat ttgtaaaata cataaattca aagctccctg gactgctcga gcttgaatat    1740
gaagggtttt ataagagggg attcttcgtt acgaagaaga ggtatgcagt aatagatgaa    1800
gaaggaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caagaaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa               2328
```

<210> SEQ ID NO 32
<211> LENGTH: 775
<212> TYPE: PRT
<213> ORGANISM: Artificial
<220> FEATURE:
<223> OTHER INFORMATION: Clone sequence

<400> SEQUENCE: 32

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

```
Met Glu Gly Glu Glu Glu Leu Lys Ile Leu Ala Phe Ala Ile Ala Thr
130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
    370                 375                 380
Tyr Thr Gly Gly Phe Val Lys Glu Pro Glu Lys Gly Leu Trp Glu Gly
385                 390                 395                 400
Ile Val Tyr Leu Asp Phe Ile Ala Leu Tyr Pro Ser Ile Ile Thr
                405                 410                 415
His Asn Val Ser Pro Asp Thr Leu Asn Leu Glu Gly Cys Glu Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu His Ala Thr Ile Pro Gly Gly Glu Ser Glu Glu Ile Lys Lys Lys
545                 550                 555                 560
```

```
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 33
<211> LENGTH: 2328
<212> TYPE: DNA
<213> ORGANISM: Artificial
<220> FEATURE:
<223> OTHER INFORMATION: Clone sequence

<400> SEQUENCE: 33
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacgggga  aaggcatgga    180 aagattgtga gaattgttga tgtagagaag gttgagaaaa gtttctcgg  caagcctatt    240 accgtgtgga actttatttt ggaacatcct caggatcagc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggaccctg acattatagt tacttataat ggagactcat cgacttccc  atatttagcg    660 aaaaggggcag aaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
```

```
gcaattttgg gaaagccaaa ggagaaggta tacgccgacg agatagcaaa agcctgggaa    900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaagac   1200
ctcgtttatc tagattttat agctctatat ccctcgatta taattaccca caatgttttct  1260 cctgatactc taaatcttga gggatgcaag aactatgata tcgctcctca agtaggccac   1320
aagttctgca aggacatccc tggttttata ccaagtctct gggacattt gttagaggaa    1380 agacaaaaga ttaagacaaa aatgaaggaa actcaggatc ctatagaaaa aatactcctt   1440
gactatagac aaaagcgat aaaactctta gcaaattctt tctacggata ttatggctat    1500 gcaaagcaa gatggtactg taaggagtgt gctgagagcg ttactgcctg gggaaggaag    1560
tacatcgagt tagtatggaa ggagctcgaa gaaaagtttg gatttaaagt catctacatt   1620
gacactgatg gtcttcacgc aactatccca ggaggagaaa gtgaggagat caagaaaaag   1680
gctctcgaat ttgtaaaata cataaattca aagctccctg gactgctcga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa               2328
```

<210> SEQ ID NO 34
<211> LENGTH: 775
<212> TYPE: PRT
<213> ORGANISM: Artificial
<220> FEATURE:
<223> OTHER INFORMATION: Clone sequence

<400> SEQUENCE: 34

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr

```
                    100                 105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Ala Ile Ala Thr
130                 135                 140
Leu Tyr His Glu Gly Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Glu Tyr Gln Arg Arg Leu Arg Glu Ser
            370                 375                 380
Tyr Thr Gly Gly Phe Val Lys Glu Pro Glu Lys Gly Leu Trp Glu Asp
385                 390                 395                 400
Leu Val Tyr Leu Asp Phe Ile Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
            515                 520                 525
```

```
Leu Glu Glu Lys Phe Gly Phe Lys Val Ile Tyr Ile Asp Thr Asp Gly
530                 535                 540

Leu His Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
                595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
                675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Arg Gln Val Gly Leu Thr Ser
                755                 760                 765

Trp Leu Asn Ile Lys Lys Ser
770                 775

<210> SEQ ID NO 35
<211> LENGTH: 2328
<212> TYPE: DNA
<213> ORGANISM: Artificial
<220> FEATURE:
<223> OTHER INFORMATION: Clone sequence

<400> SEQUENCE: 35
atgattttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga aattgttga  tgtagagaag gttgagaaaa gtttctcgg  caagcctatt    240 accgtgtgga aactttattt ggaacatcct caggatcagc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat tctctcaggat tatcagggag    600 aaggaccctg acattatagt tactctataat ggagactcat tcgacttccc atatttagcg    660
```

```
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg gaaagccaaa ggagaaggta tacgccgacg agatagcaaa agcctgggaa     900
agtggagaga accttgagag agttgccaaa tactcgatgg aagatgcaaa ggcaacttat    960
gaactcggga agaattcct tccaatgaa attcagctct caagattaat tggacaacct     1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggacgac   1200
atcgtttatc tagatttcat agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct gggacatttt gttagaggaa   1380
agacaaaaga ttaagacaaa aatgaaggaa actcaggatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tatatcgagt tagtatggaa ggagctcgaa gaaaagtttg gatttaaggt cctctacatc   1620
gacactgatg gtcttcacgc aactatccca ggaggagaaa gtgaggagat caaaaaaacg   1680
gctctagaat ttgtaaaata cataaaattca aagctccctg gactgctcga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa                2328
```

<210> SEQ ID NO 36
<211> LENGTH: 775
<212> TYPE: PRT
<213> ORGANISM: Artificial
<220> FEATURE:
<223> OTHER INFORMATION: Clone sequence

<400> SEQUENCE: 36

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

```
Thr Val Trp Lys Leu Tyr Leu Glu His Pro Gln Asp Gln Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Glu Leu Lys Ile Leu Ala Phe Ala Ile Ala Thr
            130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Arg Glu Met Ile Lys
                180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Ile Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Asp Asp
385                 390                 395                 400

Ile Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
```

```
                500             505             510
Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
        530                 535                 540

Leu His Ala Thr Ile Pro Gly Gly Glu Ser Glu Ile Lys Lys Thr
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
        770                 775

<210> SEQ ID NO 37
<211> LENGTH: 2328
<212> TYPE: DNA
<213> ORGANISM: Artificial
<220> FEATURE:
<223> OTHER INFORMATION: Clone sequence

<400> SEQUENCE: 37
atgattttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatcct caggatcagc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
```

```
gttgaggttg tatcaagcga gagagagatg ataaagagat ttctcaggat tatcagggag    600
aaggaccctg acattatagt tacttataat ggagactcat tcgacttccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg  gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagctct caagattaat tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggggt gtgggacgac    1200
atcgtttatc tagatttcat agccctatat ccctcgatta taattaccca caatgtttct    1260
cccgacactc taaatcttga gggatgcaag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaggatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtcttctcgc aactatccca ggaggagaaa gtgaggagat caagaaaaag    1680
gctctcgaat ttgtaaaata cataaattca aagctccctg gactgctcga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa               2328
```

<210> SEQ ID NO 38  
<211> LENGTH: 775  
<212> TYPE: PRT  
<213> ORGANISM: Artificial  
<220> FEATURE:  
<223> OTHER INFORMATION: Clone sequence

<400> SEQUENCE: 38

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45
```

```
Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Gln Pro Thr Ile
                    85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Ala Ile Ala Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Ile Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Asp Asp
385                 390                 395                 400

Ile Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480
```

```
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Lys Tyr Ile Glu Leu Val Trp Lys Glu
    515                 520                 525
Leu Glu Glu Lys Phe Gly Phe Lys Val Leu Tyr Ile Asp Thr Asp Gly
530                 535                 540
Leu Leu Ala Thr Ile Pro Gly Gly Glu Ser Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Gly Lys Val Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 39
<211> LENGTH: 2328
<212> TYPE: DNA
<213> ORGANISM: Artificial
<220> FEATURE:
<223> OTHER INFORMATION: Clone sequence

<400> SEQUENCE: 39
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacgggga aaggcatgga     180 aagattgtga gaattgttga tgtagagaag gttgagaaaa agtttctcgg caagcctatt     240
accgtgtgga aactttattt ggaacatcct caggatcagc ccactattag agaaaaagtt     300
agagaacatc cagcagttgt ggacatcttc gaatacgata ttccatttgc aaagagatac     360
```

```
ctcatcgaca aaggcctaat accaatggag ggggaagaag agctaaagat tcttgccttc     420
gcgatcgcga ccctctatca cgaaggagaa gagtttggaa aagcccaat  tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggaccctg acattatagt tacttataat ggagactcat tcgacttccc atatttagcg    660
aaaagggcag aaaacttgg  gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg  gaaagccaaa ggagaaggta tacgccgacg atagcaaa   agcctgggaa    900
agtggagaga accttgagag agttgccaaa tactcgatgg aagatgcaaa ggcaacttat    960
gaactcggga agaattcct  tccaatggaa attcagctct caagattaat tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaagggggtt gtgggacgac   1200
atcgtttatc tagatttcat agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaggatc ctatagaaaa aatactcctt   1440
gaccatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggag ggagctcgaa gaaaagtttg gatttaaagt cctctacatt   1620
gacactgatg gtcttcacgc aactatccca ggaggagaaa gtgaggagat caagaaaaag   1680
gctctagaat ttgtaaaata cataaattca agctccctg  gactgctcga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt  aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa atcctaa                 2328
```

<210> SEQ ID NO 40
<211> LENGTH: 775
<212> TYPE: PRT
<213> ORGANISM: Artificial
<220> FEATURE:
<223> OTHER INFORMATION: Clone sequence

<400> SEQUENCE: 40

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
```

```
                 20                  25                  30
Thr Phe Arg Pro Tyr Ile Tyr Ala Leu Leu Arg Asp Asp Ser Lys Ile
             35                  40                  45
Glu Glu Val Lys Lys Ile Thr Gly Glu Arg His Gly Lys Ile Val Arg
         50                  55                  60
Ile Val Asp Val Glu Lys Val Glu Lys Lys Phe Leu Gly Lys Pro Ile
 65                  70                  75                  80
Thr Val Trp Lys Leu Tyr Leu Glu His Pro Gln Asp Gln Pro Thr Ile
                 85                  90                  95
Arg Glu Lys Val Arg Glu His Pro Ala Val Val Asp Ile Phe Glu Tyr
            100                 105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Ala Ile Ala Thr
            130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Ile Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Tyr Gln Arg Arg Leu Arg Glu Ser
            370                 375                 380
Tyr Thr Gly Gly Phe Val Lys Glu Pro Glu Lys Gly Leu Trp Asp Asp
385                 390                 395                 400
Ile Val Tyr Leu Asp Phe Ile Ala Leu Tyr Pro Ser Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
```

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp His Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Arg Glu
        515                 520                 525

Leu Glu Glu Lys Phe Gly Phe Lys Val Leu Tyr Ile Asp Thr Asp Gly
    530                 535                 540

Leu His Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 41
<211> LENGTH: 2328
<212> TYPE: DNA
<213> ORGANISM: Artificial
<220> FEATURE:
<223> OTHER INFORMATION: Clone sequence

<400> SEQUENCE: 41
atgattttag atgtggatta cataactgaa gaaggaaaac ctgttattag gctattcaaa    60
aaagagaacg gaaaatttaa gatagagcat gatagaactt ttagaccata catttacgct   120
cttctcaggg atgattcaaa gattgaagaa gttaagaaaa taacggggga aaggcatgga   180
aagattgtga gaattgttga tgtagagaag gttgagaaaa agtttctcgg caagcctatt   240

```
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggaccctg acattatagt tacttataat ggagactcat tcgacttccc atatttagcg    660
aaaagggcag aaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaagac   1200
ctcgtttatc tagattttat agctctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct gggacatttt gttagaggaa   1380
agacaaaaga ttaagacaaa aatgaaggaa actcatgatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggaagaaag    1560 tacatcgagt tagtatggaa ggagctcgaa gaaaagtttg gatttaaagt cctctacatt   1620
gacactgatg gcctctatgc aactatccca ggaggagaaa gtgaggaaat aaagaaaaag   1680
gctctcgaat ttgtaaaata cataaattca agctccctg gactgctaga gcttgaatat    1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caagaaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcctaa               2328
```

<210> SEQ ID NO 42
<211> LENGTH: 775
<212> TYPE: PRT
<213> ORGANISM: Artificial
<220> FEATURE:
<223> OTHER INFORMATION: Clone sequence

<400> SEQUENCE: 42

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asp
385                 390                 395                 400

Leu Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr 420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
        450                 455                 460
Lys Thr Lys Met Lys Glu Thr His Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
        610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
        690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 43
<211> LENGTH: 2328
<212> TYPE: DNA
<213> ORGANISM: Artificial
<220> FEATURE:
<223> OTHER INFORMATION: Clone sequence

<400> SEQUENCE: 43
atgattttag atgtggatta cataactgaa gaaggaaaac ctgttattag gctattcaaa        60

```
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gcgatcgcga ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggaccctg acattatagt tacttataat ggagactcat tcgacttccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagctct caagattaat tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggacgac    1200
atcgtttatc tagatttcat agccctatat ccctcgatta taattaccca caatgtttct    1260
cccgatactc taaatcttga gggatgcaag aactatgata tcgctcctca gtaggccac    1320 aagttctgca aggacatccc tggttttata ccaagtctct tgggacattt gttagaggaa    1380
agacaaaaga ttaagacaaa aatgaaggaa actcaggatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gcctctatgc aactatccca ggaggagaaa gtgaggaaat aaagaaaaag    1680
gctctcgaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa               2328

<210> SEQ ID NO 44
<211> LENGTH: 775
<212> TYPE: PRT
```

<213> ORGANISM: Artificial
<220> FEATURE:
<223> OTHER INFORMATION: Clone sequence

<400> SEQUENCE: 44

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Ile Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Asp Asp
385                 390                 395                 400
```

Ile Val Tyr Leu Asp Phe Ile Ala Leu Tyr Pro Ser Ile Ile Thr
            405                 410                 415

His Asn Val Ser Pro Asp Thr Leu Asn Leu Glu Gly Cys Lys Asn Tyr
        420                 425                 430

Asp Ile Ala Pro Gln Val Gly His Lys Phe Cys Lys Asp Ile Pro Gly
    435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 45
<211> LENGTH: 2328
<212> TYPE: DNA
<213> ORGANISM: Artificial
<220> FEATURE:
<223> OTHER INFORMATION: Clone sequence

<400> SEQUENCE: 45

```
atgattttag atgtggatta cataactgaa gaaggaaaac ctgttattag gctattcaaa         60
aaagagaacg gaaaatttaa gatagagcat gatagaactt ttagaccata catttacgct        120
cttctcaggg atgattcaaa gattgaagaa gttaagaaaa taacggggga aaggcatgga        180
aagattgtga gaattgttga tgtagagaag gttgagaaaa agtttctcgg caagcctatt        240
accgtgtgga aactttattt ggaacatccc caagatgttc ccactattag agaaaaagtt        300
agagaacatc cagcagttgt ggacatcttc gaatacgata ttccatttgc aaagagatac        360
ctcatcgaca aaggcctaat accaatggag ggggaagaag agctaaagat tcttgccttc        420
gcgatcgcga ccctctatca cgaaggagaa gagtttggaa aaggcccaat tataatgatt        480
agttatgcag atgaaaatga agcaaaggtg attacttgga aaaacataga tcttccatac        540
gttgaggttg tatcaagcga gagagagatg ataaagagat ttctcaggat tatcagggag        600
aaggaccctg acattatagt tacttataat ggagactcat tcgacttccc atatttagcg        660
aaaagggcag aaaaacttgg gattaaatta accattggaa gagatggaag cgagcccaag        720
atgcagagaa taggcgatat gacggctgta gaagtcaagg gaagaataca tttcgacttg        780
tatcatgtaa taacaaggac aataaatctc ccaacataca cactagaggc tgtatatgaa        840
gcaatttttg gaaagccaaa ggagaaggta tacgccgacg agatagcaaa agcctgggaa        900
agtggagaga accttgagag agttgccaaa tactcgatgg aagatgcaaa ggcaacttat        960
gaactcggga agaattcct tccaatgaaa attcagcttt caagattagt tggacaacct       1020
ttatgggatg tttcaaggtc aagcacaggg aaccttgtag agtggttctt acttaggaaa       1080
gcctacgaaa gaacgaagt agctccaaac aagccaagtg aagaggagta tcaaagaagg       1140
ctcagggaga gctacacagg tggattcgtt aaagagccag aaaaggggtt gtgggaaggc       1200
atcgtttatc tagattttat agccctatat ccttcgatta taattaccca caatgtttct       1260
cccgatactc taaatcttga gggatgcaag aactatgata tcgctcctca gtaggccac       1320
aagttctgca aggacatccc tggttttata ccaagtctct tgggacattt gttagaggaa       1380
agacaaaaga ttaagacaaa aatgaaggaa actcaggatc ctatagaaaa aatactcctt       1440
gactatagac aaaaagcgat aaaactctta gcaaattctt tctacggata ttatggctat       1500
gcaaaagcaa gatggtactg taaggagtgt gctgagagcg ttactgcctg ggaagaaag       1560
tacatcgagt tagtatggaa ggagctcgaa gaaaagtttg gatttaaagt cctctacatt       1620
gacactgatg gcctctatgc aactatccca ggaggagaaa gtgaggaaat aaagaaaaag       1680
gctctcgaat ttgtaaaata cataaattca aagctccctg gactgctaga gcttgaatat       1740
gaaggttttt ataagagggg attcttcgtt acgaagaaga ggtatgcagt aatagatgaa       1800
gaaggaaaag tcattactcg tggtttagag atagttagga gagattggag tgaaattgca       1860
aaagaaactc aagctagagt tttggagaca atactaaaac acggagatgt tgaagaagct       1920
gtgagaatag taaaagaagt aatacaaaag cttgccaatt atgaaattcc accagagaag       1980
ctcgcaatat atgagcagat aacaagacca ttacatgagt ataaggcgat aggtcctcac       2040
gtagctgttg caaagaaact agctgctaaa ggagttaaaa taaagccagg aatggtaatt       2100
ggatacatag tacttagagg cgatggtcca attagcaata gggcaattct agctgaggaa       2160
tacgatccca aaaagcacaa gtatgacgca gaatattaca ttgagaacca ggttcttcca       2220
gcggtactta ggatattgga gggatttgga tacagaaagg aagacctcag ataccaaaag       2280
acaagacaag tcggcctaac ttcctggctt aacattaaaa aatcctaa                    2328
```

<210> SEQ ID NO 46
<211> LENGTH: 775
<212> TYPE: PRT
<213> ORGANISM: Artificial
<220> FEATURE:
<223> OTHER INFORMATION: Clone sequence

<400> SEQUENCE: 46

| Met | Ile | Leu | Asp | Val | Asp | Tyr | Ile | Thr | Glu | Glu | Gly | Lys | Pro | Val | Ile |
|---|---|---|---|---|---|---|---|---|---|---|---|---|---|---|---|
| 1 | | | | 5 | | | | | 10 | | | | | 15 | |

| Arg | Leu | Phe | Lys | Lys | Glu | Asn | Gly | Lys | Phe | Lys | Ile | Glu | His | Asp | Arg |
| | | | 20 | | | | | 25 | | | | | 30 | | |

| Thr | Phe | Arg | Pro | Tyr | Ile | Tyr | Ala | Leu | Leu | Arg | Asp | Asp | Ser | Lys | Ile |
| | | 35 | | | | | 40 | | | | | 45 | | | |

| Glu | Glu | Val | Lys | Lys | Ile | Thr | Gly | Glu | Arg | His | Gly | Lys | Ile | Val | Arg |
| | 50 | | | | | 55 | | | | | 60 | | | | |

| Ile | Val | Asp | Val | Glu | Lys | Val | Glu | Lys | Phe | Leu | Gly | Lys | Pro | Ile |
| 65 | | | | 70 | | | | | 75 | | | | | 80 |

| Thr | Val | Trp | Lys | Leu | Tyr | Leu | Glu | His | Pro | Gln | Asp | Val | Pro | Thr | Ile |
| | | | 85 | | | | | 90 | | | | | 95 | | |

| Arg | Glu | Lys | Val | Arg | Glu | His | Pro | Ala | Val | Val | Asp | Ile | Phe | Glu | Tyr |
| | | | 100 | | | | | 105 | | | | | 110 | | |

| Asp | Ile | Pro | Phe | Ala | Lys | Arg | Tyr | Leu | Ile | Asp | Lys | Gly | Leu | Ile | Pro |
| | | 115 | | | | | 120 | | | | | 125 | | | |

| Met | Glu | Gly | Glu | Glu | Gly | Leu | Lys | Ile | Leu | Ala | Phe | Ala | Ile | Ala | Thr |
| | 130 | | | | | 135 | | | | | 140 | | | | |

| Leu | Tyr | His | Glu | Gly | Glu | Glu | Phe | Gly | Lys | Gly | Pro | Ile | Ile | Met | Ile |
| 145 | | | | 150 | | | | | 155 | | | | | 160 |

| Ser | Tyr | Ala | Asp | Glu | Asn | Glu | Ala | Lys | Val | Ile | Thr | Trp | Lys | Asn | Ile |
| | | | 165 | | | | | 170 | | | | | 175 | | |

| Asp | Leu | Pro | Tyr | Val | Glu | Val | Val | Ser | Ser | Arg | Glu | Met | Ile | Lys |
| | | | 180 | | | | | 185 | | | | | 190 | |

| Arg | Phe | Leu | Arg | Ile | Ile | Arg | Glu | Lys | Asp | Pro | Asp | Ile | Ile | Val | Thr |
| | | 195 | | | | | 200 | | | | | 205 | | | |

| Tyr | Asn | Gly | Asp | Ser | Phe | Asp | Phe | Pro | Tyr | Leu | Ala | Lys | Arg | Ala | Glu |
| | 210 | | | | | 215 | | | | | 220 | | | | |

| Lys | Leu | Gly | Ile | Lys | Leu | Thr | Ile | Gly | Arg | Asp | Gly | Ser | Glu | Pro | Lys |
| 225 | | | | 230 | | | | | 235 | | | | | 240 |

| Met | Gln | Arg | Ile | Gly | Asp | Met | Thr | Ala | Val | Glu | Val | Lys | Gly | Arg | Ile |
| | | | 245 | | | | | 250 | | | | | 255 | | |

| His | Phe | Asp | Leu | Tyr | His | Val | Ile | Thr | Arg | Thr | Ile | Asn | Leu | Pro | Thr |
| | | | 260 | | | | | 265 | | | | | 270 | | |

| Tyr | Thr | Leu | Glu | Ala | Val | Tyr | Glu | Ala | Ile | Phe | Gly | Lys | Pro | Lys | Glu |
| | | 275 | | | | | 280 | | | | | 285 | | | |

| Lys | Val | Tyr | Ala | Asp | Glu | Ile | Ala | Lys | Ala | Trp | Glu | Ser | Gly | Glu | Asn |
| | 290 | | | | | 295 | | | | | 300 | | | | |

| Leu | Glu | Arg | Val | Ala | Lys | Tyr | Ser | Met | Glu | Asp | Ala | Lys | Ala | Thr | Tyr |
| 305 | | | | 310 | | | | | 315 | | | | | 320 |

| Glu | Leu | Gly | Lys | Glu | Phe | Leu | Pro | Met | Glu | Ile | Gln | Leu | Ser | Arg | Leu |
| | | | 325 | | | | | 330 | | | | | 335 | | |

| Val | Gly | Gln | Pro | Leu | Trp | Asp | Val | Ser | Arg | Ser | Ser | Thr | Gly | Asn | Leu |
| | | | 340 | | | | | 345 | | | | | 350 | | |

| Val | Glu | Trp | Phe | Leu | Leu | Arg | Lys | Ala | Tyr | Glu | Arg | Asn | Glu | Val | Ala |
| | | 355 | | | | | 360 | | | | | 365 | | | |

```
Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Gly
385                 390                 395                 400

Ile Val Tyr Leu Asp Phe Ile Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775

<210> SEQ ID NO 47
```

<211> LENGTH: 2328
<212> TYPE: DNA
<213> ORGANISM: Artificial
<220> FEATURE:
<223> OTHER INFORMATION: Clone sequence

<400> SEQUENCE: 47

| | | | | | |
|---|---|---|---|---|---|
| atgattttag | atgtggatta | cataactgaa | gaaggaaaac | ctgttattag gctattcaaa | 60 |
| aaagagaacg | gaaaatttaa | gatagagcat | gatagaactt | ttagaccata catttacgct | 120 |
| cttctcaggg | atgattcaaa | gattgaagaa | gttaagaaaa | taacggggga aaggcatgga | 180 |
| aagattgtga | gaattgttga | tgtagagaag | gttgagaaaa | agtttctcgg caagcctatt | 240 |
| accgtgtgga | aactttattt | ggaacatccc | caagatgttc | ccactattag agaaaaagtt | 300 |
| agagaacatc | cagcagttgt | ggacatcttc | gaatacgata | ttccatttgc aaagagatac | 360 |
| ctcatcgaca | aaggcctaat | accaatggag | ggggaagaag | agctaaagat tcttgccttc | 420 |
| gcgatcgcga | ccctctatca | cgaaggagaa | gagtttggaa | aaggcccaat tataatgatt | 480 |
| agttatgcag | atgaaaatga | agcaaaggtg | attacttgga | aaaacataga tcttccatac | 540 |
| gttgaggttg | tatcaagcga | gagagagatg | ataaagagat | ttctcaggat tatcagggag | 600 |
| aaggaccctg | acattatagt | tacttataat | ggagactcat | tcgacttccc atatttagcg | 660 |
| aaaagggcag | aaaacttggg | gattaaatta | accattggaa | gagatggaag cgagcccaag | 720 |
| atgcagagaa | taggcgatat | gacggctgta | gaagtcaagg | gaagaataca tttcgacttg | 780 |
| tatcatgtaa | taacaaggac | aataaatctc | ccaacataca | cactagaggc tgtatatgaa | 840 |
| gcaattttg | gaaagccaaa | ggagaaggta | tacgccgacg | agatagcaaa agcctgggaa | 900 |
| agtggagaga | acccttgagag | agttgccaaa | tactcgatgg | aagatgcaaa ggcaacttat | 960 |
| gaactcggga | agaattcct | tccaatggaa | attcagcttt | caagattagt tggacaacct | 1020 |
| ttatgggatg | tttcaaggtc | aagcacaggg | aaccttgtag | agtggttctt acttaggaaa | 1080 |
| gcctacgaaa | gaaacgaagt | agctccaaac | aagccaagtg | aagaggagta tcaaagaagg | 1140 |
| ctcagggaga | gctacacagg | tggattcgtt | aaagagccag | aaaaggggtt gtgggacggc | 1200 |
| ctggcttatc | tagattttat | agccctatac | ccctcgatta | tagttaccca caatgtttct | 1260 |
| cccgatactc | taaatcttga | gggatgcaag | aactatgata | tcgctcctca agtaggccac | 1320 |
| aagttctgca | aggacatccc | tggttttata | ccaagtctct | tgggacattt gttagaggaa | 1380 |
| agacaaaaga | ttaagacaaa | aatgaaggaa | actcaggatc | ctatagaaaa aatactcctt | 1440 |
| gactatagac | aaaaagcgat | aaaactctta | gcaaattctt | tctacggata ttatggctat | 1500 |
| gcaaaagcaa | gatggtactg | taaggagtgt | gctgagagcg | ttactgcctg gggaagaaag | 1560 |
| tacatcgagt | tagtatggaa | ggagctcgaa | gaaaagtttg | gatttaaagt cctctacatt | 1620 |
| gacactgatg | gcctctatgc | aactatccca | ggaggagaaa | gtgaggaaat aaagaaaaag | 1680 |
| gctctcgaat | ttgtaaaata | cataaattca | agctccctg | gactgctaga gcttgaatat | 1740 |
| gaagggtttt | ataagagggg | attcttcgtt | acgaagaaga | ggtatgcagt aatagatgaa | 1800 |
| gaaggaaaag | tcattactcg | tggtttagag | atagttagga | gagattggag tgaaattgca | 1860 |
| aaagaaactc | aagctagagt | tttggagaca | atactaaaac | acggagatgt tgaagaagct | 1920 |
| gtgagaatag | taaagaagt | aatacaaaag | cttgccaatt | atgaaattcc accagagaag | 1980 |
| ctcgcaatat | atgagcagat | aacaagacca | ttacatgagt | ataaggcgat aggtcctcac | 2040 |
| gtagctgttg | caaagaaact | agctgctaaa | ggagttaaaa | taaagccagg aatggtaatt | 2100 |
| ggatacatag | tacttagagg | cgatggtcca | attagcaata | gggcaattct agctgaggaa | 2160 |

```
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctaa                 2328

<210> SEQ ID NO 48
<211> LENGTH: 775
<212> TYPE: PRT
<213> ORGANISM: Artificial
<220> FEATURE:
<223> OTHER INFORMATION: Clone sequence

<400> SEQUENCE: 48
```

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu

```
                340                 345                 350
Val Glu Trp Phe Leu Leu Arg Lys Ala Tyr Glu Arg Asn Glu Val Ala
            355                 360                 365
Pro Asn Lys Pro Ser Glu Glu Glu Tyr Gln Arg Arg Leu Arg Glu Ser
        370                 375                 380
Tyr Thr Gly Gly Phe Val Lys Glu Pro Glu Lys Gly Leu Trp Asp Gly
385                 390                 395                 400
Leu Ala Tyr Leu Asp Phe Ile Ala Leu Tyr Pro Ser Ile Ile Val Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
```

Trp Leu Asn Ile Lys Lys Ser
    770             775

<210> SEQ ID NO 49
<211> LENGTH: 48
<212> TYPE: DNA
<213> ORGANISM: Artificial
<220> FEATURE:
<223> OTHER INFORMATION: Oligonucleotide primer

<400> SEQUENCE: 49
caggaaacag ctatgaccat atgattttag atgtggatta cataactg                    48

<210> SEQ ID NO 50
<211> LENGTH: 44
<212> TYPE: DNA
<213> ORGANISM: Artificial
<220> FEATURE:
<223> OTHER INFORMATION: Oligonucleotide primer

<400> SEQUENCE: 50
agtagcggcg tcgacttagg attttttaat gttaagccag gaag                        44

<210> SEQ ID NO 51
<211> LENGTH: 38
<212> TYPE: DNA
<213> ORGANISM: Artificial
<220> FEATURE:
<223> OTHER INFORMATION: Oligonucleotide primer

<400> SEQUENCE: 51 gttgttttc taatccgcat gtgatcaatt caaggccg                                38

<210> SEQ ID NO 52
<211> LENGTH: 38
<212> TYPE: DNA
<213> ORGANISM: Artificial
<220> FEATURE:
<223> OTHER INFORMATION: Oligonucleotide primer

<400> SEQUENCE: 52
cggccttgaa ttgatcacat gcggattaga aaacaac                                38

<210> SEQ ID NO 53
<211> LENGTH: 48
<212> TYPE: DNA
<213> ORGANISM: Artificial
<220> FEATURE:
<223> OTHER INFORMATION: Oligonucleotide primer

<400> SEQUENCE: 53
ctaaagattc ttgccttcgc gatcgcgacc ctctatcacg aaggagaa                    48

<210> SEQ ID NO 54
<211> LENGTH: 48
<212> TYPE: DNA
<213> ORGANISM: Artificial
<220> FEATURE:
<223> OTHER INFORMATION: Oligonucleotide primer

<400> SEQUENCE: 54
ttctccttcg tgatagaggg tcgcgatcgc gaaggcaaga atctttag                    48

<210> SEQ ID NO 55
<211> LENGTH: 47
<212> TYPE: DNA
<213> ORGANISM: Artificial

<220> FEATURE:
<223> OTHER INFORMATION: Oligonucleotide primer

<400> SEQUENCE: 55
gaggaaataa agaaaaaggc tctcgaattt gtaaaataca taaattc					47

<210> SEQ ID NO 56
<211> LENGTH: 47
<212> TYPE: DNA
<213> ORGANISM: Artificial
<220> FEATURE:
<223> OTHER INFORMATION: Oligonucleotide primer

<400> SEQUENCE: 56
gaatttatgt attttacaaa ttcgagagcc ttttcttta tttcctc					47

<210> SEQ ID NO 57
<211> LENGTH: 37
<212> TYPE: DNA
<213> ORGANISM: Artificial
<220> FEATURE:
<223> OTHER INFORMATION: Oligonucleotide primer

<400> SEQUENCE: 57
ctacattgac actgatggcc tctatgcaac tatccca					37

<210> SEQ ID NO 58
<211> LENGTH: 37
<212> TYPE: DNA
<213> ORGANISM: Artificial
<220> FEATURE:
<223> OTHER INFORMATION: Oligonucleotide primer

<400> SEQUENCE: 58
tgggatagtt gcatagaggc catcagtgtc aatgtag					37

<210> SEQ ID NO 59
<211> LENGTH: 43
<212> TYPE: DNA
<213> ORGANISM: Artificial
<220> FEATURE:
<223> OTHER INFORMATION: Oligonucleotide primer

<400> SEQUENCE: 59
caggattatc agggagaagg accctgacat tatagttact tat					43

<210> SEQ ID NO 60
<211> LENGTH: 43
<212> TYPE: DNA
<213> ORGANISM: Artificial
<220> FEATURE:
<223> OTHER INFORMATION: Oligonucleotide primer

<400> SEQUENCE: 60
ataagtaact ataatgtcag ggtccttctc cctgataatc ctg					43

<210> SEQ ID NO 61
<211> LENGTH: 44
<212> TYPE: DNA
<213> ORGANISM: Artificial
<220> FEATURE:
<223> OTHER INFORMATION: Oligonucleotide primer

<400> SEQUENCE: 61
gacaaaaatg aaggaaactc aggatcctat agaaaaaata ctcc					44

<210> SEQ ID NO 62
<211> LENGTH: 44
<212> TYPE: DNA
<213> ORGANISM: Artificial
<220> FEATURE:
<223> OTHER INFORMATION: Oligonucleotide primer

<400> SEQUENCE: 62
ggagtatttt ttctatagga tcctgagttt ccttcatttt tgtc     44

<210> SEQ ID NO 63
<211> LENGTH: 50
<212> TYPE: DNA
<213> ORGANISM: Artificial
<220> FEATURE:
<223> OTHER INFORMATION: Oligonucleotide primer

<400> SEQUENCE: 63
gaaactttat ttggaacatc ctcaggatca gcccactatt agagaaaaag     50

<210> SEQ ID NO 64
<211> LENGTH: 50
<212> TYPE: DNA
<213> ORGANISM: Artificial
<220> FEATURE:
<223> OTHER INFORMATION: Oligonucleotide primer

<400> SEQUENCE: 64
cttttctctc taatagtgggc tgatcctgag gatgttccaa ataaagtttc     50

<210> SEQ ID NO 65
<211> LENGTH: 38
<212> TYPE: DNA
<213> ORGANISM: Artificial
<220> FEATURE:
<223> OTHER INFORMATION: Oligonucleotide primer

<400> SEQUENCE: 65
caaagctccc tggactgctc gagcttgaat atgaaggg     38

<210> SEQ ID NO 66
<211> LENGTH: 38
<212> TYPE: DNA
<213> ORGANISM: Artificial
<220> FEATURE:
<223> OTHER INFORMATION: Oligonucleotide primer

<400> SEQUENCE: 66
cccttcatat tcaagctcga gcagtccagg gagctttg     38

<210> SEQ ID NO 67
<211> LENGTH: 48
<212> TYPE: DNA
<213> ORGANISM: Artificial
<220> FEATURE:
<223> OTHER INFORMATION: Oligonucleotide primer

<400> SEQUENCE: 67
gaaaacatag tatacctaga tttctcgagc cctatatccc tcgattat     48

<210> SEQ ID NO 68
<211> LENGTH: 48
<212> TYPE: DNA
<213> ORGANISM: Artificial
<220> FEATURE:
<223> OTHER INFORMATION: Oligonucleotide primer

<400> SEQUENCE: 68
ataatcgagg gatatagggc tcgagaaatc taggtatact atgttttc        48

<210> SEQ ID NO 69
<211> LENGTH: 35
<212> TYPE: DNA
<213> ORGANISM: Artificial
<220> FEATURE:
<223> OTHER INFORMATION: Oligonucleotide primer

<400> SEQUENCE: 69
gagtaggtct ctaccccttt tctggctctt taacg        35

<210> SEQ ID NO 70
<211> LENGTH: 82
<212> TYPE: DNA
<213> ORGANISM: Artificial
<220> FEATURE:
<223> OTHER INFORMATION: Oligonucleotide primer

<400> SEQUENCE: 70
ggaaaggtct cagggttgtg gramrrcmts ryytmtctag attttagagc cctatatccc        60
tcgattatar ttacccacaa tg        82

<210> SEQ ID NO 71
<211> LENGTH: 84
<212> TYPE: DNA
<213> ORGANISM: Artificial
<220> FEATURE:
<223> OTHER INFORMATION: Oligonucleotide primer

<400> SEQUENCE: 71
ggaaaggtct cagacaaaaa gcgataaaac tcttagcaaa ttctttctac ggatatwwcg        60
gctatvcsaa agcaagatgg tact        84

<210> SEQ ID NO 72
<211> LENGTH: 44
<212> TYPE: DNA
<213> ORGANISM: Artificial
<220> FEATURE:
<223> OTHER INFORMATION: Oligonucleotide primer

<400> SEQUENCE: 72
gagtaggtct cttgtctata gtcaaggagt attttttcta tagg        44

<210> SEQ ID NO 73
<211> LENGTH: 73
<212> TYPE: DNA
<213> ORGANISM: Artificial
<220> FEATURE:
<223> OTHER INFORMATION: Oligonucleotide primer

<400> SEQUENCE: 73
gagtaggtct caggatagtt gcgwgargac catcagtgtc aatgtagagg actttaaatc        60 caaactttc ttc        73

<210> SEQ ID NO 74
<211> LENGTH: 56
<212> TYPE: DNA
<213> ORGANISM: Artificial
<220> FEATURE:
<223> OTHER INFORMATION: Oligonucleotide primer

<400> SEQUENCE: 74
ggaaaggtct ctatcccagg aggagaaagt gaggagatca agaaaaaggc tctaga        56

<210> SEQ ID NO 75

<400> SEQUENCE: 75

000

<210> SEQ ID NO 76
<211> LENGTH: 43
<212> TYPE: DNA
<213> ORGANISM: Artificial
<220> FEATURE:
<223> OTHER INFORMATION: Oligonucleotide primer

<400> SEQUENCE: 76
caggaaacag ctatgacaaa cgggaaagaa ttccttccaa tgg        43

<210> SEQ ID NO 77
<211> LENGTH: 44
<212> TYPE: DNA
<213> ORGANISM: Artificial
<220> FEATURE:
<223> OTHER INFORMATION: Oligonucleotide primer

<400> SEQUENCE: 77
gtaaaacgac ggccagtacc tctataggat cctgagtttc cttc        44

<210> SEQ ID NO 78
<211> LENGTH: 20
<212> TYPE: DNA
<213> ORGANISM: Artificial
<220> FEATURE:
<223> OTHER INFORMATION: Oligonucleotide primer

<400> SEQUENCE: 78
caggaaacag ctatgacaaa        20

<210> SEQ ID NO 79
<211> LENGTH: 44
<212> TYPE: DNA
<213> ORGANISM: Artificial
<220> FEATURE:
<223> OTHER INFORMATION: Oligonucleotide primer

<400> SEQUENCE: 79
gtaaaacgac ggccagtacc cttttcttcg agctccttcc atac        44

<210> SEQ ID NO 80
<211> LENGTH: 24
<212> TYPE: DNA
<213> ORGANISM: Artificial
<220> FEATURE:
<223> OTHER INFORMATION: Oligonucleotide primer

<400> SEQUENCE: 80
cttttcttcg agctccttcc atac        24

<210> SEQ ID NO 81
<211> LENGTH: 47
<212> TYPE: DNA
<213> ORGANISM: Artificial
<220> FEATURE:
<223> OTHER INFORMATION: Oligonucleotide primer

<400> SEQUENCE: 81
gtaaaacgac ggccagtacc atattcaagc tcgagcagtc cagggag        47

```
<210> SEQ ID NO 82
<211> LENGTH: 61
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (39)..(39)
<223> OTHER INFORMATION: Biotin-modified thymidine residue

<400> SEQUENCE: 82
tagctaccag gggctccggc ttccgtcgcg accacgtttt tcgtggtcgc gacggaagcc     60
g                                                                    61

<210> SEQ ID NO 83
<211> LENGTH: 63
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (41)..(41)
<223> OTHER INFORMATION: Biotin-modified thymidine residue

<400> SEQUENCE: 83
tagctaccag ggggctccg gcttccgtcg cgaccacgtt tttcgtggtc gcgacggaag     60
ccg                                                                  63

<210> SEQ ID NO 84
<211> LENGTH: 65
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (43)..(43)
<223> OTHER INFORMATION: Biotin-modified thymidine residue

<400> SEQUENCE: 84
tagctaccag gggggggctc cggcttccgt cgcgaccacg ttttttcgtgg tcgcgacgga     60 agccg                                                                 65

<210> SEQ ID NO 85
<211> LENGTH: 20
<212> TYPE: DNA
<213> ORGANISM: Artificial
<220> FEATURE:
<223> OTHER INFORMATION: Oligonucleotide primer

<400> SEQUENCE: 85
agggaacctt gtagagtggt                                                 20

<210> SEQ ID NO 86
<211> LENGTH: 23
<212> TYPE: DNA
<213> ORGANISM: Artificial
<220> FEATURE:
<223> OTHER INFORMATION: Oligonucleotide primer

<400> SEQUENCE: 86
cttgaggagc gatatcatag ttc                                             23

<210> SEQ ID NO 87
```

```
<211> LENGTH: 25
<212> TYPE: DNA
<213> ORGANISM: Artificial
<220> FEATURE:
<223> OTHER INFORMATION: Oligonucleotide primer

<400> SEQUENCE: 87
gggtacgtgg agaccctctt cggcc                                          25

<210> SEQ ID NO 88
<211> LENGTH: 28
<212> TYPE: DNA
<213> ORGANISM: Artificial
<220> FEATURE:
<223> OTHER INFORMATION: Oligonucleotide primer

<400> SEQUENCE: 88
accaccgaac tgcgggtgac gccaagcg                                       28

<210> SEQ ID NO 89
<211> LENGTH: 43
<212> TYPE: DNA
<213> ORGANISM: Artificial
<220> FEATURE:
<223> OTHER INFORMATION: Oligonucleotide primer

<400> SEQUENCE: 89
caggaaacag ctatgacgag aaaagtgaaa tgaatagttc gac                      43

<210> SEQ ID NO 90
<211> LENGTH: 45
<212> TYPE: DNA
<213> ORGANISM: Artificial
<220> FEATURE:
<223> OTHER INFORMATION: Oligonucleotide primer

<400> SEQUENCE: 90
gtaaaacgac ggccagtacc accgaactgc gggtgacgcc aagcg                    45

<210> SEQ ID NO 91
<211> LENGTH: 48
<212> TYPE: DNA
<213> ORGANISM: Artificial
<220> FEATURE:
<223> OTHER INFORMATION: Oligonucleotide primer

<400> SEQUENCE: 91
caggaaacag ctatgaccat atgattttag atgtggatta cataactg                 48

<210> SEQ ID NO 92
<211> LENGTH: 17
<212> TYPE: DNA
<213> ORGANISM: Artificial
<220> FEATURE:
<223> OTHER INFORMATION: Oligonucleotide primer

<400> SEQUENCE: 92
gtaaaacgac ggccagt                                                   17

<210> SEQ ID NO 93
<211> LENGTH: 20
<212> TYPE: DNA
<213> ORGANISM: Artificial
<220> FEATURE:
<223> OTHER INFORMATION: Oligonucleotide primer

<400> SEQUENCE: 93
```
gcgagagaga gatgataaag                                              20

<210> SEQ ID NO 94
<211> LENGTH: 20
<212> TYPE: DNA
<213> ORGANISM: Artificial
<220> FEATURE:
<223> OTHER INFORMATION: Oligonucleotide primer

<400> SEQUENCE: 94
tcgaaatgta ttcttccctt                                              20

<210> SEQ ID NO 95
<211> LENGTH: 20
<212> TYPE: DNA
<213> ORGANISM: Artificial
<220> FEATURE:
<223> OTHER INFORMATION: Oligonucleotide primer

<400> SEQUENCE: 95
aagaggtatg cagtaataga                                              20

<210> SEQ ID NO 96
<211> LENGTH: 23
<212> TYPE: DNA
<213> ORGANISM: Artificial
<220> FEATURE:
<223> OTHER INFORMATION: Oligonucleotide primer

<400> SEQUENCE: 96
cgggaaagaa ttccttccaa tgg                                          23

<210> SEQ ID NO 97
<211> LENGTH: 67
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (45)..(45)
<223> OTHER INFORMATION: Biotin-modified thymidine residue

<400> SEQUENCE: 97
gacttccttg cctgctcgtc gtcggcatcc gtcgcgacca cgttttttcgt ggtcgcgacg    60 gatgccg                                                            67

<210> SEQ ID NO 98
<211> LENGTH: 20
<212> TYPE: DNA
<213> ORGANISM: Artificial
<220> FEATURE:
<223> OTHER INFORMATION: Oligonucleotide primer

<400> SEQUENCE: 98
ggtacgtgga gaccctcttc                                              20

<210> SEQ ID NO 99
<211> LENGTH: 21
<212> TYPE: DNA
<213> ORGANISM: Artificial
<220> FEATURE:
<223> OTHER INFORMATION: Oligonucleotide primer

<400> SEQUENCE: 99
tgttgaaggc catgcgctcg g                                            21

```
<210> SEQ ID NO 100
<211> LENGTH: 35
<212> TYPE: DNA
<213> ORGANISM: Artificial
<220> FEATURE:
<223> OTHER INFORMATION: Oligonucleotide primer

<400> SEQUENCE: 100
caggaaacag ctatgacgaa ctcgggaaag aattc                              35

<210> SEQ ID NO 101
<211> LENGTH: 48
<212> TYPE: DNA
<213> ORGANISM: Artificial
<220> FEATURE:
<223> OTHER INFORMATION: Oligonucleotide primer

<400> SEQUENCE: 101
gtaaaacgac ggccagtacc gtcgacttag gatttttaa tgttaagc                 48

<210> SEQ ID NO 102
<211> LENGTH: 54
<212> TYPE: DNA
<213> ORGANISM: Artificial
<220> FEATURE:
<223> OTHER INFORMATION: Oligonucleotide primer

<400> SEQUENCE: 102
ggaaaggtct cagtgggacg acatcgtgta tctggacttc atatccctgt atcc         54

<210> SEQ ID NO 103
<211> LENGTH: 37
<212> TYPE: DNA
<213> ORGANISM: Artificial
<220> FEATURE:
<223> OTHER INFORMATION: Oligonucleotide primer

<400> SEQUENCE: 103
gagtaggtct ctccacagtc ccctttcggg ctccttg                            37

<210> SEQ ID NO 104
<211> LENGTH: 21
<212> TYPE: DNA
<213> ORGANISM: Artificial
<220> FEATURE:
<223> OTHER INFORMATION: Oligonucleotide primer

<400> SEQUENCE: 104
gctgaggaag gcctacgaga g                                             21

<210> SEQ ID NO 105
<211> LENGTH: 25
<212> TYPE: DNA
<213> ORGANISM: Artificial
<220> FEATURE:
<223> OTHER INFORMATION: Oligonucleotide primer

<400> SEQUENCE: 105
gggtacgtgg agaccctctt cggcc                                         25

<210> SEQ ID NO 106
<211> LENGTH: 52
<212> TYPE: DNA
<213> ORGANISM: Artificial
<220> FEATURE:
<223> OTHER INFORMATION: Oligonucleotide primer
```

```
<400> SEQUENCE: 106
acaggaaaca gctatgacaa aggtctcagt taaagagcca gaaaaggggt tg              52

<210> SEQ ID NO 107
<211> LENGTH: 20
<212> TYPE: DNA
<213> ORGANISM: Artificial
<220> FEATURE:
<223> OTHER INFORMATION: Oligonucleotide primer

<400> SEQUENCE: 107
caggaaacag ctatgacaaa                                                  20

<210> SEQ ID NO 108
<211> LENGTH: 35
<212> TYPE: DNA
<213> ORGANISM: Artificial
<220> FEATURE:
<223> OTHER INFORMATION: Oligonucleotide primer

<400> SEQUENCE: 108
gagtaggtct cttaacgaat ccacctgtgt agctc                                 35

<210> SEQ ID NO 109
<211> LENGTH: 69
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (47)..(47)
<223> OTHER INFORMATION: Biotin-modified thymidine residue

<400> SEQUENCE: 109
tagctcggta aaaaaaaaaa acgccggctt ccgtcgcgac cacgttttc gtggtcgcga       60 cggaagccg                                                              69

<210> SEQ ID NO 110
<211> LENGTH: 23
<212> TYPE: DNA
<213> ORGANISM: Artificial
<220> FEATURE:
<223> OTHER INFORMATION: Oligonucleotide primer

<400> SEQUENCE: 110
acttcatctg cagagagaaa gag                                              23

<210> SEQ ID NO 111
<211> LENGTH: 23
<212> TYPE: DNA
<213> ORGANISM: Artificial
<220> FEATURE:
<223> OTHER INFORMATION: Oligonucleotide primer

<400> SEQUENCE: 111
aatattcagt atgaaaaaca ttg                                              23

<210> SEQ ID NO 112
<211> LENGTH: 21
<212> TYPE: DNA
<213> ORGANISM: Artificial
<220> FEATURE:
<223> OTHER INFORMATION: Oligonucleotide primer

<400> SEQUENCE: 112
```

-continued

| | |
|---|---|
| cctggacttg aactgtgaca c | 21 |

<210> SEQ ID NO 113
<211> LENGTH: 21
<212> TYPE: DNA
<213> ORGANISM: Artificial
<220> FEATURE:
<223> OTHER INFORMATION: Oligonucleotide primer

<400> SEQUENCE: 113

| | |
|---|---|
| cggagaagaa gccaaacttc c | 21 |

<210> SEQ ID NO 114
<211> LENGTH: 22
<212> TYPE: DNA
<213> ORGANISM: Artificial
<220> FEATURE:
<223> OTHER INFORMATION: Oligonucleotide primer

<400> SEQUENCE: 114

| | |
|---|---|
| ctattcaggc agagacagaa ag | 22 |

<210> SEQ ID NO 115
<211> LENGTH: 22
<212> TYPE: DNA
<213> ORGANISM: Artificial
<220> FEATURE:
<223> OTHER INFORMATION: Oligonucleotide primer

<400> SEQUENCE: 115

| | |
|---|---|
| aacccacagt tttcgtggga ca | 22 |

<210> SEQ ID NO 116
<211> LENGTH: 21
<212> TYPE: DNA
<213> ORGANISM: Artificial
<220> FEATURE:
<223> OTHER INFORMATION: Oligonucleotide primer

<400> SEQUENCE: 116

| | |
|---|---|
| tgttgaaggc catgcgctcg g | 21 |

<210> SEQ ID NO 117
<211> LENGTH: 44
<212> TYPE: DNA
<213> ORGANISM: Artificial
<220> FEATURE:
<223> OTHER INFORMATION: Oligonucleotide primer

<400> SEQUENCE: 117

| | |
|---|---|
| tagccccctt attagcgttt gccaagggaa ccttgtagag tggt | 44 |

<210> SEQ ID NO 118
<211> LENGTH: 47
<212> TYPE: DNA
<213> ORGANISM: Artificial
<220> FEATURE:
<223> OTHER INFORMATION: Oligonucleotide primer

<400> SEQUENCE: 118

| | |
|---|---|
| tagccccctt attagcgttt gccacttgag gagcgatatc atagttc | 47 |

<210> SEQ ID NO 119
<211> LENGTH: 21
<212> TYPE: DNA
<213> ORGANISM: Artificial
<220> FEATURE:

<223> OTHER INFORMATION: Oligonucleotide primer

<400> SEQUENCE: 119
ctaatgcacg tggagtagtg g                                     21

<210> SEQ ID NO 120
<211> LENGTH: 23
<212> TYPE: DNA
<213> ORGANISM: Artificial
<220> FEATURE:
<223> OTHER INFORMATION: Oligonucleotide primer

<400> SEQUENCE: 120
agttaactat ggtgcatcca ttg                                   23

<210> SEQ ID NO 121
<211> LENGTH: 21
<212> TYPE: DNA
<213> ORGANISM: Artificial
<220> FEATURE:
<223> OTHER INFORMATION: Oligonucleotide primer

<400> SEQUENCE: 121
gagaaagttc agtcatttgt g                                     21

<210> SEQ ID NO 122
<211> LENGTH: 23
<212> TYPE: DNA
<213> ORGANISM: Artificial
<220> FEATURE:
<223> OTHER INFORMATION: Oligonucleotide primer

<400> SEQUENCE: 122
ggacgaatct gagatttgtt aag                                   23

<210> SEQ ID NO 123
<211> LENGTH: 21
<212> TYPE: DNA
<213> ORGANISM: Artificial
<220> FEATURE:
<223> OTHER INFORMATION: Oligonucleotide primer

<400> SEQUENCE: 123
agctgtaagt agcatttgtg c                                     21

<210> SEQ ID NO 124
<211> LENGTH: 21
<212> TYPE: DNA
<213> ORGANISM: Artificial
<220> FEATURE:
<223> OTHER INFORMATION: Oligonucleotide primer

<400> SEQUENCE: 124 acagcccttacaccaaacca g                                      21

<210> SEQ ID NO 125
<211> LENGTH: 23
<212> TYPE: DNA
<213> ORGANISM: Artificial
<220> FEATURE:
<223> OTHER INFORMATION: Oligonucleotide primer

<400> SEQUENCE: 125
gatcattggt ttagatagat ccc                                   23

<210> SEQ ID NO 126

```
<211> LENGTH: 21
<212> TYPE: DNA
<213> ORGANISM: Artificial
<220> FEATURE:
<223> OTHER INFORMATION: Oligonucleotide primer

<400> SEQUENCE: 126
aggatcgctt gtgcccagaa g                                              21

<210> SEQ ID NO 127
<211> LENGTH: 21
<212> TYPE: DNA
<213> ORGANISM: Artificial
<220> FEATURE:
<223> OTHER INFORMATION: Oligonucleotide primer

<400> SEQUENCE: 127
agacatcatc cctagaggtt c                                              21

<210> SEQ ID NO 128
<211> LENGTH: 21
<212> TYPE: DNA
<213> ORGANISM: Artificial
<220> FEATURE:
<223> OTHER INFORMATION: Oligonucleotide primer

<400> SEQUENCE: 128
agacaccaga cacagaaggg c                                              21

<210> SEQ ID NO 129
<211> LENGTH: 22
<212> TYPE: DNA
<213> ORGANISM: Artificial
<220> FEATURE:
<223> OTHER INFORMATION: Oligonucleotide primer

<400> SEQUENCE: 129
caccccatat ctgcttaatc ag                                             22

<210> SEQ ID NO 130
<211> LENGTH: 21
<212> TYPE: DNA
<213> ORGANISM: Artificial
<220> FEATURE:
<223> OTHER INFORMATION: Oligonucleotide primer

<400> SEQUENCE: 130
gtgatcctct gacatcggtg g                                              21

<210> SEQ ID NO 131
<211> LENGTH: 21
<212> TYPE: DNA
<213> ORGANISM: Artificial
<220> FEATURE:
<223> OTHER INFORMATION: Oligonucleotide primer

<400> SEQUENCE: 131
gatggttttt gaaggatggt c                                              21

<210> SEQ ID NO 132
<211> LENGTH: 21
<212> TYPE: DNA
<213> ORGANISM: Artificial
<220> FEATURE:
<223> OTHER INFORMATION: Oligonucleotide primer

<400> SEQUENCE: 132
```

```
tccatgcacc ttgtgatatt c                                              21
```

<210> SEQ ID NO 133
<211> LENGTH: 2328
<212> TYPE: DNA
<213> ORGANISM: Pyrococcus furiosus

<400> SEQUENCE: 133

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgacttccc atatttagcg    660
aaaaggggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca gtaggccac    1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
```

```
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                 2328
```

<210> SEQ ID NO 134
<211> LENGTH: 775
<212> TYPE: PRT
<213> ORGANISM: Pyrococcus furiosus

<400> SEQUENCE: 134

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
```

```
                    340                 345                 350
Val Glu Trp Phe Leu Leu Arg Lys Ala Tyr Glu Arg Asn Glu Val Ala
                355                 360                 365
Pro Asn Lys Pro Ser Glu Glu Glu Tyr Gln Arg Arg Leu Arg Glu Ser
            370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
                420                 425                 430
Asp Ile Ala Pro Gln Val Gly His Lys Phe Cys Lys Asp Ile Pro Gly
                435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
            595                 600                 605
Leu Glu Ile Val Arg Arg Asp Trp Ser Glu Ile Ala Lys Glu Thr Gln
            610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
            675                 680                 685
Ala Lys Gly Val Lys Ile Lys Pro Gly Met Val Ile Gly Tyr Ile Val
            690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
            755                 760                 765
```

```
Trp Leu Asn Ile Lys Lys Ser
    770             775
```

<210> SEQ ID NO 135
<211> LENGTH: 21
<212> TYPE: DNA
<213> ORGANISM: Artificial
<220> FEATURE:
<223> OTHER INFORMATION: Oligonucleotide primer

<400> SEQUENCE: 135

```
gggtacgtgg agaccctctt c                                              21
```

<210> SEQ ID NO 136
<211> LENGTH: 7
<212> TYPE: PRT
<213> ORGANISM: Artificial
<220> FEATURE:
<223> OTHER INFORMATION: Motif

<400> SEQUENCE: 136

```
Phe Arg Ala Leu Tyr Pro Ser
1               5
```

<210> SEQ ID NO 137
<211> LENGTH: 5
<212> TYPE: PRT
<213> ORGANISM: Artificial
<220> FEATURE:
<223> OTHER INFORMATION: Motif

<400> SEQUENCE: 137

```
Glu Asn Ile Val Tyr
1               5
```

<210> SEQ ID NO 138
<211> LENGTH: 13
<212> TYPE: PRT
<213> ORGANISM: Artificial
<220> FEATURE:
<223> OTHER INFORMATION: Motif

<400> SEQUENCE: 138

```
Lys Leu Leu Ala Asn Ser Phe Tyr Gly Tyr Tyr Gly Tyr
1               5                   10
```

<210> SEQ ID NO 139
<211> LENGTH: 4
<212> TYPE: PRT
<213> ORGANISM: Artificial
<220> FEATURE:
<223> OTHER INFORMATION: Motif

<400> SEQUENCE: 139

```
Val Leu Tyr Ile
1
```

<210> SEQ ID NO 140
<211> LENGTH: 150
<212> TYPE: PRT
<213> ORGANISM: Artificial Sequence
<220> FEATURE:
<223> OTHER INFORMATION: Pfu variant AH12

<400> SEQUENCE: 140

```
Glu Phe Leu Pro Met Glu Ile Gln Leu Ser Arg Leu Val Gly Gln Pro
1               5                   10                  15
```

```
Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
        35                  40                  45

Ser Glu Glu Glu Tyr Gln Arg Arg Leu Arg Ser Tyr Thr Gly Gly
 50                  55                  60

Phe Val Lys Glu Pro Glu Lys Gly Leu Trp Asp Gly Leu Ala Tyr Leu
 65                  70                  75                  80

Asp Phe Ile Ala Leu Tyr Pro Ser Ile Ile Val Thr His Asn Val Ser
                85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
                115                 120                 125

Leu Leu Gly His Leu Leu Glu Glu Arg Gln Lys Ile Lys Thr Lys Met
                130                 135                 140

Lys Glu Thr Gln Asp Pro
145                 150

<210> SEQ ID NO 141
<211> LENGTH: 150
<212> TYPE: PRT
<213> ORGANISM: Artificial Sequence
<220> FEATURE:
<223> OTHER INFORMATION: Pfu variant 55

<400> SEQUENCE: 141

Glu Phe Leu Pro Met Glu Ile Gln Leu Ser Arg Leu Val Gly Gln Pro
 1               5                  10                  15

Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
        35                  40                  45

Ser Glu Glu Glu Tyr Gln Arg Arg Leu Arg Ser Tyr Thr Gly Gly
 50                  55                  60

Phe Val Lys Glu Pro Glu Lys Gly Leu Trp Glu Gly Ile Val Tyr Leu
 65                  70                  75                  80

Asp Phe Ile Ala Leu Tyr Pro Ser Ile Ile Ile Thr His Asn Val Ser
                85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
                115                 120                 125

Leu Leu Gly His Leu Leu Glu Glu Arg Gln Lys Ile Lys Thr Lys Met
                130                 135                 140

Lys Glu Thr Gln Asp Pro
145                 150

<210> SEQ ID NO 142
<211> LENGTH: 150
<212> TYPE: PRT
<213> ORGANISM: Artificial Sequence
<220> FEATURE:
<223> OTHER INFORMATION: Pfu variant 23

<400> SEQUENCE: 142

Glu Phe Leu Pro Met Glu Ile Gln Leu Ser Arg Leu Val Gly Gln Pro
 1               5                  10                  15
```

Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
        35                  40                  45

Ser Glu Glu Glu Tyr Gln Arg Arg Leu Arg Ser Tyr Thr Gly Gly
50                  55                  60

Phe Val Lys Glu Pro Glu Lys Gly Leu Trp Glu Asp Leu Val Tyr Leu
65                  70                  75                  80

Asp Phe Ile Ala Leu Tyr Pro Ser Ile Ile Thr His Asn Val Ser
                85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
            115                 120                 125

Leu Leu Gly His Leu Leu Glu Glu Arg Gln Lys Ile Lys Thr Lys Met
        130                 135                 140

Lys Glu Thr His Asp Pro
145                 150

<210> SEQ ID NO 143
<211> LENGTH: 150
<212> TYPE: PRT
<213> ORGANISM: Artificial Sequence
<220> FEATURE:
<223> OTHER INFORMATION: Pfu variant 15

<400> SEQUENCE: 143

Glu Phe Leu Pro Met Glu Ile Gln Leu Ser Arg Leu Ile Gly Gln Pro
1               5                   10                  15

Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
        35                  40                  45

Ser Glu Glu Glu Tyr Gln Arg Arg Leu Arg Ser Tyr Thr Gly Gly
50                  55                  60

Phe Val Lys Glu Pro Glu Lys Gly Leu Trp Asp Ile Val Tyr Leu
65                  70                  75                  80

Asp Phe Ile Ala Leu Tyr Pro Ser Ile Ile Thr His Asn Val Ser
                85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
            115                 120                 125

Leu Leu Gly His Leu Leu Glu Glu Arg Gln Lys Ile Lys Thr Lys Met
        130                 135                 140

Lys Glu Thr Gln Asp Pro
145                 150

<210> SEQ ID NO 144
<211> LENGTH: 150
<212> TYPE: PRT
<213> ORGANISM: Pyrococcus furiosus

<400> SEQUENCE: 144

Glu Phe Leu Pro Met Glu Ile Gln Leu Ser Arg Leu Val Gly Gln Pro
1               5                   10                  15

Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
            35                  40                  45

Ser Glu Glu Glu Tyr Gln Arg Arg Leu Arg Glu Ser Tyr Thr Gly Gly
 50                  55                  60

Phe Val Lys Glu Pro Glu Lys Gly Leu Trp Glu Asn Ile Val Tyr Leu
 65                  70                  75                  80

Asp Phe Arg Ala Leu Tyr Pro Ser Ile Ile Ile Thr His Asn Val Ser
            85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
            115                 120                 125

Leu Leu Gly His Leu Leu Glu Glu Arg Gln Lys Ile Lys Thr Lys Met
            130                 135                 140

Lys Glu Thr Gln Asp Pro
145                 150

<210> SEQ ID NO 145
<211> LENGTH: 150
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (76)..(76)
<223> OTHER INFORMATION: Xaa may be Gly, Asp or Asn

<400> SEQUENCE: 145

Glu Phe Leu Pro Met Glu Ile Gln Leu Ser Arg Leu Val Gly Gln Pro
 1               5                  10                  15

Leu Trp Asp Val Ser Arg Ser Ser Thr Gly Asn Leu Val Glu Trp Phe
            20                  25                  30

Leu Leu Arg Lys Ala Tyr Glu Arg Asn Glu Val Ala Pro Asn Lys Pro
            35                  40                  45

Ser Glu Glu Glu Tyr Gln Arg Arg Leu Arg Glu Ser Tyr Thr Gly Gly
 50                  55                  60

Phe Val Lys Glu Pro Glu Lys Gly Leu Trp Glu Xaa Ile Val Tyr Leu
 65                  70                  75                  80

Asp Phe Ile Ala Leu Tyr Pro Ser Ile Ile Ile Thr His Asn Val Ser
            85                  90                  95

Pro Asp Thr Leu Asn Leu Glu Gly Cys Lys Asn Tyr Asp Ile Ala Pro
                100                 105                 110

Gln Val Gly His Lys Phe Cys Lys Asp Ile Pro Gly Phe Ile Pro Ser
            115                 120                 125

Leu Leu Gly His Leu Leu Glu Glu Arg Gln Lys Ile Lys Thr Lys Met
            130                 135                 140

Lys Glu Thr Gln Asp Pro
145                 150

<210> SEQ ID NO 146
<211> LENGTH: 17
<212> TYPE: PRT
<213> ORGANISM: Pyrococcus furiosus

<400> SEQUENCE: 146

Glu Asn Ile Val Tyr Leu Asp Phe Arg Ala Leu Tyr Pro Ser Ile Ile
 1               5                  10                  15

Ile

<210> SEQ ID NO 147
<211> LENGTH: 17
<212> TYPE: PRT
<213> ORGANISM: Artificial Sequence
<220> FEATURE:
<223> OTHER INFORMATION: Pfu variant 2

<400> SEQUENCE: 147

Glu Asn Ile Val Tyr Leu Asp Phe Arg Ala Leu Tyr Pro Ser Ile Ile
1               5                   10                  15

Ile

<210> SEQ ID NO 148
<211> LENGTH: 17
<212> TYPE: PRT
<213> ORGANISM: Artificial Sequence
<220> FEATURE:
<223> OTHER INFORMATION: Pfu variant 6

<400> SEQUENCE: 148

Glu Asn Ile Val Tyr Leu Asp Phe Arg Ala Leu Tyr Pro Ser Ile Ile
1               5                   10                  15

Ile

<210> SEQ ID NO 149
<211> LENGTH: 17
<212> TYPE: PRT
<213> ORGANISM: Artificial Sequence
<220> FEATURE:
<223> OTHER INFORMATION: Pfu variant 7

<400> SEQUENCE: 149

Glu Asn Ile Val Tyr Leu Asp Phe Arg Ala Leu Tyr Pro Ser Ile Ile
1               5                   10                  15

Ile

<210> SEQ ID NO 150
<211> LENGTH: 17
<212> TYPE: PRT
<213> ORGANISM: Artificial Sequence
<220> FEATURE:
<223> OTHER INFORMATION: Pfu variant 11

<400> SEQUENCE: 150

Glu Asn Ile Val Tyr Leu Asp Phe Arg Ala Leu Tyr Pro Ser Ile Ile
1               5                   10                  15

Ile

<210> SEQ ID NO 151
<211> LENGTH: 17
<212> TYPE: PRT
<213> ORGANISM: Artificial Sequence
<220> FEATURE:
<223> OTHER INFORMATION: Pfu variant 13

<400> SEQUENCE: 151

Glu Asn Ile Val Tyr Leu Asp Phe Arg Ala Leu Tyr Pro Ser Ile Ile
1               5                   10                  15

Ile

<210> SEQ ID NO 152
<211> LENGTH: 17

```
<212> TYPE: PRT
<213> ORGANISM: Artificial Sequence
<220> FEATURE:
<223> OTHER INFORMATION: Pfu variant 3

<400> SEQUENCE: 152

Glu Gly Ile Val Tyr Leu Asp Phe Ile Ala Leu Tyr Pro Ser Ile Ile
1               5                   10                  15

Ile

<210> SEQ ID NO 153
<211> LENGTH: 17
<212> TYPE: PRT
<213> ORGANISM: Artificial Sequence
<220> FEATURE:
<223> OTHER INFORMATION: Pfu variant 4

<400> SEQUENCE: 153

Glu Asp Leu Val Tyr Leu Asp Phe Ile Ala Leu Tyr Pro Ser Ile Ile
1               5                   10                  15

Ile

<210> SEQ ID NO 154
<211> LENGTH: 17
<212> TYPE: PRT
<213> ORGANISM: Artificial Sequence
<220> FEATURE:
<223> OTHER INFORMATION: Pfu variant 5

<400> SEQUENCE: 154

Glu Gly Ile Val Tyr Leu Asp Phe Ile Ala Leu Tyr Pro Ser Ile Ile
1               5                   10                  15

Ile

<210> SEQ ID NO 155
<211> LENGTH: 17
<212> TYPE: PRT
<213> ORGANISM: Artificial Sequence
<220> FEATURE:
<223> OTHER INFORMATION: Pfu variant 8

<400> SEQUENCE: 155

Glu Asp Leu Val Tyr Leu Asp Phe Ile Ala Leu Tyr Pro Ser Ile Ile
1               5                   10                  15

Ile

<210> SEQ ID NO 156
<211> LENGTH: 17
<212> TYPE: PRT
<213> ORGANISM: Artificial Sequence
<220> FEATURE:
<223> OTHER INFORMATION: Pfu variant 9

<400> SEQUENCE: 156

Asp Asp Ile Val Tyr Leu Asp Phe Ile Ala Leu Tyr Pro Ser Ile Ile
1               5                   10                  15

Ile

<210> SEQ ID NO 157
<211> LENGTH: 17
<212> TYPE: PRT
<213> ORGANISM: Artificial Sequence
<220> FEATURE:
<223> OTHER INFORMATION: Pfu variant 10
```

```
<400> SEQUENCE: 157

Glu Gly Ile Val Tyr Leu Asp Phe Ile Ala Leu Tyr Pro Ser Ile Ile
1               5                   10                  15

Ile

<210> SEQ ID NO 158
<211> LENGTH: 17
<212> TYPE: PRT
<213> ORGANISM: Artificial Sequence
<220> FEATURE:
<223> OTHER INFORMATION: Pfu variant 12

<400> SEQUENCE: 158

Glu Gly Ile Val Tyr Leu Asp Phe Ile Ala Leu Tyr Pro Ser Ile Ile
1               5                   10                  15

Ile

<210> SEQ ID NO 159
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa may be Asn, Gly or Asp.

<400> SEQUENCE: 159

Glu Xaa Ile Val Tyr Leu Asp Phe Ile Ala Leu Tyr Pro Ser Ile Ile
1               5                   10                  15

Ile

<210> SEQ ID NO 160
<211> LENGTH: 14
<212> TYPE: PRT
<213> ORGANISM: Pyrococcus furiosus

<400> SEQUENCE: 160

Lys Leu Leu Ala Asn Ser Phe Tyr Gly Tyr Tyr Gly Tyr Ala
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Pfu variant 2

<400> SEQUENCE: 161

Lys Leu Leu Ala Asn Ser Val Tyr Gly Tyr Phe Gly Tyr Ala
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Pfu variant 6

<400> SEQUENCE: 162

Lys Leu Leu Ala Asn Ser Phe Tyr Gly Tyr Phe Gly Tyr Thr
1               5                   10

<210> SEQ ID NO 163
```

```
<211> LENGTH: 14
<212> TYPE: PRT
<213> ORGANISM: Artificial Sequence
<220> FEATURE:
<223> OTHER INFORMATION: Pfu variant 7

<400> SEQUENCE: 163

Lys Met Ala Ala Asn Ser Phe Trp Gly Tyr Ile Gly Tyr Thr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Pfu variant 11

<400> SEQUENCE: 164

Lys Leu Leu Ala Asn Ser Phe Tyr Gly Tyr Phe Gly Tyr Thr
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Pfu variant 13

<400> SEQUENCE: 165

Lys Leu Val Ala Asn Ser Phe Tyr Gly Ser Tyr Gly Tyr Pro
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Pfu variant 3

<400> SEQUENCE: 166

Lys Leu Leu Ala Asn Ser Leu Tyr Gly Tyr Tyr Gly Tyr Ala
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Pfu variant 4

<400> SEQUENCE: 167

Lys Leu Leu Ala Asn Thr Phe Tyr Gly Tyr Tyr Gly Tyr Ala
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Pfu variant 5

<400> SEQUENCE: 168

Lys Leu Leu Ala Asn Ser Phe Tyr Gly Tyr Phe Gly Tyr Pro
1               5                   10

<210> SEQ ID NO 169
<211> LENGTH: 14
<212> TYPE: PRT
```

```
<213> ORGANISM: Artificial Sequence
<220> FEATURE:
<223> OTHER INFORMATION: Pfu variant 8

<400> SEQUENCE: 169

Lys Leu Leu Ala Asn Ser Phe Tyr Gly Tyr Phe Gly Tyr Pro
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Pfu variant 9

<400> SEQUENCE: 170

Lys Leu Leu Thr Asn Ser Val Tyr Gly Tyr Tyr Gly Tyr Thr
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Pfu variant 10

<400> SEQUENCE: 171

Lys Leu Leu Ala Asn Ser Phe Tyr Gly Tyr Tyr Gly Tyr Pro
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Pfu variant 12

<400> SEQUENCE: 172

Lys Asn Leu Ala Asn Cys Phe Tyr Gly Tyr Ile Gly Phe Ala
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (11)..(11)
<223> OTHER INFORMATION: Xaa may be Tyr, Phe or Ile
<220> FEATURE:
<221> NAME/KEY: MISC_FEATURE
<222> LOCATION: (14)..(14)
<223> OTHER INFORMATION: Xaa may be Ala, Thr or Pro

<400> SEQUENCE: 173

Lys Leu Leu Ala Asn Ser Phe Tyr Gly Tyr Xaa Gly Tyr Xaa
1               5                   10

<210> SEQ ID NO 174
<211> LENGTH: 17
<212> TYPE: PRT
<213> ORGANISM: Artificial Sequence
<220> FEATURE:
<223> OTHER INFORMATION: Pfu variant E10

<400> SEQUENCE: 174

Asp Asp Ile Val Tyr Leu Asp Phe Ile Ala Leu Tyr Pro Ser Ile Ile
```

```
1               5                  10                  15

Ile

<210> SEQ ID NO 175
<211> LENGTH: 17
<212> TYPE: PRT
<213> ORGANISM: Artificial Sequence
<220> FEATURE:
<223> OTHER INFORMATION: Pfu variant 15

<400> SEQUENCE: 175

Asp Asp Ile Val Tyr Leu Asp Phe Ile Ala Leu Tyr Pro Ser Ile Ile
1               5                  10                  15

Ile

<210> SEQ ID NO 176
<211> LENGTH: 17
<212> TYPE: PRT
<213> ORGANISM: Artificial Sequence
<220> FEATURE:
<223> OTHER INFORMATION: Pfu variant 5

<400> SEQUENCE: 176

Asp Asp Ile Val Tyr Leu Asp Phe Ile Ala Leu Tyr Pro Ser Ile Ile
1               5                  10                  15

Ile

<210> SEQ ID NO 177
<211> LENGTH: 17
<212> TYPE: PRT
<213> ORGANISM: Artificial Sequence
<220> FEATURE:
<223> OTHER INFORMATION: Pfu variant 28

<400> SEQUENCE: 177

Glu Gly Ile Val Tyr Leu Asp Phe Ile Ala Leu Tyr Pro Ser Ile Ile
1               5                  10                  15

Ile

<210> SEQ ID NO 178
<211> LENGTH: 17
<212> TYPE: PRT
<213> ORGANISM: Artificial Sequence
<220> FEATURE:
<223> OTHER INFORMATION: Pfu variant 27

<400> SEQUENCE: 178

Glu Gly Ile Val Tyr Leu Asp Phe Ile Ala Leu Tyr Pro Ser Ile Ile
1               5                  10                  15

Ile

<210> SEQ ID NO 179
<211> LENGTH: 17
<212> TYPE: PRT
<213> ORGANISM: Artificial Sequence
<220> FEATURE:
<223> OTHER INFORMATION: Pfu variant 25

<400> SEQUENCE: 179

Glu Asp Leu Val Tyr Leu Asp Phe Ile Ala Leu Tyr Pro Ser Ile Ile
1               5                  10                  15

Ile
```

```
<210> SEQ ID NO 180
<211> LENGTH: 17
<212> TYPE: PRT
<213> ORGANISM: Artificial Sequence
<220> FEATURE:
<223> OTHER INFORMATION: Pfu variant 23

<400> SEQUENCE: 180

Glu Gly Ile Val Tyr Leu Asp Phe Ile Ala Leu Tyr Pro Ser Ile Ile
1               5                   10                  15

Ile

<210> SEQ ID NO 181
<211> LENGTH: 17
<212> TYPE: PRT
<213> ORGANISM: Artificial Sequence
<220> FEATURE:
<223> OTHER INFORMATION: Pfu variant 22

<400> SEQUENCE: 181

Glu Asp Leu Val Tyr Leu Asp Phe Ile Ala Leu Tyr Pro Ser Ile Ile
1               5                   10                  15

Ile

<210> SEQ ID NO 182
<211> LENGTH: 17
<212> TYPE: PRT
<213> ORGANISM: Artificial Sequence
<220> FEATURE:
<223> OTHER INFORMATION: Pfu variant 13

<400> SEQUENCE: 182

Glu Gly Ile Val Tyr Leu Asp Phe Ile Ala Leu Tyr Pro Ser Ile Ile
1               5                   10                  15

Ile

<210> SEQ ID NO 183
<211> LENGTH: 17
<212> TYPE: PRT
<213> ORGANISM: Artificial Sequence
<220> FEATURE:
<223> OTHER INFORMATION: Pfu variant 12

<400> SEQUENCE: 183

Glu Gly Ile Val Tyr Leu Asp Phe Ile Ala Leu Tyr Pro Ser Ile Ile
1               5                   10                  15

Ile

<210> SEQ ID NO 184
<211> LENGTH: 17
<212> TYPE: PRT
<213> ORGANISM: Artificial Sequence
<220> FEATURE:
<223> OTHER INFORMATION: Pfu variant 10

<400> SEQUENCE: 184

Asp Asp Ile Val Tyr Leu Asp Phe Ile Ala Leu Tyr Pro Ser Ile Ile
1               5                   10                  15

Ile

<210> SEQ ID NO 185
<211> LENGTH: 17
<212> TYPE: PRT
<213> ORGANISM: Artificial Sequence
<220> FEATURE:
```

-continued

<223> OTHER INFORMATION: Pfu variant 9

<400> SEQUENCE: 185

Asp Asp Ile Val Tyr Leu Asp Phe Ile Ala Leu Tyr Pro Ser Ile Ile
1               5                   10                  15

Ile

<210> SEQ ID NO 186
<211> LENGTH: 17
<212> TYPE: PRT
<213> ORGANISM: Pyrococcus furiosus

<400> SEQUENCE: 186

Glu Asn Ile Val Tyr Leu Asp Phe Arg Ala Leu Tyr Pro Ser Ile Ile
1               5                   10                  15

Ile

<210> SEQ ID NO 187
<211> LENGTH: 17
<212> TYPE: PRT
<213> ORGANISM: Artificial Sequence
<220> FEATURE:
<223> OTHER INFORMATION: Consensus sequence

<400> SEQUENCE: 187

Glu Asp Ile Val Tyr Leu Asp Phe Ile Ala Leu Tyr Pro Ser Ile Ile
1               5                   10                  15

Ile

<210> SEQ ID NO 188
<211> LENGTH: 10
<212> TYPE: PRT
<213> ORGANISM: Artificial Sequence
<220> FEATURE:
<223> OTHER INFORMATION: Pfu variant E10

<400> SEQUENCE: 188

Val Leu Tyr Ile Asp Thr Asp Gly Leu His
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Pfu variant 15

<400> SEQUENCE: 189

Val Ile Tyr Ile Asp Thr Asp Gly Leu Leu
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Pfu variant 5

<400> SEQUENCE: 190

Val Leu Tyr Ile Asp Thr Asp Gly Leu His
1               5                   10

<210> SEQ ID NO 191
<211> LENGTH: 10
<212> TYPE: PRT

<213> ORGANISM: Artificial Sequence
<220> FEATURE:
<223> OTHER INFORMATION: Pfu variant 28

<400> SEQUENCE: 191

Val Leu Tyr Ile Asp Thr Asp Gly Leu His
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Pfu variant 27

<400> SEQUENCE: 192

Val Leu Tyr Ile Asp Thr Asp Gly Leu His
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Pfu variant 25

<400> SEQUENCE: 193

Val Leu Tyr Ile Asp Thr Asp Gly Leu Leu
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Pfu variant 23

<400> SEQUENCE: 194

Val Leu Tyr Ile Asp Thr Asp Gly Leu His
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Pfu variant 22

<400> SEQUENCE: 195

Val Leu Tyr Ile Asp Thr Asp Gly Leu His
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Pfu variant 13

<400> SEQUENCE: 196

Val Leu Tyr Ile Asp Thr Asp Gly Leu His
1               5                   10

<210> SEQ ID NO 197
<211> LENGTH: 10
<212> TYPE: PRT
<213> ORGANISM: Artificial Sequence
<220> FEATURE:

-continued

<223> OTHER INFORMATION: Pfu variant 12

<400> SEQUENCE: 197

Val Leu Tyr Ile Asp Thr Asp Gly Leu His
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Pfu variant 10

<400> SEQUENCE: 198

Val Leu Tyr Ile Asp Thr Asp Gly Leu Leu
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Pfu variant 9

<400> SEQUENCE: 199

Val Leu Tyr Ile Asp Thr Asp Gly Leu His
1               5                   10

<210> SEQ ID NO 200
<211> LENGTH: 10
<212> TYPE: PRT
<213> ORGANISM: Pyrococcus furiosus

<400> SEQUENCE: 200

Val Leu Tyr Ile Asp Thr Asp Gly Leu Tyr
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Consensus sequence

<400> SEQUENCE: 201

Val Leu Tyr Ile Asp Thr Asp Gly Leu His
1               5                   10

<210> SEQ ID NO 202
<211> LENGTH: 17
<212> TYPE: PRT
<213> ORGANISM: Artificial Sequence
<220> FEATURE:
<223> OTHER INFORMATION: Pfu variant 5

<400> SEQUENCE: 202

Asp Asp Ile Val Tyr Leu Asp Phe Ile Ala Leu Tyr Pro Ser Ile Ile
1               5                   10                  15

Ile

<210> SEQ ID NO 203
<211> LENGTH: 17
<212> TYPE: PRT
<213> ORGANISM: Artificial Sequence
<220> FEATURE:
<223> OTHER INFORMATION: Pfu variant 4

```
<400> SEQUENCE: 203

Asp Asp Ile Val Tyr Leu Asp Phe Ile Ala Leu Tyr Pro Ser Ile Ile
1               5                   10                  15

Ile

<210> SEQ ID NO 204
<211> LENGTH: 17
<212> TYPE: PRT
<213> ORGANISM: Artificial Sequence
<220> FEATURE:
<223> OTHER INFORMATION: Pfu variant 3

<400> SEQUENCE: 204

Asp Asp Ile Val Tyr Leu Asp Phe Ile Ala Leu Tyr Pro Ser Ile Ile
1               5                   10                  15

Ile

<210> SEQ ID NO 205
<211> LENGTH: 17
<212> TYPE: PRT
<213> ORGANISM: Artificial Sequence
<220> FEATURE:
<223> OTHER INFORMATION: Pfu variant 2

<400> SEQUENCE: 205

Asp Asp Ile Val Tyr Leu Asp Phe Ile Ala Leu Tyr Pro Ser Ile Ile
1               5                   10                  15

Ile

<210> SEQ ID NO 206
<211> LENGTH: 17
<212> TYPE: PRT
<213> ORGANISM: Artificial Sequence
<220> FEATURE:
<223> OTHER INFORMATION: Pfu variant 11

<400> SEQUENCE: 206

Glu Gly Ile Val Tyr Leu Asp Phe Ile Ala Leu Tyr Pro Ser Ile Ile
1               5                   10                  15

Ile

<210> SEQ ID NO 207
<211> LENGTH: 17
<212> TYPE: PRT
<213> ORGANISM: Artificial Sequence
<220> FEATURE:
<223> OTHER INFORMATION: Pfu variant 10

<400> SEQUENCE: 207

Asp Asp Ile Val Tyr Leu Asp Phe Ile Ala Leu Tyr Pro Ser Ile Ile
1               5                   10                  15

Ile

<210> SEQ ID NO 208
<211> LENGTH: 17
<212> TYPE: PRT
<213> ORGANISM: Artificial Sequence
<220> FEATURE:
<223> OTHER INFORMATION: Pfu variant 1

<400> SEQUENCE: 208

Glu Asp Leu Val Tyr Leu Asp Phe Ile Ala Leu Tyr Pro Ser Ile Ile
1               5                   10                  15
```

Ile

```
<210> SEQ ID NO 209
<211> LENGTH: 17
<212> TYPE: PRT
<213> ORGANISM: Artificial Sequence
<220> FEATURE:
<223> OTHER INFORMATION: Pfu variant 9

<400> SEQUENCE: 209

Glu Gly Ile Val Tyr Leu Asp Phe Ile Ala Leu Tyr Pro Ser Ile Ile
1               5                   10                  15

Ile

<210> SEQ ID NO 210
<211> LENGTH: 17
<212> TYPE: PRT
<213> ORGANISM: Artificial Sequence
<220> FEATURE:
<223> OTHER INFORMATION: Pfu variant 8

<400> SEQUENCE: 210

Asp Asp Ile Val Tyr Leu Asp Phe Ile Ala Leu Tyr Pro Ser Ile Ile
1               5                   10                  15

Ile

<210> SEQ ID NO 211
<211> LENGTH: 17
<212> TYPE: PRT
<213> ORGANISM: Artificial Sequence
<220> FEATURE:
<223> OTHER INFORMATION: Pfu variant 7

<400> SEQUENCE: 211

Glu Asp Leu Val Tyr Leu Asp Phe Ile Ala Leu Tyr Pro Ser Ile Ile
1               5                   10                  15

Ile

<210> SEQ ID NO 212
<211> LENGTH: 17
<212> TYPE: PRT
<213> ORGANISM: Artificial Sequence
<220> FEATURE:
<223> OTHER INFORMATION: Pfu variant 6

<400> SEQUENCE: 212

Glu Gly Ile Val Tyr Leu Asp Phe Ile Ala Leu Tyr Pro Ser Ile Ile
1               5                   10                  15

Ile

<210> SEQ ID NO 213
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa may be Glu or Asp

<400> SEQUENCE: 213

Xaa Asp Ile Val Tyr Leu Asp Phe Ile Ala Leu Tyr Pro Ser Ile Ile
1               5                   10                  15

Ile
```

<210> SEQ ID NO 214
<211> LENGTH: 10
<212> TYPE: PRT
<213> ORGANISM: Pyrococcus furiosus

<400> SEQUENCE: 214

Val Leu Tyr Ile Asp Thr Asp Gly Leu Tyr
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Pfu variant 5

<400> SEQUENCE: 215

Val Leu Tyr Ile Asp Thr Asp Gly Leu His
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Pfu variant 4

<400> SEQUENCE: 216

Val Leu Tyr Ile Asp Thr Asp Gly Leu Leu
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Pfu variant 3

<400> SEQUENCE: 217

Val Leu Tyr Ile Asp Thr Asp Gly Leu Leu
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Pfu variant 2

<400> SEQUENCE: 218

Val Leu Tyr Ile Asp Thr Asp Gly Leu His
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Pfu variant 11

<400> SEQUENCE: 219

Val Leu Tyr Ile Asp Thr Asp Gly Leu Leu
1               5                   10

<210> SEQ ID NO 220
<211> LENGTH: 10

```
<212> TYPE: PRT
<213> ORGANISM: Artificial Sequence
<220> FEATURE:
<223> OTHER INFORMATION: Pfu variant 10

<400> SEQUENCE: 220

Val Leu Tyr Ile Asp Thr Asp Gly Leu His
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Pfu variant 1

<400> SEQUENCE: 221

Val Ile Tyr Ile Asp Thr Asp Gly Leu His
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Pfu variant 9

<400> SEQUENCE: 222

Val Ile Tyr Ile Asp Thr Asp Gly Leu His
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Pfu variant 8

<400> SEQUENCE: 223

Val Leu Tyr Ile Asp Thr Asp Gly Leu Leu
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Pfu variant 7

<400> SEQUENCE: 224

Val Leu Tyr Ile Asp Thr Asp Gly Leu His
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Pfu variant 6

<400> SEQUENCE: 225

Val Leu Tyr Ile Asp Thr Asp Gly Leu Leu
1               5                   10

<210> SEQ ID NO 226
<211> LENGTH: 10
<212> TYPE: PRT
<213> ORGANISM: Artificial Sequence
```

```
<220> FEATURE:
<223> OTHER INFORMATION: Consensus sequence
<220> FEATURE:
<221> NAME/KEY: MISC_FEATURE
<222> LOCATION: (10)..(10)
<223> OTHER INFORMATION: Xaa may be Tyr, His or Leu

<400> SEQUENCE: 226

Val Leu Tyr Ile Asp Thr Asp Gly Leu Xaa
1               5                   10

<210> SEQ ID NO 227
<211> LENGTH: 17
<212> TYPE: PRT
<213> ORGANISM: Artificial Sequence
<220> FEATURE:
<223> OTHER INFORMATION: Pfu variant F1

<400> SEQUENCE: 227

Glu Asn Ile Val Tyr Leu Asp Phe Arg Ala Leu Tyr Pro Ser Ile Ile
1               5                   10                  15

Ile

<210> SEQ ID NO 228
<211> LENGTH: 17
<212> TYPE: PRT
<213> ORGANISM: Artificial Sequence
<220> FEATURE:
<223> OTHER INFORMATION: Pfu variant G2

<400> SEQUENCE: 228

Glu Gly Ile Val Tyr Leu Asp Phe Ile Ala Leu Tyr Pro Ser Ile Ile
1               5                   10                  15

Ile

<210> SEQ ID NO 229
<211> LENGTH: 17
<212> TYPE: PRT
<213> ORGANISM: Artificial Sequence
<220> FEATURE:
<223> OTHER INFORMATION: Pfu variant F2

<400> SEQUENCE: 229

Glu Gly Ile Val Tyr Leu Asp Phe Ile Ala Leu Tyr Pro Ser Ile Ile
1               5                   10                  15

Ile

<210> SEQ ID NO 230
<211> LENGTH: 17
<212> TYPE: PRT
<213> ORGANISM: Artificial Sequence
<220> FEATURE:
<223> OTHER INFORMATION: Pfu variant E2

<400> SEQUENCE: 230

Glu Asp Leu Val Tyr Leu Asp Phe Ile Ala Leu Tyr Pro Ser Ile Ile
1               5                   10                  15

Ile

<210> SEQ ID NO 231
<211> LENGTH: 17
<212> TYPE: PRT
<213> ORGANISM: Artificial Sequence
<220> FEATURE:
<223> OTHER INFORMATION: Pfu variant E1
```

-continued

```
<400> SEQUENCE: 231

Glu Gly Ile Val Tyr Leu Asp Phe Ile Ala Leu Tyr Pro Ser Ile Ile
1               5                   10                  15

Ile

<210> SEQ ID NO 232
<211> LENGTH: 17
<212> TYPE: PRT
<213> ORGANISM: Artificial Sequence
<220> FEATURE:
<223> OTHER INFORMATION: Pfu variant D2

<400> SEQUENCE: 232

Glu Gly Ile Val Tyr Leu Asp Phe Ile Ala Leu Tyr Pro Ser Ile Ile
1               5                   10                  15

Ile

<210> SEQ ID NO 233
<211> LENGTH: 17
<212> TYPE: PRT
<213> ORGANISM: Artificial Sequence
<220> FEATURE:
<223> OTHER INFORMATION: Pfu variant D1

<400> SEQUENCE: 233

Glu Gly Ile Val Tyr Leu Asp Phe Ile Ala Leu Tyr Pro Ser Ile Ile
1               5                   10                  15

Ile

<210> SEQ ID NO 234
<211> LENGTH: 17
<212> TYPE: PRT
<213> ORGANISM: Artificial Sequence
<220> FEATURE:
<223> OTHER INFORMATION: Pfu variant C2

<400> SEQUENCE: 234

Glu Asp Leu Val Tyr Leu Asp Phe Ile Ala Leu Tyr Pro Ser Ile Ile
1               5                   10                  15

Ile

<210> SEQ ID NO 235
<211> LENGTH: 17
<212> TYPE: PRT
<213> ORGANISM: Artificial Sequence
<220> FEATURE:
<223> OTHER INFORMATION: Pfu variant A3

<400> SEQUENCE: 235

Asp Asp Ile Val Tyr Leu Asp Phe Ile Ala Leu Tyr Pro Ser Ile Ile
1               5                   10                  15

Ile

<210> SEQ ID NO 236
<211> LENGTH: 17
<212> TYPE: PRT
<213> ORGANISM: Artificial Sequence
<220> FEATURE:
<223> OTHER INFORMATION: Pfu variant A2

<400> SEQUENCE: 236

Asp Asp Ile Val Tyr Leu Asp Phe Ile Ala Leu Tyr Pro Ser Ile Ile
1               5                   10                  15
```

Ile

<210> SEQ ID NO 237
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa may be Asn, Gly or Asp

<400> SEQUENCE: 237

Glu Xaa Ile Val Tyr Leu Asp Phe Ile Ala Leu Tyr Pro Ser Ile Ile
1               5                   10                  15

Ile

<210> SEQ ID NO 238
<211> LENGTH: 14
<212> TYPE: PRT
<213> ORGANISM: Artificial Sequence
<220> FEATURE:
<223> OTHER INFORMATION: Pfu variant F1

<400> SEQUENCE: 238

Lys Leu Leu Ala Asn Ser Phe Tyr Gly Tyr Lys Gly Tyr Pro
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Pfu variant G2

<400> SEQUENCE: 239

Lys Leu Leu Ala Asn Ser Phe Tyr Gly Tyr Phe Gly Tyr Ala
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Pfu variant F2

<400> SEQUENCE: 240

Lys Leu Leu Ala Asn Ser Phe Tyr Gly Tyr Phe Gly Tyr Ala
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Pfu variant E2

<400> SEQUENCE: 241

Lys Arg Leu Ala Asn Ser Phe Tyr Gly Tyr Phe Ser Tyr Thr
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Pfu variant E1

<400> SEQUENCE: 242

Lys Leu Leu Ala Asn Ser Phe Tyr Gly Tyr Phe Gly Tyr Thr
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Pfu variant D2

<400> SEQUENCE: 243

Lys Leu Leu Ala Asn Ser Phe Tyr Gly Tyr Phe Gly Tyr Thr
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Pfu variant D1

<400> SEQUENCE: 244

Lys Leu Leu Ala Asn Ser Phe Tyr Gly Tyr Tyr Gly Tyr Ala
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Pfu variant C2

<400> SEQUENCE: 245

Lys Leu Phe Ala Asn Ser Phe Tyr Gly Tyr Tyr Gly Tyr Pro
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Pfu variant A3

<400> SEQUENCE: 246

Lys Leu Leu Thr Asn Ser Leu Tyr Gly Tyr Phe Gly Tyr Pro
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Pfu variant A2

<400> SEQUENCE: 247

Lys Leu Phe Ala Asn Ser Phe Tyr Glu Tyr Tyr Gly Tyr Ala
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE

```
<222> LOCATION: (14)..(14)
<223> OTHER INFORMATION: Xaa may be Ala, Pro or Thr

<400> SEQUENCE: 248

Lys Leu Leu Ala Asn Ser Phe Tyr Gly Tyr Phe Gly Tyr Xaa
1               5                   10

<210> SEQ ID NO 249
<211> LENGTH: 17
<212> TYPE: PRT
<213> ORGANISM: Thermococcus gorgonarius

<400> SEQUENCE: 249

Glu Asn Ile Val Tyr Leu Asp Phe Arg Ser Leu Tyr Pro Ser Ile Ile
1               5                   10                  15

Ile

<210> SEQ ID NO 250
<211> LENGTH: 17
<212> TYPE: PRT
<213> ORGANISM: Artificial Sequence
<220> FEATURE:
<223> OTHER INFORMATION: Tgo variant E10AMo

<400> SEQUENCE: 250

Asp Asp Ile Val Tyr Leu Asp Phe Ile Ser Leu Tyr Pro Ser Ile Ile
1               5                   10                  15

Ile

<210> SEQ ID NO 251
<211> LENGTH: 17
<212> TYPE: PRT
<213> ORGANISM: Artificial Sequence
<220> FEATURE:
<223> OTHER INFORMATION: Tgo variant TgoT E10AMo

<400> SEQUENCE: 251

Asp Asp Ile Val Tyr Leu Asp Phe Ile Ser Leu Tyr Pro Ser Ile Ile
1               5                   10                  15

Ile

<210> SEQ ID NO 252
<211> LENGTH: 17
<212> TYPE: PRT
<213> ORGANISM: Artificial Sequence
<220> FEATURE:
<223> OTHER INFORMATION: Consensus sequence

<400> SEQUENCE: 252

Asp Asp Ile Val Tyr Leu Asp Phe Ile Ser Leu Tyr Pro Ser Ile Ile
1               5                   10                  15

Ile

<210> SEQ ID NO 253
<211> LENGTH: 20
<212> TYPE: PRT
<213> ORGANISM: Thermococcus gorgonarius

<400> SEQUENCE: 253

Tyr Arg Gln Arg Ala Ile Lys Ile Leu Ala Asn Ser Phe Tyr Gly Tyr
1               5                   10                  15

Tyr Gly Tyr Ala
            20
```

```
<210> SEQ ID NO 254
<211> LENGTH: 20
<212> TYPE: PRT
<213> ORGANISM: Artificial Sequence
<220> FEATURE:
<223> OTHER INFORMATION: Tgo variant E10AMo

<400> SEQUENCE: 254

Tyr Arg Gln Arg Ala Ile Lys Ile Leu Ala Asn Ser Phe Tyr Gly Tyr
1               5                   10                  15

Tyr Gly Tyr Ala
            20

<210> SEQ ID NO 255
<211> LENGTH: 20
<212> TYPE: PRT
<213> ORGANISM: Artificial Sequence
<220> FEATURE:
<223> OTHER INFORMATION: Tgo variant TgoT E10AMo

<400> SEQUENCE: 255

Tyr Arg Gln Arg Leu Ile Lys Ile Leu Ala Asn Ser Phe Tyr Gly Tyr
1               5                   10                  15

Tyr Gly Tyr Ala
            20

<210> SEQ ID NO 256
<211> LENGTH: 20
<212> TYPE: PRT
<213> ORGANISM: Artificial Sequence
<220> FEATURE:
<223> OTHER INFORMATION: Consensus sequence

<400> SEQUENCE: 256

Tyr Arg Gln Arg Ala Ile Lys Ile Leu Ala Asn Ser Phe Tyr Gly Tyr
1               5                   10                  15

Tyr Gly Tyr Ala
            20

<210> SEQ ID NO 257
<211> LENGTH: 20
<212> TYPE: PRT
<213> ORGANISM: Pyrococcus furiosus

<400> SEQUENCE: 257

Gly Leu Trp Glu Asn Ile Val Tyr Leu Asp Phe Arg Ala Leu Tyr Pro
1               5                   10                  15

Ser Ile Ile Ile
            20

<210> SEQ ID NO 258
<211> LENGTH: 20
<212> TYPE: PRT
<213> ORGANISM: Artificial Sequence
<220> FEATURE:
<223> OTHER INFORMATION: Pfu variant Bio32

<400> SEQUENCE: 258

Gly Leu Trp Asn Asp Leu Val Tyr Leu Asp Phe Ile Ala Leu Tyr Pro
1               5                   10                  15

Ser Ile Ile Ile
            20

<210> SEQ ID NO 259
```

-continued

```
<211> LENGTH: 20
<212> TYPE: PRT
<213> ORGANISM: Artificial Sequence
<220> FEATURE:
<223> OTHER INFORMATION: Pfu variant Bio120

<400> SEQUENCE: 259

Gly Leu Trp Glu Asp Ile Val Tyr Leu Asp Phe Arg Ala Gln Tyr Pro
1               5                   10                  15

Ser Ile Ile Ile
            20

<210> SEQ ID NO 260
<211> LENGTH: 20
<212> TYPE: PRT
<213> ORGANISM: Artificial Sequence
<220> FEATURE:
<223> OTHER INFORMATION: Pfu variant Bio187

<400> SEQUENCE: 260

Gly Leu Trp Glu Gly Ile Val Tyr Leu Asp Phe Ile Ala Leu Tyr Pro
1               5                   10                  15

Ser Ile Ile Ile
            20

<210> SEQ ID NO 261
<211> LENGTH: 20
<212> TYPE: PRT
<213> ORGANISM: Artificial Sequence
<220> FEATURE:
<223> OTHER INFORMATION: Pfu variant Bio33

<400> SEQUENCE: 261

Gly Leu Trp Asp Ser Ile Val Tyr Leu Asp Phe Ile Ala Leu Tyr Pro
1               5                   10                  15

Ser Ile Ile Ile
            20

<210> SEQ ID NO 262
<211> LENGTH: 20
<212> TYPE: PRT
<213> ORGANISM: Artificial Sequence
<220> FEATURE:
<223> OTHER INFORMATION: Pfu variant Bio56

<400> SEQUENCE: 262

Gly Leu Trp Asp Asn Ile Val Tyr Leu Asp Phe Ile Ala Leu Tyr Pro
1               5                   10                  15

Ser Ile Ile Ile
            20

<210> SEQ ID NO 263
<211> LENGTH: 20
<212> TYPE: PRT
<213> ORGANISM: Artificial Sequence
<220> FEATURE:
<223> OTHER INFORMATION: Pfu variant Bio80

<400> SEQUENCE: 263

Gly Leu Trp Asp Ser Leu Val Tyr Leu Asp Phe Ile Ala Leu Tyr Pro
1               5                   10                  15

Ser Ile Ile Ile
            20

<210> SEQ ID NO 264
```

```
<211> LENGTH: 20
<212> TYPE: PRT
<213> ORGANISM: Artificial Sequence
<220> FEATURE:
<223> OTHER INFORMATION: Pfu variant Bio94

<400> SEQUENCE: 264

Gly Leu Trp Asp Asp Leu Ala Tyr Leu Asp Phe Lys Ala Leu Tyr Pro
1               5                   10                  15

Ser Ile Ile Ile
            20

<210> SEQ ID NO 265
<211> LENGTH: 20
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Xaa may be Glu, Asn or Asp
<220> FEATURE:
<221> NAME/KEY: MISC_FEATURE
<222> LOCATION: (5)..(5)
<223> OTHER INFORMATION: Xaa may be Asn, Asp, Gly or Ser

<400> SEQUENCE: 265

Gly Leu Trp Xaa Xaa Ile Val Tyr Leu Asp Phe Ile Ala Leu Tyr Pro
1               5                   10                  15

Ser Ile Ile Ile
            20
```